United States Patent
Lindsley et al.

(10) Patent No.: US 9,453,017 B2
(45) Date of Patent: Sep. 27, 2016

(54) ANTIVIRAL THERAPIES WITH PHOSPHOLIPASE D INHIBITORS

(71) Applicants: Craig W. Lindsley, Brentwood, TN (US); Alex H. Brown, Franklin, TN (US)

(72) Inventors: Craig W. Lindsley, Brentwood, TN (US); Alex H. Brown, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/348,036

(22) PCT Filed: Sep. 30, 2012

(86) PCT No.: PCT/US2012/058192
§ 371 (c)(1),
(2) Date: Mar. 27, 2014

(87) PCT Pub. No.: WO2013/049773
PCT Pub. Date: Apr. 4, 2013

(65) Prior Publication Data
US 2015/0025041 A1 Jan. 22, 2015

Related U.S. Application Data

(60) Provisional application No. 61/541,935, filed on Sep. 30, 2011.

(51) Int. Cl.
*A61K 31/44* (2006.01)
*A61K 31/70* (2006.01)
(Continued)

(52) U.S. Cl.
CPC ............. *C07D 471/10* (2013.01); *A61K 31/05* (2013.01); *A61K 31/138* (2013.01);
(Continued)

(58) Field of Classification Search
CPC .................................................... A61K 31/435
USPC .......................................................... 514/278
See application file for complete search history.

(56) References Cited

U.S. PATENT DOCUMENTS 6,187,559 B1   2/2001  Steed et al. .................. 435/69.1
7,396,546 B2   7/2008  Rosenbloom
(Continued)

FOREIGN PATENT DOCUMENTS

AU   2010275526   3/2012
AU   2012315569   5/2014
(Continued)

OTHER PUBLICATIONS

Alessi, D.R., et al. "Characterization of a 3-phosphoinositide-dependent protein kinase which phosphorylates and activates protein kinase bα," Curr. Biol., vol. 7, pp. 261-269 (1997).
(Continued)

*Primary Examiner* — Shengjun Wang
(74) *Attorney, Agent, or Firm* — Ballard Spahr LLP

(57) ABSTRACT

Disclosed are methods of treating viral infections comprising, in one aspect, administering compounds that are phospholipase D inhibitors. This abstract is intended as a scanning tool for purposes of searching in the particular art and is not intended to be limiting of the present invention. In accordance with the purpose(s) of the invention, as embodied and broadly described herein, the invention, in one aspect, relates to antiviral therapies. For example, compounds having Phospholipase D activity (e.g., isoform selective Phospholipase D inhibitors) can be useful in antiviral therapies (e.g., influenza treatments).

21 Claims, 38 Drawing Sheets

(51) Int. Cl.

| | | |
|---|---|---|
| A61K 31/35 | (2006.01) | |
| A61K 31/215 | (2006.01) | |
| A61K 31/13 | (2006.01) | |
| C07D 471/10 | (2006.01) | |
| A61K 45/06 | (2006.01) | |
| A61K 31/05 | (2006.01) | |
| A61K 31/138 | (2006.01) | |
| A61K 31/4535 | (2006.01) | |
| A61K 31/454 | (2006.01) | |
| A61K 31/435 | (2006.01) | |
| A61K 31/4709 | (2006.01) | |
| A61K 31/498 | (2006.01) | |
| C07D 401/04 | (2006.01) | |
| C07D 401/14 | (2006.01) | |
| C07D 405/14 | (2006.01) | |
| C07D 409/14 | (2006.01) | |
| A61K 31/231 | (2006.01) | |
| A61K 31/661 | (2006.01) | |

(52) U.S. Cl.
CPC .......... *A61K 31/231* (2013.01); *A61K 31/435* (2013.01); *A61K 31/454* (2013.01); *A61K 31/4535* (2013.01); *A61K 31/4709* (2013.01); *A61K 31/498* (2013.01); *A61K 31/661* (2013.01); *A61K 45/06* (2013.01); *C07D 401/04* (2013.01); *C07D 401/14* (2013.01); *C07D 405/14* (2013.01); *C07D 409/14* (2013.01)

(56) References Cited

U.S. PATENT DOCUMENTS

| | | | | |
|---|---|---|---|---|
| 2004/0029244 | A1 | 2/2004 | Williger | 514/310 |
| 2004/0265999 | A1 | 12/2004 | Yoon et al. | 435/375 |
| 2005/0239906 | A1* | 10/2005 | Garaci et al. | 514/733 |
| 2006/0030536 | A1 | 2/2006 | Yu et al. | 514/44 A |
| 2006/0172363 | A1 | 8/2006 | Ryu et al. | 435/198 |
| 2008/0300298 | A1 | 12/2008 | Arbiser et al. | 514/450 |
| 2009/0155349 | A1* | 6/2009 | Heller | A61K 31/085 424/450 |
| 2010/0009970 | A1 | 1/2010 | Johansen et al. | 514/183 |
| 2010/0105698 | A1* | 4/2010 | Bar-Or | C07D 241/08 514/255.02 |
| 2011/0178080 | A1 | 7/2011 | Shi et al. | 514/278 |
| 2012/0184600 | A1 | 7/2012 | Liu et al. | 514/278 |

FOREIGN PATENT DOCUMENTS

| | | |
|---|---|---|
| BR | 112012001586.9 | 3/2012 |
| CA | 2768940 | 1/2011 |
| CA | 2850597 | 4/2013 |
| CN | 102573474 | 7/2012 |
| EP | 2456307 | 5/2012 |
| EP | 2760447 | 8/2014 |
| IL | 217720 | 1/2012 |
| IN | 1661/DELNP/2012 | 2/2012 |
| JP | 2003-535863 | 12/2003 |
| JP | 2008-252478 | 10/2008 |
| JP | 2013-500260 | 1/2013 |
| KR | 2012-7004698 | 2/2012 |
| MX | A/2012/001064 | 1/2012 |
| RU | 2012106657 | 8/2013 |
| SG | 201200525-2 | 1/2012 |
| WO | WO 96/41634 | 12/1996 |
| WO | WO 01/12228 | 2/2001 |
| WO | WO-01/89449 A2 | 11/2001 |
| WO | WO 01/94346 | 12/2001 |
| WO | WO-2004/112724 A2 | 12/2004 |
| WO | WO-2006/019841 A2 | 3/2006 |
| WO | WO 2006/071730 | 7/2006 |
| WO | WO 2007/134958 | 11/2007 |
| WO | WO 2010/138869 | 12/2010 |
| WO | WO 2011/011680 | 1/2011 |
| WO | WO 2013/049773 | 4/2013 |
| WO | WO 2014/093553 | 6/2014 |
| WO | WO 2014/093557 | 6/2014 |

OTHER PUBLICATIONS

Andresen, B.T., et al. "The role of phosphatidic acid in the regulation of the ras/mek/erk signaling cascade," FEBS Lett., vol. 531(1), pp. 65-68 (2002).
Bellacosa, A., et al. "A retroviral oncogene, akt, encoding a serine-threonine kinase containing an sh2-like region," Science, vol. 254, pp. 274-277 (1991).
Berge, S.M., et al. "Pharmaceutical salts," J. Pharmaceutical Sciences, vol. 66, pp. 1-19 (1977).
Bertrand, R., et al. "Induction of a common pathway of apoptosis by staurosporine." Exp. Cell Res., vol. 211, pp. 314-321 (1994).
Brown, H.A., et al. "ADP-ribosylation factor (arf), a small gtp-dependent regulatory protein, stimulates phospholipase d activity," Cell, vol. 75, pp. 1137-1144 (1993).
Brown, H.A., et al. "Biochemical analysis of phospholipase d," In Methods in Enzymology, Lipidomics and Bioactive Lipids: Lipids and Cell Signaling, vol. 434, pp. 49-87 (2007).
Bundgaard, et al. "Glycolamide esters as biolabile prodrugs of carboxylic acid agents: synthesis, stability, bioconversion, and physicochemical properties," J. of Pharmaceutical Sciences, vol. 77, pp. 285-298 (1988).
Bundgaard, et al. Means to enhance penetration: (1) prodrugs as a means to improve the delivery of peptide drugs, Advanced Drug Delivery Reveiws, vol. 8, pp. 1-38 (1992).
Campbell, I.G., et al. "Mutation of the PIK3CA gene in ovarian and breast cancer," Cancer Res., vol. 64, pp. 7678-7681 (2004).
Cantley, L.C., "The phosphoinositide 3-kinase pathway," Science, vol. 296, pp. 1655-1657 (2002).
Cheng, et al. "PI3K signaling in glioma-animal models and therapeutic challenges," Brain Pathol., vol. 19, pp. 112-120 (2009).
Chung, J., et al. "Rapamycin-fkbp specifically blocks growth-dependent activation of and signaling by the 70 kd s6 protein kinases," Cell, vol. 69, pp. 1227-1236 (1992).
Colley, et al. "Phospholipase d2, a distinct phospholipase d isoform with novel regulatory properties that provokes cytoskeletal reorganization." Curr. Biol., vol. 7, pp. 191-201 (1997).
Datta, et al. "Akt phosphorylation of bad couples survival signals to the cell-intrinsic death machinery," Cell, vol. 91, pp. 231-241 (1997).
Dowler, S., et al. "Protein lipid overlay assay," Sci. STKE, p1-6 (2002).
Edwards, et al. "Neisseria gonorrhoeae pld directly interacts with akt kinase upon infection of primary, human, cervical, epithelial cells," Cell Microbiol., vol. 8, pp. 1253-1271 (2006).
Egan, D.F., et al. "Phosphorylation of ulk1 (hatg1) by amp-activated protein kinase connects energy sensing to mitophagy," Science, vol. 331, pp. 456-461 (2011).
Elias, M., et al. "Molecular diversity of phospholipase d in angiosperms," BMC Genomics, vol. 3(1) (2002).
Fang, Y. et al. "Phosphatidic acid-mediated mitogenic activation of mtor signaling," Science, vol. 294, pp. 1942-1945 (2001).
Foster, D., et al. "Phospholipase d in cell proliferation and cancer1 1national cancer institute, and the institutional support from the research centers in minority institutions (rcmi) program of the nih," Mol. Cancer Res., vol. 1, pp. 789-800 (2003).
Foster, D.A. "Regulation of mtor by phosphatidic acide?" Cancer Res., vol. 67(1), pp. 1-4 (2007).
Foster, D.A. "Phosphatidic acid signaling to mtor: signals for the survival of human cancer cells," Biochim. Biophys. Actas, vol. 1791, pp. 949-955 (2009).
Franke, T.F., et al. "The protein kinase encoded by the akt proto-oncogene is a target of the pdgf-activated phosphatidylinositol 3-kinase," Cell, vol. 81, pp. 727-736 (1995).
Furnari, F.B., et al. "Malignant astrocytic glioma: genetics, biology, and paths to treatment," Gene. Dev., vol. 21, pp. 2683-2710 (2007).

(56) References Cited

OTHER PUBLICATIONS

Garcia-Calvo M., et al., Inhibition of human caspases by peptide-based and macromolecular inhibitors. J Biol Chem. 1998;273: 32608-32613.
Giannone, R., et al. "Dual-tagging system for the affinity purification of mammalian protein complexes," Biotech., vol. 43, pp. 296-302 (2007).
Grant No. U54 MH084659 awarded by the National Institute of Health (NIH).
Grant No. P01 ESO013125 awarded by the National Institute of Health (NIH)—Abstract.
Grant No. NIAID HHSN2722008000058C awarded by the National Institute of Health (NIH)—Abstract.
Ha, J., et al. "Critical phosphorlyation sites for acetyl-coa carboxylase activity," J. Biol. Chem., vol. 269, pp. 22162-22168 (1994).
Haas-Kogan, et al. "Protein kinase b (pkb/akt) activity is elevated in glioblastoma cells due to mutation of the tumor suppressor pten/mmac," Curr. Biol., vol. 8, pp. 1195-1198 (1998).
Hahn-Windgassen, A., et al. "Mechanisms of signal transduction: akt activates the mammalian target of rapamycin by regulating cellular atp level and ampk activity," J. Biolog., Chem., vol. 280, pp. 32081-32089 (2005).
Hammond, et al. "Human ADP-ribosylation factor-activated phosphatidylcholine-specific phospholipase D defines a new and highly conserved gene family," J. Biol. Chem., vol. 270, pp. 29640-29643 (1995).
Hardie, D.G. Amp-activated/snfl protein kinase Nat. Rev. Mol. Cell Bio., vol. 8, pp. 774-785 (2007).
Hawley, S.A., et al. "Cell biology and metabolism: characterization of the amp-activated protein kinase kinase from rat liver and identification of threonine 172 as the major site of which it phosphorylates amp-activated protein kinase," J. Biol. Chem., vol. 271, pp. 27879-27887 (1996).
Henage, L., et al. "Kinetic analysis of a mammalian phospholipase d: kinetic analysis of a mammalian phospholipase d: allosteric modulation by monomeric gtpases, protein kinase c and polyphosphoinosites," J. Biol. Chem., vol. 281, pp. 3408-3417 (2006).
Stella, V., et al. "The chemistry of a novel 5,5-diphenylhydantoin pro-drug," Prodrugs as Novel Drug Delivery Systems, American Chemical Society, Ch. 3, pp. 154-183 (1975).
Hirai, H., et al. "MK-2206, an allosteric Akt inhibitor, enhances antitumor efficacy by standard chemotherapeutic agents or molecular targeted drugs in vitro and in vivo." Mol. Cancer Ther., vol. 9, pp. 1956-1967 (2010).
Hsu, et al. "Phospholipase d signaling pathway is involved in lung cancer-derived il-8 increased osteoclastogenesis," Carcinogenesis, vol. 31(4), pp. 587-596 (2010).
Ivanova, P.T., et al. "Glycerophospholipid identification and quantitation by electrospray ionation mass spectrometry," in Methods in Enzymology, 432, Lipidomics and Bioactive Lipids: Mass spectrometry based lipid analysis, pp. 21-57 (2007).
Jacobsen, M.D., et al. "Role of ced-3/ice-family proteases in staurosporine-induced programmed cell death," J. Cell Biol., vol. 133, pp. 1041-1051 (1996).
James, et al. "Specific binding of the Akt-1 protein kinase to phosphatidylinositol 3,4,5-trisphosphate without subsequent activation." Biocem. J., vol. 315, pp. 709-713 (1996).
Jung, C.H., et al. "mTor regulation of autophagy," FEBS Lett., vol. 584, pp. 1287-1295 (2010).
Kabeya, Y., et al. "Lc3, a mammalian homologue of yeast apg8p, is localized in autophagosome membranes after processing," EMBO J., vol. 19, pp. 5720-5728 (2000).
Ha, U., et al. "A novel role for ikb kinase (ikk) ? and ikk B in erk-dependent up-regulation of muc5ac mucin transcription by streptococcus pneumoniae," J. Immunol., vol. 178(5), pp. 1737-1745 (2007).

Kennedy, S.G., et al. The pi 3-kinase/akt signaling pathway delivers an anti-apoptotic signal, Genes & Development, vol. 11, pp. 701-713 (1997).
Kihara, A., et al. "Beclin-phosphatidylinositol 3-kinase complex functionsat the trans-golgi network," EMBO Reports, vol. 2, pp. 330-335 (2001).
Kim, J., et al. "Ampk and mtor regulate autophagy through direct phosphorylation of ulk1," Nature Cell Bio., vol. 13, pp. 132-141 (2011).
Kimura, S., et al. Proc. Natl. Acad. Sci. U.S.A., vol. 105, pp. 19211-19216 (2007).
Kohn, A.D., et al. "Expression of a constitutively active akt ser/thr kinase in 3t3-11 adipocytes stimulates glucose uptake and glucose transporter 4 translocation," J. Biol. Chem., vol. 271, pp. 31372-31378 (1996b).
Komatsu, M., et al. "Impairment of starvation-induced and constitutive autophagy in atg7-deificient mice," J. Cell Biol., vol. 169, pp. 425-434 (2005).
Korolkovas, "Essentials of medicinal chemistry, isosteric substitutions," in Essentials of Medicinal Chemistry 1988, New York, Wiley & Sons, pp. 78-82.
Kroemer, G., et al. "Autophagy and the integrated stress response," Mol. Cell, vol. 40, pp. 280-293 (2010).
Kumar, C., et al., "Expression, purification, characterization and homology modeling of active Akt/PKB, a key enzyme involved in cell survival signaling." Biochim. Biophys. Acta. 1526: 257-268 (2001).
Lakadamyali, M., et al. "Endocytosis of influenze viruses," Microbes Infect., vol. 6(10), pp. 929-936 (2004).
Lam, et al. "Arrested spread of vesicular stomatitis virus infections in vitro depends on interferon-mediated antiviral activity," Biotechnol Bioeng., vol. 90(7), pp. 793-804 (2005).
Lavieri, R., et al. "Design and synthesis of isoform-selective phospholipase D (PLD) inhibitiros. Part II. Identification of the 1,3,8-triazaspiro[4,5]decan-4-one privileged structure that engenders PLD2 selectivity," Bioorg. Med. Chem., vol. 19, pp. 2240-2243 (2009).
Lavieri, R., et al. "Design, synthesis, and biological evaluation of halogenated n-(2-(4-Oxo-1-phenyl-1,3,8-triazaspiro[4.5]decan-8-yl)ethyl)benzamides: discovery of an isoform-selective small molecule phospholipase d2 inhibitor," J. Med. Chem., vol. 53, pp. 6706-6719 (2010).
Lewis, J.A., et al. "Design and synthesis of isoform-selective phospholipase D (PLD) inhibitors. Part I: Impact of alternative halogenated privileged structures for PLD1 specificity." Bioorg. Med. Chem., vol. 19, pp. 1916-1920 (2009).
Liang, X.H., et al. Nature, vol. 402, pp. 672-676 (1999).
Libermann, T.A., et al. Nature, vol. 313, pp. 144-147 (1985).
Mahajan, K., et al. "Ack1 mediated AKT/PKB tyrosine 176 phosphorylation regulates its activation." PloS ONE, vol. 5, e9646 (2010).
Manning, B.D., et al. "AKT/PKB signaling: navigating downstream." Cell, vol. 129, pp. 1261-1274 (2007).
Matsunaga, K., et al. Nat. Cell Biol., vol. 11, pp. 385-396 (2009).
Myers, et al. (2011) Biochim. Biophys. Acta 1811: 748-757.
Nozawa, et al. "Inhibition of platelet-derived growth factor-induced cell growth signaling by a short interfering rna for ews-fli1 via down-regulation of phospholipase d2 in ewing sarcoma cells," The Journal of Biological Chemistry, vol. 280(30), pp. 27544-27551 (2005).
Paruch, et al. "CCR5 signaling through phospholipase d involves p44/42 map-kinases and promotes hiv-1 ltr-directed gene expression," The FASEB Journal, vol. 21(14), pp. 4038-4046 (2007).
Ponting, C.P., et al. "A novel family of phospholipase d homologues that includes phospholipid synthases and putative endonucleases: identification of duplicated repeats and potential active site residues," Protein Sci., vol. 5(5), pp. 914-922 (1996).
Ravikumar, B., et al. "Mammalian macroautophagy at a glance." J. Cell Sci., vol. 122, pp. 1707-1711 (2009).
Sarbassov, D.D., et al. "Phosphorylation and regulation of Akt/PKB by the Rictor-mTOR Complex." Science, vol. 307, pp. 1098-1101 (2005).

(56) References Cited

OTHER PUBLICATIONS

Scott, S., et al. "Design of isoform-selective phospholipase D inhibitors that modulate cancer cell invasiveness," Nat. Chem. Biol. vol. 5(2), pp. 108-117 (2009).
Scott, S.A., et al. Regulation of phospholipase d activity and phosphatidic acid production after purinergic (p2y6) receptor stimulation, J. Biol. Chem., vol. 288, pp. 20477-20487 (2013).
Selvy, et al., "Phospholipase D: Enzymology, Functionality, and Chemical Modulation," Chemical Reviews 2011, 111: 6064-6119.
Shin, S.I., et al. Proc. Natl. Acad. Sci. U.S.A., vol. 72, pp. 4435-4439 (1975).
Singh, S.K. et al. "Identification of human brain tumour initiating cells." Nat. Cell Biol., vol. 432, pp. 396-401 (2004).
Stuckey, J.A. "Crystal structure of a phospholipase d family member," Nat. Struct. Biol., vol. 6(3), pp. 278-284 (1999).
Sun, H., et al. Proc. Natl. Acad. Sci. U.S.A., vol. 96, pp. 6199-6204 (1999).
Sun, Q., et al. "Identification of Barkor as a mammalian autophagy-specific factor for Beclin 1 and class III phosphatidylinositol 3-kinase." Proc. Natl. Acad. Sci. U.S.A., vol. 105, pp. 19211-19216 (2008).
Sun, Y., et al. "mtor signaling: pld takes center stage," Cell Cycle, vol. 7(2), pp. 3118-3123 (2008).
Thomas, C., et al. Curr. Biol., vol. 12, pp. 1256-1262 (2002).
Thoreen, C.C., et al. "An ATP-competitive mammalian target of rapamycin." J. Biol. Chem., vol. 284, pp. 8023-8032 (2009).
Tsujimoto, "Another way to die: autophagic programmed cell death." Cell Death Differ., vol. 12 Suppl 2, pp. 1528-1534 (2005).
Vance, et al. J. Lipid Res., vol. 50 Suppl, S132-7 (2008).
Vander Heidan, M.G., et al. "Understanding the warburg effect: the metabolic requirements of cell proliferation," Science, vol. 324(5930), pp. 1029-1033 (2009).
Walker, S.J., et al. "Measurement of g protein stimulated phospholipase d activity in intact cells," In Methods in Molecular Biology, G Protein Signaling: Methods and Protocols, vol. 237 (2004).
Wang, et al. "Notch promotes radioresistance of glioma stem cells." Stem Cells, vol. 28, pp. 17-28 (2010).
Wang, Q.J., et al. "Induction of autophagy in axonal dystrophy and degeneration."J. Neurosci., vol. 26, pp. 8057-8068 (2006).
Wang, R.C., et al. Science, vol. 338, pp. 956-959 (2012).
Wermuth, "Molecular variations based on Isosteric Replacements," Practice of Medicinal Chemistry 1996, 203-237.
Widder, et al. Methods in Enzymology, vol. 4, Academic Press (1985).
Yamamoto, A et al., "Bafilomycin A1 prevents maturation of autophagic vacuoles by inhibiting fusion between autophagosomes and lysosomes in rat hepatoma cell line, H-4-II-E cells," Cell Structure and Function, vol. 23, No. 1, pp. 33-42, 1998.
Yang, S.F., et al. "Transphosphatidylation by phospholipase d," J. Biol. Chem., vol. 242(3), pp. 477-484 (1967).
Yao, F, et al. Tetracycline repressor, tetR, rather than the tetR-mammalian cell transcription factor fusion derivatives, regulates inducible gene expression in mammalian cells. Human Gene Therapy, Sep. 1998, vol. 9, No. 13, p. 1939-1950.—Abstract.
Yap, T. A. et al. First-in-man clinical trial of the oral pan-AKT inhibitor MK-2206 in patients with advanced solid tumors. J. Clin. Oncol. 29, 4688-4695 (2011).
Zheng, Y, et al. (2006) Phospholipase D couples survival and migration signals in stress response of human cancer cells. J Biol Chem 281:15862-15868.
Zhong, Q. J. Wang, X. Li et al., "Distinct regulation of autophagic activity by Atg14L and Rubicon associated with Beclin 1-phosphatidylinositol-3-kinase complex," Nature Cell Biology, vol. 11, No. 4, pp. 468-476, 2009.
Extended European Search Report issued Dec. 13, 2012 for European Patent Application No. EP 10802947.1, which was filed on Jul. 23, 2010 and published as EP 2456307 on May 30, 2012 (Inventor—Brown // Applicant—Vanderbilt University) (pp. 1-8).

International Search Report and Written Opinion issued Sep. 17, 2010 for International Patent Application No. PCT/US2010/043045, which was filed on Jul. 23, 2010 and published as WO 2011/011680 on Jan. 27, 2011 (Inventor—Brown // Applicant—Vanderbilt University) (pp. 1-7).
International Preliminary Report on Patentability issued Jan. 24, 2012 for International Patent Application No. PCT/US2010/043045, which was filed on Jul. 23, 2010 and published as WO 2011/011680 on Jan. 27, 2011 (Inventor—Brown // Applicant—Vanderbilt University) (pp. 1-6).
Restriction Requirement issued Jun. 19, 2014 for U.S. Appl. No. 13/386,397, filed May 1, 2012 and published as U.S. 2012/0214832 on Aug. 23, 2012 (Inventor—Brown // Applicant—Vanderbilt University) (pp. 1-9).
International Search Report and Written Opinion issued Dec. 4, 2012 for International Patent Application No. PCT/US2012/058192, which was filed on Sep. 30, 2012 and published as WO 2013/049773 on Apr. 4, 2013 (Inventor—Lindsley // Applicant—Vanderbilt University) (pp. 1-8).
International Preliminary Report on Patentability issued Apr. 1, 2014 for International Patent Application No. PCT/US2012/058192, which was filed on Sep. 30, 2012 and published as WO 2013/049773 on Apr. 4, 2013 (Inventor—Lindsley // Applicant—Vanderbilt University) (pp. 1-6).
International Search Report issued Apr. 15, 2014 for International Patent Application No. PCT/US2013/074502, which was filed on Dec. 11, 2013 and published as WO 2014/093557 on Jun. 19, 2014 (Inventor—Brown // Applicant—Vanderbilt University) (pp. 1-2).
International Search Report issued Apr. 25, 2014 for International Patent Application No. PCT/US2013/074496, which was filed on Dec. 11, 2013 and published as WO 2014/093553 on Jun. 19, 2014 (Inventor—Brown // Applicant—Vanderbilt University) (pp. 1-2).
Restriction Requirement issued Apr. 1, 2014 for U.S. Appl. No. 14/103,795, filed Dec. 11, 2013 and published as U.S. 2014/0163055 on Jun. 12, 2014 (Inventor—Brown // Applicant—Vanderbilt University) (pp. 1-7).
Response to Restriction Requirement filed Jun. 2, 2014 for U.S. Appl. No. 14/103,795, filed Dec. 11, 2013 and published as U.S. 2014/0163055 on Jun. 12, 2014 (Inventor—Brown // Applicant—Vanderbilt University) (pp. 1-7).
Non-Final Office Action issued Aug. 25, 2014 for U.S. Appl. No. 14/103,795, filed Dec. 11, 2013 and published as U.S. 2014/0163055 on Jun. 12, 2014 (Inventor—Brown // Applicant—Vanderbilt University) (pp. 1-7).
Response to Restriction Requirement submitted Sep. 19, 2014 for U.S. Appl. No. 13/386,397, filed May 1, 2012 and published as U.S. 2012/0214832 on Aug. 23, 2012 (Inventor—Brown // Applicant—Vanderbilt University) (13 pages).
Non-Final Office Action issued Nov. 20, 2014 for U.S. Appl. No. 13/386,397, filed May 1, 2012 and published as U.S. 2012/0214832 on Aug. 23, 2012 (Inventor—Brown // Applicant—Vanderbilt University) (10 pages).
Response to Non-Final Office Action submitted Mar. 20, 2015 for U.S. Appl. No. 13/386,397, filed May 1, 2012 and published as U.S. 2012/0214832 on Aug. 23, 2012 (Inventor—Brown // Applicant—Vanderbilt University) (16 pages).
Notice of Allowance issued Apr. 14, 2015 for U.S. Appl. No. 13/386,397, filed May 1, 2012 and published as U.S. 2012/0214832 on Aug. 23, 2012 (Inventor—Brown // Applicant—Vanderbilt University) (7 pages).
Response to Non-Final Office Action submitted Nov. 25, 2014 for U.S. Appl. No. 14/103,795, filed Dec. 11, 2013 and published as U.S. 2014/0163055 on Jun. 12, 2014 (Inventor—Brown // Applicant—Vanderbilt University) (15 pages).
Restriction Requirement issued Feb. 9, 2015 for U.S. Appl. No. 14/103,795, filed Dec. 11, 2013 and published as U.S. 2014/0163055 on Jun. 12, 2014 (Inventor—Brown // Applicant—Vanderbilt University) (10 pages).
Restriction Requirement issued Mar. 16, 2015 for U.S. Appl. No. 14/103,819, filed Dec. 11, 2013 and published as US 2014/0378524 A1 on Dec. 25, 2014 (Inventor—Brown // Applicant—Vanderbilt University) (7 pages).

(56) References Cited

OTHER PUBLICATIONS

U.S. Appl. No. 61/228,492, filed Jul. 24, 2009, H. Alex Brown (Vanderbilt University).
U.S. Appl. No. 61/541,935, filed Sep. 30, 2011, H. Alex Brown (Vanderbilt University).
U.S. Appl. No. 61/736,003, filed Dec. 11, 2012, H. Alex Brown (Vanderbilt University).
U.S. Appl. No. 61/735,998, filed Dec. 11, 2012, H. Alex Brown (Vanderbilt University).
Alessi, D. R. et al. (1997) Characterization of a 3-phosphoinositide-dependent protein kinase which phosphorylates and activates protein kinase bα. *Curr/ Biol.* 7: 261-269.
Andresen, B. T. et al. (2002) The role of phosphatidic acid in the regulation of the ras/mek/erk signaling cascade. *FEBS Lett.* 531(1): 65-68.
Bellacosa, A. et al. (1991) A retroviral oncogene, akt, encoding a serine-threonine kinase containing an sh2-like region. *Science* 254: 274-277.
Berge, S. M. et al. (1977) Pharmaceutical salts. *J. Pharmaceutical Sciences* 66: 1-19.
Bertrand, R. et al. (1994) Induction of a common pathway of apoptosis by staurosporine. *Exp. Cell Res.* 211: 314-321.
Brown, H. A. et al. (1993) ADP-ribosylation factor (arf), a small gtp-dependent regulatory protein, stimulates phospholipase d activity. *Cell* 75: 1137-1144.
Brown, H. A. et al. (2007) Biochemical analysis of phospholipase d. In *Methods in Enzymology, Lipidomics and Bioactive Lipids: Lipids and Cell Signaling* 434: 49-87.
Bundgaard et al. (1988) Glycolamide esters as biolabile prodrugs of carboxylic acid agents: synthesis, stability, bioconversion, and physicochemical properties. *J. of Pharmaceutical Sciences* 77: 285-298.
Bundgaard et al. (1992) Means to enhance penetration: (1) prodrugs as a means to improve the delivery of peptide drugs. *Advanced Drug Delivery Reviews* 8: 1-38.
Campbell, I. G. et al. (2004) Mutation of the PIK3CA gene in ovarian and breast cancer. *Cancer Res.* 64: 7678-7681.
Cantley, L. C. (2002) The phosphoinositide 3-kinase pathway. *Science* 296: 1655-1657.
Cheng et al. (2009) PI3K signaling in glioma-animal models and therapeutic challenges. *Brain Pathol.* 19: 112-120.
Chung, J. et al. (1992) Rapamycin-fkbp specifically blocks growth-dependent activation of and signaling by the 70 kd s6 protein kinases. *Cell* 69: 1227-1236.
Colley et al. (1997) Phospholipase d2, a distinct phospholipase d isoform with novel regulatory properties that provokes cytoskeletal reorganization. *Curr. Biol.* 7: 191-201.
Datta et al. (1997) Akt phosphorylation of bad couples survival signals to the cell-intrinsic death machinery. *Cell* 91: 231-241.
Dowler, S. et al. (2002) Protein lipid overlay assay. *Science STKE* : 1-6.
Edwards et al. (2006) Neisseria gonorrhoeae pld directly interacts with akt kinase upon infection of primary, human, cervical, epithelial cells. *Cells Microbiol.* 8: 1253-1271.
Egan, D. F. et al. (2011) Phosphorylation of ulk1 (hatg1) by amp-activated protein kinase connects energy sensing to mitophagy. *Science* 331: 456-461.
Elias, M. et al. (2002) Molecular diversity of phospholipase d in angiosperms. *BMC Genomics* 3(1).
Fang, Y. et al. (2001) Phosphatidic acid-mediated mitogenic activation of mtor signaling. *Science* 294: 1942-1945.
Foster and Xu (2003) Phospholipase d in cell proliferation and cancer. *Mol. Cancer Res.* 1: 789-800.
Foster, D.A. (2007) Regulation of mtor by phosphatidic acid? *Cancer Res.* 67(1): 1-4.
Foster, D. A. (2009) Phosphatidic acid signaling to mtor: signals for the survival of human cancer cells. *Biochim. Biophys. Acta* 1791: 949-955.

Franke, T. F. et al. (1995) The protein kinase encoded by the akt proto-oncogene is a target of the pdgf-activated phosphatidylinositol 3-kinase. *Cell* 81: 727-736.
Furnari, F. B. et al. (2007) Malignant astrocytic glioma: genetics, biology, and paths to treatment. *Gene Dev.* 21: 2683-2710.
Garcia-Calvo, M. et al. (1998) Inhibition of human caspases by peptide-based and macromolecular inhibitors. *J. Biol. Chem.* 273: 32608-32613.
Giannone, R. et al. (2007) Dual-tagging system for the affinity purification of mammalian protein complexes. *Biotech.* 43: 296-302.
Grant No. P01 ESO013125 awarded by the National Institute of Health (NIH).
Ha, J. et al. (1994) Critical phosphorylation sites for acetyl-coa carboxylase activity. *J. Biol. Chem.* 269: 22162-22168.
Haas-Kogan et al. (1998) Protein kinase b (pkb/akt) activity is elevated in glioblastoma cells due to mutation of the tumor suppressor pten/mmac. *Curr. Biol.* 8: 1195-1198.
Hahn-Windgassen, A. et al. (2005) Mechanisms of signal transduction: akt activates the mammalian target of rapamycin by regulating cellular atp level and ampk activity. *J. Biol. Chem.* 280: 32081-32089.
Hardie, D. G. (2007) Amp-activated/snfl protein kinase. *Nat. Rev. Mol. Cell Bio.* 8: 774-785.
Hawley, S. A. et al. (1996) Cell biology and metabolism: characterization of the amp-activated protein kinase from rat liver and identification of threonine 172 as the major site of which it phosphorylates amp-activated protein kinase. *J. Biol. Chem.* 271: 27879-27877.
Henage, L. et al. (2006) Kinetic analysis of a mammalian phospholipase d: kinetic analysis of a mammalian phospholipase d: allosteric modulation by monomeric gtpases, protein kinase c and polyphosphoinosites. *J. Biol. Chem.* 281: 3408-3417.
Stella, V. et al. (1975) The chemistry of a novel 5,5-diphenylhydantoin pro-drug. *Prodrugs as Novel Drug Delivery Systems, American Chemical Society,* Chp. 3: 154-183.
Hirai, H. et al. (201) MK-2206, an allosteric Akt inhibitor, enhances antitumor efficacy by standard chemotherapeutic agents or molecular targeted drugs in vitro and in vivo. *Mol. Cancer Ther.* 9: 1956-1967.
Hsu et al. (2001) Phospholipase d signaling pathway is involved in lung cancer-derived il-8 increased osteoclastogenesis. *Carcinogenesis* 31(4): 587-596.
Ivanova, P. T. et al. (2007) Glycerophospholipid identification and quantitation by electrospray ionation mass spectrometry. In *Methods in Enzymology, Lipidomics and Bioactive Lipids: Mass spectrometry based lipid analysis.* 432: 21-57.
Jacobsen, M. D. et al. (1996) Role of ced-3/ice-family proteases in staurosporine-induced programmed cell death. *J. Cell Biol.* 133: 1041-1051.
James et al. (1996) Specific binding of the Akt-1 protein kinase to phosphatidylinositol 3,4,5-triphosphate without subsequent activation. *Biochem. J.* 315: 709-713.
Jung, C. H. et al. (2010) mTor regulation of autophagy. *FEBS Lett.* 584: 1287-1295.
Kabeya, Y. et al. (2000) Le3, a mammalian homologue of yeast apg8p, is localized in autophagosome membranes after processing. *EMBO J.* 19: 5720-5728.
Ha, U. et al. (2007) A novel role for ikb kinase and IKK B in erk-dependent up-regulation of muc5ac mucin transcription by streptococcus pneumonia. *J. Immunol.* 178(5): 1737-1745.
Kennedy, S. G. et al. (1997) The pi 3-kinase/akt signaling pathway delivers an anti-apoptotic signal. *Genes & Development* 11: 701-713.
Kihara, A. et al. (2001) Beclin-phosphatidylinositol 3-kinase complex functions at the trans-golgi network. *EMBO Reports* 2: 330-335.
Kim, J. et al. (2011) AMPL and mTOR regulate autophagy through direct phosphorylation of ulk1. *Nature Cell Bio.* 13: 132-141.
Kimura, S. et al. (2007) *Proc. Natl. Acad. Sci. U. S. A.* 105: 19211-19216.

(56) References Cited

OTHER PUBLICATIONS

Kohn, A. D. et al. (1996) Expression of a constitutively active akt ser-thr kinase in 3t3-l1 adipocytes stimulates glucose uptake and glucose transporter 4 translocation. *J. Biol. Chem.* 271: 31372-31378.

Komatsu, M. et al. (2005) Impairment of starvation-induced and constitutive autophagy in atg7-deficient mice. *J. Cell Biol.* 169: 425-434.

Korolkovas (1988) Essentials of medicinal chemistry, isosteric substitutions in *Essentials of Medicinal Chemistry* New York, Wiley & Sons, pp. 78-82.

Kroemer, G. et al. (2010) Autophagy and the integrated stress response. *Mol. Cell* 40: 280-293.

Kumar, C. et al. (2001). Expression, purification, characterization and homology modeling of active Akt/PKB, a key enzyme involved in cell survival signaling. *Biochim. Biophys. Acta.* 1526: 257-268.

Lakadamyali, M. et al. (2004) Endocytosis of influenza viruses. *Microbes Infect.* 6(10): 929-936.

Lam et al. (2005) Arrested spread of vesicular stomatitis virus infections in vitro depends on interferon-mediated antiviral activity. *Biotechnol. Bioeng.* 90(7): 793-804.

Lavieri, R. et al. (2009) Design and synthesis of isoform-selective phospholipase D (PLD) inhibitors. Part II. Identification of the 1,3,8-triazaspiro[4,5]decan-4-one privileged structure that engenders PLD2 selectivity. *Bioorg. Med. Chem.* 19: 2240-2243.

Lavieri, R. et al. (2010) Design, synthesis, and biological evaluation of halogenated n-(2-(4-oxo-1-phenyl-1,3,8-triazaspiro[4.5]decan-8-yl)ethyl)benzamides: discovery of an isoform-selective small molecule phospholipase d2 inhibitor. *J. Med. Chem.* 53: 6706-6719.

Lewis, J. A. et al. (2009) Design and synthesis of isoform-selective phospholipase D (PLD) inhibitors. Part I: Impact of alternative halogenated privileged structures for PLD1 specificity. *Bioorg. Med. Chem.* 19: 1916-1920.

Liang, X. H. et al. (1999) *Nature* 402: 672-676.

Libermann, T. A. et al. (1985) *Nature* 313: 144-147.

Mahajan, K. et al. (2010) Ack1 mediated AKT/PKB tyrosine 176 phosphorylation regulates its activation. *PloS ONE* 5: e9646.

Manning, B. D. et al. (2007) AKT/PKB signaling: navigating downstream. *Cell* 129: 1261-1274.

Matsunaga, K. et al. (2009) *Nat. Cell Biol.* 11: 385-396.

Myers et al. (2011) *Biochim. Biophys. Acta* 1811: 748-757.

Nozawa et al. (2005) Inhibition of platelet-derived growth factor-induced cell growth signaling by a short interfering ma for ews-flil via down-regulation of phospholipase d2 in ewing sarcoma cells. *The Journal of Biological Chemistry* 280(30): 27544-27551.

Paruch et al. (2007). CCR5 signaling through phospholipase d involves p44/42 map-kinases and promotes hiv-1 ltr-directed gene expression. *The FASEB Journal* 21(4): 4038-4046.

Ponting, C. P. et al. (1996) A novel family of phospholipase d homologues that includes phospholipid synthases and putative endonucleases: identification of duplicated repeats and potential active site residues. *Protein Sci.* 5(5): 914-922.

Ravikumar, B. et al. (2009) Mammalian macroautophagy at a glance. *J. Cell Sci.* 122: 1707-1711.

Sarvassov, D. D. et al. (2005) Phosphorylation and regulation of Akt/PKB by the Rictor-mTOR complex. *Science* 307: 1098-1101.

Scott, S. et al. (2009) Design of isoform-selective phospholipase D inhibitors that modulate cancer cell invasiveness. *Nat. Chem. Biol.* 5(2): 108-117.

Scott, S. A. (2013) Regulation of phospholipase d activity and phosphatidic acid production after purinergic (p2y6) receptor stimulation. *J. Biol. Chem.* 288: 20477-20487.

Selvy et al. (2011) Phospholipase D: Enzymology, Functionality, and Chemical Modulation. 111: 6064-6119.

Shin, S. I. et al. (1975) *Proc. Natl. Acad. Sci. U. S. A.* 72: 4435-4439.

Singh, S. K. et al. (2004) Identification of human brain tumor initiating cells. *Nat. Cell Biol.* 432: 396-401.

Stuckey, J. A. (1999) Crystal structure of a phospholipase d family member. *Nat. Struct. Biol.* 6(3): 278-284.

Sun, H. et al. (1999) *Proc. Natl. Acad. Sci. U. S. A.* 96: 6199-6204.

Sun, Q. et al. (2008) Identification of Barkor as a mammalian autophagy-specific factor for Beclin 1 and class III phosphatidylinositol 3-kinase. *Proc. Natl. Acad. Si. U. S. A.* 105: 19211-19216.

Sun, Y. et al. (2008) Motor signaling: pld takes center stage. *Cell Cycle* 7(2): 3118-3123.

Thomas, C. et al. (2002) *Curr. Biol.* 12: 1256-1262.

Thoreen, C. C. et al. (2009) An ATP-competitive mammalian target of rapamycin. *J. Biol. Chem.* 284: 8023-8032.

Tsujimoto (2005) Another way to die: autophagic programmed cell death. *Cell Death Differ.* 12(2): 1528-1534.

Vance et al. (2008) *J. Lipid Res.* 50: S132-137.

Vander Heidan, M. G. et al. (2009) Understanding the Warburg effect: the metabolic requirements of cell proliferation. *Science* 324(5930): 1029-1033.

Walker, S. J. et al. (2004) Measurement of g protein stimulated phospholipase d activity in intact cells. In *Methods in Molecular Biology, G Protein Signaling: Methods and Protocols* 237.

Wang et al. (2010) Notch promotes radioresistance of glioma stem cells. *Stem Cells* 28: 17-28.

Wang, Q. J. et al. (2006) Induction of autophagy in axonal dystrophy and degeneration. *J. Neurosci.* 26: 8057-8068.

Wang, R. C. et al. (2012) *Science* 338: 956-959.

Wermuth (1996) Molecular variations based on isosteric replacements. *Practice of Medicinal Chemistry* 203-237.

Widder et al. (1985) *Methods in Enzymology*, vol. 4, Academic Press.

Yamamoto, A. et al. (1998) Bafilomycin A1 prevents maturation of autophagic vacuoles by inhibiting fusion between autophagosomes and lysosomes in rat hepatoma cell line, H-4-II-E cells. *Cell Structure and Function* 23(1): 33-42.

Yang, S. F. et al. (1967) Transphosphatidylation by phospholipase d. *J. Biol. Chem.* 242(3): 477-484.

Yao, F. et al. (1998) Tetracycline repressor, tetR, rather than the tetR-mammalian cell transcription factor fusion derivatives, regulates inducible gene expression in mammalian cells. *Human Gene Therapy*, 9(13): 1939-1950. Abstract.

Yap, T. A. et al. (2011) First-in-man clinical trial of the oral pan-AKT inhibitor MK-2206 in patients with advanced solid tumors. *J. Clin. Oncol.* 29: 4688-4695.

Zheng, Y. et al. (2006) Phospholipase D couples survival and migration signals in stress response of human cancer cells. *J. Biol. Chem.* 281: 15862-15868.

Zhong, Q. J. et al. (2009) Distinct regulation of autophagiz activity by Atg14L and Rubicon associated with Beclin 1-phosphatidylinositol-3-kinase complex. *Nature Cell Biology* 11(4): 468-476.

Extended European Search Report issued Dec. 13, 2012 for European Patent Application No. EP 10802947.1, which was filed on Jul. 23, 2010 and published as EP 2456307 on May 30, 2012 (Inventor—Brown // Applicant—Vanderbilt University) (pp. 1-7).

Communication issued Aug. 29, 2014 for European Patent Application No. EP 10802947.1, which was filed on Jul. 23, 2010 and published as EP 2456307 on May 30, 2012 (Inventor—Brown // Applicant—Vanderbilt University) (pp. 1-6).

Reply to Communication filed Mar. 20, 2015 for European Patent Application No. EP 10802947.1, which was filed on Jul. 23, 2010 and published as EP 2456307 on May 30, 2012 (Inventor—Brown // Applicant—Vanderbilt University) (pp. 1-14).

Communication issued Jun. 24, 2015 for European Patent Application No. EP 10802947.1, which was filed on Jul. 23, 2010 and published as EP 2456307 on May 30, 2012 (Inventor—Brown // Applicant—Vanderbilt University) (pp. 1-3).

Response to Restriction filed Sep. 19, 2014 for U.S. Appl. No. 13/386,397, filed May 1, 2012 and published as U.S. 2012/0214832 on Aug. 23, 2012 (Inventor—Brown // Applicant—Vanderbilt University) (pp. 1-13).

Non-Final Office Action issued Nov. 20, 2014 for U.S. Appl. No. 13/386,397, filed May 1, 2012 and published as U.S. 2012/0214832 on Aug. 23, 2012 (Inventor—Brown // Applicant—Vanderbilt University) (pp. 1-10).

Response to Non-Final Office Action filed Mar. 20, 2015 for U.S. Appl. No. 13/386,397, filed May 1, 2012 and published as U.S.

(56) References Cited

OTHER PUBLICATIONS

2012/0214832 on Aug. 23, 2012 (Inventor—Brown // Applicant—Vanderbilt University) (pp. 1-16).
Notice of Allowance issued Apr. 14, 2015 for U.S. Appl. No. 13/386,397, filed May 1, 2012 and published as U.S. 2012/0214832 on Aug. 23, 2012 (Inventor—Brown // Applicant—Vanderbilt University) (pp. 1-7).
European Search Report issued Jun. 22, 2015 for European Patent Application No. 12835711.8, which was filed on Sep. 30, 2012 and published as 2760447 on Aug. 6, 2014 (Inventor—Lindsley // Applicant—Vanderbilt University) (pp. 1-9).
International Search Report and Written Opinion issued Apr. 15, 2014 for International Patent Application No. PCT/US2013/074502, which was filed on Dec. 11, 2013 and published as WO 2014/093557 on Jun. 19, 2014 (Inventor—Brown // Applicant—Vanderbilt University) (pp. 1-6).
Restriction Requirement issued Mar. 16, 2015 for U.S. Appl. No. 14/103,819, filed Dec. 11, 2013 and published as U.S. 2014/0378524 A1 on Dec. 25, 2014 (Inventor—Brown // Applicant—Vanderbilt University) (pp. 1-7).
Response to Restriction Requirement filed Jun. 8, 2015 for U.S. Appl. No. 14/103,819, filed Dec. 11, 2013 and published as U.S. 2014/0378524 A1 on Dec. 25, 2014 (Inventor—Brown // Applicant—Vanderbilt University) (pp. 1-16).
Restriction Requirement issued Apr. 1, 2014 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-7).
Response to Restriction filed Jun. 2, 2014 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-7).
Non-Final Office Action issued Aug. 25, 2014 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-7).
Response to Non-Final Office Action filed Nov. 25, 2014 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-15).
Restriction Requirement issued Feb. 9, 2015 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-10).
Response to Restriction filed May 15, 2015 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-15).
Final Office Action issued Jun. 11, 2015 for U.S. Appl. No. 14/103,795, filed Dec. 11, 2013 and published as US 2014/0163055 A1 on Jun. 12, 2014 (Inventor—Brown // Applicant—Vanderbilt University) (pp. 1-7).
Extended European Search Report issued by the European Patent Office on Sep. 17, 2015 for application EP 12835711.8, filed on Sep. 30, 2012 and published as EP 2760447 on Aug. 6, 2014 (Applicant—Vanderbilt University // Inventor—Brown, et al.) (16 pages).
"Special Issue on Phospholipase D", Biochimica et Biophysica Acta 1791 (2009) 837-838.
Arbabi, et al., "Alcohol (Ethanol) Inhibits IL-8 and TNF: Role of the p38 Pathway", 1999 by The American Association of Immunologists (6 pages).
Aye, et al., "Ethanol-Induced in vitro Invasion of Breast Cancer Cells: The Contribution of MMP-2 by Fibroblasts," Int. J. Cancer: 112, 738-746 (2004).
Benagiano, et al., "Chlamydophila pneumoniae phospholipase D (CpPLD) drives Th17 inflammation in human atherosclerosis", pp. 1222-1227, PNAS, Jan. 24, 2012, vol. 109, No. 4.
Billah, et al., "Regulation of Phospholipase D in HL-60 Granulocytes", vol. 264. No. 15. Issue of pp. 9069-9076, 1989.
Birichevskaya, et al., "Substrate Requirements of Phospholipase D from Streptomyces Netropis", Chemistry of Natural Compounds, vol. 42, No. 1, 2006.
Blitterswijk, et al., "Rapid attenuation of receptor-induced diacylglycerol and phosphatidic acid by phospholipase D-mediated transphosphatidylation: formation of bisphosphatidic acid", The EMBO Journal vol. 12 No. 7 pp. 2655-2662, 1993.
Bocckino, et al., "Ca2+-mobilizing hormones elicit phosphatidylethanol accumulation via phospholipase D activation", vol. 225, 201-204.
Bruhl, et al., "Degradation of phosphatidylethanol counteracts the apparent phospholipase D-mediated formation in heart and other organs", Biochimica et Biophysica Acta 1633 (2003) 84-89.
Cheung, et al., "Ablation of Matrix Metalloproteinase-9 Increases Severity of Viral Myocarditis in Mice", Downloaded from http://circ.ahajou1rn5a7ls4.org/ by guest on Feb. 23, 2016 (10 pages).
Dippe, et al., "Phospholipase D-catalyzed synthesis of new phospholipids with polar head groups", Chemistry and Physics of Lipids 152 (2008) 71-77.
D'Souza-Schorey, et al., "Tumor-derived microvesicles: shedding light on novel microenvironment modulators and prospective cancer biomarkers", Genes & Development, vol. 26:1287-1299 (2012).
Elkington, et al., "The paradox of matrix metalloproteinase in infectious disease", 2005 British Society for Immunology, Clinical and Experimental Immunology, vol. 142, pp. 12-20.
Ella, et al., "Utilization of Alcohols by Plant and Mammalian Phospholipase D", Biochem. and Mol. Bio. Int'l., pp. 715-724 (1997).
Exton, et al., "New Developments in Phospholipase D", J. Bio. Chem., vol. 272, No. 25, Issue of Jun. 20, pp. 15579-15582, 1997.
Frohman, "The phospholipase D superfamily as therapeutic targets", TIPS-1200; No. of pp. 8 (2015).
Hagishita, et al.,"A Spectrophotometric Assay for the Transphosphatidylation Activity of Phospholipase D Enzyme", Analytical Biochemistry 276, 161-165 (1999).
Henkels, et al., "Phospholipase D (PLD) drives cell invasion, tumor growth and metastasis in a human breast cancer xenograph model", Oncogene (2013) 32, 5551-5562.
Kato, et al. "Acidic extracellular microenvironment and cancer", Cancer Cell International 2013, 13:89-94.
Knizhnik, et al., "Arf6Q1 Promotes Cell Proliferation Via the PLD-mTORC1 and p38MAPK Pathways", Journal of Cellular Biochemistry, 9999:1-12 (2011).
Liscovitch, et al., "Ca2+ inhibits guanine nucleotide-activated phospholipase D in neural-derived NG108-15 cells", Cell Regulation, vol. 2, 1011-1019, Dec. 1991.
Liu, et al., "Monitoring Phosphatides Acid Formation in Intact Phosphatidylcholine Bilayers upon Phospholipase D Catalysis", dx.doi.org/10.1021/ac403580r, Anal. Chem. (7 pages).
Mayr, et al., "Identification of a novel, Ca2+-dependent phospholipase D with preference for phosphatidylserine and phosphatidylethanolamine in *Saccharomyces cerevisiae*", FEBS Letters 393 (1996) 236-240.
Nakazawa, et al., "Isolation and characterization of actinomycetes strains that produce phospholipase D having high transphosphatidylation activity", Microbiological Research, 2006 (6 pages).
Nakka, et al., "The imidazolidone analogs as phospholipase D1 inhibitors: analysis of the three-dimensional quantitative structure—activity relationship", Med Chem Res, 2011 (9 pages).
Pai, et al., "Phospholipase D Catalyzes Phospholipid Metabolism in Chemotactic Peptide-stimulated HL-60 Granulocytes", J. Bio. Chem. vol. 264, No. 26, pp. 12472-12477 (1988).
Pappan, et al., "Substrate Selectivities and Lipid Modulation of Plant Phospholipase Da, -b, and -g", Arch. of Biochem. and Biophysics, vol. 353, No. 1, 1988 (10 pages).
Peacock, et al., "Abscisic acid signal transduction in the barley aleurone is mediated by phospholipase D activity", Proc. Natl. Acad. Sci. USA vol. 95, pp. 2697-2702, Mar. 1998.
Pend, et al., "Mammalian phospholipase D physiological and pathological roles", Acta Physiol 2012, 204, 219-226.

(56) References Cited

OTHER PUBLICATIONS

Petersen, et al., "N-acylphosphatidylethanolamine-hydrolyzing phospholipase D lacks the ability to transphosphatidylate", FEBS Letters 455 (1999) 41-44.
Pettit, et al., "Phospholipase D1b and D2a generate structurally identical phosphatidic acid species in mammalian cells", Biochem. J. (2001) 360, 707-715.
Randall, et al., "A novel and sensitive assay for phospholipase D in intact cells", vol. 264, No. 1, 87-90 (1990).
Reich, et al., "Expression and Clinical Role of Protein of Regenerating Liver (PRL) Phosphatases in Ovarian Carcinoma", Int. J. Mol. Sci. 2011, 12, 1133-1145.
Reich, et. al., "Carbamoylphosphonates Control Tumor Cell Proliferation and Dissemination by Simultaneously Inhibiting Carbonic Anhydrase IX and Matrix Metalloproteinase-2. Toward Nontoxic Chemotherapy Targeting Tumor Microenvironment",(2012) dx.doi.org/10.1021/jm300981b |J. Med. Chem. 2012, 55, 7875-7882.
Rich, et al., "Phospholipase D-Catalyzed Transphosphatidylation in Anhydrous Organic Solvents", 2000, John Wiley (4 pages).
Sanchez, et al., "The molecular connections between the cannabinoid system and endometriosis", Molecular Human Reproduction, vol. 18, No. 12 pp. 563-571, 2012.
Shimbo, et al., "Two *Streptomyces* Strains that Produce Phospholipase D with High Transphosphatidylation Activity", Agricultural and Biological Chemistry, 53 (11), 3083-3085, 1989.
Su, et al., "FIPI, a Phospholipase D pharmacological inhibitor that alters cell spreading and inhibits chemotaxis", American Society for Pharmacology and Experimental Therapeutics, 2008 (36 pages).
Takami, et al., "Synthesis of Novel Phosphatidyldihydroxyacetone via Transphosphatidylation Reaction by Phospholipase D", Bioscience, Biotechnology, and Biochemistry, 58 (12), 2136-2139, 1994.
Urtreger, et al., "Contribution of Individual PKC Isoforms to Breast Cancer Progression", IUBMB Life, 64(1): Jan. 18-26, 2012.
Van der Bend, et al., "The biologically active phospholipid, lysophosphatidic acid, induces phosphatidylcholine breakdown in fibroblasts via activation of phospholipase D", Biochem. J. (1992) 285, 235-240.
Vandenbroucke, et al., "Is there new hope for therapeutic matrix metalloproteinase inhibition?", Dec. 2014, vol. 13 (2014) (24 pages).

Kang, et al., "Autoregulation of phospholipase D activity is coupled to selective induction of phospholipase D1 expression to promote invasion of breast cancer cells", Int. J. Cancer: 128, 805-816 (2011).
Yu, et al., "The transphosphatidylation activity of phospholipase D", Molecular and Cellular Biochemistry 157: 101-105, 1996.
Non-Final Office Action issued Jul. 28, 2015 for U.S. Appl. No. 14/103,819, filed Dec. 22, 2013 and published as U.S. 2014/0378524 A1 on Dec. 25, 2014 (Inventor—Brown // Applicant—Vanderbilt University) (pp. 1-7).
Response to Final Office Action filed on Sep. 9, 2015 for U.S. Appl. No. 14/103,795, which was filed on Dec. 11, 2013 and published as US 2014/0163055 A1 on Jun. 12, 2014 (Inventor—Brown // Applicant—Vanderbilt University) (pp. 1-12).
Advisory Action issued on Sep. 24, 2015 for U.S. Appl. No. 14/103,795, filed Dec. 11, 2013 and published as US 2014/0163055 A1 on Jun. 12, 2014 (Inventor—Brown // Applicant—Vanderbilt University) No. (pp. 1-3).
Final Office Action issued Mar. 18, 2016 for U.S. Appl. No. 14/103,819, filed Dec. 22, 2013 and published as U.S. Pat. No. 2014/0378524 A1 on Dec. 25, 2014 (Inventor—Brown//Applicant—Vanderbilt University) (pp. 1-8).
Final Office Action issued Mar. 31, 2016 for U.S. Appl. No. 14/103,795, filed Dec. 11, 2013 and published as U.S. Pat. No. 2014/0163055 A1 on Jun. 12, 2014 (Inventor—Brown//Applicant—Vanderbilt University) (pp. 1-9).
Schneider, et al., "Signal Transduction Underlying Carbachol-Induced Contraction of Human Urinary Bladder," 2004, J. of Pharmacology and Experimental Therap., vol. 309, pp. 1148-1153.
Office Action was issued on May 9, 2016 by the Canadian Patent Office for Canadian Application 2,768,940, which was filed on Jul. 23, 2010 (Inventor—H. Alex Brown et al; Applicant—Vanderbilt University) (4 pages).
Supplementary European Search Report issued on Jun. 10, 2016 for EP Application No. 13862832.6, which was filed on Dec. 11, 2013 and published as 2931040 on Oct. 21, 2015 (Applicant—Vanderbilt University) (15 Pages).
Supplementary European Search Report issued on Jun. 29, 2016 for EP Application No. 13863529.7, which was filed on Dec. 11, 2013 and published as 2931277 on Oct. 21, 2015 (Applicant—Vanderbilt University) (8 Pages).
Amblard, et al., "Facile Purification of Honokiol and Its Antiviral and Cytotoxic Properties," J. Med. Chemistry, vol. 49, No. 11, Jun. 2006, pp. 3426-3427.

\* cited by examiner

| mean±sem in nmol/mg protein | * unconfirmed by MS/MS | Mock-infected time (hrs) | | | | |
|---|---|---|---|---|---|---|
| class | species | 0 | 1 | 2 | 4 | 6 |
| PA | 32:1 * | 0.74±0.08 | 0.66±0.12 | 1.12±0.12 | 1.47±0.25 | 1.37±0.28 |
| PA | 34:2 * | 0.21±0.06 | 0.19±0.05 | 0.24±0.05 | 0.48±0.14 | 0.43±0.13 |
| PA | 34:1 | 0.88±0.23 | 0.79±0.2 | 1.14±0.24 | 1.87±0.53 | 1.74±0.49 |
| PA | 36:2 | 1.03±0.09 | 0.93±0.15 | 1.37±0.17 | 1.91±0.31 | 1.86±0.35 |
| PA | 36:1 * | 1.03±0.13 | 0.94±0.18 | 1.53±0.25 | 1.68±0.27 | 1.84±0.45 |
| PC | 28:0 | 0.39±0.09 | 0.27±0.06 | 0.38±0.08 | 0.66±0.17 | 0.6±0.12 |
| PC | 30:1 | 1.23±0.23 | 0.89±0.16 | 1.19±0.15 | 1.82±0.32 | 1.62±0.11 |
| PC | 30:0 | 2.84±0.6 | 1.94±0.45 | 2.67±0.41 | 3.87±0.81 | 4.81±1.26 |
| PC | 32:1 | 14.84±3.07 | 9.81±1.84 | 12.05±1.47 | 17.91±3.23 | 15.42±1.11 |
| PC | 32:0 | 5.51±0.74 | 4.03±0.62 | 5.5±0.8 | 8.72±1.93 | 8.24±1.33 |
| PC | 34:2e | 2.59±0.58 | 1.57±0.28 | 1.76±0.15 | 3.46±0.66 | 2.94±0.19 |
| PC | 34:1e | 8.71±2.02 | 5.51±1.18 | 7.02±1.06 | 11.23±2.4 | 9.73±1.3 |
| PC | 34:2 | 6.72±1.31 | 4.81±0.86 | 6.12±0.87 | 9.59±2.07 | 8.11±0.94 |
| PC | 34:1 | 13.45±2.71 | 9.03±1.59 | 10.99±1.45 | 17.11±3.8 | 14.45±1.85 |
| PC | 34:0 | 3.62±0.57 | 3.17±0.45 | 4.52±0.89 | 8.27±2.81 | 7.3±2.11 |
| PC | 36:4e * | 2.03±0.39 | 1.3±0.2 | 1.94±0.2 | 2.89±0.51 | 2.31±0.19 |
| PC | 36:3e | 2.68±0.55 | 1.9±0.3 | 2.68±0.29 | 4.33±1.08 | 3.38±0.53 |
| PC | 36:2e | 4.41±0.98 | 3.02±0.55 | 4.07±0.46 | 6.05±1.45 | 4.98±0.85 |
| PC | 36:1e | 3.72±0.8 | 2.63±0.5 | 3.77±0.52 | 5.4±1.52 | 4.74±1.14 |
| PC | 36:4 | 3.22±0.68 | 2.44±0.46 | 3.31±0.59 | 5.55±1.53 | 4.12±0.87 |
| PC | 36:3 | 8.9±1.82 | 6.87±1.25 | 8.99±1.5 | 15.24±4.14 | 13.35±2.81 |
| PC | 36:2 | 25.06±4.86 | 18±2.78 | 22.79±2.79 | 34.65±8.32 | 32.01±6.63 |
| PC | 36:1 | 10.88±2.1 | 8.68±1.27 | 12.3±2.42 | 19.99±6.4 | 16.82±6.29 |
| PC | 38:5 * | 2.3±0.33 | 1.89±0.22 | 2.63±0.35 | 3.96±1.13 | 3.78±1.01 |
| PC | 38:4 | 4.3±0.61 | 3.39±0.41 | 4.77±0.63 | 6.67±1.84 | 6.05±1.55 |
| PC | 38:3 | 5.27±0.9 | 4.16±0.51 | 5.75±0.77 | 8.6±2.67 | 7.55±2.1 |
| PC | 38:2 | 2.78±1.18 | 1.66±0.74 | 2.84±1.32 | 5.38±2.53 | 4.37±1.93 |
| PC | 40:4 * | 2.96±0.63 | 2.22±0.29 | 3.24±0.49 | 4.62±1.61 | 4.3±1.31 |
| LPC | 16:0e * | 0.2±0.06 | 0.25±0.08 | 0.33±0.08 | 0.6±0.21 | 0.65±0.19 |
| LPC | 16:0 | 0.81±0.17 | 0.85±0.19 | 1.53±0.35 | 1.58±0.54 | 2.36±0.8 |
| LPC | 18:1 | 0.79±0.13 | 1±0.21 | 2.53±0.65 | 2.3±0.85 | 3.55±1.39 |
| LPC | 18:0 | 0.27±0.1 | 0.26±0.09 | 0.17±0.05 | 0.52±0.18 | 0.48±0.11 |
| PE | 32:1 | 1.73±0.31 | 1.35±0.27 | 2.04±0.2 | 2.26±0.58 | 1.94±0.41 |
| PE | 34:1p | 1.61±0.53 | 1.08±0.29 | 0.88±0.19 | 1.43±0.49 | 0.77±0.12 |
| PE | 34:2 | 2.73±0.54 | 2.2±0.52 | 3.29±0.36 | 3.6±1 | 3.12±0.76 |
| PE | 34:1 | 5.02±0.76 | 3.83±0.87 | 5.86±0.53 | 5.75±1.37 | 5.29±1.13 |
| PE | 36:4p | 4.65±1.39 | 3.23±0.93 | 2.33±0.6 | 4.65±1.56 | 2.27±0.46 |
| PE | 36:3p | 3.36±0.81 | 2.44±0.63 | 2.4±0.4 | 4.31±1.41 | 2.47±0.22 |
| PE | 36:3p | 1.19±0.29 | 0.91±0.23 | 1.06±0.12 | 1.68±0.56 | 1.17±0.18 |
| PE | 36:1p * | 0.96±0.26 | 0.71±0.22 | 0.79±0.07 | 1.14±0.39 | 0.74±0.12 |
| PE | 36:4 * | 2.76±0.48 | 2.11±0.48 | 3.28±0.28 | 3.09±0.84 | 2.55±0.54 |
| PE | 36:3 | 2.6±0.39 | 2.1±0.46 | 3.6±0.39 | 3.4±0.93 | 3.06±0.72 |
| PE | 36:2 | 6.4±1.03 | 4.82±0.87 | 8.05±1.03 | 6.95±1.7 | 5.98±1.2 |
| PE | 36:1 | 5.84±0.73 | 4.05±0.71 | 7.29±1.23 | 5.44±1.33 | 5.08±1.17 |
| PE | 38:6p/36:0 * | 2.94±0.6 | 2.05±0.46 | 2.26±0.3 | 2.59±0.78 | 1.74±0.21 |

Figure 16

| mean±sem in nmol/mg protein | * unconfirmed by MS/MS | Mock-infected time (hrs) | | | | |
|---|---|---|---|---|---|---|
| class | species | 0 | 1 | 2 | 4 | 6 |
| PE | 38:5p | 3.58±1 | 2.56±0.75 | 2.75±0.52 | 4.79±1.69 | 3.1±0.49 |
| PE | 38:4p | 3.96±0.85 | 3.05±0.62 | 3.02±0.63 | 5.43±1.67 | 3±0.45 |
| PE | 38:6 * | 1.17±0.19 | 0.82±0.19 | 1.33±0.14 | 1.28±0.41 | 1.06±0.31 |
| PE | 38:5 | 5.24±0.85 | 3.77±0.69 | 6.46±0.7 | 5.53±1.45 | 4.75±1.17 |
| PE | 38:4 | 11.58±1.66 | 8.18±1.59 | 15.19±1.78 | 11.64±3.06 | 11.22±3.05 |
| PE | 38:3 | 5.68±0.51 | 4.23±0.75 | 9.81±1.51 | 6.49±1.91 | 7.74±2.64 |
| PE | 40:6p * | 1.89±0.39 | 1.47±0.25 | 1.78±0.49 | 2.18±0.73 | 1.06±0.29 |
| PE | 40:5p * | 1.44±0.34 | 1.03±0.25 | 1.42±0.19 | 1.91±0.63 | 1.31±0.3 |
| PE | 40:4p * | 1.08±0.23 | 0.89±0.17 | 1.33±0.27 | 1.53±0.36 | 1.15±0.24 |
| PE | 40:6 * | 1.15±0.13 | 0.76±0.14 | 1.65±0.29 | 0.99±0.3 | 1.09±0.36 |
| PE | 40:5 * | 0.68±0.08 | 0.45±0.09 | 1.22±0.24 | 0.72±0.21 | 0.84±0.31 |
| PE | 40:4 * | 0.53±0.11 | 0.35±0.08 | 1.07±0.29 | 0.49±0.13 | 0.65±0.24 |
| LPE | 16:1 * | 0.04±0.02 | 0.07±0.04 | 0.43±0.17 | 0.34±0.17 | 0.65±0.31 |
| LPE | 18:2 * | 0.04±0.02 | 0.06±0.04 | 0.31±0.12 | 0.3±0.14 | 0.51±0.24 |
| LPE | 18:1 | 0.45±0.13 | 0.49±0.16 | 1.35±0.4 | 1.11±0.48 | 1.4±0.65 |
| LPE | 18:0 | 0.12±0.06 | 0.05±0.03 | 0.04±0.02 | 0.14±0.07 | 0.14±0.06 |
| LPE | 20:4 | 1.41±0.36 | 1.6±0.46 | 4.92±1.54 | 3.7±1.56 | 4.94±2.3 |
| LPE | 20:3 | 0.51±0.14 | 0.62±0.19 | 2.14±0.65 | 1.66±0.74 | 2.47±1.17 |
| LPE | 22:6 | 0.35±0.09 | 0.38±0.12 | 1.31±0.43 | 0.86±0.38 | 1.22±0.58 |
| LPE | 22:5 * | 0.1±0.04 | 0.11±0.05 | 0.55±0.18 | 0.38±0.18 | 0.62±0.29 |
| LPE | 22:4 | 0.12±0.03 | 0.09±0.04 | 0.37±0.11 | 0.24±0.11 | 0.38±0.17 |
| PG | 34:2 | 0.32±0.14 | 0.2±0.09 | 0.25±0.08 | 0.47±0.23 | 0.21±0.08 |
| PG | 34:1 | 1.27±0.19 | 0.91±0.13 | 1.38±0.16 | 1.59±0.29 | 1.33±0.19 |
| PG | 36:3 | 0.27±0.12 | 0.19±0.09 | 0.15±0.08 | 0.61±0.27 | 0.24±0.05 |
| PG | 36:2 | 1.63±0.68 | 0.85±0.39 | 1.45±0.49 | 2.84±1.19 | 1.58±0.37 |
| PG | 36:1 | 0.24±0.06 | 0.21±0.07 | 0.16±0.07 | 0.39±0.13 | 0.18±0.12 |
| PG | 40:7 | 3.82±1.36 | 1.82±0.62 | 3.69±0.83 | 4.95±2.38 | 2.55±0.81 |
| PG | 40:6 * | 0.96±0.38 | 0.4±0.24 | 0.96±0.27 | 1.21±0.67 | 0.54±0.27 |
| PI | 34:2 | 0.69±0.17 | 0.63±0.15 | 0.82±0.11 | 1.05±0.31 | 0.92±0.2 |
| PI | 34:1 * | 0.58±0.18 | 0.51±0.15 | 0.65±0.1 | 0.86±0.26 | 0.79±0.18 |
| PI | 36:4 | 0.36±0.09 | 0.33±0.08 | 0.46±0.07 | 0.58±0.15 | 0.46±0.08 |
| PI | 36:3 | 0.9±0.22 | 0.81±0.17 | 1.11±0.17 | 1.53±0.4 | 1.32±0.24 |
| PI | 36:2 | 1.95±0.51 | 1.63±0.35 | 2.11±0.32 | 2.75±0.7 | 2.55±0.47 |
| PI | 36:1 * | 0.82±0.25 | 0.57±0.12 | 0.81±0.11 | 1.11±0.31 | 1.03±0.22 |
| PI | 38:5 | 1.09±0.35 | 0.91±0.22 | 1.33±0.3 | 1.87±0.55 | 1.49±0.33 |
| PI | 38:4 | 4.46±1.22 | 3.46±0.55 | 4.56±0.68 | 6.17±1.37 | 5.53±0.9 |
| PI | 38:3 | 5.23±1.15 | 3.87±0.46 | 5.82±0.68 | 6.51±1.37 | 6.01±0.98 |
| PI | 38:2 * | 1.17±0.31 | 0.74±0.09 | 1.29±0.23 | 1.37±0.38 | 1.27±0.32 |
| PI | 40:6 * | 0.23±0.08 | 0.14±0.03 | 0.2±0.04 | 0.22±0.07 | 0.14±0.04 |
| PI | 40:5 * | 0.3±0.1 | 0.19±0.03 | 0.32±0.06 | 0.34±0.1 | 0.28±0.07 |
| PI | 40:4 | 0.4±0.11 | 0.25±0.03 | 0.42±0.06 | 0.42±0.11 | 0.38±0.09 |
| PI | 40:3 | 0.35±0.06 | 0.24±0.04 | 0.41±0.08 | 0.33±0.06 | 0.32±0.06 |
| LPI | 18:1 * | 0.06±0.02 | 0.06±0.02 | 0.22±0.05 | 0.21±0.04 | 0.35±0.1 |
| LPI | 18:0 | 0.2±0.03 | 0.18±0.06 | 0.55±0.15 | 0.51±0.07 | 0.63±0.09 |
| LPI | 20:4 * | 0.12±0.03 | 0.08±0.02 | 0.19±0.04 | 0.18±0.05 | 0.34±0.08 |

Figure 16 (continued)

| mean±sem in nmol/mg protein | * unconfirmed by MS/MS | Mock-infected time (hrs) | | | | |
|---|---|---|---|---|---|---|
| class | species | 0 | 1 | 2 | 4 | 6 |
| PS | 32:1 | 1.2±0.35 | 1.06±0.18 | 1.06±0.18 | 1.51±0.3 | 1.25±0.31 |
| PS | 34:2 * | 1.29±0.21 | 1.05±0.17 | 1.42±0.15 | 1.57±0.27 | 1.45±0.16 |
| PS | 34:1 | 7.91±1.31 | 6.04±0.98 | 7.97±0.75 | 9.39±1.74 | 8.59±0.92 |
| PS | 36:4 | 1±0.1 | 0.75±0.12 | 0.82±0.13 | 1.06±0.12 | 1±0.17 |
| PS | 36:3 * | 0.63±0.06 | 0.52±0.09 | 0.73±0.07 | 0.91±0.17 | 0.84±0.11 |
| PS | 36:2 | 4.57±0.95 | 3.35±0.56 | 4.64±0.47 | 6.03±1.39 | 5.46±0.82 |
| PS | 36:1 | 13.98±2.59 | 10.38±1.62 | 13.99±1.41 | 17.22±4.12 | 15.37±2.33 |
| PS | 36:0 | 2.68±0.3 | 2.79±0.45 | 3.59±0.53 | 4.47±1.63 | 3.53±0.96 |
| PS | 38:5 * | 1.01±0.11 | 0.83±0.13 | 1.05±0.12 | 1.37±0.28 | 1.15±0.18 |
| PS | 38:4 | 3.62±0.44 | 3.03±0.46 | 3.96±0.45 | 4.77±1 | 4.18±0.58 |
| PS | 38:3 | 2.48±0.27 | 2.14±0.38 | 3.02±0.43 | 3.3±0.8 | 2.88±0.48 |
| PS | 38:2 | 1.72±0.26 | 1.42±0.24 | 2.03±0.26 | 2.24±0.62 | 1.9±0.37 |
| PS | 38:1 | 1.06±0.19 | 0.88±0.16 | 1.14±0.14 | 1.38±0.45 | 1.18±0.28 |
| PS | 40:6 * | 0.55±0.06 | 0.48±0.12 | 0.56±0.15 | 0.55±0.1 | 0.5±0.12 |
| PS | 40:5 * | 0.36±0.04 | 0.29±0.08 | 0.38±0.1 | 0.35±0.08 | 0.32±0.08 |
| PS | 40:4 * | 0.48±0.04 | 0.43±0.09 | 0.59±0.13 | 0.53±0.11 | 0.47±0.09 |
| PS | 40:3 | 0.81±0.09 | 0.69±0.16 | 1±0.24 | 0.84±0.16 | 0.77±0.13 |
| PS | 40:2 | 0.72±0.1 | 0.62±0.12 | 0.85±0.13 | 0.82±0.25 | 0.7±0.15 |
| PS | 40:1 | 0.67±0.1 | 0.54±0.1 | 0.72±0.09 | 0.7±0.23 | 0.61±0.13 |
| LPS | 18:1 * | 0.13±0 | 0.13±0.02 | 0.16±0.04 | 0.15±0.03 | 0.32±0.12 |
| LPS | 18:0 | 0.11±0.01 | 0.11±0.02 | 0.19±0.05 | 0.2±0.06 | 0.28±0.11 |
| SM | d18:1/14:0 | 1.03±0.2 | 0.91±0.19 | 1.28±0.17 | 1.89±0.52 | 1.75±0.41 |
| SM | d18:2/16:0 | 0.97±0.15 | 0.89±0.15 | 1.22±0.14 | 1.76±0.4 | 1.61±0.25 |
| SM | d18:1/16:0 | 10.48±1.75 | 9.03±1.49 | 12.14±1.72 | 17.99±4.59 | 15.88±2.73 |

Figure 16 (continued)

| mean±sem in nmol/mg protein | * unconfirmed |  | | Infected time (hrs) | | |
|---|---|---|---|---|---|---|
| class | species | 0 | 1 | 2 | 4 | 6 |
| PA | 32:1 * | 0.74±0.08 | 1.01±0.16 | 0.86±0.06 | 0.85±0.08 | 1.18±0.19 |
| PA | 34:2 * | 0.38±0.08 | 0.27±0.07 | 0.22±0.05 | 0.28±0.05 | 0.37±0.15 |
| PA | 34:1 | 1.36±0.21 | 1.06±0.26 | 0.93±0.2 | 1.06±0.16 | 1.46±0.54 |
| PA | 36:2 | 1.15±0.14 | 1.31±0.25 | 1.12±0.1 | 1.34±0.15 | 1.8±0.16 |
| PA | 36:1 * | 1.43±0.23 | 1.4±0.27 | 1.21±0.16 | 1.15±0.1 | 1.75±0.16 |
| PC | 28:0 | 0.3±0.03 | 0.37±0.1 | 0.32±0.06 | 0.45±0.03 | 0.4±0.12 |
| PC | 30:1 | 1.55±0.19 | 1.15±0.22 | 1.1±0.15 | 1.51±0.09 | 1.29±0.3 |
| PC | 30:0 | 3.38±0.28 | 2.57±0.56 | 2.43±0.44 | 2.91±0.14 | 3.13±0.88 |
| PC | 32:1 | 17.47±1.12 | 12.59±2.61 | 10.96±1.35 | 15.02±1.05 | 12.46±1.77 |
| PC | 32:0 | 4.53±0.38 | 5.23±0.87 | 5.12±0.59 | 6.69±0.29 | 7.55±1.7 |
| PC | 34:2e | 3.2±0.28 | 2.03±0.36 | 1.67±0.18 | 3.02±0.24 | 2.51±0.35 |
| PC | 34:1e | 10.1±0.88 | 7.57±1.82 | 6.68±1.16 | 9.08±0.89 | 8.63±2.06 |
| PC | 34:2 | 7.92±0.44 | 6.53±1.35 | 5.86±0.87 | 7.71±0.53 | 7.63±1.52 |
| PC | 34:1 | 14.43±0.95 | 12.73±2.69 | 11.13±1.82 | 13.97±1.11 | 14.15±3.08 |
| PC | 34:0 | 2.41±0.57 | 5.24±1.27 | 4.73±0.89 | 4.99±0.92 | 7.22±2.88 |
| PC | 36:4e * | 2.07±0.14 | 1.86±0.31 | 1.65±0.15 | 2.51±0.1 | 2.15±0.3 |
| PC | 36:3e | 2.57±0.23 | 2.63±0.41 | 2.39±0.28 | 3.29±0.2 | 3.23±0.7 |
| PC | 36:2e | 4.11±0.42 | 3.95±0.72 | 3.7±0.48 | 4.67±0.4 | 4.8±1.23 |
| PC | 36:1e | 3.36±0.33 | 3.66±0.76 | 3.5±0.56 | 3.82±0.64 | 4.48±1.39 |
| PC | 36:4 | 3.15±0.36 | 3.5±0.72 | 3.22±0.59 | 3.95±0.46 | 4.03±1.21 |
| PC | 36:3 | 8.71±0.97 | 9.72±2.04 | 9.05±1.64 | 11.23±1.46 | 12.15±3.59 |
| PC | 36:2 | 24.86±2.19 | 26.07±5.16 | 23.14±3.65 | 26.88±2.54 | 27.96±6.98 |
| PC | 36:1 | 9.05±1.38 | 13.82±2.83 | 12.8±2.27 | 12.36±2.29 | 18.73±6.81 |
| PC | 38:5 * | 2.17±0.17 | 2.93±0.42 | 2.63±0.3 | 2.69±0.26 | 3.28±0.9 |
| PC | 38:4 | 3.97±0.36 | 5.14±0.7 | 4.74±0.54 | 4.78±0.51 | 5.94±1.64 |
| PC | 38:3 | 4.85±0.57 | 6.37±1.01 | 5.68±0.73 | 5.4±0.83 | 7.45±2.52 |
| PC | 38:2 | 2.06±0.87 | 2.86±1.31 | 2.64±1.13 | 2.21±1.25 | 4.35±2.52 |
| PC | 40:4 * | 2.66±0.43 | 3.5±0.59 | 3.03±0.4 | 2.87±0.7 | 4.01±1.48 |
| LPC | 16:0e * | 0.15±0.05 | 0.35±0.13 | 0.39±0.09 | 0.34±0.07 | 0.54±0.29 |
| LPC | 16:0 | 0.74±0.13 | 1.34±0.41 | 1.63±0.34 | 1±0.33 | 1.92±1 |
| LPC | 18:1 | 0.49±0.09 | 1.84±0.62 | 2.52±0.61 | 1.24±0.66 | 2.96±1.67 |
| LPC | 18:0 | 0.33±0.11 | 0.29±0.07 | 0.2±0.03 | 0.41±0.07 | 0.34±0.12 |
| PE | 32:1 | 1.54±0.13 | 2.2±0.36 | 1.86±0.28 | 1.45±0.19 | 1.74±0.54 |
| PE | 34:1p | 1.53±0.17 | 1.15±0.17 | 0.79±0.12 | 1.06±0.26 | 0.71±0.12 |
| PE | 34:2 | 2.51±0.2 | 3.67±0.8 | 3.29±0.66 | 2.45±0.42 | 2.65±0.86 |
| PE | 34:1 | 4.41±0.46 | 6.35±1.11 | 5.67±0.93 | 4.35±0.52 | 4.8±1.26 |
| PE | 36:4p | 4.93±0.41 | 3.27±0.53 | 1.9±0.5 | 3.17±0.68 | 2.15±0.64 |
| PE | 36:3p | 3.44±0.3 | 2.88±0.35 | 2.16±0.33 | 2.86±0.29 | 2.56±0.27 |
| PE | 36:3p | 1.24±0.14 | 1.2±0.13 | 1.06±0.14 | 1.15±0.12 | 1.32±0.28 |
| PE | 36:1p * | 1.03±0.15 | 0.94±0.15 | 0.8±0.15 | 0.73±0.12 | 0.81±0.18 |
| PE | 36:4 * | 2.4±0.26 | 3.32±0.49 | 2.99±0.5 | 2.28±0.36 | 2.32±0.59 |
| PE | 36:3 | 2.15±0.25 | 3.51±0.52 | 3.4±0.61 | 2.92±0.53 | 3.4±1.02 |
| PE | 36:2 | 5.78±0.57 | 7.44±1.05 | 7.2±0.98 | 5.94±0.67 | 6.66±1.57 |
| PE | 36:1 | 4.34±0.53 | 6.13±0.93 | 5.87±0.71 | 4.6±0.56 | 5.95±1.37 |
| PE | 38:6p/36:0 * | 2.67±0.24 | 2.43±0.4 | 1.65±0.33 | 1.98±0.11 | 2.1±0.26 |

Figure 16 (continued)

| mean±sem in nmol/mg protein | * unconfirmed by MS/MS | Infected +VU0364739 time (hrs) | | | |
|---|---|---|---|---|---|
| class | species | 0 | 1 | 2 | 4 | 6 |
| PE | 38:5p | 3.77±0.86 | 3.41±0.43 | 6.2±1.94 | 4.86±0.49 |
| PE | 38:4p | 4.37±0.92 | 3.94±0.75 | 5.37±1.23 | 5.07±0.84 |
| PE | 38:6 * | 1.52±0.24 | 1.45±0.09 | 1.48±0.33 | 1.77±0.24 |
| PE | 38:5 | 5.82±1 | 5.64±0.43 | 5.97±1.06 | 6.82±0.5 |
| PE | 38:4 | 12.83±2.24 | 12.65±0.98 | 12.26±2.24 | 14.36±0.84 |
| PE | 38:3 | 7.66±1.72 | 7.35±0.87 | 5.96±1.25 | 8.26±0.95 |
| PE | 40:6p * | 2.84±0.69 | 2.54±0.61 | 2.3±0.63 | 2.8±0.66 |
| PE | 40:5p * | 1.91±0.43 | 1.9±0.2 | 2.43±0.88 | 2.88±0.18 |
| PE | 40:4p * | 1.54±0.42 | 1.6±0.26 | 1.46±0.22 | 2.65±0.49 |
| PE | 40:6 * | 1.65±0.43 | 1.47±0.23 | 1.12±0.22 | 1.73±0.17 |
| PE | 40:5 * | 1±0.28 | 0.97±0.16 | 0.78±0.19 | 1.22±0.15 |
| PE | 40:4 * | 0.82±0.29 | 0.82±0.17 | 0.54±0.13 | 0.86±0.15 |
| LPE | 16:1 * | 0.09±0.04 | 0.46±0.22 | 0.34±0.19 | 0.49±0.27 |
| LPE | 18:2 * | 0.06±0.02 | 0.29±0.15 | 0.28±0.15 | 0.34±0.19 |
| LPE | 18:1 | 0.62±0.08 | 1.45±0.49 | 1.32±0.58 | 1.3±0.58 |
| LPE | 18:0 | 0.39±0.07 | 0.28±0.06 | 0.42±0.12 | 0.35±0.01 |
| LPE | 20:4 | 1.57±0.31 | 4.08±1.5 | 3.47±1.74 | 3.36±1.71 |
| LPE | 20:3 | 0.72±0.2 | 1.88±0.74 | 1.42±0.74 | 1.69±0.9 |
| LPE | 22:6 | 0.46±0.13 | 1.35±0.54 | 1.14±0.6 | 1.16±0.62 |
| LPE | 22:5 * | 0.17±0.08 | 0.58±0.25 | 0.47±0.27 | 0.58±0.32 |
| LPE | 22:4 | 0.15±0.05 | 0.37±0.14 | 0.26±0.15 | 0.34±0.18 |
| PG | 34:2 | 0.7±0.12 | 0.64±0.06 | 1.1±0.17 | 0.7±0.01 |
| PG | 34:1 | 2.18±0.33 | 1.97±0.21 | 3.87±0.56 | 2.49±0.16 |
| PG | 36:3 | 0.75±0.17 | 0.53±0.11 | 1.31±0.24 | 0.68±0.15 |
| PG | 36:2 | 2.36±0.67 | 2.25±0.5 | 4.95±1.05 | 3.17±0.23 |
| PG | 36:1 | 0.63±0.12 | 0.4±0.13 | 0.56±0.18 | 0.57±0.06 |
| PG | 40:7 | 4.06±1.03 | 3.68±0.98 | 3.64±1.01 | 3.26±0.21 |
| PG | 40:6 * | 1.05±0.34 | 0.91±0.33 | 0.73±0.26 | 0.78±0.09 |
| PI | 34:2 | 1.38±0.16 | 1.36±0.13 | 1.91±0.33 | 1.62±0.2 |
| PI | 34:1 * | 1.05±0.18 | 1.05±0.15 | 1.41±0.28 | 1.27±0.21 |
| PI | 36:4 | 0.68±0.11 | 0.71±0.09 | 1.01±0.17 | 0.73±0.1 |
| PI | 36:3 | 1.63±0.27 | 1.76±0.28 | 2.64±0.49 | 2.04±0.3 |
| PI | 36:2 | 2.88±0.48 | 3.02±0.44 | 4.59±0.87 | 3.52±0.45 |
| PI | 36:1 * | 1.12±0.18 | 1.17±0.15 | 1.69±0.32 | 1.44±0.21 |
| PI | 38:5 | 1.56±0.32 | 1.8±0.35 | 2.76±0.56 | 2.13±0.32 |
| PI | 38:4 | 4.52±0.64 | 4.94±0.62 | 7.81±1.18 | 6.16±0.72 |
| PI | 38:3 | 5.42±0.67 | 5.95±0.49 | 7.57±1.11 | 6.66±0.83 |
| PI | 38:2 * | 1.27±0.13 | 1.52±0.26 | 1.52±0.36 | 1.43±0.26 |
| PI | 40:6 * | 0.26±0.04 | 0.3±0.06 | 0.35±0.09 | 0.29±0.06 |
| PI | 40:5 * | 0.35±0.04 | 0.43±0.08 | 0.52±0.12 | 0.44±0.09 |
| PI | 40:4 | 0.45±0.05 | 0.54±0.08 | 0.58±0.11 | 0.52±0.07 |
| PI | 40:3 | 0.46±0.08 | 0.45±0.02 | 0.44±0.05 | 0.43±0.04 |
| LPI | 18:1 * | 0.14±0.06 | 0.31±0.04 | 0.58±0.1 | 0.71±0.25 |
| LPI | 18:0 | 0.53±0.15 | 0.79±0.1 | 1.3±0.16 | 1.32±0.25 |
| LPI | 20:4 * | 0.14±0.02 | 0.2±0.03 | 0.39±0.07 | 0.44±0.16 |

Figure 16 (continued)

| mean±sem in nmol/mg protein | * unconfirmed by MS/MS | Infected +VU0364739 time (hrs) | | | | |
|---|---|---|---|---|---|---|
| class | species | 0 | 1 | 2 | 4 | 6 |
| PS | 32:1 | | 1.48±0.19 | 1.5±0.35 | 2.56±0.42 | 1.69±0.06 |
| PS | 34:2 * | | 1.56±0.06 | 1.48±0.25 | 2.32±0.15 | 1.84±0.07 |
| PS | 34:1 | | 8.86±0.39 | 8.28±1.64 | 13.19±0.96 | 10.33±0.22 |
| PS | 36:4 | | 1.15±0.11 | 0.89±0.19 | 1.61±0.11 | 1.2±0.06 |
| PS | 36:3 * | | 0.88±0.05 | 0.79±0.17 | 1.22±0.06 | 1.09±0.05 |
| PS | 36:2 | | 5.02±0.32 | 4.77±1.2 | 7.64±0.67 | 6.49±0.19 |
| PS | 36:1 | | 15.09±0.62 | 13.02±3.48 | 18.71±1.52 | 16.15±0.17 |
| PS | 36:0 | | 4.97±0.33 | 3.48±0.89 | 3.11±0.28 | 3.21±0.45 |
| PS | 38:5 * | | 1.3±0.08 | 1.02±0.19 | 1.47±0.1 | 1.36±0.05 |
| PS | 38:4 | | 4.5±0.21 | 3.53±0.69 | 4.75±0.16 | 4.3±0.08 |
| PS | 38:3 | | 3.59±0.26 | 2.87±0.48 | 3.17±0.14 | 3.12±0.22 |
| PS | 38:2 | | 2.44±0.13 | 1.94±0.42 | 2.16±0.1 | 2.14±0.14 |
| PS | 38:1 | | 1.38±0.06 | 1.08±0.3 | 1.19±0.12 | 1.14±0.13 |
| PS | 40:6 * | | 0.98±0.12 | 0.71±0.08 | 0.76±0.12 | 0.85±0.06 |
| PS | 40:5 * | | 0.59±0.07 | 0.45±0.05 | 0.44±0.08 | 0.52±0.04 |
| PS | 40:4 * | | 0.75±0.09 | 0.56±0.05 | 0.53±0.08 | 0.63±0.05 |
| PS | 40:3 | | 1.22±0.16 | 0.94±0.09 | 0.81±0.13 | 0.91±0.08 |
| PS | 40:2 | | 1.01±0.07 | 0.82±0.18 | 0.76±0.05 | 0.78±0.05 |
| PS | 40:1 | | 0.84±0.05 | 0.63±0.18 | 0.67±0.04 | 0.59±0.05 |
| LPS | 18:1 * | | 0.2±0.04 | 0.2±0.07 | 0.21±0.11 | 0.29±0.23 |
| LPS | 18:0 | | 0.18±0.03 | 0.16±0.05 | 0.14±0.07 | 0.21±0.17 |
| SM | d18:1/14:0 | | 1.42±0.15 | 1.34±0.13 | 1.85±0.33 | 1.73±0.27 |
| SM | d18:2/16:0 | | 1.3±0.14 | 1.25±0.13 | 1.94±0.22 | 1.48±0.13 |
| SM | d18:1/16:0 | | 13.45±1.52 | 12.55±1.2 | 19.01±2.31 | 16.44±2.31 |

Figure 16 (continued)

ANTIVIRAL THERAPIES WITH PHOSPHOLIPASE D INHIBITORS

CROSS-REFERENCE TO RELATED APPLICATIONS

This application claims the benefit of U.S. Provisional Application No. 61/541,935, filed on Sep. 30, 2011, which is incorporated herein by reference in its entirety.

STATEMENT REGARDING FEDERALLY SPONSORED RESEARCH

This invention was made with government support under grant numbers U54 MH084659, P01 ESO013125, NIAID HHSN2722008000058C awarded by the National Institutes of Health (NIH). The United States government has certain rights in the invention.

BACKGROUND

Infectious diseases, particularly those caused by viruses, presently result in a significant burden on human populations in terms of economic cost, morbidity and mortality. Many of viral diseases, including chickenpox, influenza, herpes, human immunodeficiency virus (HIV/AIDS), human papillomavirus (HPV), infectious mononucleosis, mumps, measles, rubella, shingles, viral gastroenteritis, viral hepatitis, viral meningitis, or viral pneumonia, can be fatal, particularly in vulnerable populations such as children or the elderly. Of particular concern is that the risk of various viral infections to humans rapidly spreading and potentially becoming pandemics has significantly increased in the last fifty years, in large part due to phenomenal increase in air travel. For example, in 2009, there were over 2.5 billion air travelers worldwide, with nearly 1 billion of those as international travelers crossing national borders. These concerns were borne out in 2009 with the rapid spread of a new strain of H1N1 influenza virus creating a pandemic.

Viruses are minute microorganisms having no cell structure, and they are broadly classified as DNA viruses or RNA viruses. In some sense, viruses are not living organisms in their own right since they completely depend upon host cells for all aspects that characterize living cells. For example, viruses require host cells for protein synthesis and energy production mechanisms, and viruses completely lack their own metabolic pathways. In short, viruses cannot exist without the cellular machinery of a host cell. Thus, viral infection presents a particularly difficult therapeutic challenge, in part due to the significant difficulty of designing therapeutic agents that attack the various without significant collateral damage to the host cells and other cells in the body.

Examples of an RNA virus causing a human disease include Japanese encephalitis virus, hepatitis C virus (HCV), and the like of the family Flaviviridae, Rotavirus and the like of the family Reoviridae, mumps virus, measles virus, and the like of the family Paramyxoviridae, influenza virus and the like of the family Orthomyxoviridae, and human immunodeficiency virus (HIV) and the like of the family Retroviridae. There exist three modes of viral infection: acute infection with significant disintegration of host cells; persistent infection with clinical symptoms that remain at relatively minor levels but become chronic; and latent infection with viruses that remain in a state in which no observable viral protein synthesis takes place for a long time period, although cancer is induced in some cases.

As noted above, influenza is caused by an RNA virus of the Orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza type C viruses also infect only humans. They infect most people when they are young and rarely causes serious illness.

Influenza viruses are enveloped viruses containing negative single-stranded RNA's which are segmented and encapsidated. The influenza virus envelope is characterized by the presence of two surface glycoproteins: hemagglutinin and neuraminidase. The influenza A and B virions are pleomorphic and are usually 80-120 nm in diameter. The influenza C virion has many distinctive properties and is thus distinguished from the closely related A and B virions.

It is estimated that millions of people in the United States—about 10% to 20% of U.S. residents—get influenza each year. The majority of this population generally recovers in one to two weeks. In some cases, however, complications can arise from an influenza infection. Those persons at highest risk for contracting complications from the flu include: persons over 50 years of age, children aged 6 to 23 months, women more than 3 months pregnant, persons living in a long-term care facility or institution, persons with chronic heart, lung, or kidney conditions, diabetes, or weakened immune system. Pneumonia, bronchitis, encephalitis, otitis media, rhinitis, and sinusitis are only a few examples of complications that result from an influenza infection. Moreover, the flu can make chronic health problems worse. For example, people with asthma may experience asthma attacks while they have the flu, and people with chronic congestive heart failure may have worsening of this condition that is triggered by the flu.

An average of about 36,000 people per year in the United States die from influenza, and 114,000 per year have to be admitted to the hospital as a result of the infection. Thus, influenza viruses have a major impact on morbidity leading to increases in hospitalization and in visits to health care providers. For example, high rates of hospitalization are often observed for subjects over 65 years of age and also for children less than 5 years of age.

Furthermore, the spread of influenza virus through a population can result in epidemics, which have considerable economic impact. High rates of mortality were observed due to influenza infection during the influenza epidemics of 1957, 1968 and 1977 (Fields Virology, Second Edition, Volume 1, pp. 1075-1152 (1990)). Periodically, the influenza virus causes a worldwide epidemic. For example, the influenza pandemic of 1918 reportedly caused about 20 million deaths worldwide and about 500,000 deaths in the United States (Medical Microbiology, Fourth Edition, University of Texas Medical Branch at Galveston (1996)).

Despite advances in the understanding of the biology of viruses, there is still a scarcity of compounds that are both potent, efficacious, and selective therapeutic agents for the treatment of viral diseases. These needs and other needs are satisfied by the present invention.

SUMMARY

In accordance with the purpose(s) of the invention, as embodied and broadly described herein, the invention, in one aspect, relates to antiviral therapies. For example, compounds having Phospholipase D activity (e.g., isoform selective Phospholipase D inhibitors) can be useful in antiviral therapies (e.g., influenza treatments).

Disclosed are methods for treating a subject for viral infection, the method comprising the step of administering to the subject an effective amount of a compound having a structure represented by a formula:

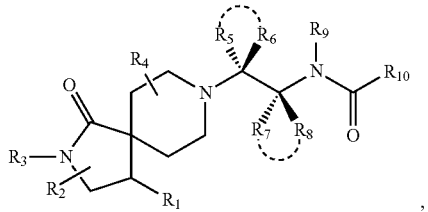

wherein each ---- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

Also disclosed are methods for treating a subject for viral infection, the method comprising the step of administering to the subject an effective amount of a compound having a structure represented by a formula:

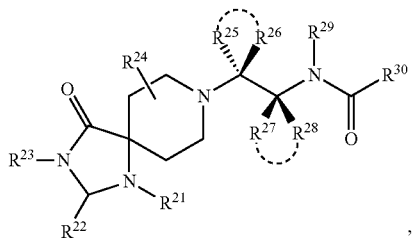

wherein each ---- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

Also disclosed are methods for treating a subject for viral infection, the method comprising the step of administering to the subject an effective amount of a compound having a structure represented by a formula:

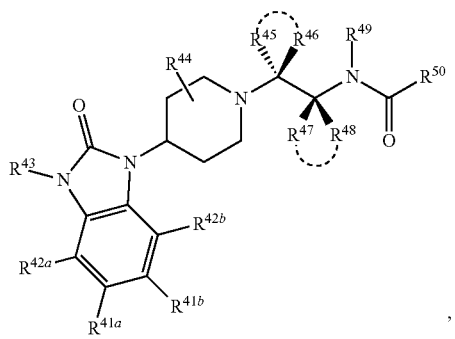

wherein each ---- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

Also disclosed are method for treating a subject for viral infection, the method comprising the step of administering to the subject an effective amount of a compound selected from: trans-diethylstilbestrol, resveratrol, honokiol, SCH420789, presqualene diphosphate, raloxifene, 4-hydroxytamoxifen, 5-fluoro-2-indoyl des-chlorohalopemide, and halopemide, or a pharmaceutically acceptable salt, hydrate, solvate, or polymorph thereof, thereby treating the subject for viral infection.

Also disclosed are methods for treating a subject for viral infection, the method comprising the step of administering to the subject an effective amount of a phospholipase D (PLD) inhibitor, thereby treating the subject for viral infection.

Also disclosed are methods for inhibiting viral entry into a cell, the method comprising the step of contacting the cell with an effective amount of a phospholipase D (PLD) inhibitor, thereby inhibiting viral entry into the cell.

Also disclosed are methods for inhibiting viral replication within a cell, the method comprising the step of contacting the cell with an effective amount of a phospholipase D (PLD) inhibitor, thereby inhibiting viral replication within the cell.

Also disclosed are methods for treating a subject for viral infection, the method comprising the step of administering to the subject an effective amount of a binding agent of phospholipase D (PLD), wherein the binding agent binds to at least one amino acid in a non-catalytic domain of PLD, thereby inhibiting viral entry into the cell.

Also disclosed are methods for treating a subject for viral infection, the method comprising the step of administering to the subject an effective amount of an allosteric binding agent of phospholipase D (PLD), thereby treating the subject for viral infection.

Also disclosed are methods for inhibiting viral entry into a cell, the method comprising the step of contacting the cell an effective amount of a binding agent of phospholipase D (PLD), wherein the binding agent binds to at least one amino acid in a non-catalytic domain of PLD, thereby inhibiting viral entry into the cell.

Also disclosed are methods for inhibiting viral entry into a cell, the method comprising the step of contacting the cell with an effective amount of an allosteric binding agent of phospholipase D (PLD), thereby inhibiting viral entry into the cell.

Also disclosed are methods for inhibiting viral replication within a cell, the method comprising the step of contacting the cell with an effective amount of a binding agent of phospholipase D (PLD), wherein the binding agent binds to at least one amino acid residue in a binding domain comprising amino acids 1-505 of PLD1, or the homologous amino acids of PLD2, thereby inhibiting viral replication within the cell.

Also disclosed are methods for inhibiting viral replication within a cell, the method comprising the step of contacting the cell with an effective amount of an allosteric binding agent of phospholipase D (PLD), thereby inhibiting viral replication within the cell.

Also disclosed are pharmaceutical compositions comprising a pharmaceutically acceptable carrier and an effective amount of a disclosed compound, or a pharmaceutically acceptable salt, hydrate, solvate, or polymorph thereof, wherein the pharmaceutical composition is administered for the treatment of a viral infection.

Also disclosed are kits comprising at least one disclosed compound and one or more of at least one agent known to decrease phospholipase D activity; at least one agent known to increase phospholipase D activity; at least one agent known to treat a viral infection; or instructions for treating a viral infection.

Also disclosed are methods for manufacturing a medicament comprising combining at least one disclosed compound with a pharmaceutically acceptable carrier or diluent, wherein the medicament is used to treat a viral infection.

Also disclosed are uses of a disclosed for the treatment of a viral infection in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 16 shows representative data (means and standard errors) for phospholipid species in A549 cells following infection with influenza virus.

Figure 1:
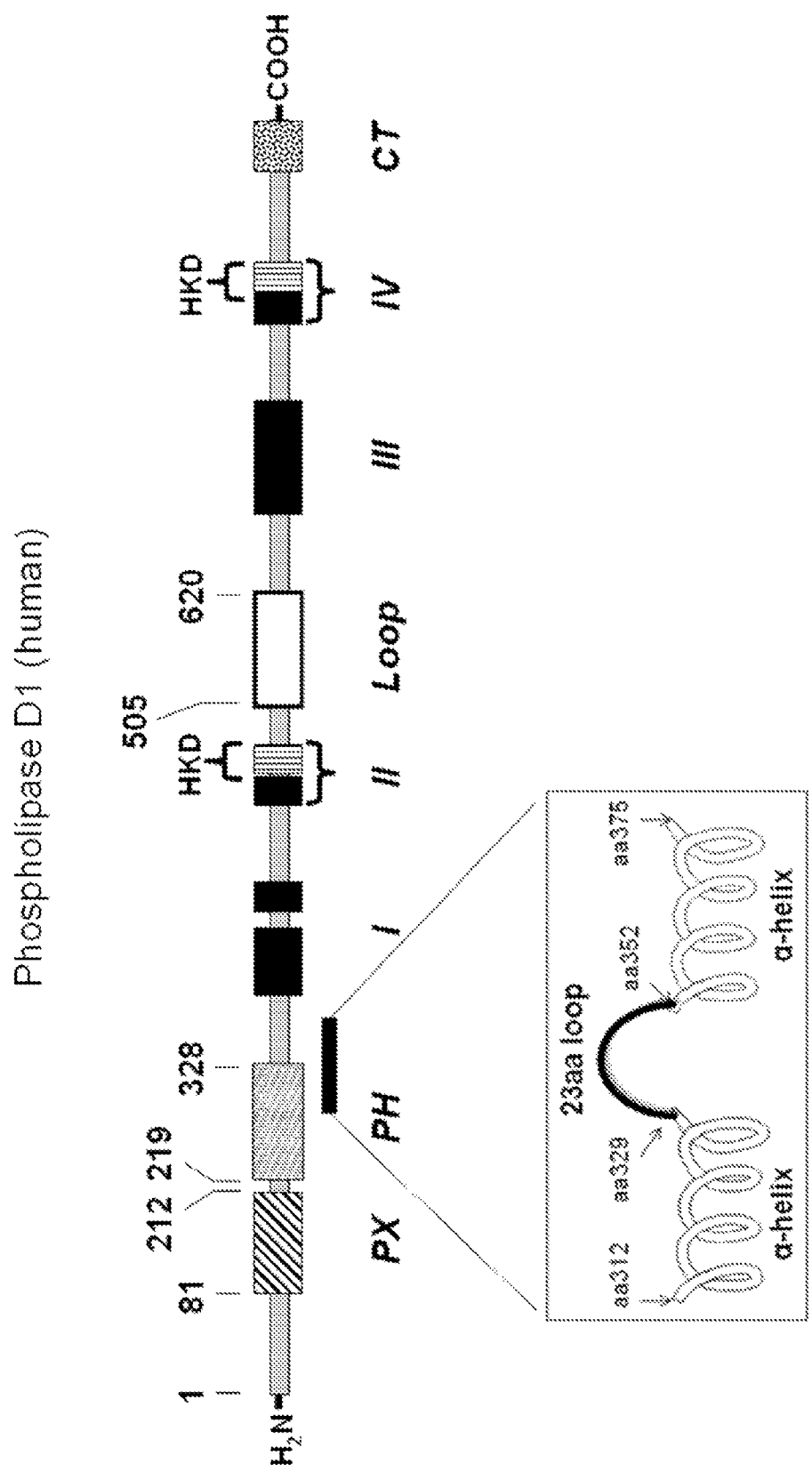
FIG. 1 shows representative schematic structure of the primary and domain structure of PLD1 with a domain that can bind representative disclosed compounds.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "phospholipase D" and "PLD" can be used interchangeably, and refer to a protein family comprising at least the following members: PLD1 and PLD2. Activation of PLDs occurs as a consequence of agonist stimulation of both tyrosine kinase and G protein-coupled receptors. PC-specific PLDs have been proposed to function in regulated secretion, cytoskeletal reorganization, transcriptional regulation, and cell cycle control. PLDs may also be involved in the regulation of perinuclear intravesicular membrane traffic. Several domains are described for the protein, with the overall primary domain structure for PLD1 as given in FIG. 1. PLD2 lacks the "loop" domain, but otherwise has the same domains located at about the same relative positions in the protein.

The PLD protein family catalyzes a variety of reaction. The most well-characterized reaction is the hydrolysis of phosphatidylcholine to produce phosphatidic acid and choline, as follows:

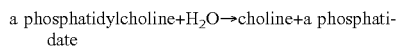

Although the foregoing is the most well-characterized reaction catalyzed by PLD, there are additional reactions which are also catalyzed by PLD. These reactions include:

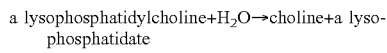

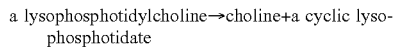

The reactions catalyzed by PLD can involve headgroups other than choline. For example, hydrolysis of the headgroup can be generalized as follows:

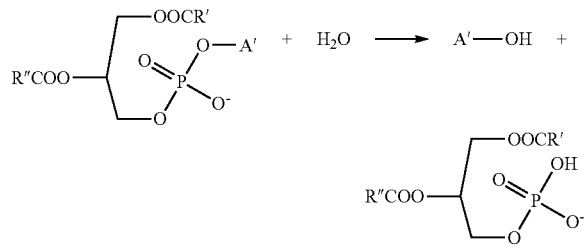

In the foregoing reaction scheme, the R'COO and R"COO moieties derive from fatty acids, e.g. $C_{16}$-$C_{22}$ saturated and unsaturated fatty acids (including polyenoic acids). It should be understood that A' represents an amine containing moiety, e.g. choline.

Alternatively, PLD can also catalyze a transphosphatidylation reaction as follows:

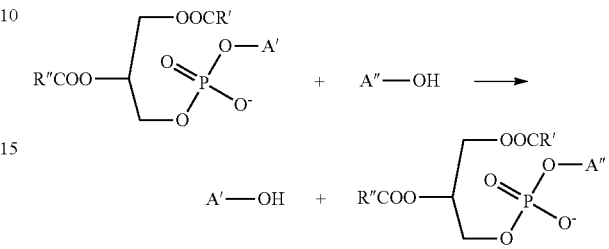

In the foregoing reaction scheme, the R'COO, R"COO, and A' moieties have the same meaning as in the previous reaction. In addition, the A"-OH moiety represents is a primary alcohol.

As used herein, the terms "phospholipase D1" and "PLD1" refer to the phospholipase D1 protein encoded by a gene designated in human as the PLD1 gene, which has a human gene map locus described by Entrez Gene cytogenetic band: 3q26; Ensembl cytogenetic band: 3q26.31; and, HGNC cytogenetic band: 3q26. The term PLD1 refers to a human protein that has about 1074 amino acids and has a molecular weight of about 124,184 Da. The term is inclusive of splice isoforms or mRNA transcript variants, e.g. the alternative mRNA splicing products that code for the isoforms designated as PLD1A, PLD1B, PLD1C, and PLD1D. The term is also inclusive of that protein referred to by such alternative designations as: "PLD1", "phospholipase D1, phosphatidylcholine-specific", "choline phosphatase 1", "phosphatidylcholine-hydrolyzing phospholipase D1", "PLD1", "PLD 1", "EC 3.1.4.4", "phospholipase D1", and "phospholipase D1, phophatidylcholine-specific", as used by those skilled in the art to refer to that protein encoded by human gene PLD1 or to the gene itself. The term is also inclusive of the non-human orthologs or homologs thereof, as well as splice variants and alternative transcripts of the PLD1 gene.

As used herein, the terms "phospholipase D2" and "PLD2" refer to the phospholipase D2 protein encoded by a gene designated in human as the PLD2 gene, which has a human gene map locus described by Entrez Gene cytogenetic band: 17p13.1; Ensembl cytogenetic band: 17p13.2; and, HGNC cytogenetic band: 17p13.3. The term PLD2 refers to a human protein that has about 933 amino acids and has a molecular weight of about 105,987 Da. The term is inclusive of splice isoforms or mRNA transcript variants, e.g. the alternative mRNA splicing products that code for the isoforms designated as PLD2A, PLD2B, and PLD2C. The term is also inclusive of that protein referred to by such alternative designations as: "PLD2", "phospholipase D2", "Choline phosphatase 2", "Phosphatidylcholine-hydrolyzing phospholipase D2", "PLD1C", "hPLD2", "PLD 2", and "EC 3.1.4.4", as used by those skilled in the art to refer to that protein encoded by human gene PLD2 or to the gene itself. The term is also inclusive of the non-human orthologs or homologs thereof, as well as splice variants and alternative transcripts of the PLD2 gene.

As used herein, the term "PLD inhibitor" refers to any exogenously administered compound or agent that directly inhibits the activity of a PLD gene product. In this context, an inhibitor is understood to directly decrease the activity of the target PLD gene product compared to the activity of the gene product in the absence of the exogenously administered compound or agent. Examples of directly acting compounds or agents are allosteric inhibitors, competitive inhibitors, noncompetitive inhibitors, irreversible inhibitors, and uncompetitive inhibitors.

As used herein, the term "PLD1 inhibitor" refers to any exogenously administered compound or agent that directly inhibits the activity of a PLD1 gene product. In this context, an inhibitor is understood to directly decrease the activity of the target PLD1 gene product compared to the activity of the gene product in the absence of the exogenously administered compound or agent. Examples of directly acting compounds or agents are allosteric inhibitors, competitive inhibitors, noncompetitive inhibitors, irreversible inhibitors, and uncompetitive inhibitors.

As used herein, the term "PLD2 inhibitor" refers to any exogenously administered compound or agent that directly inhibits the activity of a PLD2 gene product. In this context, an inhibitor is understood to directly decrease the activity of the target PLD2 gene product compared to the activity of the gene product in the absence of the exogenously administered compound or agent. Examples of directly acting compounds or agents are allosteric inhibitors, competitive inhibitors, noncompetitive inhibitors, irreversible inhibitors, and uncompetitive inhibitors.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

As used herein, "gene product" refers to transcription or translation products that are derived from a specific gene locus or gene. The "gene locus" or "gene" includes coding sequences as well as regulatory, flanking and intron sequences.

The term "viral infection" refers to the introduction of a virus into cells or tissues, e.g., an influenza virus. In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an particular organ, e.g., lung, and cause disease, e.g., localized effects such as respiratory impairment and edema, and systemic effects.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder, e.g. an infection with an influenza virus. The term "patient" includes human and veterinary subjects. In some aspects of the disclosed methods, the subject has been diagnosed with a need for treatment of one or more viral infections prior to the administering step. In some aspects of the disclosed method, the subject has been diagnosed with a need for inhibition of PLD1, PLD2, or both PLD1 and PLD2 activity prior to the administering step. In some aspects of the disclosed method, the subject has been diagnosed with a viral infection, e.g. an influenza virus such as H5N1. In some aspects of the disclosed method, the subject has been identified with a disorder treatable by inhibition of PLD1, PLD2, or both PLD1 and PLD2 activity prior to the administering step. In one aspect, a subject can be treated prophylactically with a compound or composition disclosed herein, as discussed herein elsewhere. It is understood that a subject can be a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; supportive treatment, that is, treatment employed to supplement another specific therapy directed toward the improvement of the associated disease, pathological condition, or disorder; and prophylactic treatment, that is, treatment directed to preventing a disease or disorder in a subject, preventing the occurrence of symptoms in a subject with a disease or disorder, preventing the recurrence of symptoms in a subject with a disease or disorder, and/or decreasing the severity of frequency of outward symptoms of disease or disorder in a subject. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prophylaxis" refers to the complete prevention of infection, the prevention of occurrence of symptoms in an infected subject, the prevention of recurrence of symptoms in an infected subject, or a decrease in severity or frequency of outward symptoms of viral infection or disease in the subject.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by selective inhibition of Phospholipase D1" means having been subjected to a physical examination by a person of skill, for example, a physician, and found to have a condition that can be diagnosed or treated by a compound or composition that can inhibit PLD1. As a further example, "diagnosed with a need for selective inhibition of Phospholipase D2" refers to having been subjected to a physical examination by a person of skill, for example, a physician, and found to have a condition characterized by PLD2 activity. Such a diagnosis can be in reference to a disorder, such as a disease of uncontrolled cellular proliferation, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to PLD2 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The terms "co-administer(s)", "co-administering", and "co-administration" all refer to with respect to compounds or compositions, is meant either simultaneous administration or any manner of separate sequential administration of one or more PLD inhibitor compounds, e.g. a PLD1 selective inhibitor, a PLD2 selective inhibitor, or a non-selective inhibitor of PLD1 and PLD2, with one or more pharmaceutically active agents, such as, but not limited to, those agents included in antiviral therapy. Preferably, if the administration is not simultaneous, the compounds are administered in a close time proximity to each other. Furthermore, it does not matter if the compounds are administered in the same dosage form, e.g. one compound may be administered topically and another compound may be administered orally. "Substantially simultaneously" means that the compound, i.e. a PLD inhibitor compound, is typically administered during or within a reasonably short time either before or after the administration of other compounds, such as a pharmaceutically active agent that treats the disease in question. Additionally, "co-administration", "co-administer(s)", and "co-administering" include administering more than one dose of the pharmaceutically active agent within 24 hours after a dose of a PLD inhibitor compound. In other words, PLD inhibitors need not be administered again before or with every administration of a pharmaceutically active agent, but may be administered intermittently during the course of treatment. "Co-administration", "co-administer(s)", and "co-administering" also includes administering a pharmaceutically active agent and a PLD inhibitor compound as a part of one or more pharmaceutical compositions, and such one or more pharmaceutical compositions may contain a co-formulation of a PLD inhibitor compound and a pharmaceutically active agent or individual formulations of a pharmaceutically active agent and a PLD inhibitor compound.

It is understood that co-administration a PLD inhibitor compound and an anti-viral agent or other therapeutic agent can be independently co-administered by any appropriate route of administration. The active agents, i.e. a PLD inhibitor compound and an anti-viral agent or other therapeutic agent, can be administered by the same or different routes of administration, as appropriate. For example, one of the active ingredients can be administered orally and the other administered orally or by some other appropriate route of administration. Alternatively, the combination of active ingredients can be concurrently orally administered. In a further example, consistent with this understanding, one of the active ingredients can be administered parenterally, for example, intravenously, intramuscularly, subcutaneously, topically, intravaginally, rectally, intranasally, inhalationally, intrathecally, intraocularly, and one or more of the other active ingredients administrated by a similar or distinct route of administration. Moreover, it is understood, that a PLD inhibitor compound and an anti-viral agent or other therapeutic agent can be co-administered or independently administered by distinct routes of administration such as parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

As used herein, "combination therapy" (or "co-therapy") refers to the administration of a PLD inhibitor compound and an anti-viral agent or other therapeutic agent during the course of therapy or treatment for a viral infection. Such combination therapy may involve the administration of the PLD inhibitor compound before, during, and/or after the administration of the anti-viral agent or other therapeutic agent administered to ameliorate, treat, reverse, or cure the viral infection or symptoms associated with the viral infection. The administration of the PLD inhibitor compound may be separated in time from the administration of anti-viral agent or other therapeutic agent by up to several weeks, and may precede it or follow it, but more commonly the administration of the PLD inhibitor compound will accompany at least one aspect of the administration of the anti-viral agent or other therapeutic agent.

As used herein, "concurrently" means (1) simultaneously in time, or (2) at different times during the course of a common treatment schedule.

The term "contacting" as used herein refers to bringing a disclosed compound and a cell, target histamine receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount or dosage that can effectively prevent a disease or disorder in a subject, prevent the occurrence of symptoms in a subject with a disease or disorder, prevent the recurrence of symptoms in a subject with a disease or disorder, and/or decrease the severity of frequency of outward symptoms of a disease or disorder in a subject.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound that is metabolized, for example hydrolyzed or oxidized, in the host to form the compound of the present invention without forming fragments with toxicological liabilities. Typical examples of prodrugs include compounds that have biologically labile protecting groups linked to a functional moiety of the active compound. For example, a prodrug can comprise alkylation, acylation or other lipophilic modification of one or more hydroxy group(s) present in a compound of the invention, e.g. a PLD inhibitor compound. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

The term "immune modulator" refers to any substance meant to alter the working of the humoral or cellular immune system of a subject. Such immune modulators include inhibitors of mast cell-mediated inflammation, interferons, interleukins, prostaglandins, steroids, corticosteroids, colony-stimulating factors, chemotactic factors, etc.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the terms "optional" or "optionally" means that the subsequently described event or circumstance may or may not occur, and that the description includes instances where said event or circumstance occurs and instances where it does not.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" refers to a non-aromatic carbon-based moiety. Aliphatic can include both acyclic or cyclic moieties (e.g., alkyl and cycloalkyl) and can include both saturated and unsaturated moieties (e.g., alkyl, alkenyl, and alkynyl).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of from 1 to 24 carbon atoms, for example from 1 to 12 carbons, from 1 to 8 carbons, from 1 to 6 carbons, or from 1 to 4 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including optionally substituted alkyl, cycloalkyl, alkoxy, amino, ether, halide, hydroxy, nitro, silyl, sulfo-oxo, or thiol, as described herein.

A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The cycloalkyl group can be substituted or unsubstituted. The cycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein. A specific example of amino is —$NH_2$.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, 1,2-oxazol-4-yl, 1,2-oxazol-5-yl, 1,3-oxazolyl, 1,2,4-oxadiazol-5-yl, 1,2,3-triazolyl, 1,3-thiazol-4-yl, pyridinyl, and pyrimidin-5-yl.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "heterocycloalkyl" as used herein is a non-aromatic carbon-based ring composed of at least two carbon atoms and at least one non-carbon heteroatom. For example, the non-carbon heteroatom can include, but is not limited to, oxygen, nitrogen, sulphur, phosphorus and the like. Examples of heterocycloalkyl groups include, aziridine, oxirane, thiirane, azetidine, oxetane, thietane, pyrrolidine, tetrahydrofuran, tetrahydrothiophene, piperidine, thetrahydro-2H-pyran, tetrahydro-2H-thipyran, azepane, oxepane, thiepane, azocane, oxocane, thiocane, pyrazolidine, imidazolidine, diazetidine, hexahydropyridazine, piperazine, diazepane, oxazinane, oxazepane, oxazolidine, oxazetine, and the like. The heterocycloalkyl group can be substituted or unsubstituted. The heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined herein above. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

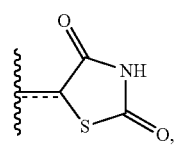

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

In some aspects, a structure of a compound can be represented by a formula:

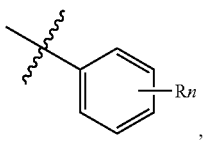

which is understood to be equivalent to a formula:

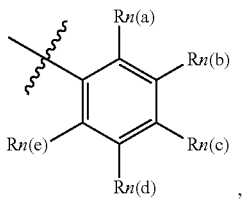

wherein n is typically an integer. That is, R″ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain instances of the above defined terms may occur more than once in the structural formulae, and upon such occurrence each term shall be defined independently of the other.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "hydrolysable residue" is meant to refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (ee). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Phospholipase D Inhibitors

In one aspect, the invention relates to compounds, or pharmaceutically acceptable derivatives thereof, useful as isoform selective phospholipase D inhibitors. In general, it is contemplated that each disclosed compound or derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect, the compounds of the invention are useful in the treatment of viral infection. In a further aspect, the compounds are useful in the treatment of disease associated with a viral infection. In a still further aspect, the compounds are useful in treating a viral infection comprising an RNA virus.

1. Compounds Useful in the Disclosed Methods, Uses, and Pharmaceutical Compositions In one aspect, the invention relates to phospholipase D inhibitors comprising a compound with a structure represented by a formula:

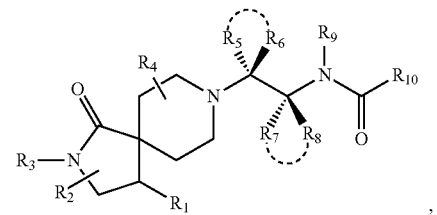

, wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein R³ comprises hydrogen, an optionally substituted C1 to C6 alkyl, an optionally substituted C3 to C₆ cycloalkyl, or a hydrolysable residue; wherein R⁴ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of R⁵ and R⁶ independently comprises hydrogen, trifluoromethyl, carboxamido, alkylsulfonyl, an optionally substituted C1 to C6 alkyl, or an optionally substituted C3 to C6 cycloalkyl or R⁵ and R⁶, together with the intermediate carbon, comprise an optionally substituted C3 to C6 cycloalkyl; wherein each of R⁷ and R⁸ independently comprises hydrogen, trifluoromethyl, carboxamido, alkylsulfonyl, an optionally substituted C1 to C6 alkyl, or an optionally substituted C3 to C6 cycloalkyl or R⁷ and R⁸, together with the intermediate carbon, comprise an optionally substituted C3 to C6 cycloalkyl; wherein R⁹ comprises hydrogen, an optionally substituted C1 to C6 alkyl, an optionally substituted C3 to C6 cycloalkyl, or a hydrolysable residue; wherein R¹⁰ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof.

In a further aspect, the compound has a structure represented by a formula:

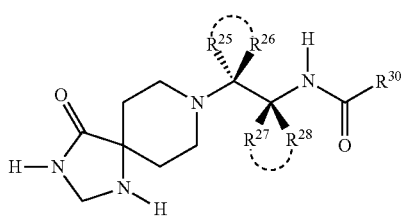

In one aspect, the invention relates to phospholipase D inhibitors comprising a compound with a structure represented by a formula:

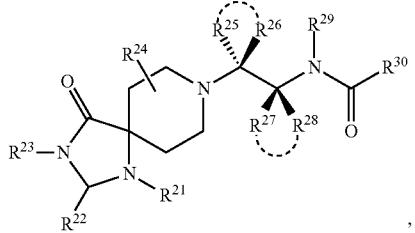

wherein each ---- independently comprises an optional covalent bond; wherein R²¹ is an optionally substituted C3 to C9 organic residue selected from aryl, heteroaryl, cycloalkyl, heterocycloalkyl, cycloalkenyl, and heterocycloalkenyl; wherein R²² comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein R²³ comprises hydrogen, an optionally substituted C1 to C6 alkyl, an optionally substituted C3 to C₆ cycloalkyl, or a hydrolysable residue; wherein R²⁴ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of R²⁵ and R²⁶ independently comprises hydrogen, trifluoromethyl, carboxamido, alkylsulfonyl, an optionally substituted C1 to C6 alkyl, or an optionally substituted C3 to C6 cycloalkyl or R²⁵ and R²⁶, together with the intermediate carbon, comprise an optionally substituted C3 to C6 cycloalkyl; wherein each of R²⁷ and R²⁸ independently comprises hydrogen, trifluoromethyl, carboxamido, alkylsulfonyl, an optionally substituted C1 to C6 alkyl, or an optionally substituted C3 to C₆ cycloalkyl or R²⁷ and R²⁸, together with the intermediate carbon, comprise an optionally substituted C3 to C6 cycloalkyl; wherein R²⁹ comprises hydrogen, an optionally substituted C1 to C6 alkyl, an optionally substituted C3 to C₆ cycloalkyl, or a hydrolysable residue; wherein R³⁰ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof.

In a further aspect, the compound has a structure represented by a formula:

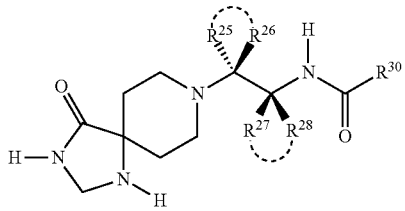

In one aspect, the invention relates to phospholipase D inhibitors comprising a compound with a structure represented by a formula:

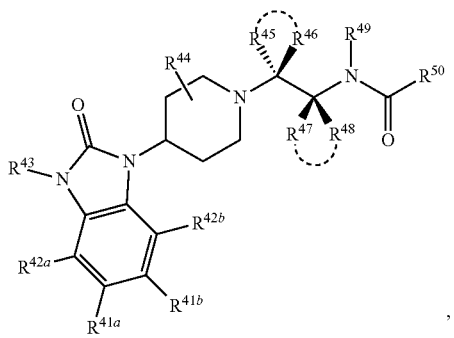

wherein each ---- independently comprises an optional covalent bond; wherein each of R⁴¹ᵃ and R⁴¹ᵇ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of R⁴²ᵃ and R⁴²ᵇ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein R⁴³ comprises hydrogen, an optionally substituted C1 to C6 alkyl, an optionally substituted C3 to C6 cycloalkyl, or a hydrolysable residue; wherein R⁴⁴ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, halide, hydroxyl, trifluoromethyl, amino, cyano, nitro, azide, carboxamido, alkoxy, thiol, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to $C_6$ cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the compound has a structure represented by a formula:

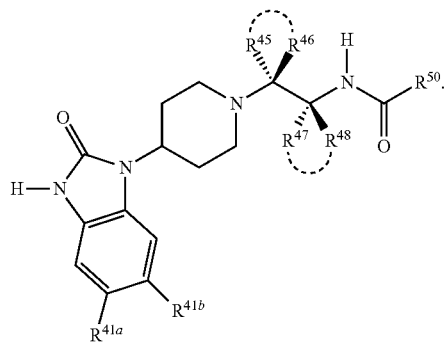

It is understood that the disclosed compounds can be used in connection with the disclosed methods, compositions, kits, and uses.

2. $R^1$ Groups

In one aspect, $R^1$ is an optionally substituted C3 to C9 organic residue selected from aryl, heteroaryl, cycloalkyl, heterocycloalkyl, cycloalkenyl, and heterocycloalkenyl.

In a further aspect, $R^1$ is optionally substituted aryl selected from phenyl and naphthyl.

In a further aspect, $R^1$ is optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophenyl, indolyl, indazolyl, quinolinyl, naphthyridinyl, benzothiazolyl, benzooxazolyl, benzoimidazolyl, and benzotriazolyl.

In a further aspect, $R^1$ is optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^1$ is optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^1$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, $R^1$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^1$ is halophenyl, for example 4-fluorophenyl.

3. $R^2$ Groups

In one aspect, $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^2$ is hydrogen. In a further aspect, each $R^2$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^2$ is independently selected from halide, hydroxyl, trifluoromethyl, amino, cyano, nitro, azide, carboxamido, alkoxy, thiol, and alkylsulfonyl. In a further aspect, at least one $R^2$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

4. $R^3$ Groups

In one aspect, $R^3$ comprises hydrogen, an optionally substituted C1 to C6 alkyl, an optionally substituted C3 to C6 cycloalkyl, or a hydrolysable residue.

In a further aspect, $R^3$ is hydrogen. In a further aspect, $R^3$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^3$ is an optionally substituted C3 to C6 cycloalkyl selected from cyclopropyl, cyclobutyl, cyclopentyl, cyclohexyl, and bicyclo[3.1.0]hexyl. In a further aspect, $R^3$ is a hydrolysable residue.

5. $R^4$ Groups

In one aspect, $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^4$ is hydrogen. In a further aspect, each $R^4$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^4$ is independently selected from halide, hydroxyl, trifluoromethyl, amino, cyano, nitro, azide, carboxamido, alkoxy, thiol, and alkylsulfonyl. In a further aspect, at least one $R^4$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

6. $R^5$ and $R^6$ Groups

In one aspect, each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl.

In a further aspect, $R^5$ is hydrogen. In a further aspect, $R^5$ is selected from trifluoromethyl, carboxamido, alkylsulfonyl, and an optionally substituted C1 to C6 organic residue. In a further aspect, $R^5$ is selected from trifluoromethyl, carboxamido, and alkylsulfonyl. In a further aspect, $R^5$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^6$ is hydrogen. In a further aspect, $R^6$ is selected from trifluoromethyl, carboxamido, alkylsulfonyl, and an optionally substituted C1 to C6 organic residue. In a further aspect, $R^6$ is selected from trifluoromethyl, carboxamido, and alkylsulfonyl. In a further aspect, $R^6$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^6$ is hydrogen and wherein $R^5$ is selected from trifluoromethyl, carboxamido, alkylsulfonyl, and an optionally substituted C1 to C6 organic residue. In a further aspect, $R^6$ is hydrogen and wherein $R^5$ is selected from trifluoromethyl, carboxamido, and alkylsulfonyl. In a further aspect, $R^6$ is hydrogen and wherein $R^5$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^5$ is hydrogen and wherein $R^6$ is selected from trifluoromethyl, carboxamido, alkylsulfonyl, and an optionally substituted C1 to C6 organic residue. In a further aspect, $R^5$ is hydrogen and wherein $R^6$ is selected from trifluoromethyl, carboxamido, and alkylsulfonyl. In a further aspect, $R^5$ is hydrogen and wherein $R^6$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^5$ and $R^6$, together with the intermediate carbon, comprise an optionally substituted C3 to C6 cycloalkyl. In a further aspect, wherein $R^5$ and $R^6$, together with the intermediate carbon, comprise cyclopropyl, cyclobutyl, cyclopentyl, or cyclohexyl.

7. $R^7$ and $R^8$ Groups

In one aspect, each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl.

In a further aspect, $R^7$ is hydrogen. In a further aspect, $R^7$ is selected from trifluoromethyl, carboxamido, alkylsulfonyl, and an optionally substituted C1 to C6 organic residue. In a further aspect, $R^7$ is selected from trifluoromethyl, carboxamido, and alkylsulfonyl. In a further aspect, $R^7$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^7$ is methyl.

In a further aspect, $R^8$ is hydrogen. In a further aspect, $R^8$ is selected from trifluoromethyl, carboxamido, alkylsulfonyl, and an optionally substituted C1 to C6 organic residue. In a further aspect, $R^8$ is selected from trifluoromethyl, carboxamido, and alkylsulfonyl. In a further aspect, $R^8$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^8$ is methyl.

In a further aspect, $R^8$ is hydrogen and wherein $R^7$ is selected from trifluoromethyl, carboxamido, alkylsulfonyl, and an optionally substituted C1 to C6 organic residue. In a further aspect, $R^8$ is hydrogen and wherein $R^7$ is selected from trifluoromethyl, carboxamido, and alkylsulfonyl. In a further aspect, $R^8$ is hydrogen and wherein $R^7$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^7$ is hydrogen and wherein $R^8$ is selected from trifluoromethyl, carboxamido, alkylsulfonyl, and an optionally substituted C1 to C6 organic residue. In a further aspect, $R^7$ is hydrogen and wherein $R^8$ is selected from trifluoromethyl, carboxamido, and alkylsulfonyl. In a further aspect, $R^7$ is hydrogen and wherein $R^8$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^7$ and $R^8$, together with the intermediate carbon, comprise an optionally substituted C3 to $C_6$ cycloalkyl. In a further aspect, $R^7$ and $R^8$, together with the intermediate carbon, comprise cyclopropyl, cyclobutyl, cyclopentyl, or cyclohexyl.

8. $R^9$ Groups

In one aspect, $R^9$ comprises hydrogen, an optionally substituted C1 to C6 alkyl, an optionally substituted C3 to $C_6$ cycloalkyl, or a hydrolysable residue.

In a further aspect, $R^9$ is hydrogen. In a further aspect, $R^9$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^9$ is an optionally substituted C3 to $C_6$ cycloalkyl selected from cyclopropyl, cyclobutyl, cyclopentyl, and cyclohexyl. In a further aspect, $R^9$ is a hydrolysable residue.

9. $R^{10}$ Groups

In one aspect, $R^{10}$ comprises an optionally substituted C1 to C12 organic residue selected from alkyl, aryl, heteroaryl, cycloalkyl, heterocycloalkyl, cycloalkenyl, and heterocycloalkenyl.

In a further aspect, $R^{10}$ is an optionally substituted alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, cyclohexyl, heptyl, cycloheptyl, octyl, cyclooctyl, nonyl, cyclononyl, decyl, cyclodecyl, undecyl, cycloundecyl, dodecyl, or cyclododecyl.

In a further aspect, $R^{10}$ is an optionally substituted aryl selected from phenyl and naphthyl.

In a further aspect, $R^{10}$ is an optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, $R^{10}$ is an optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^{10}$ is an optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{10}$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, $R^{10}$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{10}$ is phenylethynyl, indolyl, quinolinyl, naphthyl, phenylcyclopropyl, or fluorophenyl.

10. $R^{21}$ Groups

In one aspect, $R^{21}$ is an optionally substituted C3 to C9 organic residue selected from aryl, heteroaryl, cycloalkyl, heterocycloalkyl, cycloalkenyl, and heterocycloalkenyl.

In a further aspect, $R^{21}$ is optionally substituted aryl selected from phenyl and naphthyl.

In a further aspect, $R^{21}$ is optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, $R^{21}$ is optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^{21}$ is optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{21}$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, $R^{21}$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{21}$ is halophenyl, for example 4-fluorophenyl.

11. $R^{22}$ Groups

In one aspect, $R^{22}$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^{22}$ is hydrogen. In a further aspect, each $R^{22}$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^{22}$ is independently selected from halide, hydroxyl, trifluoromethyl, amino, cyano, nitro, azide, carboxamido, alkoxy, thiol, and alkylsulfonyl. In a further aspect, at least one $R^{22}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

12. $R^{23}$ Groups

In one aspect, $R^{23}$ comprises hydrogen, an optionally substituted C1 to C6 alkyl, an optionally substituted C3 to C6 cycloalkyl, or a hydrolysable residue.

In a further aspect, $R^{23}$ is hydrogen. In a further aspect, $R^{23}$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^{23}$ is an optionally substituted C3 to C6 cycloalkyl selected from cyclopropyl, cyclobutyl, cyclopentyl, cyclohexyl, and bicyclo[3.1.0]hexyl. In a further aspect, $R^{23}$ is a hydrolysable residue.

13. $R^{24}$ Groups

In one aspect, $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^{24}$ is hydrogen. In a further aspect, each $R^{24}$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^{24}$ is independently selected from halide, hydroxyl, trifluoromethyl, amino, cyano, nitro, azide, carboxamido, alkoxy, thiol, and alkylsulfonyl. In a further aspect, at least one $R^{24}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

14. $R^{25}$ and $R^{26}$ Groups

In one aspect, each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl.

In a further aspect, $R^{25}$ is hydrogen. In a further aspect, $R^{25}$ is selected from trifluoromethyl, carboxamido, alkylsulfonyl, and an optionally substituted C1 to C6 organic residue. In a further aspect, $R^{25}$ is selected from trifluoromethyl, carboxamido, and alkylsulfonyl. In a further aspect, $R^{25}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{26}$ is hydrogen. In a further aspect, $R^{26}$ is selected from trifluoromethyl, carboxamido, alkylsulfonyl, and an optionally substituted C1 to C6 organic residue. In a further aspect, $R^{26}$ is selected from trifluoromethyl, carboxamido, and alkylsulfonyl. In a further aspect, $R^{26}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{26}$ is hydrogen and wherein $R^{25}$ is selected from trifluoromethyl, carboxamido, alkylsulfonyl, and an optionally substituted C1 to C6 organic residue. In a further aspect, $R^{26}$ is hydrogen and wherein $R^{25}$ is selected from trifluoromethyl, carboxamido, and alkylsulfonyl. In a further aspect, $R^{26}$ is hydrogen and wherein $R^{25}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{25}$ is hydrogen and wherein $R^{26}$ is selected from trifluoromethyl, carboxamido, thiol, alkylsulfonyl, and an optionally substituted C1 to C6 organic residue. In a further aspect, $R^{25}$ is hydrogen and wherein $R^{26}$ is selected from trifluoromethyl, carboxamido, and alkylsulfonyl. In a further aspect, $R^{25}$ is hydrogen and wherein $R^{26}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{25}$ and $R^{26}$, together with the intermediate carbon, comprise an optionally substituted C3 to C6 cycloalkyl. In a further aspect, wherein $R^{25}$ and $R^{26}$, together with the intermediate carbon, comprise cyclopropyl, cyclobutyl, cyclopentyl, or cyclohexyl.

15. $R^{27}$ and $R^{28}$ Groups

In one aspect, each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl.

In a further aspect, $R^{27}$ is hydrogen. In a further aspect, $R^{27}$ is selected from trifluoromethyl, carboxamido, alkylsulfonyl, and an optionally substituted C1 to C6 organic residue. In a further aspect, $R^{27}$ is selected from trifluoromethyl, carboxamido, and alkylsulfonyl. In a further aspect, $R^{27}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^{27}$ is methyl.

In a further aspect, $R^{28}$ is hydrogen. In a further aspect, $R^{28}$ is selected from trifluoromethyl, carboxamido, alkylsulfonyl, and an optionally substituted C1 to C6 organic residue. In a further aspect, $R^{28}$ is selected from trifluoromethyl, carboxamido, and alkylsulfonyl. In a further aspect, $R^{28}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^{28}$ is methyl.

In a further aspect, $R^{28}$ is hydrogen and wherein $R^{27}$ is selected from trifluoromethyl, carboxamido, alkylsulfonyl, and an optionally substituted C1 to C6 organic residue. In a further aspect, $R^{28}$ is hydrogen and wherein $R^{27}$ is selected from trifluoromethyl, carboxamido, and alkylsulfonyl. In a further aspect, $R^{28}$ is hydrogen and wherein $R^{27}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{27}$ is hydrogen and wherein $R^{28}$ is selected from trifluoromethyl, carboxamido, alkylsulfonyl, and an optionally substituted C1 to C6 organic residue. In a further aspect, $R^{27}$ is hydrogen and wherein $R^{28}$ is selected from trifluoromethyl, carboxamido, and alkylsulfonyl. In a further aspect, $R^{27}$ is hydrogen and wherein $R^{28}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{27}$ and $R^{28}$, together with the intermediate carbon, comprise an optionally substituted C3 to C6 cycloalkyl. In a further aspect, $R^{27}$ and $R^{28}$, together with the intermediate carbon, comprise cyclopropyl, cyclobutyl, cyclopentyl, or cyclohexyl.

16. $R^{29}$ Groups

In one aspect, $R^{29}$ comprises hydrogen, an optionally substituted C1 to C6 alkyl, an optionally substituted C3 to C6 cycloalkyl, or a hydrolysable residue.

In a further aspect, $R^{29}$ is hydrogen. In a further aspect, $R^{29}$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^{29}$ is an optionally substituted C3 to C6 cycloalkyl selected from cyclopropyl, cyclobutyl, cyclopentyl, and cyclohexyl. In a further aspect, $R^9$ is a hydrolysable residue.

17. $R^{30}$ Groups

In one aspect, $R^{30}$ comprises an optionally substituted C1 to C12 organic residue selected from alkyl, aryl, heteroaryl, cycloalkyl, heterocycloalkyl, cycloalkenyl, and heterocycloalkenyl.

In a further aspect, $R^{30}$ is an optionally substituted alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, cyclohexyl, heptyl, cycloheptyl, octyl, cyclooctyl, nonyl, cyclononyl, decyl, cyclodecyl, undecyl, cycloundecyl, dodecyl, or cyclododecyl.

In a further aspect, $R^{30}$ is an optionally substituted aryl selected from phenyl and naphthyl.

In a further aspect, $R^{30}$ is an optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, $R^{30}$ is an optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^{30}$ is an optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{30}$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, $R^{30}$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^{30}$ is phenylethynyl, indolyl, quinolinyl, naphthyl, phenylcyclopropyl, or fluorophenyl.

18. $R^{41A}$ and $R^{41B}$ Groups

In one aspect, each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each of $R^{41a}$ and $R^{41b}$ is hydrogen. In a further aspect, each of $R^{41a}$ and $R^{41b}$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each of $R^{41a}$ and $R^{41b}$ is independently selected from halide, hydroxyl, trifluoromethyl, amino, cyano, nitro, azide, carboxamido, alkoxy, thiol, and alkylsulfonyl. In a further aspect, at least one of $R^{41a}$ and $R^{41b}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

19. $R^{42A}$ and $R^{42B}$ Groups

In one aspect, each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each of $R^{42a}$ and $R^{42b}$ is hydrogen. In a further aspect, each of $R^{42a}$ and $R^{42b}$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each of $R^{42a}$ and $R^{42b}$ is independently selected from halide, hydroxyl, trifluoromethyl, amino, cyano, nitro, azide, carboxamido, alkoxy, thiol, and alkylsulfonyl. In a further aspect, at least one of $R^{42a}$ and $R^{42b}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

20. $R^{43}$ Groups

In one aspect, $R^{43}$ comprises hydrogen, an optionally substituted C1 to C6 alkyl, an optionally substituted C3 to C6 cycloalkyl, or a hydrolysable residue.

In a further aspect, $R^{43}$ is hydrogen. In a further aspect, $R^{43}$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^{43}$ is an optionally substituted C3 to C6 cycloalkyl selected from cyclopropyl, cyclobutyl, cyclopentyl, cyclohexyl, and bicyclo[3.1.0] hexyl. In a further aspect, $R^{43}$ is a hydrolysable residue.

21. $R^{44}$ Groups

In one aspect, $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue.

In a further aspect, each $R^{44}$ is hydrogen. In a further aspect, each $R^{44}$ is independently selected from halide, hydroxyl, trifluoromethyl, amino, cyano, nitro, azide, carboxamido, alkoxy, thiol, alkylsulfonyl, and an optionally substituted C1 to C6 organic residue. In a further aspect, each $R^{44}$ is independently selected from halide, hydroxyl, trifluoromethyl, amino, cyano, nitro, azide, carboxamido, alkoxy, thiol, and alkylsulfonyl. In a further aspect, at least one $R^{44}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

22. $R^{45}$ and $R^{46}$ Groups

In one aspect, each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl.

In a further aspect, $R^{45}$ is hydrogen. In a further aspect, $R^{45}$ is selected from trifluoromethyl, carboxamido, alkylsulfonyl, and an optionally substituted C1 to C6 organic residue. In a further aspect, $R^{45}$ is selected from trifluoromethyl, carboxamido, and alkylsulfonyl. In a further aspect, $R^{45}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{46}$ is hydrogen. In a further aspect, $R^{46}$ is selected from trifluoromethyl, alkoxy, thiol, alkylsulfonyl, and an optionally substituted C1 to C6 organic residue. In a further aspect, $R^{46}$ is selected from trifluoromethyl, carboxamido, and alkylsulfonyl. In a further aspect, $R^{46}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{46}$ is hydrogen and wherein $R^{45}$ is selected from trifluoromethyl, carboxamido, alkylsulfonyl, and an optionally substituted C1 to C6 organic residue. In a further aspect, $R^{46}$ is hydrogen and wherein $R^{45}$ is selected from trifluoromethyl, carboxamido, and alkylsulfonyl. In a further aspect, $R^{46}$ is hydrogen and wherein $R^{45}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{45}$ is hydrogen and wherein $R^{46}$ is selected from trifluoromethyl, carboxamido, alkylsulfonyl, and an optionally substituted C1 to C6 organic residue. In a further aspect, $R^{45}$ is hydrogen and wherein $R^{46}$ is selected from trifluoromethyl, carboxamido, and alkylsulfonyl. In a further aspect, $R^{45}$ is hydrogen and wherein $R^{46}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{45}$ and $R^{46}$, together with the intermediate carbon, comprise an optionally substituted C3 to C6 cycloalkyl. In a further aspect, wherein $R^{45}$ and $R^{46}$, together with the intermediate carbon, comprise cyclopropyl, cyclobutyl, cyclopentyl, or cyclohexyl.

23. $R^{47}$ and $R^{48}$ Groups

In one aspect, each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl.

In a further aspect, $R^{47}$ is hydrogen. In a further aspect, $R^{47}$ is selected from trifluoromethyl, carboxamido, alkylsulfonyl, and an optionally substituted C1 to C6 organic residue. In a further aspect, $R^{47}$ is selected from trifluoromethyl, carboxamido, and alkylsulfonyl. In a further aspect, $R^{47}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^{47}$ is methyl.

In a further aspect, $R^{48}$ is hydrogen. In a further aspect, $R^{48}$ is selected from trifluoromethyl, carboxamido, alkylsulfonyl, and an optionally substituted C1 to C6 organic residue. In a further aspect, $R^{48}$ is selected from trifluoromethyl, carboxamido, and alkylsulfonyl. In a further aspect, $R^{48}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl. In a further aspect, $R^{48}$ is methyl.

In a further aspect, $R^{48}$ is hydrogen and wherein $R^{47}$ is selected from trifluoromethyl, carboxamido, alkoxy, thiol, alkylsulfonyl, and an optionally substituted C1 to C6 organic residue. In a further aspect, $R^{48}$ is hydrogen and wherein $R^{47}$ is selected from trifluoromethyl, carboxamido, and alkylsulfonyl. In a further aspect, $R^{48}$ is hydrogen and wherein $R^{47}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{47}$ is hydrogen and wherein $R^{48}$ is selected from trifluoromethyl, carboxamido, alkylsulfonyl, and an optionally substituted C1 to C6 organic residue. In a further aspect, $R^{47}$ is hydrogen and wherein $R^{48}$ is selected from trifluoromethyl, carboxamido, and alkylsulfonyl. In a further aspect, $R^{47}$ is hydrogen and wherein $R^{48}$ is methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

In a further aspect, $R^{47}$ and $R^{48}$, together with the intermediate carbon, comprise an optionally substituted C3 to C6 cycloalkyl. In a further aspect, $R^{47}$ and $R^{48}$, together with the intermediate carbon, comprise cyclopropyl, cyclobutyl, cyclopentyl, or cyclohexyl.

24. $R^{49}$ Groups

In one aspect, $R^{49}$ comprises hydrogen, an optionally substituted C1 to C6 alkyl, an optionally substituted C3 to C6 cycloalkyl, or a hydrolysable residue.

In a further aspect, $R^{49}$ is hydrogen. In a further aspect, $R^{49}$ is an optionally substituted C1 to C6 alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, and cyclohexyl. In a further aspect, $R^{49}$ is an optionally substituted C3 to C6 cycloalkyl selected from cyclopropyl, cyclobutyl, cyclopentyl, and cyclohexyl. In a further aspect, $R^9$ is a hydrolysable residue.

25. R$^{50}$ Groups

In one aspect, R$^{50}$ comprises an optionally substituted C1 to C16 organic residue selected from alkyl, aryl, heteroaryl, cycloalkyl, heterocycloalkyl, cycloalkenyl, and heterocycloalkenyl.

In a further aspect, R$^{50}$ is an optionally substituted alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, cyclohexyl, heptyl, cycloheptyl, octyl, cyclooctyl, nonyl, cyclononyl, decyl, cyclodecyl, undecyl, cycloundecyl, dodecyl, or cyclododecyl.

In a further aspect, R$^{50}$ is an optionally substituted aryl selected from phenyl and naphthyl.

In a further aspect, R$^{50}$ is an optionally substituted heteroaryl selected from furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, R$^{50}$ is an optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, R$^{50}$ is an optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, R$^{50}$ is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, R$^{50}$ is optionally substituted heterocycloalkenyl comprising a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, R$^{50}$ is phenylethynyl, indolyl, quinolinyl, naphthyl, phenylcyclopropyl, or fluorophenyl.

26. Exemplary Compounds

In one aspect, the invention relates to phospholipase D inhibitors comprising one or more compounds selected from:

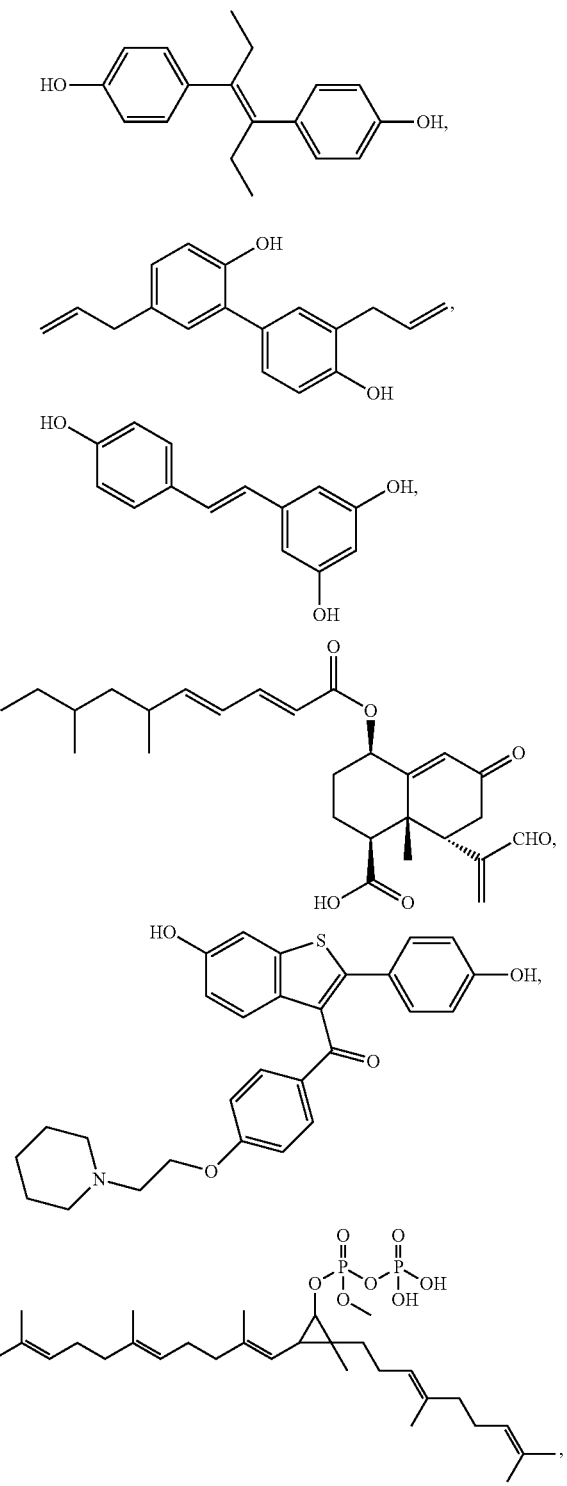

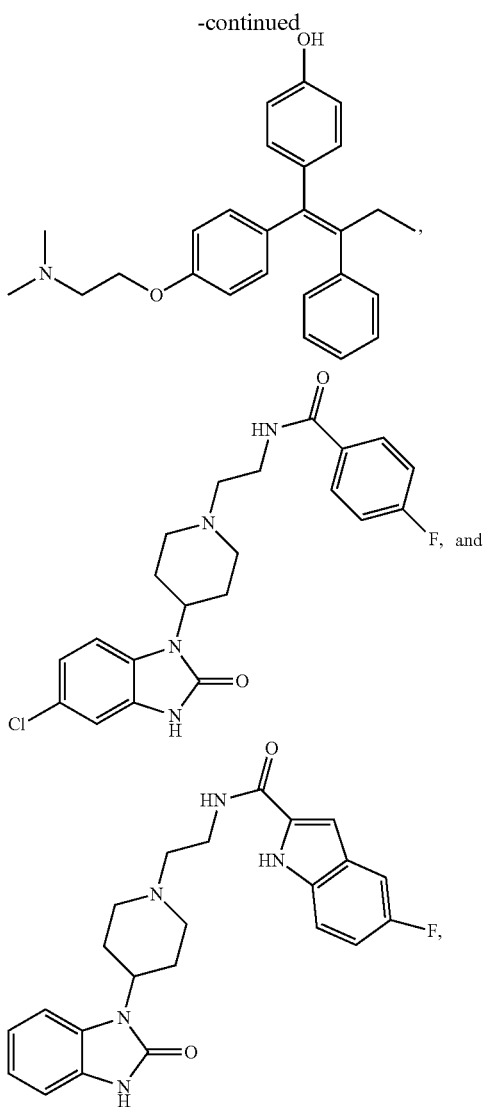

or a subgroup thereof.

In a further aspect, the invention relates to phospholipase D inhibitors comprising a compound selected from trans-diethylstilbestrol ((E)-4,4'-(hex-3-ene-3,4-diyl)diphenol); resveratrol (5-[2-(4-hydroxyphenyl)ethenyl]benzene-1,3-diol); honokiol (3',5-diallyl-[1,1'-biphenyl]-2,4'-diol); SCH420789 ((1S,4R,8S,8aR)-4-(2E,4E)-6,8-dimethyldeca-2,4-dienoyl)oxy)-8a-methyl-6-oxo-8-(3-oxoprop-1-en-2-yl)-1,2,3,4,6,7,8,8a-octahydronaphthalene-1-carboxylic acid); presqualene diphosphate ([[2-(4,8-dimethylnona-3,7-dienyl)-2-methyl-3-(2,6,10-trimethylundeca-1,5,9-trienyl) cyclopropyl]methoxy-hydroxy-phosphoryl]oxyphosphonic acid); raloxifene ((6-hydroxy-2-(4-hydroxyphenyl)benzo[b] thiophen-3-yl)(4-(2-(piperidin-1-yl)ethoxy)phenyl)methanone); 4-hydroxytamoxifen (4-[(Z)-1-[4-[2-(dimethyl-amino)ethoxy]phenyl]-2-phenylbut-1-enyl]phenol); 5-fluoro-2-indoyl des-chlorohalopemide (N-[2-[4-(2,3-di-hydro-2-oxo-1H-benzimidazol-1-yl)-1-piperidinyl]ethyl]-5-fluoro-1H-indole-2-carboxamide), and halopemide (N-[2-[4-(5-Chloro-2,3-dihydro-2-oxo-1H-benzimidazol-1-yl) piperidino]ethyl]-4-fluorobenzamide).

In various aspects, a phospholipase D inhibitor compound can be present as:

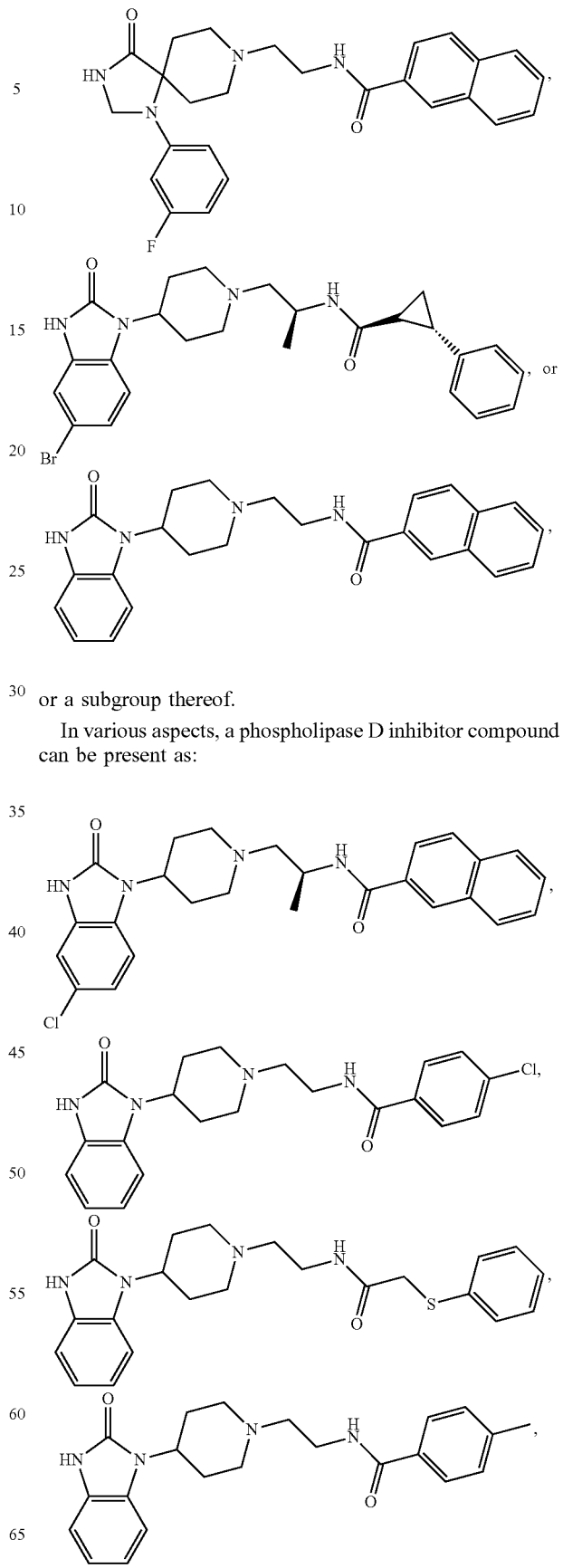

or a subgroup thereof.

In various aspects, a phospholipase D inhibitor compound can be present as:

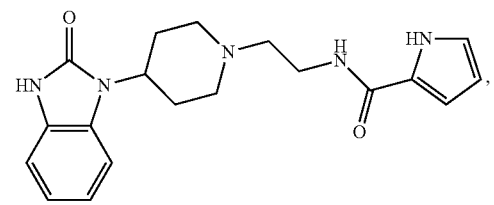
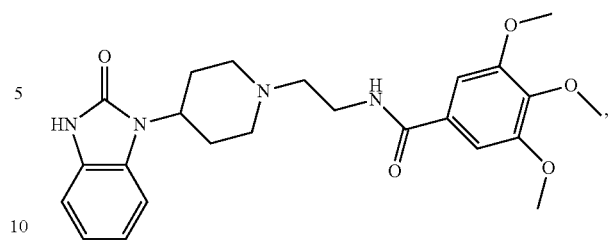
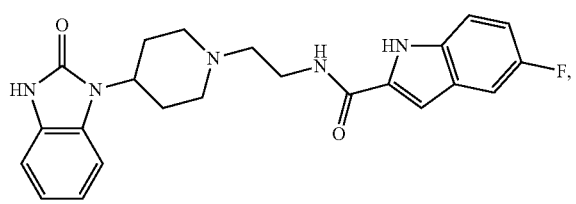
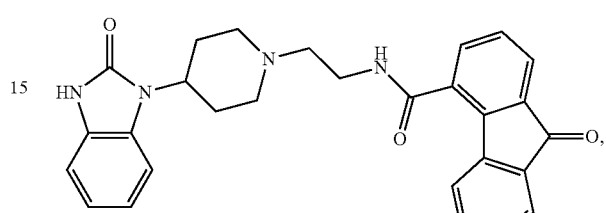
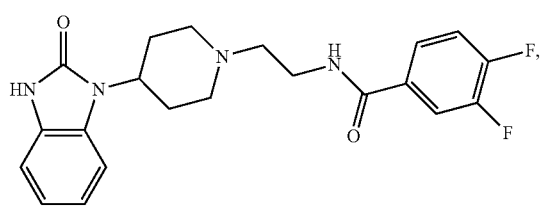
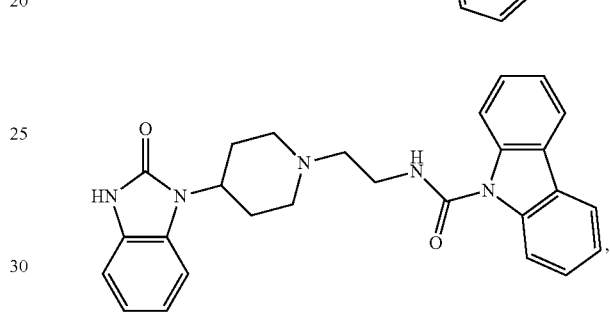
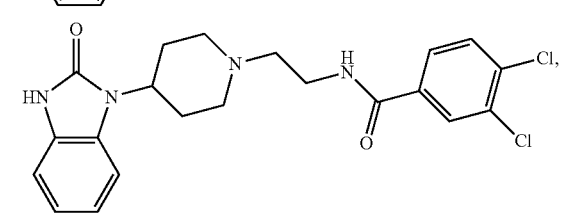
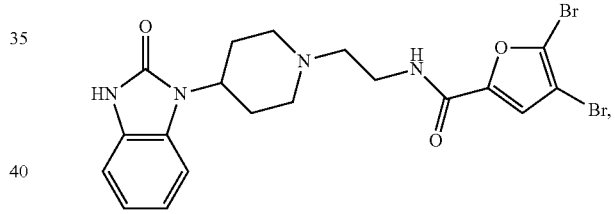
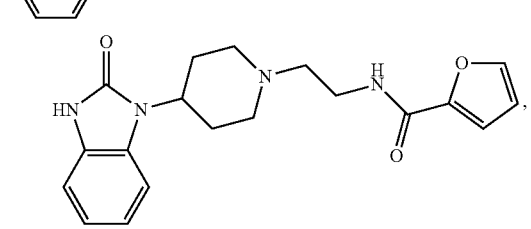
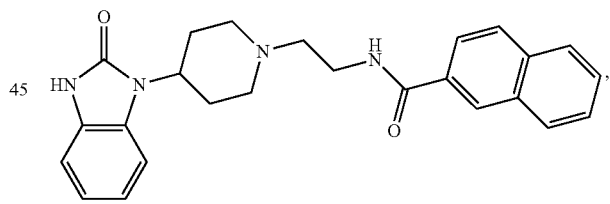
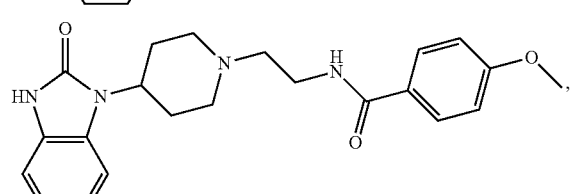
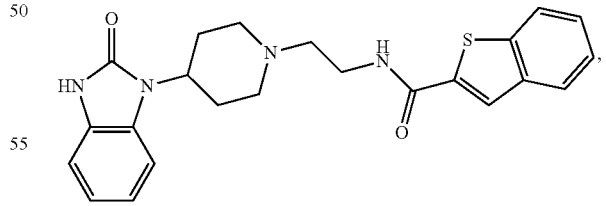
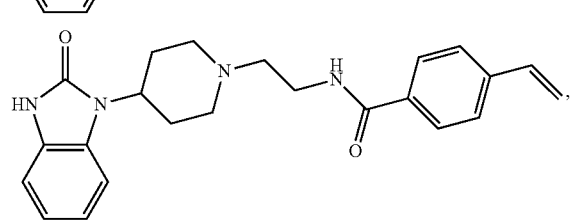
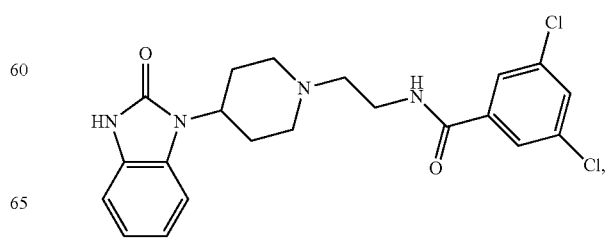

49
-continued
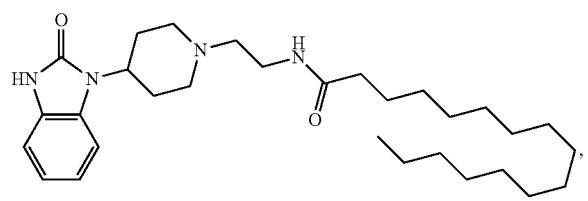
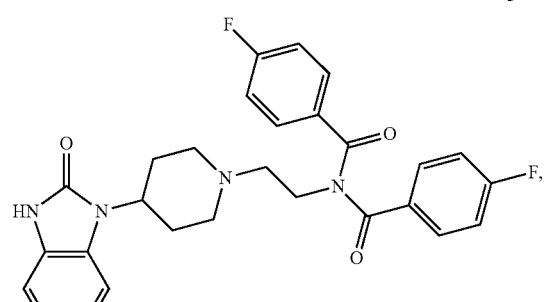
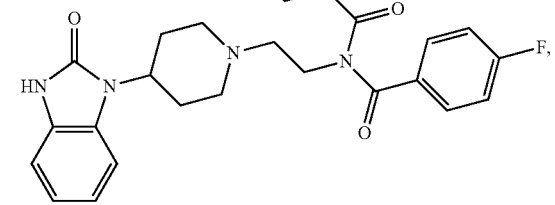
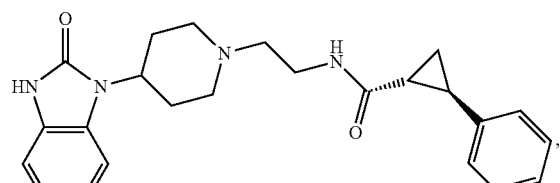
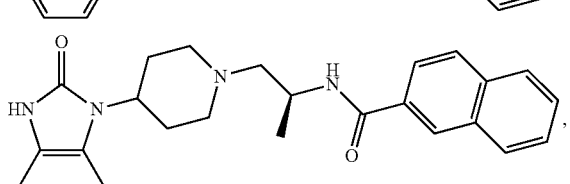
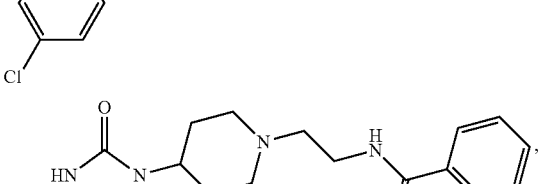
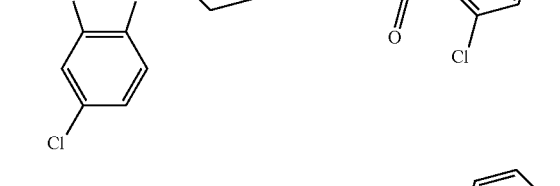
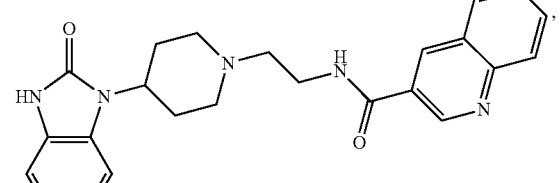
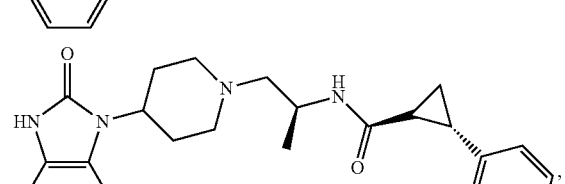
50
-continued
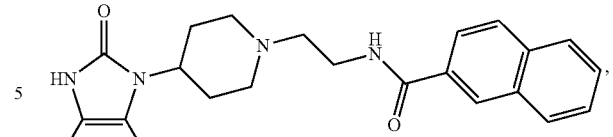
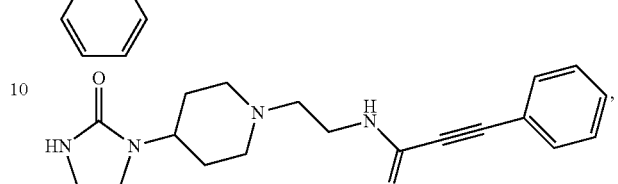
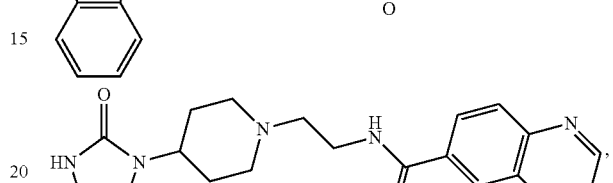
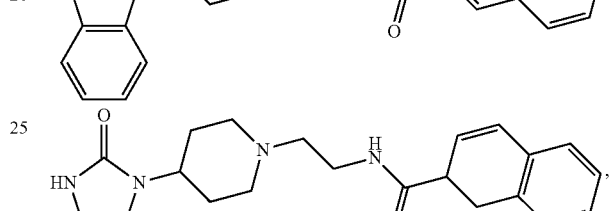
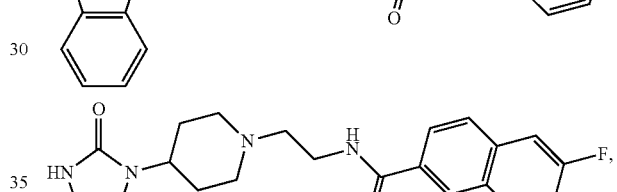
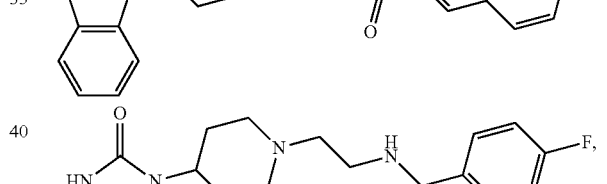
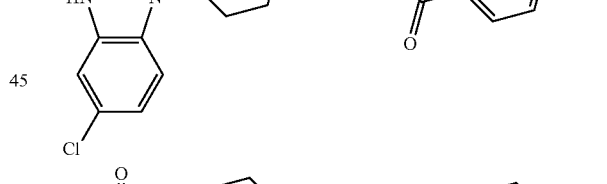
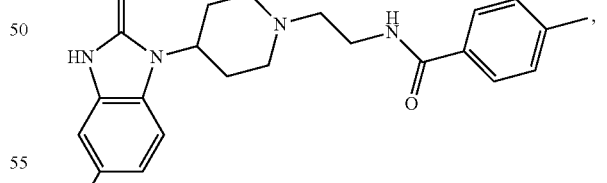
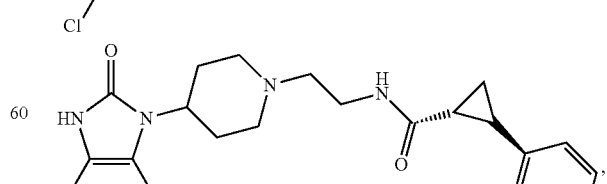

-continued
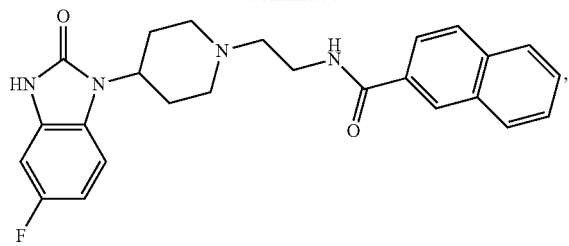
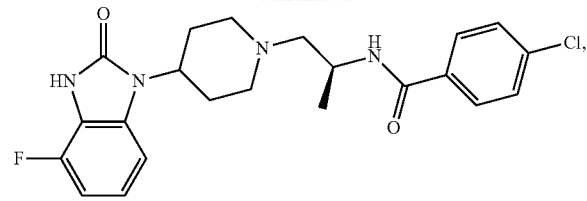
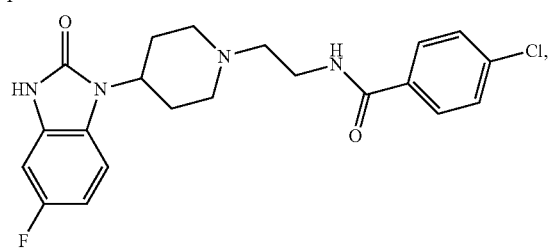
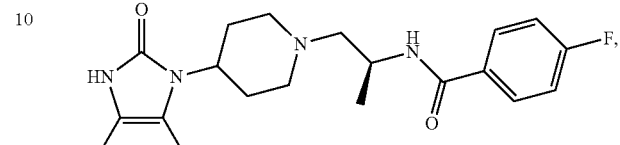
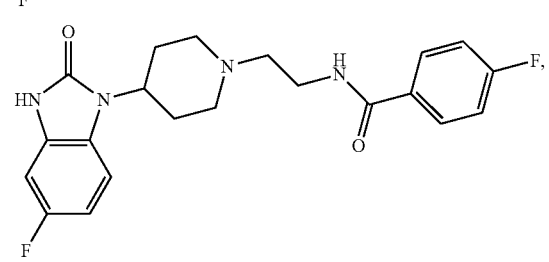
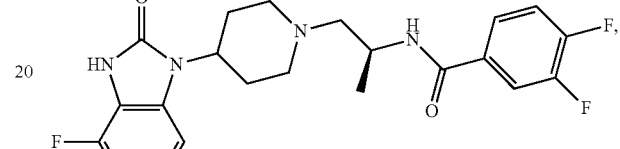
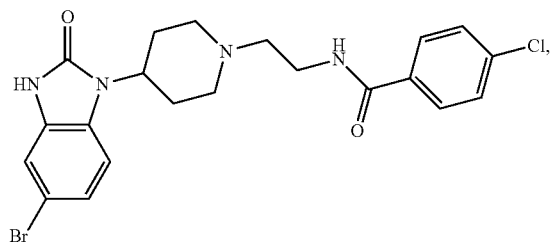
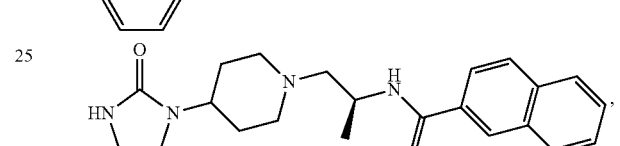
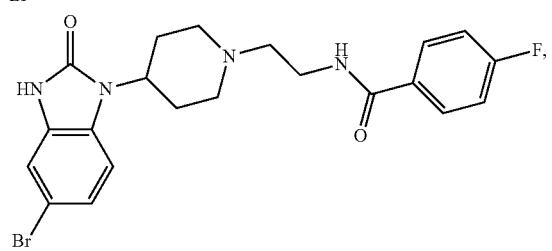
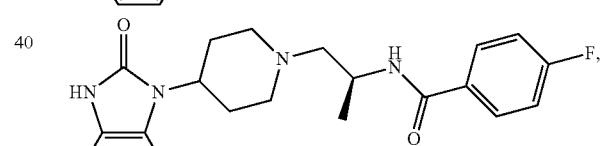
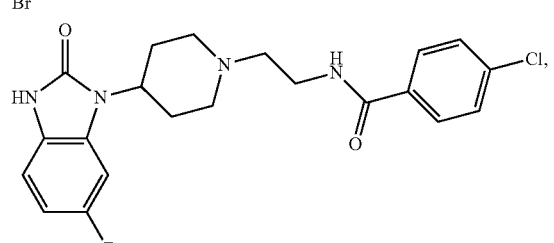
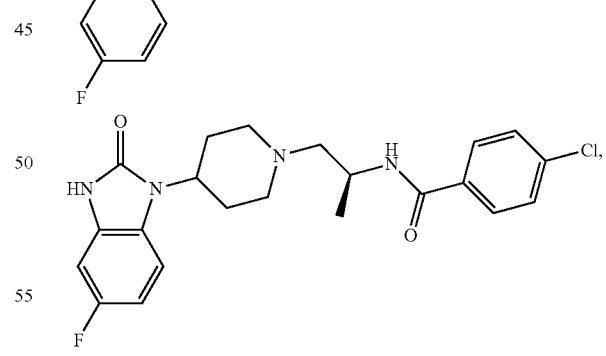
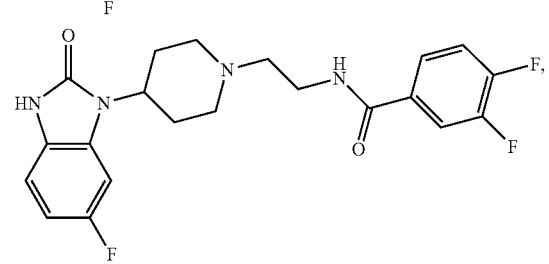
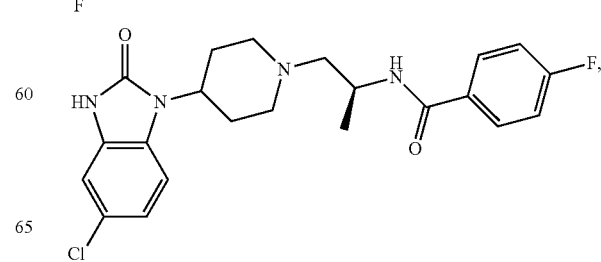

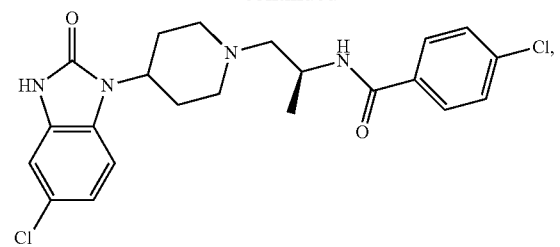
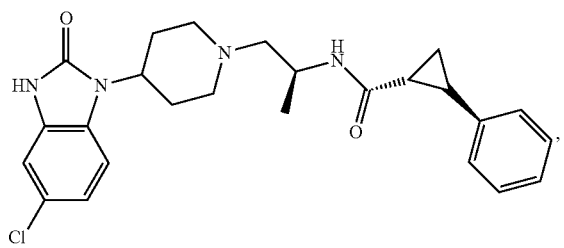
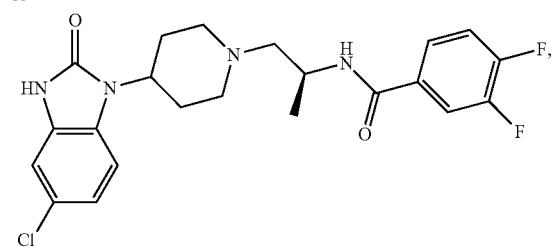
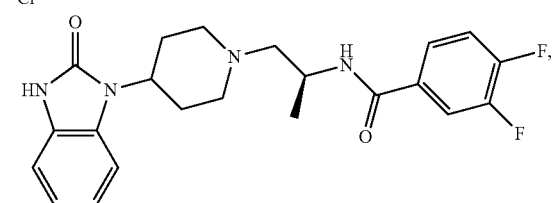
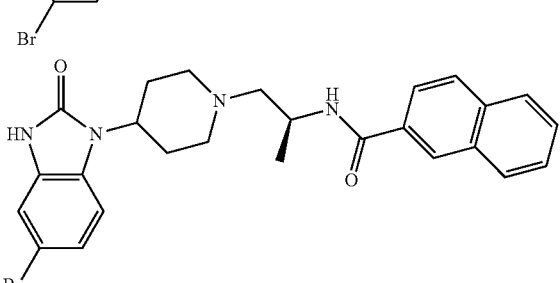
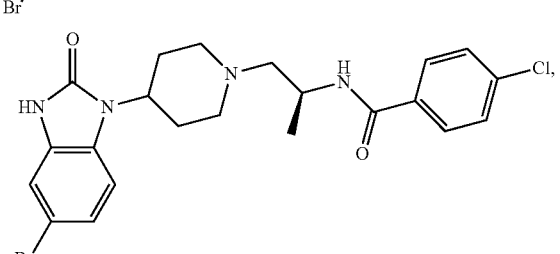
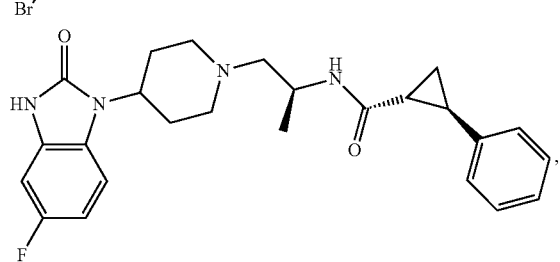
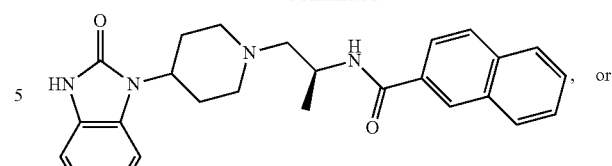
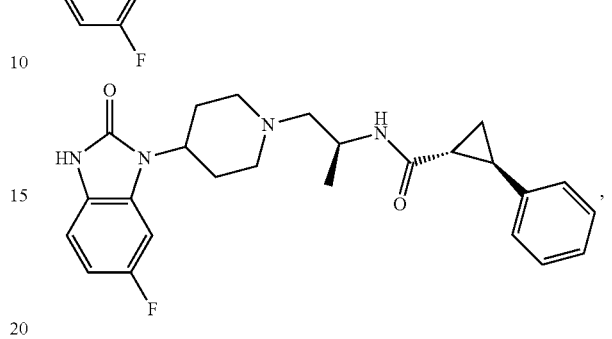
a subgroup thereof.
In various aspects, a phospholipase D inhibitor compound can be present as:
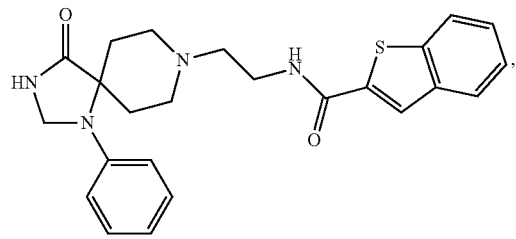
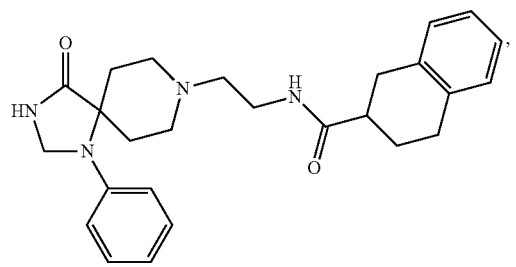
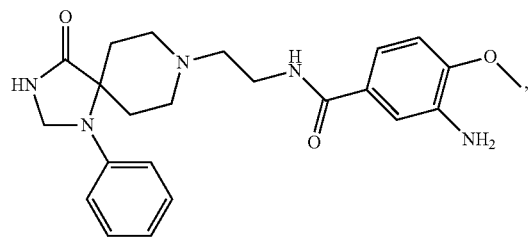
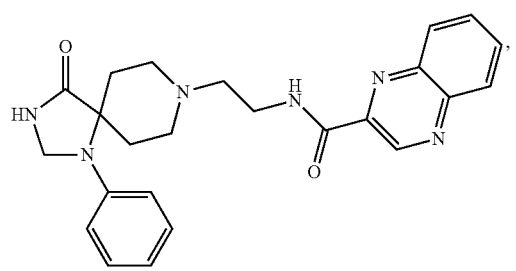

-continued
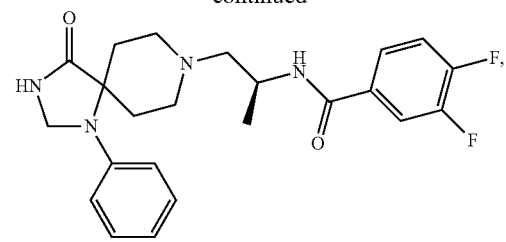
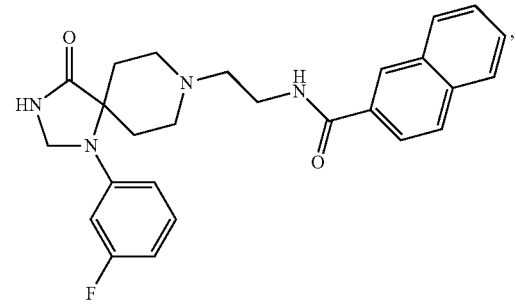
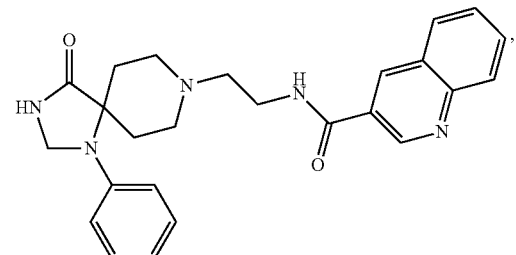
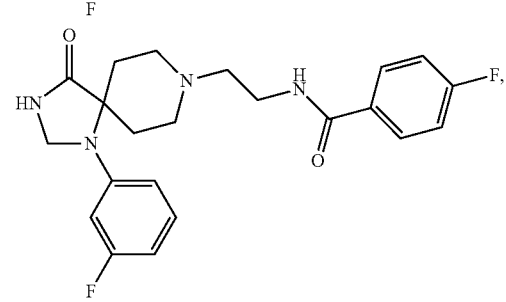
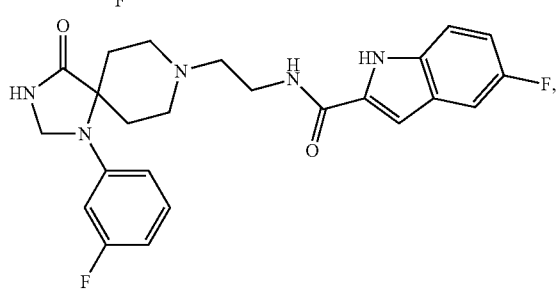
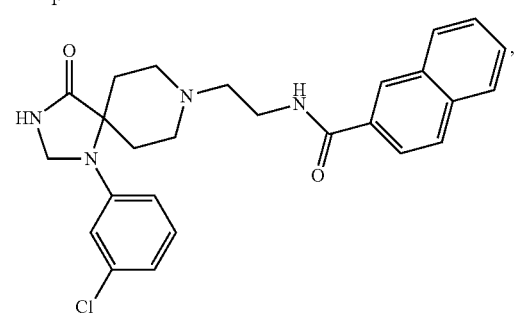
-continued
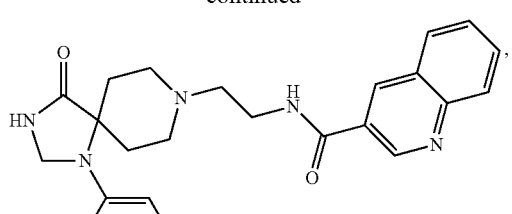
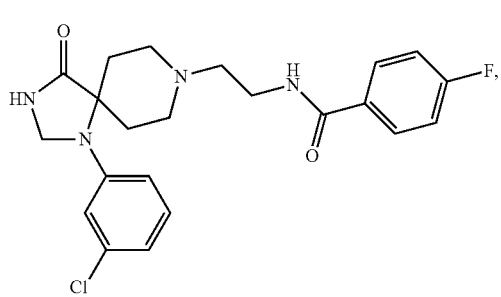
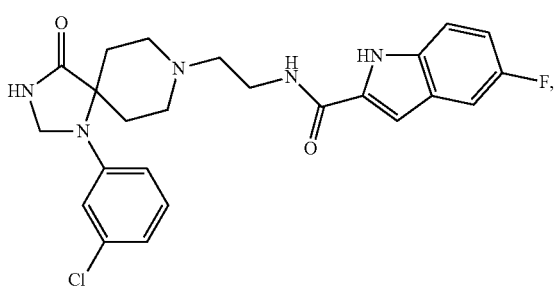
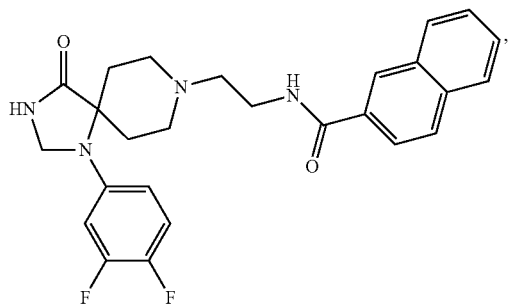
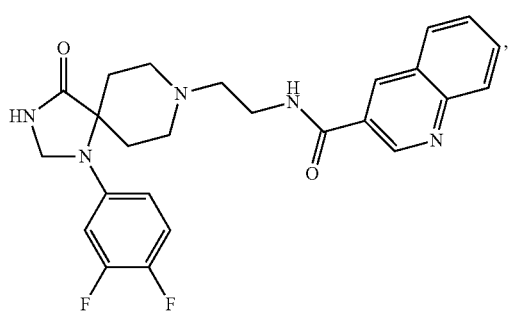

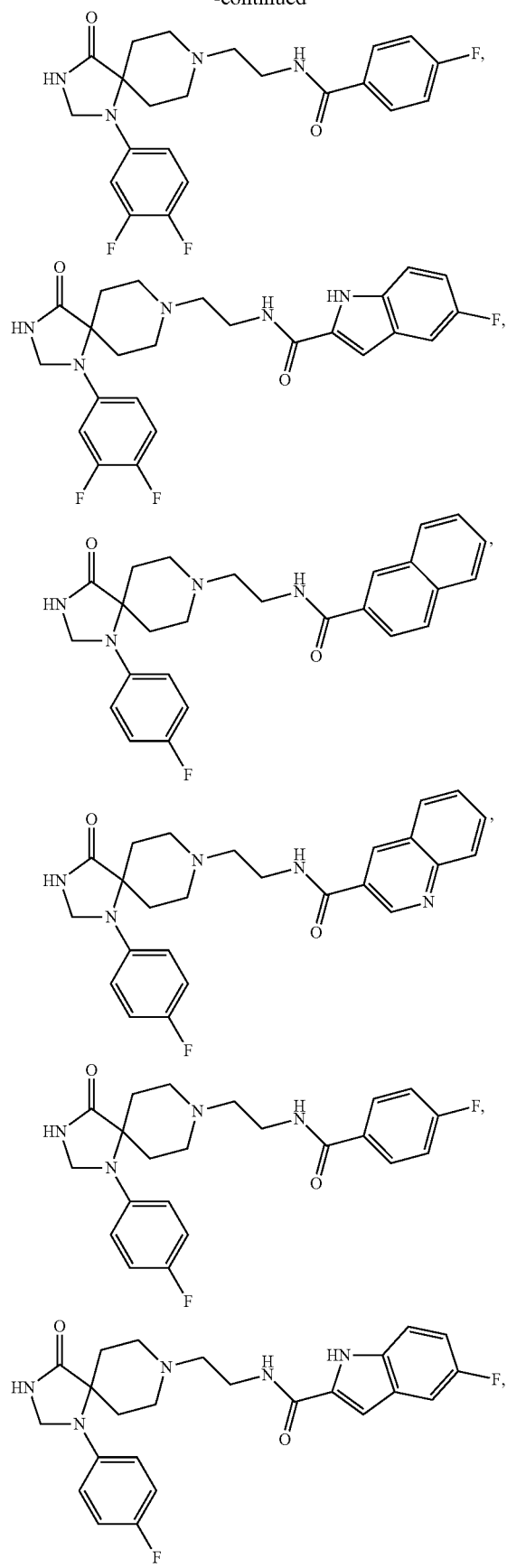
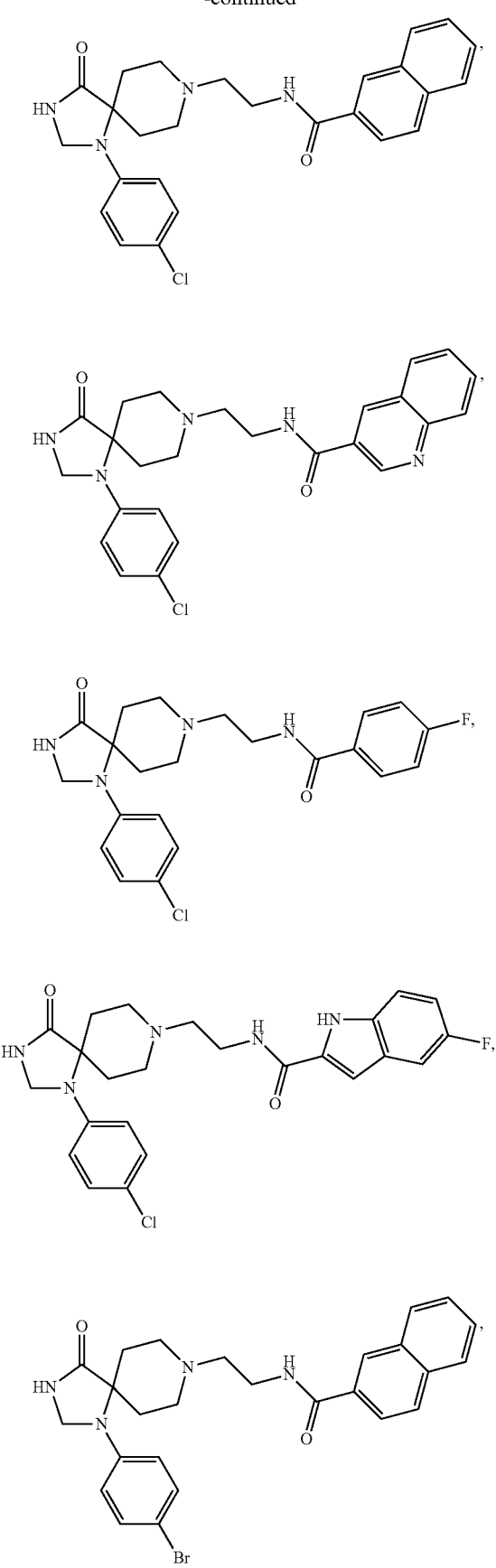

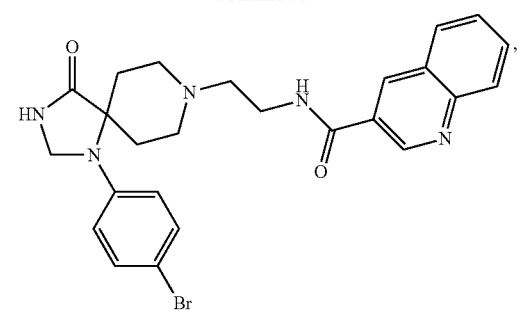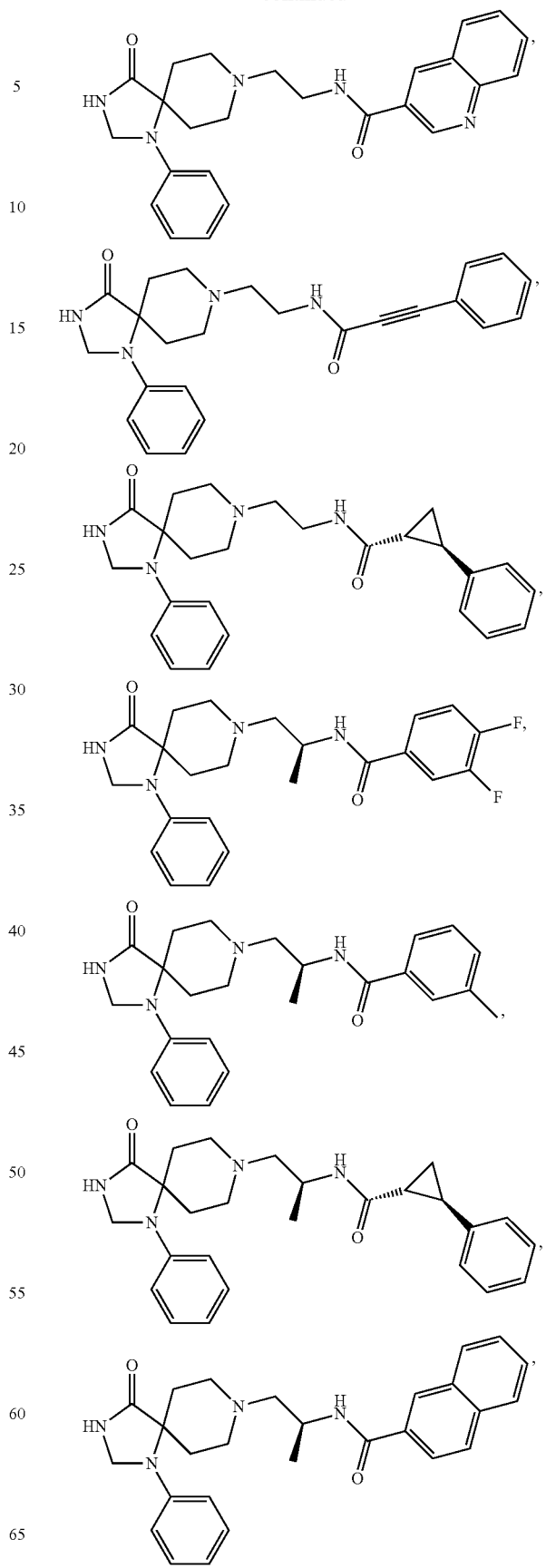

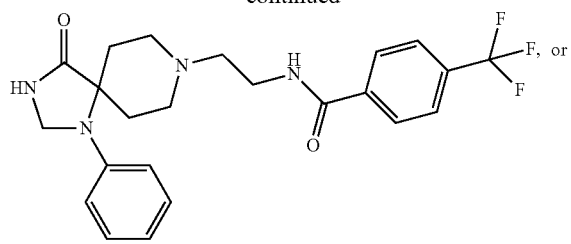
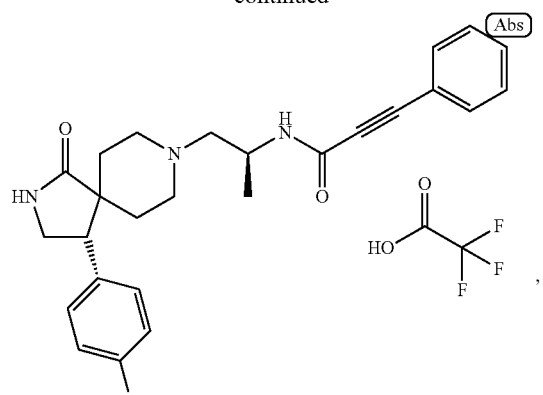
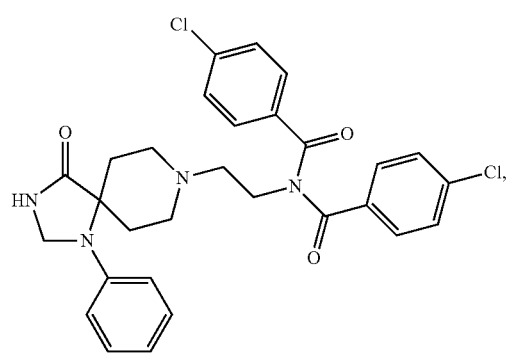
or a subgroup thereof.
In various aspects, a phospholipase D inhibitor compound can be present as:
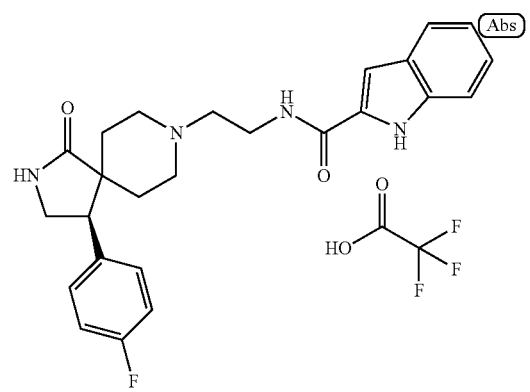
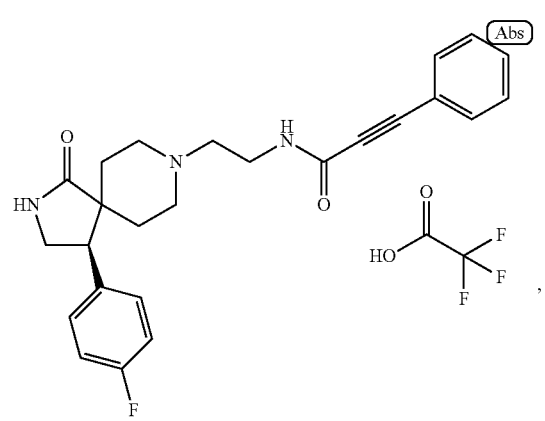
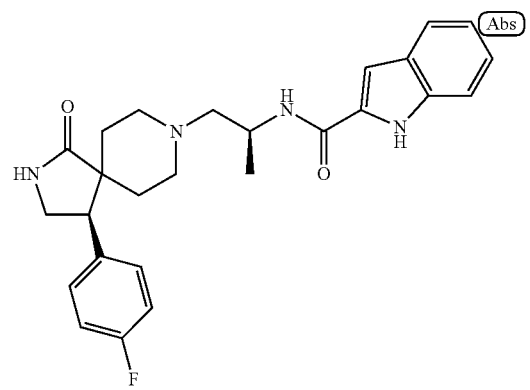
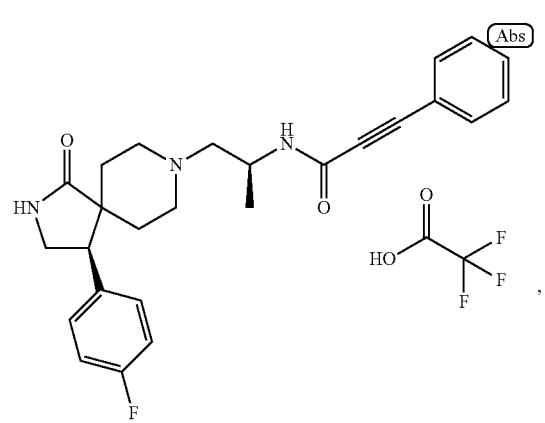
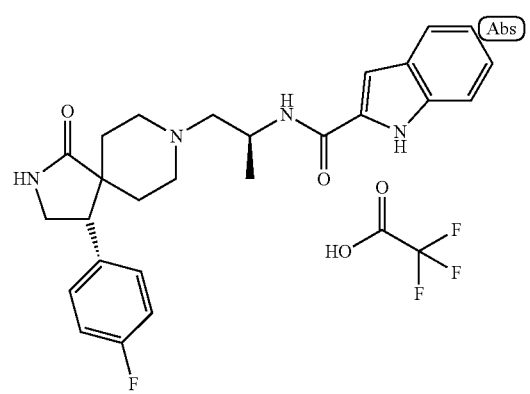

63
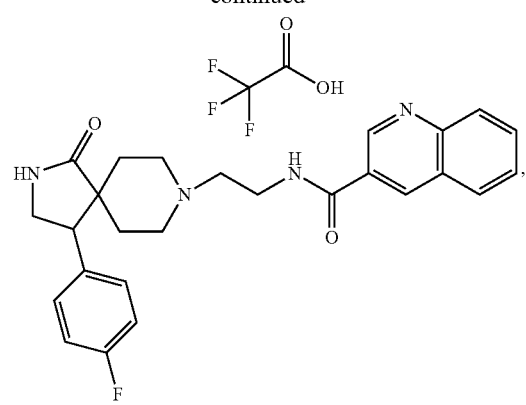
64
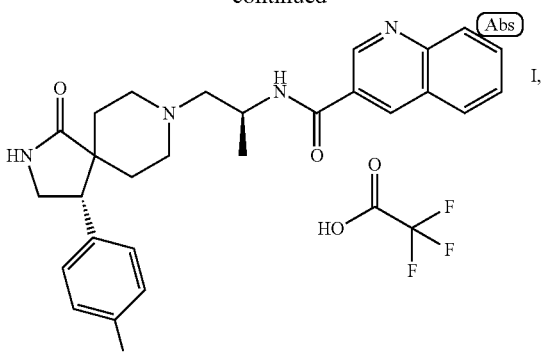
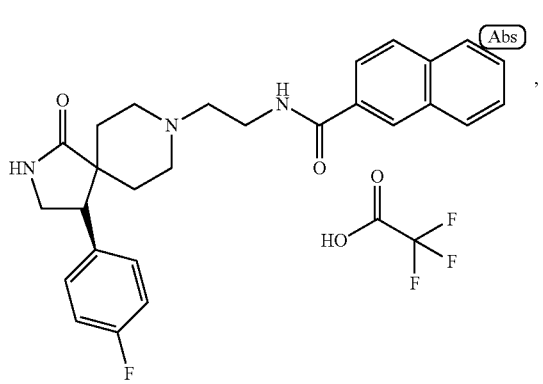
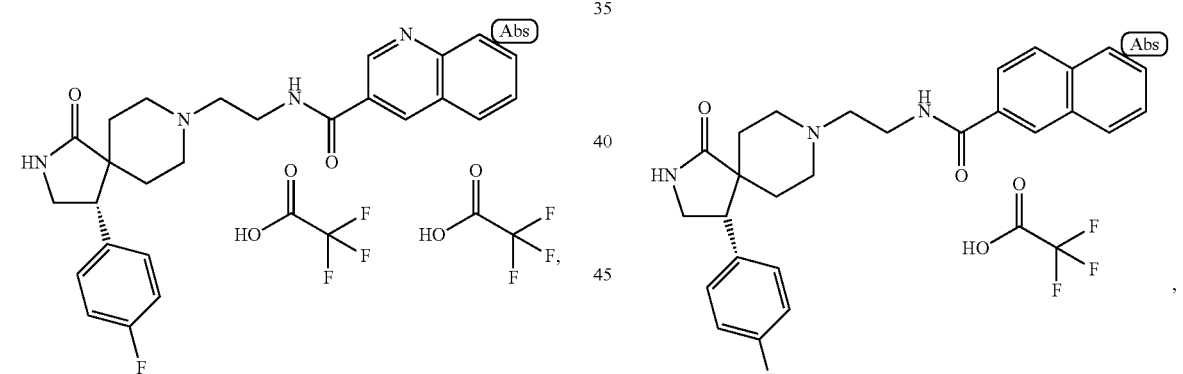
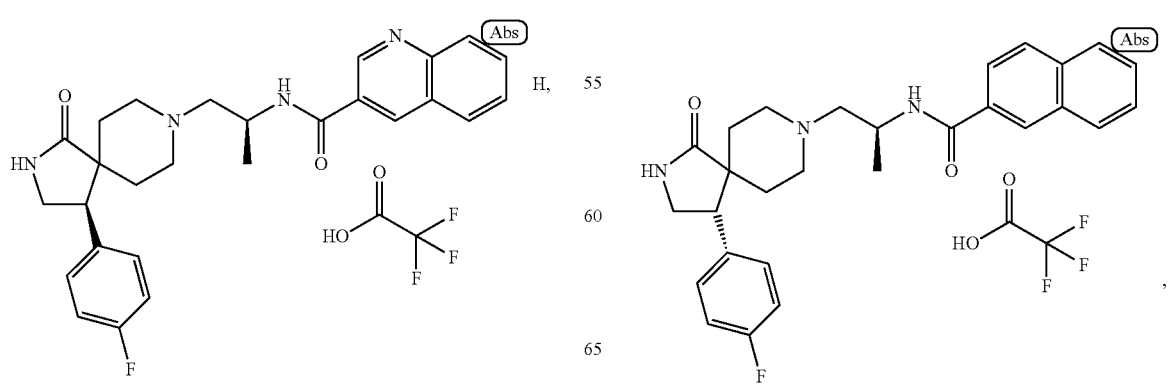

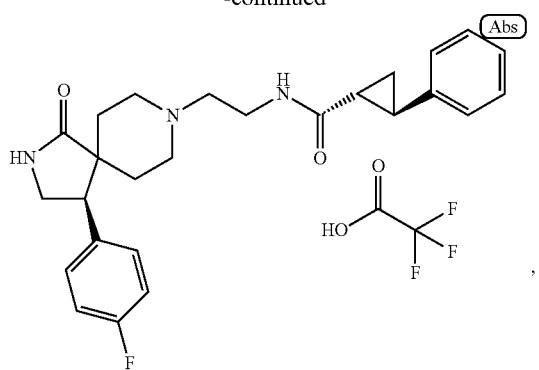
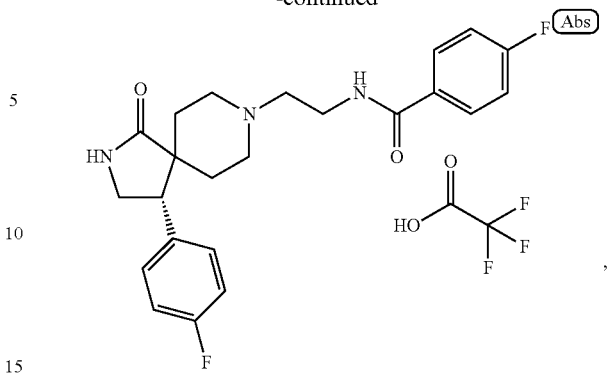
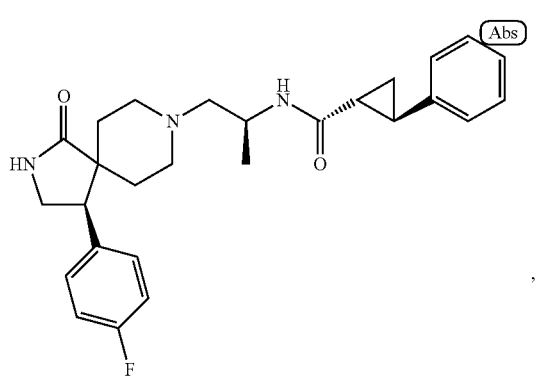
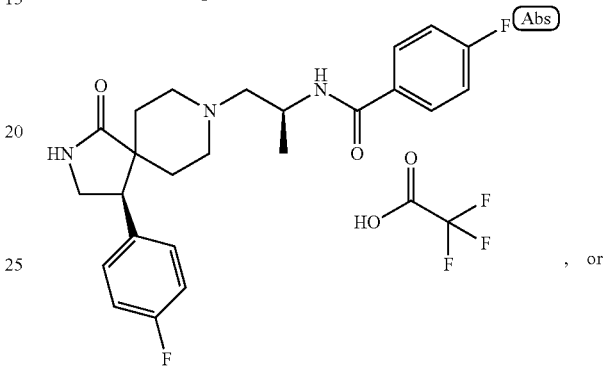
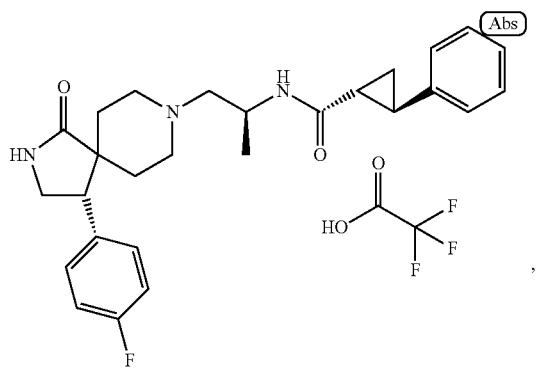
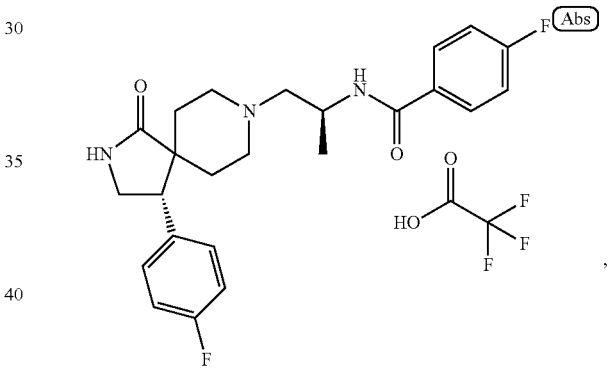

, or or a subgroup thereof.

C. Phospholipase D Inhibition Activity

In a further aspect, the invention relates to compounds that inhibit a phospholipase D selected from PLD1 and PLD2. In a still further aspect, the compounds inhibit PLD1. In a yet further aspect, the compounds inhibit PLD2. In an even further aspect, the compounds inhibit one or more PLD1 proteins selected from PLD1A, PLD1B, PLD1C, and PLD1D. In a yet further aspect, the compounds inhibit one or more PLD2 selected from PLD2A, PLD2B, and PLD2C.

In one aspect, the compound inhibits PLD activity, i.e. a compound can inhibit PLD1 activity and/or PLD2 activity. In a further aspect, the compound inhibits PLD1 response in Calu-1 cells. In a further aspect, the compound inhibits PLD2 response in HEK293gfpPLD2 cells. In a further aspect, the compound inhibits in vitro PLD1 response. In a further aspect, the compound inhibits in vitro PLD2 response. For example, the compound can have a PLD1 $IC_{50}$ of less than about 10 µM, of less than about 5 µM, of less than about 1 µM, of less than about 500 nM, of less than about 100 nM, or of less than about 50 nM. As further examples, the compound can have a PLD2 $IC_{50}$ of less than about 10 µM, of less than about 5 µM, of less than about 1 µM, of less than about 500 nM, of less than about 100 nM, or of less than about 50 nM.

In a further aspect, the compound can have a PLD1 $IC_{50}$ of less than about 10 µM, of less than about 1 µM, of less than about 500 nM, of less than about 100 nM, of less than about 60 nM, or of less than about 20 nM. In a further aspect, the compound can have a PLD2 $IC_{50}$ of less than about 10 µM, of less than about 1 µM, of less than about 500 nM, of less than about 100 nM, of less than about 60 nM, or of less than about 20 nM.

D. Methods of Making the Compounds

The compounds of this invention can be prepared by employing reactions as shown in the disclosed schemes below, in addition to other standard manipulations that are known in the literature, exemplified in the experimental sections or clear to one skilled in the art. For clarity, examples having a fewer substituent can be shown where multiple substituents are allowed under the definitions disclosed herein. The compounds of this invention can be prepared by employing reactions as disclosed in the references cited herein. For example, suitable methods for synthesizing the disclosed compounds are provided in WO/2011/011680; Scott, S., et al. (2009) Nat. Chem. Biol. 5(2):108-117; Lewis, J. A., et al. (2009) Bioorg. Med. Chem. 19:1916-1920; Lavieri, R., et al. (2009) Bioorg. Med. Chem. 19:2240-2243; and Lavieri, R. R., et al. (2010) J. Med. Chem. 53:6706-6719.

1. Route I

In one aspect, substituted 1-oxo-2,8-diazaspiro[4.5]decanyl analogs of the present invention can be prepared generically by the synthetic scheme as shown below.

Compounds are represented in generic form, with substituents as noted in compound descriptions elsewhere herein. A more specific example is set forth below.

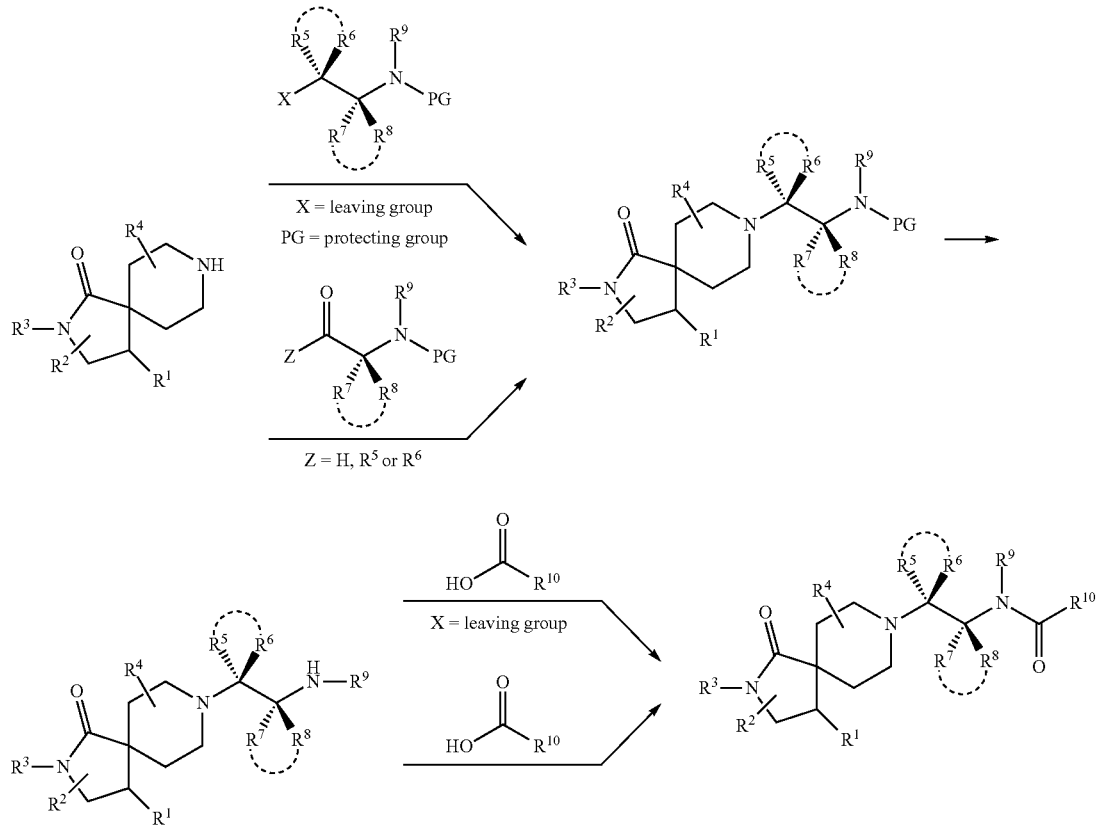

-continued

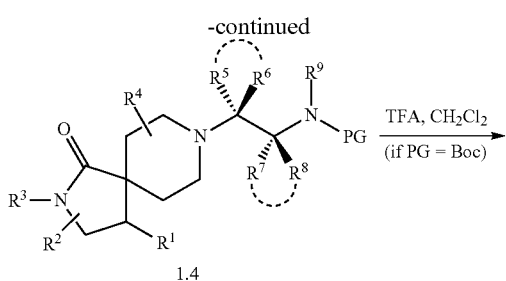

1.4

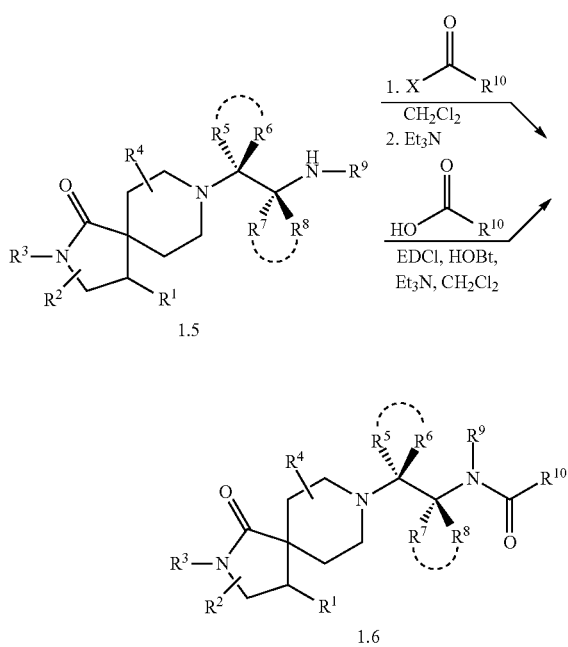

X = leaving group
PG = protecting group

In one aspect, Route I begins with a suitable substituted 2,8-diazaspiro[4.5]decan-1-one (1.1). A suitable 2,8-diazaspiro[4.5]decan-1-one (1.1) is commercially available or can be readily prepared by one skilled in the art. The first reaction of 1.1 and a suitable substituted N-protected amino derivative (1.2) involves a nucleophilic substitution reaction resulting in a N-protected product (1.4). Alternately, the reaction of 1.1 and compound 1.3 [e.g., where $R^5$ or $R^6$=H, alkyl group, or aryl group] is a reductive amination reaction resulting in a N-protected product (1.4).

In one aspect, the reaction of 1.1 and 1.2 is typically carried out under a suitable reaction atmosphere and in a suitable solvent that supports substitution reactions such as DMF in the presence of an appropriate base such as $K_2CO_3$. The reaction is conducted at a suitable temperature and for a time sufficient to complete the reaction and to provide compounds of type 1.4 as shown above. The product, a compound of type 1.4, is isolated by methods known to one skilled in the art (e.g., extraction, washing, drying, and concentration under a vacuum; followed by purification, e.g., chromatography, if necessary).

In one aspect, the reaction of 1.1 and 1.3 is typically carried out under a suitable reaction condition that supports reductive amination of carbonyl compounds known to one skilled in the art to give products of type 1.4. Reaction components 1.1 and 1.3 are dissolved in a suitable solvent, e.g., dichloromethane, and stirred at ambient temperature (about 15-30° C.) for about 15 min. Then, the reducing agent, [e.g., macroporous polystyrene triacetoxyborohydride, MP-B(O$_2$CCH$_3$)$_3$H. or other suitable reducing agent] is added to the reaction mixture. The reaction is carried out for a time sufficient to complete the reaction, e.g., overnight (about 8-18 h), to provide compounds of type 1.4 as shown above. The product, a compound of type 1.4, is isolated by methods known to one skilled in the art (e.g., filtered, and concentration under a vacuum; followed by purification, e.g., chromatography, if necessary).

In one aspect, compounds of type 1.5 can be prepared by the conversion of the N-protected compound (e.g., N-Boc compound type 1.4) to the corresponding amine derivative (1.5). For example, a reaction of this type is commonly carried out by dissolving the N-Boc derivative (1.4) in a suitable solvent, e.g., CH$_2$Cl$_2$, and then TFA is added. The mixture is stirred for a time sufficient, e.g., about overnight (8-18 h), at ambient room temperature (about 15-30° C.) to complete the reaction. The product (1.8) is isolated by methods known to one skilled in the art (e.g., concentration under a vacuum; followed by purification, e.g., chromatography, if necessary).

In one aspect, compounds of type 1.6 can be prepared by the acylation of 1.5 with an appropriate acid halide of type $R^{10}C(O)X$ under a standard amine acylation procedure known to one skilled in the art. In an example, $R^{10}C(O)X$ and the appropriate amine of type 1.5, dissolved in a suitable solvent such as dichloromethane, then an appropriate base, e.g., triethylamine, is added. The reaction is stirred at an appropriate temperature (about 0-30° C.) for about 24-36 h. The product (1.6) is isolated by methods known to one skilled in the art (e.g., concentration under a vacuum; followed by purification, e.g., chromatography, if necessary).

In one aspect, compounds of type 1.6 can be prepared by the acylation of 1.5 with an appropriate carboxylic acid of type $R^{10}CO_2H$ under a standard carboxylic acid and amine coupling procedure known to one skilled in the art. In an example, $R^{10}CO_2H$, EDCI, HOBt, triethylamine are dissolved in a suitable solvent such as dichloromethane, and allowed to stir for a period of time, e.g., about 15 min. Then, a solution of 1.5, in a solvent, e.g., dichloromethane, is added to the reaction mixture, and the reaction is stirred at ambient temperature (about 15-30° C.) for about 24-36 h. The product (1.6) is isolated by methods known to one skilled in the art (e.g., concentration under a vacuum; followed by purification, e.g., chromatography, if necessary).

2. Route II

In one aspect, substituted 4-oxo-1,3,8-triazaspiro[4.5]decanyl analogs of the present invention can be prepared generically by the synthetic scheme as shown below.

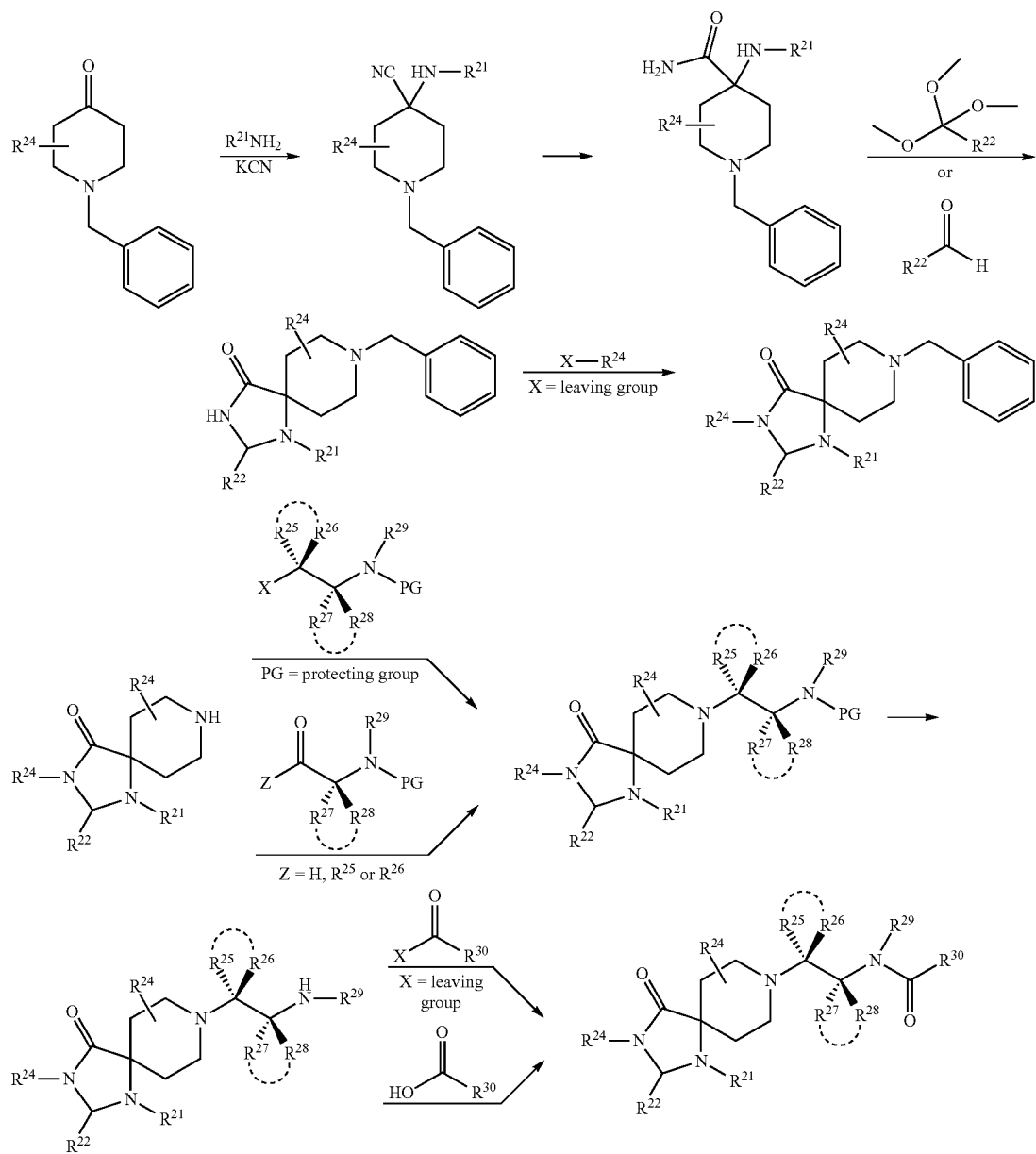
Compounds are represented in generic form, with substituents as noted in compound descriptions elsewhere herein. A more specific example is set forth below.
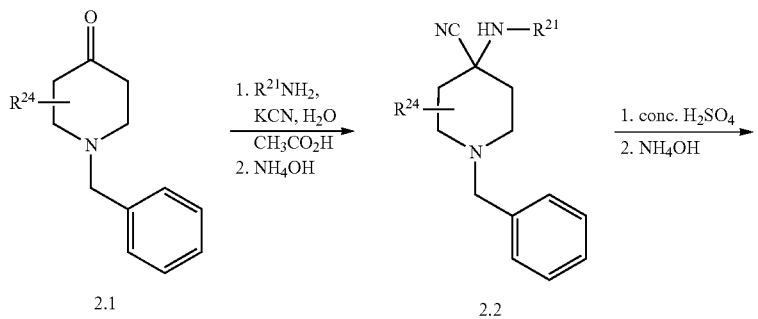

-continued
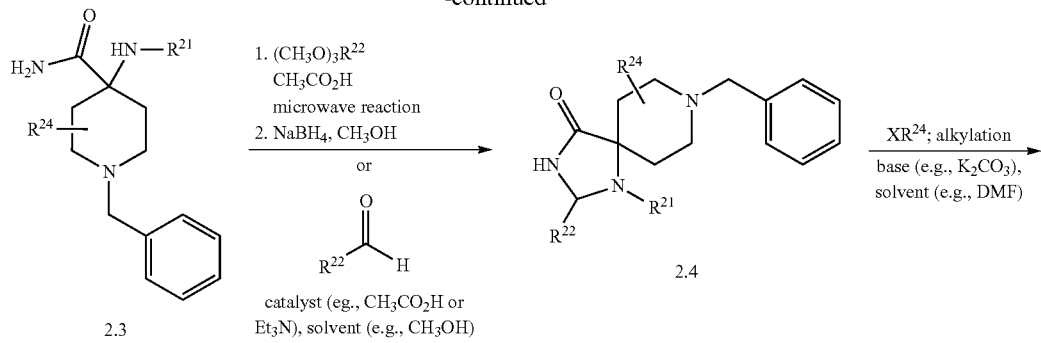
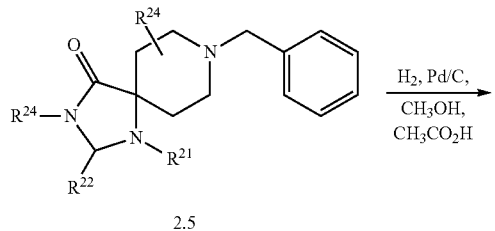
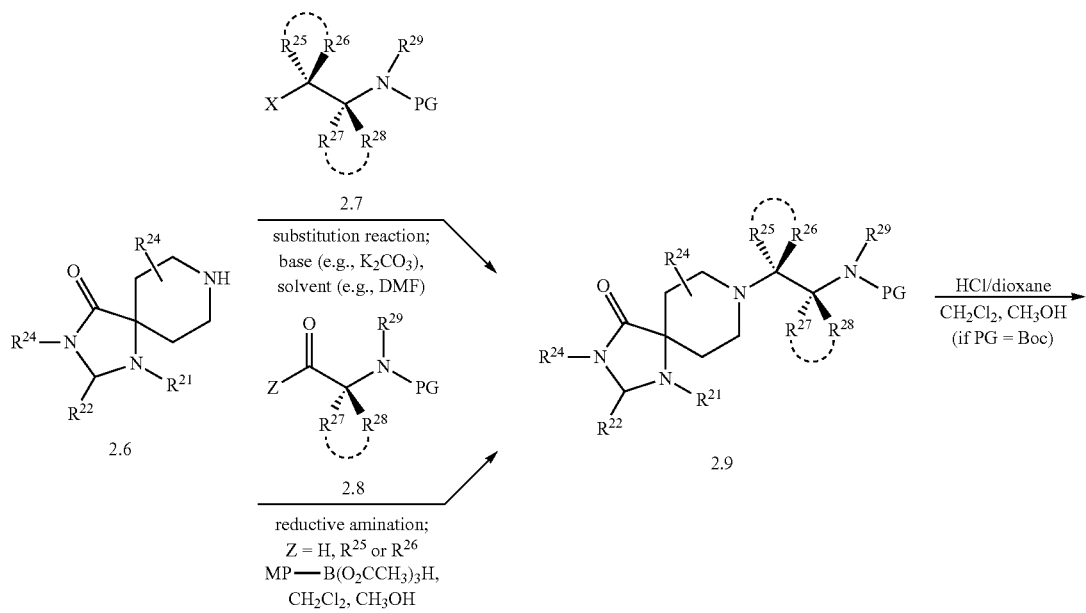
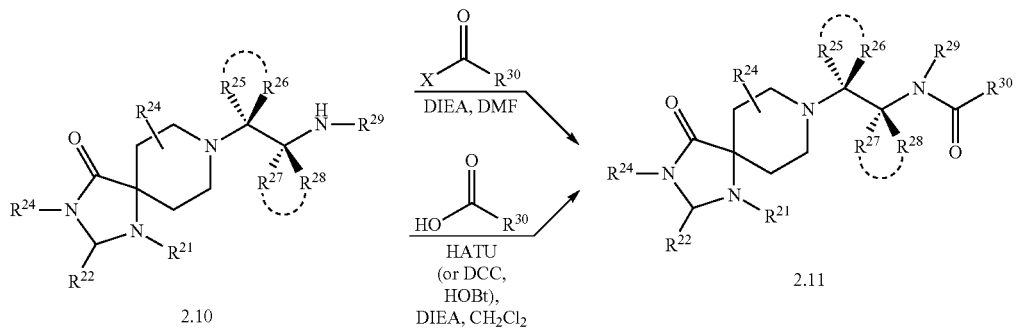
X = leaving group
PG = protecting group In one aspect, Route II begins with a suitable substituted 1-benzylpiperidine-4-one. A suitable 1-benzylpiperidine-4-one derivatives (2.1) are commercially available or can be readily prepared by one skilled in the art. To a solution of 2.1 in acetic acid and water at about 0° C. is added the amine, $R^{21}NH_2$, and potassium cyanide. The reaction is allowed to warm to about ambient temperature (about 15-30° C.) and agitated/stirred for sufficient time to allow complete reaction to occur (e.g., about 12 h). The reaction is mixture is cooled to about 0° C. and concentrated ammonium hydroxide is added until about pH≥11 is reached. The product (2.2) is isolated by methods known to one skilled in the art (e.g., extraction, and concentration under a vacuum). Immediately following, the unpurified 2.2 is cooled to about 0° C. and concentrated sulfuric acid is added slowly. The reaction is allowed to warm to ambient temperature (about 15-30° C.) with stirring for about 12 h. The reaction is mixture is cooled to about 0° C. and concentrated ammonium hydroxide is added until about pH≥11 is reached. The product (2.3) is isolated by methods known to one skilled in the art (e.g., extraction, and concentration under a vacuum, followed by purification, e.g., chromatography, if necessary).

In one aspect, compounds of type 2.4 can be prepared by the reaction of an appropriate orthoformate derivative [e.g., $(CH_3O)_3R^{22}$] and 2.3. Compound 2.3, $(CH_3O)_3R^{22}$, and acetic acid are combined and subjected to microwave irradiation at an appropriate temperature to effect reaction, e.g., about 150° C., for about 15 min or sufficient time to complete the reaction. Then ammonium hydroxide is added until about pH=12 and extracted with dichloromethane and concentrated under vacuum. The resulting material is added to a suspension of sodium borohydride in methanol and stirred for about 3 h or sufficient time to complete the reaction. The reaction is quenched with water. The product (2.4) is isolated by methods known to one skilled in the art (e.g., extraction, and concentration under a vacuum, followed by purification, e.g., chromatography, if necessary).

In one aspect, compounds of type 2.4 can be prepared by the reaction of an appropriate aldehyde ($R^{22}CHO$) under in the presence of a suitable acid (e.g., acetic acid) or base (e.g., triethylamine) catalyst in a suitable solvent (e.g., methanol) at suitable reaction temperature and sufficient time to complete the reaction. The product (2.4) is isolated by methods known to one skilled in the art (e.g., extraction, washing, drying, filtering, and concentration under a vacuum, followed by purification, e.g., chromatography, if necessary).

In one aspect, compounds of type 2.5 can be prepared from 2.4 (where $R^{24}$=H) by alkylation with an appropriate alkyl halide (or similar $XR^{24}$ where X is an appropriate leaving group or other electrophile to afford the substituent, $R^{24}$). Compound 2.4 is reacted with an appropriate base (e.g., $K_2CO_3$) in an appropriate solvent (e.g., DMF) at a sufficient reaction temperature and for sufficient time to allow for complete reaction to afford a product (2.5). The product (2.5) is isolated by methods known to one skilled in the art (e.g., extraction, washing, drying, filtering, and concentration under a vacuum, followed by purification, e.g., chromatography, if necessary).

In one aspect, compounds of type 2.6 can be prepared from 2.5 by hydrogenation. Compound 2.5 is dissolved in a appropriate solvent(s) (e.g., methanol, acetic acid) and treated with an appropriate metal catalyst (e.g., Pd/C) under an atmosphere of hydrogen gas. The reaction is allowed to stir at an appropriate temperature and sufficient time (e.g., about 36 h) to allow for complete reaction to occur. The product (2.6) is isolated by methods known to one skilled in the art (e.g., filtering, adjusting the pH, washing, extraction, drying, filtering, and concentration under a vacuum, followed by purification, e.g., chromatography, if necessary).

In one aspect, the reaction of 2.6 and 2.7 is typically carried out under a suitable reaction atmosphere and in a suitable solvent that supports substitution reactions such as DMF in the presence of an appropriate base such as $K_2CO_3$. The reaction is conducted at a suitable temperature and for a time sufficient to complete the reaction, to provide compounds of type 2.9 as shown above. The product, a compound of type 2.9, is isolated by methods known to one skilled in the art (e.g., extraction, washing, drying, and concentration under a vacuum; followed by purification, e.g., chromatography, if necessary).

In one aspect, the reaction of 2.6 and 2.8 is typically carried out under a suitable reaction condition that supports reductive amination of carbonyl compounds known to one skilled in the art to give products of type 2.9. Reaction components 2.6 and 2.8 are dissolved in a suitable solvent, e.g., dichloromethane and stirred at ambient temperature (about 15 to 30° C.) for about 15 min. Then, the reducing agent, [e.g., macroporous polystyrene triacetoxyborohydride, $MP-B(O_2CCH_3)_3H$. or other suitable reducing agent] is added to the reaction mixture. The reaction is carried out for a time sufficient to complete the reaction, e.g., overnight (about 8-18 h), to provide compounds of type 2.9 as shown above. The product, a compound of type 2.9, is isolated by methods known to one skilled in the art (e.g., filtered, and concentration under a vacuum; followed by purification, e.g., chromatography, if necessary).

In one aspect, compounds of type 2.10 can be prepared by the conversion of the N-protected compound (e.g., N-Boc compound type 2.9) to the corresponding amine derivative (2.10). For example, a reaction of this type is commonly carried out by dissolving the N-Boc derivative (2.9) in a suitable solvent(s) (e.g., $CH_2Cl_2$, $CH_3OH$) and then HCl (e.g., 4 M HCl in dioxane) is added. The mixture is stirred for a time sufficient, e.g., about 36 h, at ambient room temperature (about 15 to 30° C.) to complete the reaction. The product (2.10) is isolated by methods known to one skilled in the art (e.g., concentration under a vacuum; followed by purification, e.g., chromatography, if necessary).

In one aspect, compounds of type 2.11 can be prepared by the acylation of 2.10 with an appropriate acid halide of type $R^{30}C(O)X$ under a standard amine acylation procedure known to one skilled in the art. In an example, $R^{30}C(O)X$ and the appropriate amine of type 2.10, dissolved in a suitable solvent such as DMF, then an appropriate base, e.g., N,N-diisopropylamine (DIEA), is added at an appropriate temperature (about 0° C.). The mixture is allowed to stir for about 12 h or sufficient time to complete the reaction while slowly warming to ambient temperature (about 15-30° C.). The product (2.11) is isolated by methods known to one skilled in the art (e.g., concentration under a vacuum; followed by purification, e.g., chromatography, if necessary).

In one aspect, compounds of type 2.11 can be prepared by the acylation of 2.10 with an appropriate carboxylic acid of type $R^{30}CO_2H$ under a standard carboxylic acid and amine coupling procedure known to one skilled in the art. In an example, compound 2.10, $R^{30}CO_2H$, HATU (or other appropriate amine-carboxylic acid coupling agent, e.g., DCC or PS-DCC in the presence of HOBt) are combined, and then DIEA is added. The mixture is diluted with an appropriate solvent(s) (e.g., 2:1 $CH_2Cl_2$:DMF) to an appropriate solution concentration, and allowed to stir at ambient temperature (about 15-30° C.) for a period of time sufficient to complete the reaction, e.g., about 4 h. The product (2.11) is isolated by methods known to one skilled in the art (e.g., filtering by vacuum to collect the precipitated product; followed by purification, e.g., chromatography, if necessary).

3. Route III

In one aspect, substituted 2-oxo-2,3-dihydro-1H-benzo[d]imidazol-1-yl analogs of the present invention can be prepared generically by the synthetic scheme as shown below.

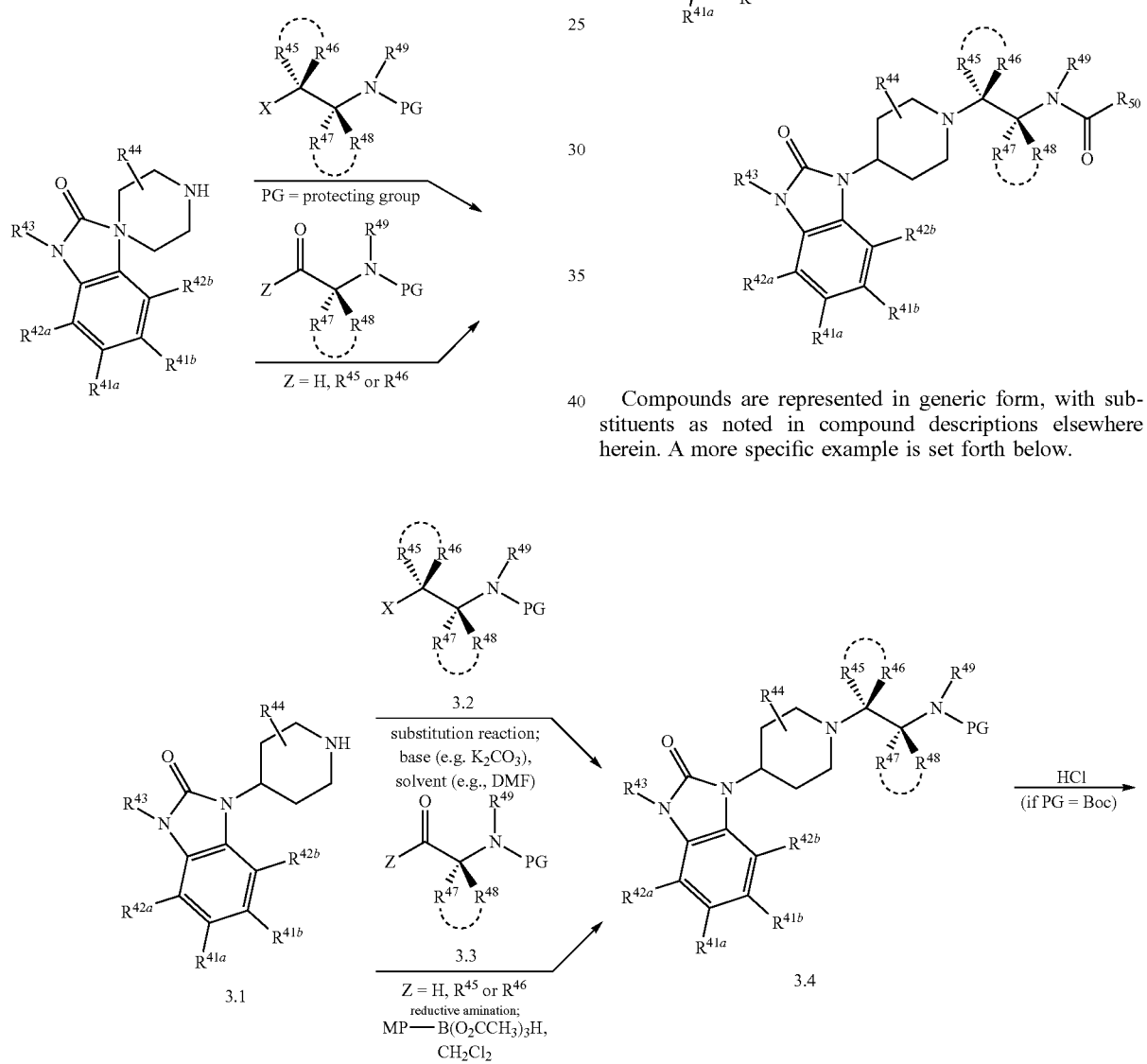

Compounds are represented in generic form, with substituents as noted in compound descriptions elsewhere herein. A more specific example is set forth below.

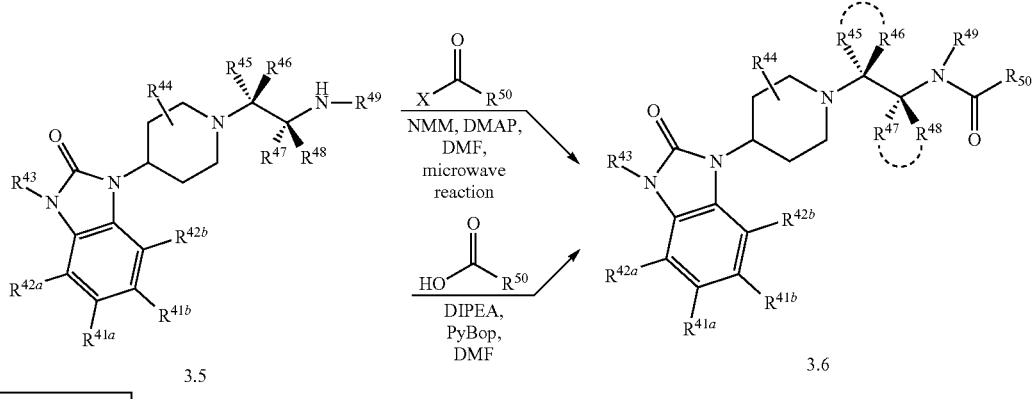

In one aspect, Route III begins with a suitable substituted compound of type 3.1. A suitable 1-(piperidin-4-yl)-1H-benzo[d]imidazol-2(3H)-one derivative (3.1) is commercially available or can be readily prepared by one skilled in the art. In one aspect, the reaction of 3.1 and 3.2 is typically carried out under a suitable reaction atmosphere and in a suitable solvent that supports substitution reactions such as DMF in the presence of an appropriate base such as $K_2CO_3$. The reaction is conducted at a suitable temperature and for a time sufficient to complete the reaction, to provide compounds of type 3.4 as shown above. The product, a compound of type 3.4, is isolated by methods known to one skilled in the art (e.g., extraction, washing, drying, and concentration under a vacuum; followed by purification, e.g., chromatography, if necessary).

In one aspect, the reaction of 3.1 and 3.3 is typically carried out under a suitable reaction condition that supports reductive amination of carbonyl compounds known to one skilled in the art to give products of type 3.4. Reaction components 3.1 and 3.3 are dissolved in a suitable solvent, e.g., dichloromethane and stirred Then, the reducing agent, [e.g., macroporous polystyrene triacetoxyborohydride, MP-B(O$_2$CCH$_3$)$_3$H. or other suitable reducing agent] is added to the reaction mixture. The reaction is carried out for a time sufficient to complete the reaction, e.g., 16 h, to provide compounds of type 3.4 as shown above. The product, a compound of type 3.4, is isolated by methods known to one skilled in the art (e.g., filtered, extracted, and concentration under a vacuum; followed by purification, e.g., chromatography, if necessary).

In one aspect, compounds of type 3.5 can be prepared by the conversion of the N-protected compound (e.g., N-Boc compound type 3.4) to the corresponding amine derivative (3.5). For example, a reaction of this type is commonly carried out by dissolving the N-Boc derivative (2.9) in a suitable solvent(s) (e.g., 1,2-dichloroethane/methanol) and then HCl (e.g., 4 M HCl in dioxane) is added. The mixture is stirred for a time sufficient, e.g., about 16 h, at ambient room temperature (about 15 to 30° C.) to complete the reaction. The product (3.5) is isolated by methods known to one skilled in the art (e.g., concentration under a vacuum; followed by purification, e.g., chromatography).

In one aspect, compounds of type 3.6 can be prepared by the acylation of 3.5 with an appropriate acid halide of type $R^{50}C(O)X$ under a standard amine acylation procedure known to one skilled in the art. In an example, compound 3.5 is dissolved in a suitable solvent such as DMF; N-methylmorpholine is added, $R^{50}C(O)X$ is added; and a catalytic amount of DMAP is added. The mixture is reacted under microwave irradiation for about 17 min or sufficient time and at an appropriate temperature (about 155° C.) to complete the reaction. The product (3.6) is isolated by methods known to one skilled in the art (e.g., concentration under a vacuum; followed by purification, e.g., chromatography).

In one aspect, compounds of type 3.6 can be prepared by the acylation of 3.5 with an appropriate carboxylic acid of type $R^{50}CO_2H$ under a standard amine acylation procedure known to one skilled in the art. In an example, compound 3.5 is dissolved in a suitable solvent such as DMF; $R^{50}CO_2H$ is added; an appropriate base, e.g., N,N-diisopropylamine (DIEA), is added; and (benzotriazol-1-lyoxy)tripyrrolidinophosphonium hexafluorophosphate (PyBOP) is added. The mixture is allowed to stir/rotate for about 16 h. or sufficient time and at ambient temperature (about 15-30° C.) to complete the reaction. The product (3.6) is isolated by methods known to one skilled in the art (e.g., concentration under a vacuum; followed by purification, e.g., chromatography).

It is understood that the disclosed methods of making can be used in connection with the disclosed compounds, compositions, kits, and uses.

E. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable derivatives (e.g., salt(s)) thereof) as an active ingredient, a pharmaceutically acceptable carrier, and, optionally, other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In one aspect, the invention relates to pharmaceutical compositions comprising an effective amount of a phospholipase D inhibitor, or a pharmaceutically acceptable salt, solvate, or polymorph thereof; an effective amount of at least one compound selected from: a) a viral protein M2 ion channel inhibitor, or a pharmaceutically acceptable prodrug, salt, solvate, or polymorph thereof; b) a neuraminidase inhibitor, or a pharmaceutically acceptable prodrug, salt, solvate, or polymorph thereof; and c) a nucleoside analog, or a pharmaceutically acceptable prodrug, salt, solvate, or polymorph thereof; and a pharmaceutically acceptable carrier.

In a further aspect, the phospholipase D inhibitor is a disclosed compound or a product of a disclosed method of making. In a still further aspect, the phospholipase D inhibitor is a PLD1 selective inhibitor. In a yet further aspect, the phospholipase D inhibitor is a PLD2 selective inhibitor. In an even further aspect, the phospholipase D inhibitor is a non-selective PLD inhibitor. In a still further aspect, the phospholipase D inhibitor is a disclosed phospholipase D inhibitor.

In a further aspect, an effective amount is a therapeutically effective amount. In a still further aspect, an effective amount is a prophylactically effective amount. That is, a prophylactically effective amount is an amount or dosage that can effectively prevent an infection in a subject, prevent the occurrence of symptoms in an infected subject, prevent the recurrence of symptoms in an infected subject, and/or decrease the severity of frequency of outward symptoms of a viral infection or disease in a subject. In a yet further aspect, an effective amount of a phospholipase D inhibitor blocks or delays entry of an influenza virus into a cell of a subject. In an even further aspect, an effective amount of a phospholipase D inhibitor blocks or delays budding of an influenza virus from infected cells of a subject. In a still further aspect, an effective amount of a phospholipase D inhibitor increases accumulation of innate immune effector protein Mx1. In a yet further aspect, an effective amount of a phospholipase D inhibitor decreases endosome maturation in an infected cell of a subject.

In a further aspect, the phospholipase D inhibitor inhibits PLD1 and/or PLD2. In a still further aspect, the phospholipase D inhibitor inhibits PLD1. In a yet further aspect, the phospholipase D inhibitor inhibits PLD2.

In a further aspect, the phospholipase D inhibitor of the pharmaceutical composition is a compound having a structure represented by a formula:

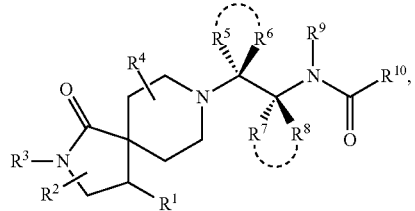

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the pharmaceutical composition is a compound having a structure represented by a formula:

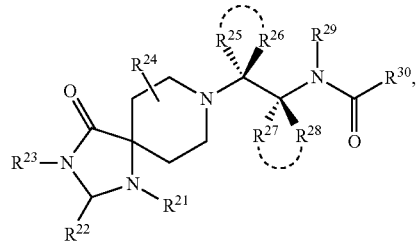

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the pharmaceutical composition is a compound having a structure represented by a formula:

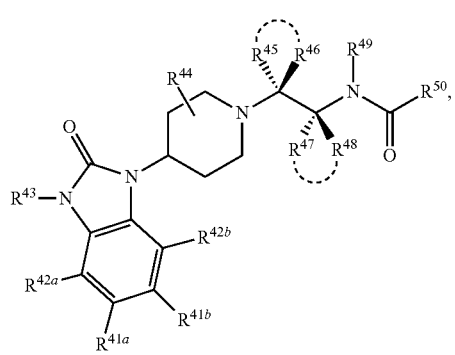

wherein each ---- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the pharmaceutical composition is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the phospholipase D inhibitor of the pharmaceutical composition is selected from:

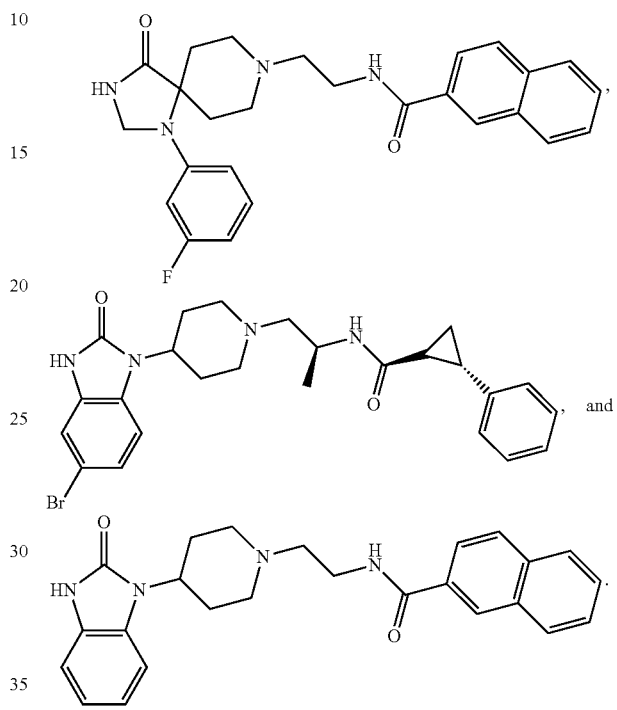

In a further aspect, the viral protein M2 ion channel inhibitor is an amino-adamantane compound. In a yet further aspect, the amino-adamantane compound is selected from 1-amino-adamantane and 1-(1-aminoethyl)adamantane. In a still further aspect, the viral protein M2 ion channel inhibitor is selected from amantadine and rimantadine, or a pharmaceutically acceptable prodrug, salt, solvate, or polymorph thereof. In an even further aspect, the viral protein M2 ion channel inhibitor is an analog of amantadine or rimantadine.

In a further aspect, the amantadine analog is selected from 1-amino-1,3,5-trimethylcyclohexane, 1-amino-1(trans),3 (trans),5-trimethylcyclohexane, 1-amino-1 (cis),3 (cis),5-trimethylcyclohexane, 1-amino-1,3,3,5-tetramethylcyclohexane, 1-amino-1,3,3,5,5-pentamethylcyclohexane (neramexane), 1-amino-1,3,5,5-tetramethyl-3-ethylcyclohexane, 1-amino-1,5,5-trimethyl-3,3-diethylcyclohexane, 1-amino-1,5,5-trimethyl-cis-3-ethylcyclohexane, 1-amino-(1S,5S)cis-3-ethyl-1,5,5-trimethylcyclohexane, 1-amino-1,5,5-trimethyl-trans-3-ethylcyclohexane, 1-amino-(1R,5S)trans-3-ethyl-1,5,5-trimethylcyclohexane, 1-amino-1-ethyl-3,3,5,5-tetramethylcyclohexane, 1-amino-1-propyl-3,3,5,5-tetramethylcyclohexane, N-methyl-1-amino-1,3,3,5,5-pentamethylcyclohexane, N-ethyl-1-amino-1,3,3,5,5-pentamethyl-cyclohexane, N-(1,3,3,5,5-pentamethylcyclohexyl)pyrrolidine, 3,3,5,5-tetramethylcyclohexylmethylamine, 1-amino-1-propyl-3,3,5,5-tetramethylcyclohexane, 1 amino-1,3,3,5(trans)-tetramethylcyclohexane (axial amino group), 3-propyl-1,3,5,5-tetramethylcyclohexylamine semihydrate, 1-amino-1,3, 5,5-tetramethyl-3-ethylcyclohexane, 1-amino-1,3,5-trimethylcyclohexane, 1-amino-1,3-dimethyl-3-propylcyclohexane, 1-amino-1,3(trans),5(trans)-trimethyl-3 (cis)-propylcyclohexane, 1-amino-1,3-dimethyl-3-ethylcyclohexane, 1-amino-1,3,3-trimethylcyclohexane, cis-3-ethyl-1(trans)-3(trans)-5-trimethylcyclohexamine, 1-amino-1,3(trans)-dimethylcyclohexane, 1,3,3-trimethyl-5,5-dipropylcyclohexylamine, 1-amino-1-methyl-3(trans)-propylcyclohexane, 1-methyl-3 (cis)-propylcyclohexylamine, 1-amino-1-methyl-3 (trans)-ethylcyclohexane, 1-amino-1,3,3-trimethyl-5(cis)-ethylcyclohexane, 1-amino-1,3,3-trimethyl-5 (trans)-ethylcyclohexane, cis-3-propyl-1,5,5-trimethylcyclohexylamine, trans-3-propyl-1,5,5-trimethylcyclohexylamine, N-ethyl-1,3,3,5,5-pentamethylcyclohexylamine, N-methyl-1-amino-1,3,3,5,5-pentamethylcyclohexane, 1-amino-1-methylcyclohexane, N,N-dimethyl-1-amino-1,3,3,5,5-pentamethylcyclohexane, 2-(3,3,5,5-tetramethylcyclohexyl)ethylamine, 2-methyl-1-(3,3,5,5-tetramethylcyclohexyl)propyl-2-amine, 2-(1,3,3,5,5-pentamethylcyclohexyl-1)-ethylamine semihydrate, N-(1,3,3,5,5-pentamethylcyclohexyl)-pyrrolidine, 1-amino-1,3 (trans),5(trans)-trimethylcyclohexane, 1-amino-1,3(cis),5(cis)-trimethylcyclohexane, 1-amino-(1R,5S)trans-5-ethyl-1,3,3-trimethylcyclohexane, 1-amino-(1S,5S)cis-5-ethyl-1,3,3-trimethylcyclohexane, 1-amino-1,5,5-trimethyl-3(cis)-isopropyl-cyclohexane, 1-amino-1,5,5-trimethyl-3(trans)-isopropyl-cyclohexane, 1-amino-1-methyl-3 (cis)-ethylcyclohexane, 1-amino-1-methyl-3 (cis)-methyl-cyclohexane, 1-amino-5,5-diethyl-1,3,3-trimethyl-cyclohexane, 1-amino-1,3,3,5,5-pentamethylcyclohexane, 1-amino-1,5,5-trimethyl-3,3-diethylcyclohexane, 1-amino-1-ethyl-3,3,5,5-tetramethylcyclohexane, N-ethyl-1-amino-1,3,3,5,5-pentamethylcyclohexane, N-(1,3,5-trimethylcyclohexyl)pyrrolidine, N-(1,3,5-trimethylcyclohexyl)piperidine, N-[1,3(trans),5(trans)-trimethylcyclohexyl]pyrrolidine, N-[1,3(trans),5(trans)-trimethylcyclohexyl]piperidine, N-[1,3(cis),5(cis)-trimethylcyclohexyl]pyrrolidine, N-[1,3(cis),5(cis)-trimethylcyclohexyl]piperidine, N-(1,3,3,5-tetramethylcyclohexyl)pyrrolidine, N-(1,3,3,5-tetramethylcyclohexyl)piperidine, N-(1,3,3,5,5-pentamethylcyclohexyl)pyrrolidine, N-(1,3,3,5,5-pentamethylcyclohexyl)piperidine, N-(1,3,5,5-tetramethyl-3-ethylcyclohexyl)pyrrolidine, N-(1,3,5,5-tetramethyl-3-ethylcyclohexyl)piperidine, N-(1,5,5-trimethyl-3,3-diethylcyclohexyl)pyrrolidine, N-(1,5,5-trimethyl-3,3-diethylcyclohexyl)piperidine, N-(1,3,3-trimethyl-cis-5-ethylcyclohexyl)pyrrolidine, N-(1,3,3-trimethyl-cis-5-ethylcyclohexyl)piperidine, N-[(1S,5S)cis-5-ethyl-1,3,3-trimethylcyclohexyl]pyrrolidine, N-[(1S,5S)cis-5-ethyl-1,3,3-trimethylcyclohexyl]piperidine, N-(1,3,3-trimethyl-trans-5-ethylcyclohexyl)pyrrolidine, N-(1,3,3-trimethyl-trans-5-ethylcyclohexyl)piperidine, N-[(1R,5S)trans-5-ethyl-3,3-trimethylcyclohexyl]pyrrolidine, N-[(1R,5S)trans-5-ethyl-1,3,3-trimethylcyclohexyl]piperidine, N-(1-ethyl-3,3,5,5-tetramethylcyclohexyl)pyrrolidine, N-(1-ethyl-3,3,5,5-tetramethylcyclohexyl)piperidine, N-(1-propyl-3,3,5,5-tetramethylcyclohexyl)pyrrolidine, N-(1-propyl-3,3,5,5-tetramethylcyclohexyl)piperidine, N-(1,3,3,5,5-pentamethylcyclohexyl)pyrrolidine, spiro[cyclopropane-1,2-adamantan]-2-amine, spiro[pyrrolidine-2,2'-adamantane], spiro[piperidine-2,2-adamantane], 2-(2-adamantyl)piperidine, 3-(2-adamantyl)pyrrolidine, 2-(1-adamantyl)piperidine, 2-(1-adamantyl)pyrrolidine, and 2-(1-adamantyl)-2-methyl-pyrrolidine.

In a further aspect, the amantadine analog is selected from 1-amino-3-phenyl adamantane, 1-amino-methyl adamantane, 1-amino-3-ethyl adamantane, 1-amino-3-isopropyl adamantane, 1-amino-3-n-butyl adamantane, 1-amino-3,5-diethyl adamantane, 1-amino-3,5-diisopropyl adamantane, 1-amino-3,5-di-n-butyl adamantane, 1-amino-3-methyl-5-ethyl adamantane, 1-N-methylamino-3,5-dimethyl adamantane, 1-N-ethylamino-3,5-dimethyl adamantane, 1-N-isopropyl-amino-3,5-dimethyl adamantane, 1-N,N-dimethyl-amino-3,5-dimethyl adamantane, 1-N-methyl-N-isopropyl-amino-3-methyl-5-ethyl adamantane, 1-amino-3-butyl-5-phenyl adamantane, 1-amino-3-pentyl adamantane, 1-amino-3,5-dipentyl adamantane, 1-amino-3-pentyl-5-hexyl adamantane, 1-amino-3-pentyl-5-cyclohexyl adamantane, 1-amino-3-pentyl-5-phenyl adamantane, 1-amino-3-hexyl adamantane, 1-amino-3,5-dihexyl adamantane, 1-amino-3-hexyl-5-cyclohexyl adamantane, 1-amino-3-hexyl-5-phenyl adamantane, 1-amino-3-cyclohexyl adamantane, 1-amino-3,5-dicyclohexyl adamantane, 1-amino-3-cyclohexyl-5-phenyl adamantane, 1-amino-3,5-diphenyl adamantane, 1-amino-3,5,7-trimethyl adamantane, 1-amino-3,5-dimethyl-7-ethyl adamantane, 1-amino-3,5-diethyl-7-methyl adamantane, 1-N-pyrrolidino and 1-N-piperidine derivatives, 1-amino-3-methyl-5-propyl adamantane, 1-amino-3-methyl-5-butyl adamantane, 1-amino-3-methyl-5-pentyl adamantane, 1-amino-3-methyl-5-hexyl adamantane, 1-amino-3-methyl-5-cyclohexyl adamantane, 1-amino-3-methyl-5-phenyl adamantane, 1-amino-3-ethyl-5-propyl adamantane, 1-amino-3-ethyl-5-butyl adamantane, 1-amino-3-ethyl-5-pentyl adamantane, 1-amino-3-ethyl-5-hexyl adamantane, 1-amino-3-ethyl-5-cyclohexyl adamantane, 1-amino-3-ethyl-5-phenyl adamantane, 1-amino-3-propyl-5-butyl adamantane, 1-amino-3-propyl-5-pentyl adamantane, 1-amino-3-propyl-5-hexyl adamantane, 1-amino-3-propyl-5-cyclohexyl adamantane, 1-amino-3-propyl-5-phenyl adamantane, 1-amino-3-butyl-5-pentyl adamantane, 1-amino-3-butyl-5-hexyl adamantane, and 1-amino-3-butyl-5-cyclohexyl adamantine.

The composition of claim 1, wherein the neuraminidase inhibitor is selected from oseltamivir, zanamivir, peramivir, laninamivir octanoate, 2,3-didehydro-2-deoxy-N-acetyl-neuraminic acid (DANA), 2-deoxy-2,3-dehydro-N-trifluoroacetylneuraminic acid (FANA), N-[(1R,2S)-2-methoxy-2-methyl-1-[(2R,3S,5R)-5-(2-methylpropanoyl)-3-[(Z)-prop-1-enyl]pyrrolidin-2-yl]pentyl]acetamide (A-322278), and (2R,4S,5R)-5-[(1R,2S)-1-acetamido-2-methoxy-2-methyl-pentyl]-4-[(Z)-prop-1-enyl]pyrrolidine-2-carboxylic acid (A-315675), or a pharmaceutically acceptable salt, solvate, or polymorph thereof.

In a further aspect, neuraminidase inhibitor is selected from oseltamivir, zanamivir, peramivir, laninamivir octanoate, or a pharmaceutically acceptable salt, solvate, or polymorph thereof. In a still further aspect, the neuraminidase inhibitor is oseltamivir, oseltamivir phosphate, or oseltamivir carboxylate. In a yet further aspect, the neuraminidase inhibitor is oseltamivir phosphate. In an even further aspect, the neuraminidase inhibitor is zanamivir. In a still further aspect, the neuraminidase inhibitor is peramivir. In a yet further aspect, the neuraminidase inhibitor is laninamivir octanoate.

In a further aspect, the nucleoside analog is selected from ribavirin, viramidine, 6-fluoro-3-hydroxy-2-pyrazinecarboxamide, 2'-deoxy-2'-fluoroguanosine, pyrazofurin, carbodine, and cyclopenenyl cytosine. In a still further aspect, the nucleoside analog is selected from ribavirin and viramidine. In a yet further aspect, the nucleoside analog is ribavirin. In an even further aspect, the nucleoside analog is viramidine.

In a further aspect, the pharmaceutical composition further comprises a prostaglandin E2 receptor agonist, or a pharmaceutically acceptable prodrug, salt, solvate, or polymorph thereof. In a still further aspect, the prostaglandin E2 receptor agonist is selected from a prostaglandin E receptor 4 (subtype EP4) selective agonist, a prostaglandin E receptor 2 (subtype EP2) selective agonist, and a mixed agonist for prostaglandin E receptor 4 (subtype EP4) and prostaglandin E receptor 2 (subtype EP2). In a yet further aspect, the prostaglandin E2 receptor agonist is a prostaglandin E receptor 4 (subtype EP4) agonist. In an even further aspect, the prostaglandin E receptor 4 (subtype EP4) agonist is selected from beraprost, nileprost, iloprost, cicaprost, eptaloprost, and ciprosten, or a pharmaceutically acceptable prodrug, salt, solvate, or polymorph thereof. In a still further aspect, the prostaglandin E receptor 4 (subtype EP4) agonist is beraprost. In a yet further aspect, the prostaglandin E receptor 4 (subtype EP4) agonist is nileprost.

In a further aspect, the pharmaceutical composition further comprises an interferon, or an isoform, mutein or fused protein thereof. In a still further aspect, the interferon is a pegylated interferon, a recombinant interferon, or a natural interferon. In a yet further aspect, the interferon is recombinant human interferon-beta, recombinant human interfone-beta which has a CHO cell-derived glycosylation, or consensus interferon-beta. In an even further aspect, the interferon is pegylated interferon-beta or interferon-beta Fc-fusion protein.

In a further aspect, the pharmaceutical composition further comprises an effective amount of an antiviral agent selected from a replication inhibitor, an IMP dehydrogenase inhibitor, an RNA polymerase inhibitor, and an influenza-specific interfering oligonucleotide. In a still further aspect, the IMP dehydrogenase inhibitor is selected from ribavirin, viramidine, merimepodib (VX-497), mycophenolic acid, mycophenolate mofetil, benzamide riboside, tiazofurin, mizoribine, and 3-deazaguanosine. In a yet further aspect, the IMP dehydrogenase inhibitor is selected from ribavirin, viramidine, merimepodib (VX-497), mycophenolic acid, and mycophenolate mofetil. In an even further aspect, the IMP dehydrogenase inhibitor is selected from ribavirin, viramidine, mycophenolic acid, and mycophenolate mofetil. In a still further aspect, the RNA polymerase inhibitor is favipiravir.

In a further aspect, the pharmaceutical composition further comprises an effective amount of an influenza virus absorption inhibitor selected from a hemagglutinin-specific antibody, a polyoxometalate, a sulfated polysaccharide, a sialidase fusion protein, and an O-glycoside of sialic acid. In a still further aspect, the influenza virus absorption inhibitor is a recombinant sialidase fusion protein. In a yet further aspect, the recombinant sialidase fusion protein is Fludase (DAS181).

In a further aspect, the pharmaceutical composition further comprises an effective amount of a cysteamine compound. In a still further aspect, the cysteamine compound is selected from cysteamine, cysteamine salts, prodrugs of cysteamine, analogs of cysteamine, derivatives of cysteamine, conjugates of cysteamine, metabolic precursors of cysteamine, and metabolites of cysteamine. In a yet further aspect, the cysteamine salt is cysteamine hydrochloride. In an even further aspect, the metabolic precursor of cysteamine is selected from cysteine, cystamine, and pantethine. In a still further aspect, the cysteamine metabolite is selected from taurine and hypotaurine.

In a further aspect, the pharmaceutical composition further comprises an effective amount of a therapeutic agent selected from an antitussive, a mucolytic, an expectorant, an antipyretic, an analgesic, and a nasal decongestant.

In a further aspect, the pharmaceutical composition further comprises an effective amount of an immunomodulator, or a pharmaceutically acceptable prodrug, salt, solvate, or polymorph thereof. In a still further aspect, an effective amount of an immunomodulator is an amount effective to reduce or inhibit one or more symptoms of inflammation of a subject. In a yet further aspect, the immunomodulator is polyoxidonium.

In a further aspect, the immunomodulator is an anti-inflammatory agent. In a still further aspect, the anti-inflammatory agent is non-steroidal, steroidal, or a combination thereof. In a yet further aspect, the anti-inflammatory agent is a non-steroidal anti-inflammatory agent. In an even further aspect, the non-steroidal anti-inflammatory agent is selected from a COX2 inhibitor, an aminosalicylate drug, a PPAR ligand.

In a further aspect, the non-steroidal anti-inflammatory agent is selected from an oxicam, a salicylate, an acetic acid derivative, a fenamate, a propionic acid derivative, and a pyrazole. In a yet further aspect, the non-steroidal anti-inflammatory agent comprises one or more of piroxicam, isoxicam, tenoxicam, sudoxicam, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, mefenamic acid, meclofenamic acid, flufenamic acid, niflumic acid, tolfenamic acid, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, tiaprofenic, phenylbutazone, oxyphenbutazone, feprazone, azapropazone, and trimethazone.

In a further aspect, the non-steroidal anti-inflammatory agent is a COX2 inhibitor. In a still further aspect, the COX2 inhibitor is celecoxib.

In a further aspect, the non-steroidal anti-inflammatory agent is an aminosalicylate. In a still further aspect, the aminosalicylate drug is selected from mesalazine and sulfasalazine.

In a further aspect, the non-steroidal anti-inflammatory agent is a PPAR ligand. In a still further aspect, the PPAR ligand is a fibrate. In a yet further aspect, the fibrate is selected from gemfibrozil, bezafibrate, ciprofibrate, clofibrate, and renofibrate, or combinations thereof.

In a further aspect, the anti-inflammatory agent is a steroidal anti-inflammatory agent. In a still further aspect, the steroidal anti-inflammatory agent is selected from hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, predisone, beclomethasone dipropionate, triamcinolone, and mixtures thereof.

In a further aspect, the pharmaceutical composition comprising a phospholipase D inhibitor, or a pharmaceutically acceptable salt, solvate, or polymorph thereof an effective amount of at least one compound selected from: a) a viral protein M2 ion channel inhibitor, or a pharmaceutically acceptable prodrug, salt, solvate, or polymorph thereof b) a neuraminidase inhibitor, or a pharmaceutically acceptable prodrug, salt, solvate, or polymorph thereof; and c) a nucleoside analog; is formulated for oral administration. In a still further aspect, the pharmaceutical composition comprising a phospholipase D inhibitor, or a pharmaceutically acceptable salt, solvate, or polymorph thereof; an effective amount of at least one compound selected from: a) a viral protein M2 ion channel inhibitor, or a pharmaceutically acceptable prodrug, salt, solvate, or polymorph thereof; b) a neuraminidase inhibitor, or a pharmaceutically acceptable prodrug, salt, solvate, or polymorph thereof; and c) a nucleoside analog; is formulated for intravenous administration.

In one aspect, the invention pertains to pharmaceutical compositions comprising: a) a first antiviral agent comprising an effective amount of a phospholipase D inhibitor, or a pharmaceutically acceptable salt, solvate, or polymorph thereof; b) a second antiviral agent comprising a viral protein M2 ion channel inhibitor, or a pharmaceutically acceptable prodrug, salt, solvate, or polymorph thereof; c) a third antiviral agent comprising a neuraminidase inhibitor, or a pharmaceutically acceptable prodrug, salt, solvate, or polymorph thereof; and d) a fourth antiviral agent comprising a nucleoside analog, or a pharmaceutically acceptable prodrug, salt, solvate, or polymorph thereof; and a pharmaceutically acceptable carrier.

In a further aspect, the first antiviral agent is a disclosed phospholipase D inhibitor; the second antiviral agent is selected from amantadine and rimantadine, or a pharmaceutically acceptable prodrug, salt, solvate, or polymorph thereof; the third antiviral agent is selected from oseltamivir, zanamivir, peramivir, laninamivir octanoate, or a pharmaceutically acceptable prodrug, salt, solvate, or polymorph thereof; and the fourth antiviral agent is selected from ribavirin and viramidine, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is oseltamivir, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is zanamivir, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is peramivir, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is laninamivir octanoate, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is oseltamivir, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is zanamivir, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is peramivir, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is laninamivir octanoate, or a pharmaceutically acceptable prodrug, salt, solvate, or polymorph thereof; and the fourth antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is oseltamivir, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is zanamivir, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is peramivir, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is laninamivir octanoate, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is oseltamivir, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is zanamivir, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is peramivir, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is laninamivir octanoate, or a pharmaceutically acceptable prodrug, salt, solvate, or polymorph thereof; and the fourth antiviral agent is viramidine, or a pharmaceutically acceptable prodrug, salt, solvate, or polymorph thereof.

In a further aspect, the pharmaceutical composition comprising the first antiviral agent, the second antiviral agent, the third antiviral agent, and the fourth antiviral agent is formulated for oral administration. In a still further aspect, the pharmaceutical composition comprising the first antiviral agent, the second antiviral agent, the third antiviral agent, and the fourth antiviral agent is formulated intravenous administration.

In one aspect, the invention pertains to pharmaceutical compositions comprising: a) a first antiviral agent comprising an effective amount of a phospholipase D inhibitor, or a pharmaceutically acceptable salt, solvate, or polymorph thereof; b) a second antiviral agent comprising a viral protein M2 ion channel inhibitor, or a pharmaceutically acceptable prodrug, salt, solvate, or polymorph thereof; and c) a third antiviral agent comprising a neuraminidase inhibitor, or a pharmaceutically acceptable prodrug, salt, solvate, or polymorph thereof.

In a further aspect, the first antiviral agent is a disclosed phospholipase D inhibitor; the second antiviral agent is selected from amantadine and rimantadine, or a pharmaceutically acceptable prodrug, salt, solvate, or polymorph thereof; and the third antiviral agent is selected from oseltamivir, zanamivir, peramivir, laninamivir octanoate, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof and the third antiviral agent is oseltamivir, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; and the third antiviral agent is zanamivir, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; and the third antiviral agent is peramivir, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; and the third antiviral agent is laninamivir octanoate, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; and the third antiviral agent is oseltamivir, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; and the third antiviral agent is zanamivir, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; and the third antiviral agent is peramivir, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; and the third antiviral agent is laninamivir octanoate, or a pharmaceutically acceptable prodrug, salt, solvate, or polymorph thereof.

In a further aspect, the pharmaceutical composition comprising the first antiviral agent, the second antiviral agent, and the third antiviral agent is formulated for oral administration. In a still further aspect, the pharmaceutical composition comprising the first antiviral agent, the second antiviral agent, and the third antiviral agent is formulated intravenous administration.

In one aspect, the present invention pertains to pharmaceutical compositions comprising: a) a first antiviral agent comprising an effective amount of a phospholipase D inhibitor, or a pharmaceutically acceptable salt, solvate, or polymorph thereof; b) a second antiviral agent comprising a viral protein M2 ion channel inhibitor, or a pharmaceutically acceptable prodrug, salt, solvate, or polymorph thereof; and c) a third antiviral agent comprising a nucleoside analog, or a pharmaceutically acceptable prodrug, salt, solvate, or polymorph thereof; and a pharmaceutically acceptable carrier.

In a further aspect, the first antiviral agent is a disclosed phospholipase D inhibitor; the second antiviral agent is selected from amantadine and rimantadine, or a pharmaceutically acceptable prodrug, salt, solvate, or polymorph thereof; the third antiviral agent is selected from ribavirin and viramidine, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is amantadine, or a pharmaceutically acceptable prodrug, salt, solvate, or polymorph thereof; the third antiviral agent is viramidine, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is rimantadine, or a pharmaceutically acceptable prodrug, salt, solvate, or polymorph thereof; the third antiviral agent is viramidine, or a pharmaceutically acceptable prodrug, salt, solvate, or polymorph thereof.

In a further aspect, the pharmaceutical composition comprising the first antiviral agent, the second antiviral agent, and the third antiviral agent is formulated for oral administration. In a still further aspect, the pharmaceutical composition comprising the first antiviral agent, the second antiviral agent, and the third antiviral agent is formulated intravenous administration.

In one aspect, the present invention pertains to pharmaceutical compositions comprising: a) a first antiviral agent comprising an effective amount of a phospholipase D inhibitor, or a pharmaceutically acceptable salt, solvate, or polymorph thereof; b) a second antiviral agent comprising a neuraminidase inhibitor, or a pharmaceutically acceptable prodrug, salt, solvate, or polymorph thereof; and c) a third antiviral agent comprising a nucleoside analog, or a pharmaceutically acceptable prodrug, salt, solvate, or polymorph thereof; and a pharmaceutically acceptable carrier.

In a further aspect, the first antiviral agent is a disclosed phospholipase D inhibitor; the second antiviral agent is selected from oseltamivir, zanamivir, peramivir, laninamivir octanoate, or a pharmaceutically acceptable prodrug, salt, solvate, or polymorph thereof; and wherein third antiviral agent is selected from ribavirin and viramidine, or a pharmaceutically acceptable prodrug, salt, solvate, or polymorph thereof.

In a further aspect, the first antiviral agent is a disclosed phospholipase D inhibitor; the second antiviral agent is oseltamivir, or a pharmaceutically acceptable prodrug, salt, solvate, or polymorph thereof; and wherein third antiviral agent is selected from ribavirin, or a pharmaceutically acceptable prodrug, salt, solvate, or polymorph thereof.

In a further aspect, the first antiviral agent is a disclosed phospholipase D inhibitor; the second antiviral agent is zanamivir, or a pharmaceutically acceptable prodrug, salt, solvate, or polymorph thereof; and wherein third antiviral agent is selected from ribavirin, or a pharmaceutically acceptable prodrug, salt, solvate, or polymorph thereof.

In a further aspect, the first antiviral agent is a disclosed phospholipase D inhibitor; the second antiviral agent is peramivir, or a pharmaceutically acceptable prodrug, salt, solvate, or polymorph thereof; and wherein third antiviral agent is selected from ribavirin, or a pharmaceutically acceptable prodrug, salt, solvate, or polymorph thereof.

In a further aspect, the first antiviral agent is a disclosed phospholipase D inhibitor; the second antiviral agent is laninamivir octanoate, or a pharmaceutically acceptable prodrug, salt, solvate, or polymorph thereof; and wherein third antiviral agent is selected from ribavirin, or a pharmaceutically acceptable prodrug, salt, solvate, or polymorph thereof.

In a further aspect, the first antiviral agent is a disclosed phospholipase D inhibitor; the second antiviral agent is oseltamivir, or a pharmaceutically acceptable prodrug, salt, solvate, or polymorph thereof; and wherein third antiviral agent is selected from viramidine, or a pharmaceutically acceptable prodrug, salt, solvate, or polymorph thereof.

In a further aspect, the first antiviral agent is a disclosed phospholipase D inhibitor; the second antiviral agent is zanamivir, or a pharmaceutically acceptable prodrug, salt, solvate, or polymorph thereof; and wherein third antiviral agent is selected from viramidine, or a pharmaceutically acceptable prodrug, salt, solvate, or polymorph thereof.

In a further aspect, the first antiviral agent is a disclosed phospholipase D inhibitor; the second antiviral agent is peramivir, or a pharmaceutically acceptable prodrug, salt, solvate, or polymorph thereof; and wherein third antiviral agent is selected from viramidine, or a pharmaceutically acceptable prodrug, salt, solvate, or polymorph thereof.

In a further aspect, the first antiviral agent is a disclosed phospholipase D inhibitor; the second antiviral agent is laninamivir octanoate, or a pharmaceutically acceptable prodrug, salt, solvate, or polymorph thereof; and wherein third antiviral agent is selected from viramidine, or a pharmaceutically acceptable prodrug, salt, solvate, or polymorph thereof.

In a further aspect, the pharmaceutical composition comprising the first antiviral agent, the second antiviral agent, and the third antiviral agent is formulated for oral administration. In a still further aspect, the pharmaceutical composition comprising the first antiviral agent, the second antiviral agent, and the third antiviral agent is formulated intravenous administration.

In one aspect, the present invention pertains to pharmaceutical compositions comprising: a) a first antiviral agent comprising an effective amount of a phospholipase D inhibitor, or a pharmaceutically acceptable salt, solvate, or polymorph thereof; and b) a second antiviral agent comprising a nucleoside analog, or a pharmaceutically acceptable prodrug, salt, solvate, or polymorph thereof; and a pharmaceutically acceptable carrier.

In a further aspect, the first antiviral agent is a disclosed phospholipase D inhibitor; and the second antiviral agent is selected from ribavirin and viramidine, or a pharmaceutically acceptable prodrug, salt, solvate, or polymorph thereof.

In a further aspect, the first antiviral agent is a disclosed phospholipase D inhibitor; the second antiviral agent is ribavirin, or a pharmaceutically acceptable prodrug, salt, solvate, or polymorph thereof.

In a further aspect, the first antiviral agent is a disclosed phospholipase D inhibitor; the second antiviral agent is viramidine, or a pharmaceutically acceptable prodrug, salt, solvate, or polymorph thereof.

In a further aspect, the pharmaceutical composition comprising the first antiviral agent and the second antiviral agent is formulated for oral administration. In a still further aspect, the pharmaceutical composition comprising the first antiviral agent and the second antiviral agent is formulated intravenous administration.

In one aspect, the present invention pertains to pharmaceutical compositions comprising: a) a first antiviral agent comprising an effective amount of a phospholipase D inhibitor, or a pharmaceutically acceptable salt, solvate, or polymorph thereof; and b) a second antiviral agent comprising a neuraminidase inhibitor, or a pharmaceutically acceptable prodrug, salt, solvate, or polymorph thereof.

In a further aspect, the first antiviral agent is a disclosed phospholipase D inhibitor; and the second antiviral agent is selected from oseltamivir, zanamivir, peramivir, laninamivir octanoate, or a pharmaceutically acceptable prodrug, salt, solvate, or polymorph thereof.

In a further aspect, the first antiviral agent is a disclosed phospholipase D inhibitor; and the second antiviral agent is oseltamivir, or a pharmaceutically acceptable prodrug, salt, solvate, or polymorph thereof.

In a further aspect, the first antiviral agent is a disclosed phospholipase D inhibitor; and the second antiviral agent is zanamivir, or a pharmaceutically acceptable prodrug, salt, solvate, or polymorph thereof.

In a further aspect, the first antiviral agent is a disclosed phospholipase D inhibitor; and the second antiviral agent is peramivir, or a pharmaceutically acceptable prodrug, salt, solvate, or polymorph thereof.

In a further aspect, the first antiviral agent is a disclosed phospholipase D inhibitor; and the second antiviral agent is laninamivir octanoate, or a pharmaceutically acceptable prodrug, salt, solvate, or polymorph thereof.

In a further aspect, the pharmaceutical composition comprising the first antiviral agent and the second antiviral agent is formulated for oral administration. In a still further aspect, the pharmaceutical composition comprising the first antiviral agent and the second antiviral agent is formulated intravenous administration.

In one aspect, the present invention pertains to pharmaceutical compositions comprising: a) a first antiviral agent comprising an effective amount of a phospholipase D inhibitor, or a pharmaceutically acceptable salt, solvate, or polymorph thereof; and b) a second antiviral agent comprising a viral protein M2 ion channel inhibitor, or a pharmaceutically acceptable prodrug, salt, solvate, or polymorph thereof.

In a further aspect, the first antiviral agent is a disclosed phospholipase D inhibitor; the second antiviral agent is selected from amantadine and rimantadine, or a pharmaceutically acceptable prodrug, salt, solvate, or polymorph thereof.

In a further aspect, the first antiviral agent is a disclosed phospholipase D inhibitor; and the second antiviral agent is amantadine, or a pharmaceutically acceptable prodrug, salt, solvate, or polymorph thereof.

In a further aspect, the first antiviral agent is a disclosed phospholipase D inhibitor; and the second antiviral agent is rimantadine, or a pharmaceutically acceptable prodrug, salt, solvate, or polymorph thereof.

In a further aspect, the pharmaceutical composition comprising the first antiviral agent and the second antiviral agent is formulated for oral administration. In a still further aspect, the pharmaceutical composition comprising the first antiviral agent and the second antiviral agent is formulated intravenous administration.

In a further aspect, the pharmaceutical compositions of the present invention comprising a first antiviral agent, wherein the first antiviral agent comprises an effective amount of a phospholipase D inhibitor, or a pharmaceutically acceptable salt, solvate, or polymorph thereof, the phospholipase D inhibitor is a compound having a structure represented by a formula:

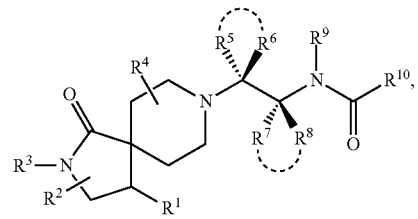

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the pharmaceutical compositions of the present invention comprising a first antiviral agent, wherein the first antiviral agent comprises an effective amount of a phospholipase D inhibitor, or a pharmaceutically acceptable salt, solvate, or polymorph thereof, the phospholipase D inhibitor is a compound having a structure represented by a formula:

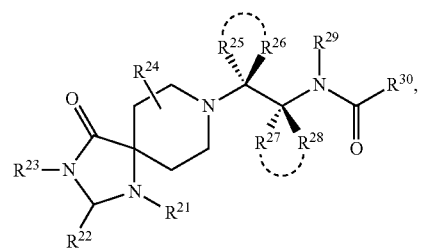

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the pharmaceutical compositions of the present invention comprising a first antiviral agent, wherein the first antiviral agent comprises an effective amount of a phospholipase D inhibitor, or a pharmaceutically acceptable salt, solvate, or polymorph thereof, the phospholipase D inhibitor is a compound having a structure represented by a formula:

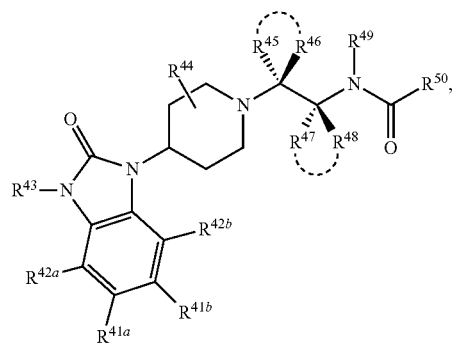

wherein each ----- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the pharmaceutical compositions of the present invention comprising a first antiviral agent, wherein the first antiviral agent comprises an effective amount of a phospholipase D inhibitor, or a pharmaceutically acceptable salt, solvate, or polymorph thereof, the phospholipase D inhibitor is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the pharmaceutical compositions of the present invention comprising a first antiviral agent, wherein the first antiviral agent comprises an effective amount of a phospholipase D inhibitor, or a pharmaceutically acceptable salt, solvate, or polymorph thereof, the phospholipase D inhibitor is a selected from:

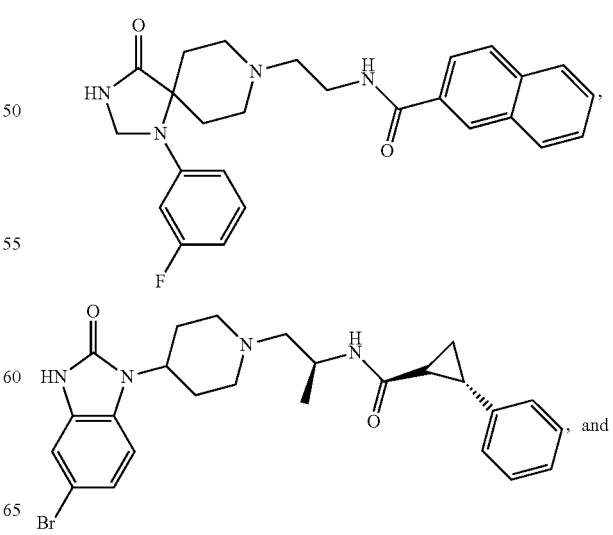

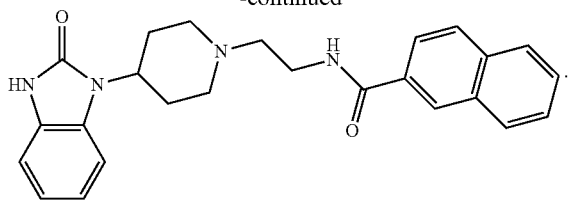

The disclosed compounds can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and can be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions encompass any composition made by admixing a compound of the present invention and a pharmaceutically acceptable carrier.

As used herein, the term "pharmaceutically acceptable salts" refers to salts prepared from pharmaceutically acceptable non-toxic bases or acids. When a disclosed compound is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable derivatives thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment of the disclosed conditions, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The disclosed pharmaceutical compositions can further comprise other therapeutically active compounds, as discussed further herein, which are usually applied in the treatment of the above mentioned pathological conditions.

In a further aspect, a pharmaceutical composition can comprise a therapeutically effective amount of any one or more disclosed compound and a pharmaceutically acceptable carrier. In a further aspect, a pharmaceutical composition can comprise a therapeutically effective amount of one or more product of any disclosed method and a pharmaceutically acceptable carrier. In one aspect, the invention relates to a method for manufacturing a medicament comprising combining at least one disclosed compound or at least one product of a disclosed method with a pharmaceutically acceptable carrier or diluent.

It is understood that the disclosed compositions can be prepared from the disclosed compounds. It is also understood that the disclosed compositions can be employed in the disclosed methods of using.

F. Kits

In one aspect, the invention relates to a kit comprising at least one disclosed compound or at least one product of a disclosed method and at least one agent known to increase PLD activity. In a further aspect, a kit comprises at least one disclosed compound or at least one product of a disclosed method and at least one agent known to decrease PLD activity. In a further aspect, the at least one compound or the at least one product and the at least one agent are co-formulated. In a further aspect, the at least one compound or the at least one product and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

G. Methods of Treating a Viral Infection

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Treating a Viral Infection by Administering a 1-Oxo-2,8-Diazaspiro[4.5]Decanyl Analog In one aspect, the invention relates to a method for treating a subject for viral infection, the method comprising the step of administering to the subject an effective amount of a compound having a structure represented by a formula:

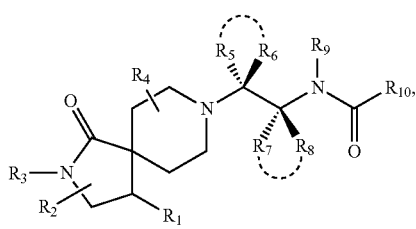

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the compound of the method for treating a subject for viral infection has a structure represented by a formula:

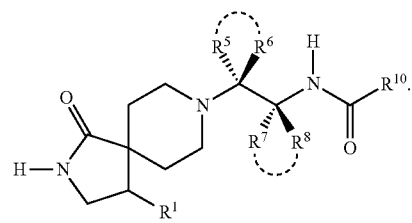

In a further aspect, the subject of the method is mammalian. In a yet further aspect, the subject of the method is human. In a still further aspect, the subject of the method has been diagnosed with a need of treatment for viral infection prior to the administering step. In an even further aspect, the method further comprises the step of identifying the subject as having a need of treatment for viral infection.

In a further aspect, the amount of the method is a therapeutically effective amount. In a still further aspect, the amount of the method is a prophylactically effective amount.

In a further aspect, the compound of the method inhibits PLD1 and/or PLD2 response. In a still further aspect, the compound inhibits PLD1 and/or PLD2 activity in an in vitro assay. In a yet further aspect, the compound inhibits PLD1 and/or PLD2 activity in a cell-based assay.

In a further aspect, the compound of the method inhibits PLD1. In a yet further aspect, the compound is a PLD1-selective inhibitor. In an even further aspect, the compound inhibits PLD1 response in Calu-1 cells.

In a further aspect, the compound of the method inhibits PLD2. In a yet further aspect, the compound is a PLD2-selective inhibitor. In an even further aspect, the compound inhibits PLD2 response in HEK293gfpPLD2 cells.

In a further aspect, the compound of the method inhibits in vitro PLD1 response. In a yet further aspect, the compound has a PLD1 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the compound inhibits in vitro PLD2 response. In a yet further aspect, the compound has a PLD2 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the method further comprises assessing viral load in the subject following administration.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

2. Treating a Viral Infection by Administering a 4-Oxo-1,3,8-Triazaspiro[4.5]Decanyl Analog In various aspects, the invention relates to a method for treating a subject for viral infection, the method comprising the step of administering to the subject an effective amount of a compound having a structure represented by a formula:

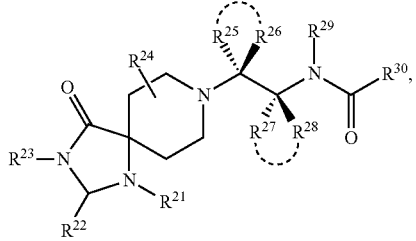

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the compound of the method for treating a subject for viral infection has a structure represented by a formula:

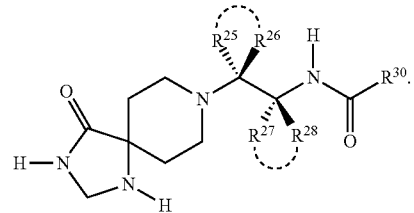

In a further aspect, the subject of the method is mammalian. In a yet further aspect, the subject of the method is human. In a still further aspect, the subject of the method has been diagnosed with a need of treatment for viral infection prior to the administering step. In an even further aspect, the method further comprises the step of identifying the subject as having a need of treatment for viral infection.

In a further aspect, the amount of the method is a therapeutically effective amount. In a still further aspect, the amount of the method is a prophylactically effective amount.

In a further aspect, the compound of the method inhibits PLD1 and/or PLD2 response. In a still further aspect, the compound inhibits PLD1 and/or PLD2 activity in an in vitro assay. In a yet further aspect, the compound inhibits PLD1 and/or PLD2 activity in a cell-based assay.

In a further aspect, the compound of the method inhibits PLD1. In a yet further aspect, the compound is a PLD1-selective inhibitor. In an even further aspect, the compound inhibits PLD1 response in Calu-1 cells.

In a further aspect, the compound of the method inhibits PLD2. In a yet further aspect, the compound is a PLD2-selective inhibitor. In an even further aspect, the compound inhibits PLD2 response in HEK293gfpPLD2 cells.

In a further aspect, the compound of the method inhibits in vitro PLD1 response. In a yet further aspect, the compound has a PLD1 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the compound inhibits in vitro PLD2 response. In a yet further aspect, the compound has a PLD2 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the method further comprises assessing viral load in the subject following administration.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

3. Treating a Viral Infection by Administering a Substituted 2-Oxo-2,3-Dihydro-1H-Benzo[D]Imidazol-1-yl Analog In one aspect, the invention relates to a method for treating a subject for viral infection, the method comprising the step of administering to the subject an effective amount of a compound having a structure represented by a formula:

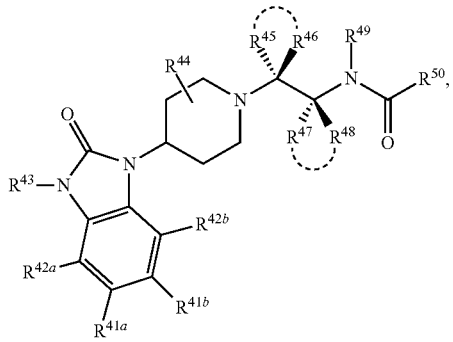

wherein each ----- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the compound of the method for treating a subject for viral infection has a structure represented by a formula:

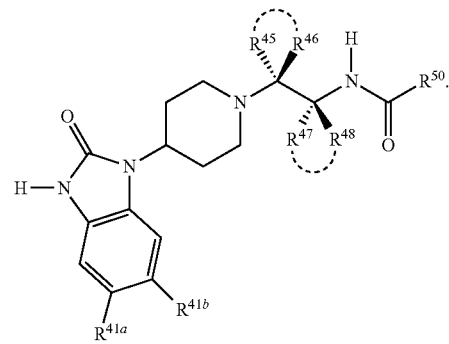

In a further aspect, the subject of the method is mammalian. In a yet further aspect, the subject of the method is human. In a still further aspect, the subject of the method has been diagnosed with a need of treatment for viral infection prior to the administering step. In an even further aspect, the method further comprises the step of identifying the subject as having a need of treatment for viral infection.

In a further aspect, the amount of the method is a therapeutically effective amount. In a still further aspect, the amount of the method is a prophylactically effective amount.

In a further aspect, the compound of the method inhibits PLD1 and/or PLD2 response. In a still further aspect, the compound inhibits PLD1 and/or PLD2 activity in an in vitro assay. In a yet further aspect, the compound inhibits PLD1 and/or PLD2 activity in a cell-based assay.

In a further aspect, the compound of the method inhibits PLD1. In a yet further aspect, the compound is a PLD1-selective inhibitor. In an even further aspect, the compound inhibits PLD1 response in Calu-1 cells.

In a further aspect, the compound of the method inhibits PLD2. In a yet further aspect, the compound is a PLD2- selective inhibitor. In an even further aspect, the compound inhibits PLD2 response in HEK293gfpPLD2 cells.

In a further aspect, the compound of the method inhibits in vitro PLD1 response. In a yet further aspect, the compound has a PLD1 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the compound inhibits in vitro PLD2 response. In a yet further aspect, the compound has a PLD2 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the method further comprises assessing viral load in the subject following administration.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

4. Treating a Viral Infection by Administering a Selected Compound

In one aspect, the invention relates to a method for treating a subject for viral infection, the method comprising the step of administering to the subject an effective amount of a compound selected from: trans-diethylstilbestrol, resveratrol, honokiol, SCH420789, presqualene diphosphate, raloxifene, 4-hydroxytamoxifen, 5-fluoro-2-indoyl deschlorohalopemide, and halopemide, or a pharmaceutically acceptable salt, hydrate, solvate, or polymorph thereof, thereby treating the subject for viral infection.

In a further aspect, the subject of the method is mammalian. In a yet further aspect, the subject of the method is human. In a still further aspect, the subject of the method has been diagnosed with a need of treatment for viral infection prior to the administering step. In an even further aspect, the method further comprises the step of identifying the subject as having a need of treatment for viral infection.

In a further aspect, the effective amount of the method is a therapeutically effective amount. In a still further aspect, the amount of the method is a prophylactically effective amount.

In a further aspect, the compound of the method inhibits PLD1 and/or PLD2 response. In a still further aspect, the compound inhibits PLD1 and/or PLD2 activity in an in vitro assay. In a yet further aspect, the compound inhibits PLD1 and/or PLD2 activity in a cell-based assay.

In a further aspect, the compound of the method inhibits PLD1. In a yet further aspect, the compound is a PLD1-selective inhibitor. In an even further aspect, the compound inhibits PLD1 response in Calu-1 cells.

In a further aspect, the compound of the method inhibits PLD2. In a yet further aspect, the compound is a PLD2-selective inhibitor. In an even further aspect, the compound inhibits PLD2 response in HEK293gfpPLD2 cells.

In a further aspect, the compound of the method inhibits in vitro PLD1 response. In a yet further aspect, the compound has a PLD1 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the compound inhibits in vitro PLD2 response. In a yet further aspect, the compound has a PLD2 $IC_{50}$ of less than about 10 µM, of less than about 1 µM, of less than about 500 nM, of less than about 100 nM, of less than about 60 nM, or of less than about 20 nM. In a still further aspect, the compound exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the method further comprises assessing viral load in the subject following administration.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

5. Treating a Viral Infection by Administering a PLD Inhibitor

In various aspects, the invention relates to a method for treating a subject for viral infection, the method comprising the step of administering to the subject an effective amount of a phospholipase D (PLD) inhibitor, thereby treating the subject for viral infection.

In a further aspect, the subject of the method is mammalian. In a still further aspect, the subject of the method is human. In a yet further aspect, the subject has been diagnosed with a need of treatment for viral infection prior to the administering step. In an even further aspect, the method further comprises the step of identifying the subject as having a need of treatment for viral infection.

In a further aspect, the amount of the method is a therapeutically effective amount. In a yet further aspect, the amount of the method is a prophylactically effective amount.

In a further aspect, the method further comprises assessing viral load in the subject following administration.

In a further aspect, the PLD inhibited is PLD1. In a still further aspect, the phospholipase D (PLD) inhibitor is a PLD1-selective inhibitor. In a yet further aspect, the phospholipase D (PLD) inhibitor inhibits PLD1 response in Calu-1 cells.

In a further aspect, the PLD inhibited is PLD2. In a still further aspect, the phospholipase D (PLD) inhibitor is a PLD2-selective inhibitor. In a yet further aspect, the phospholipase D (PLD) inhibitor inhibits PLD2 response in HEK293gfpPLD2 cells.

In a further aspect, the phospholipase D (PLD) inhibitor inhibits in vitro PLD1 response. In a still further aspect, the phospholipase D (PLD) inhibitor has a PLD1 $IC_{50}$ of less than about 10 μM, of less than about 1 μM, of less than about 500 nM, of less than about 100 nM, of less than about 60 nM, or of less than about 20 nM. In a yet further aspect, the phospholipase D (PLD) inhibitor exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the phospholipase D (PLD) inhibitor inhibits in vitro PLD2 response. In a still further aspect, the phospholipase D (PLD) inhibitor has a PLD2 $IC_{50}$ of less than about 10 μM, of less than about 1 μM, of less than about 500 nM, of less than about 100 nM, of less than about 60 nM, or of less than about 20 nM. In a yet further aspect, the phospholipase D (PLD) inhibitor exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the phospholipase D (PLD) inhibitor of the method for treating a subject for viral infection is a compound having a structure represented by a formula:

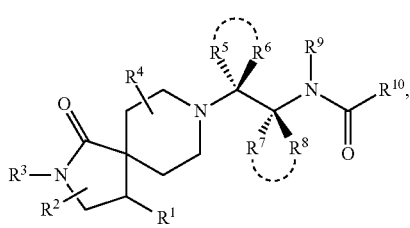

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for treating a subject for viral infection is a compound having a structure represented by a formula:

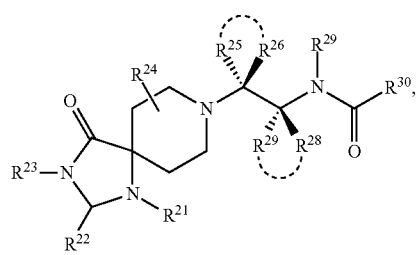

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for treating a subject for viral infection is a compound having a structure represented by a formula:

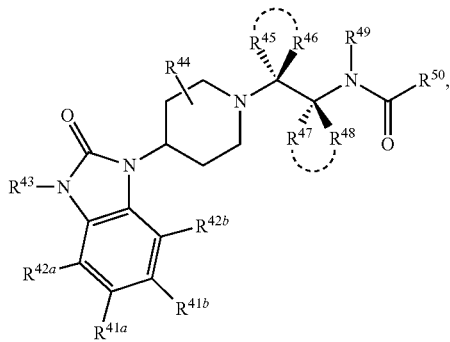

wherein each ----- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for treating a subject for viral infection is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

6. Treating a Viral Infection by Inhibiting Viral Entry into a Cell

In one aspect, the invention relates to a method for inhibiting viral entry into a cell, the method comprising the step of contacting the cell with an effective amount of a phospholipase D (PLD) inhibitor, thereby inhibiting viral entry into the cell.

In a further aspect, the cell of the method is mammalian. In a still further aspect, the cell of the method is human. In a yet further aspect, the cell of the method has been isolated from a mammal prior to the contacting step.

In a further aspect, the PLD inhibited is PLD1. In a still further aspect, the phospholipase D (PLD) inhibitor is a PLD1-selective inhibitor. In a yet further aspect, the phospholipase D (PLD) inhibitor inhibits PLD1 response in Calu-1 cells.

In a further aspect, the PLD inhibited is PLD2. In a still further aspect, the phospholipase D (PLD) inhibitor is a PLD2-selective inhibitor. In a yet further aspect, the phospholipase D (PLD) inhibitor inhibits PLD2 response in HEK293gfpPLD2 cells.

In a further aspect, the phospholipase D (PLD) inhibitor inhibits in vitro PLD1 response. In a still further aspect, the phospholipase D (PLD) inhibitor has a PLD1 $IC_{50}$ of less than about 10 μM, of less than about 1 μM, of less than about 500 nM, of less than about 100 nM, of less than about 60 nM, or of less than about 20 nM. In a yet further aspect, the phospholipase D (PLD) inhibitor exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the phospholipase D (PLD) inhibitor inhibits in vitro PLD2 response. In a still further aspect, the phospholipase D (PLD) inhibitor has a PLD2 $IC_{50}$ of less than about 10 μM, of less than about 1 μM, of less than about 500 nM, of less than about 100 nM, of less than about 60 nM, or of less than about 20 nM. In a yet further aspect, the phospholipase D (PLD) inhibitor exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the phospholipase D (PLD) inhibitor of the method for inhibiting viral entry into a cell is a compound having a structure represented by a formula:

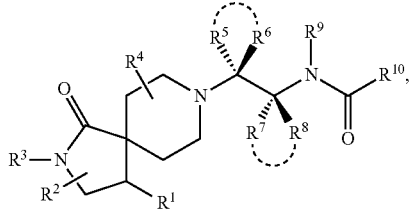

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for inhibiting viral entry into a cell is a compound having a structure represented by a formula:

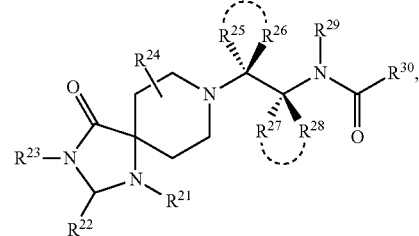

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for inhibiting viral entry into a cell is a compound having a structure represented by a formula:

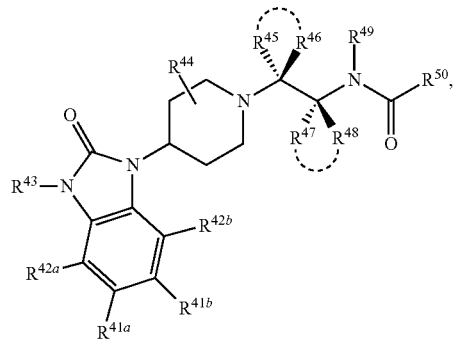

wherein each ----- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for inhibiting viral entry into a cell is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

7. Treating a Viral Infection by Inhibiting Viral Replication in a Cell

In one aspect, the invention relates to a method for inhibiting viral replication within a cell, the method comprising the step of contacting the cell with an effective amount of a phospholipase D (PLD) inhibitor, thereby inhibiting viral replication within the cell.

In a further aspect, the cell of the method is mammalian. In a still further aspect, the cell of the method is human. In a yet further aspect, the cell of the method has been isolated from a mammal prior to the contacting step.

In a further aspect, the PLD inhibited is PLD1. In a still further aspect, the phospholipase D (PLD) inhibitor is a PLD1-selective inhibitor. In a yet further aspect, the phospholipase D (PLD) inhibitor inhibits PLD1 response in Calu-1 cells.

In a further aspect, the PLD inhibited is PLD2. In a still further aspect, the phospholipase D (PLD) inhibitor is a PLD2-selective inhibitor. In a yet further aspect, the phospholipase D (PLD) inhibitor inhibits PLD2 response in HEK293gfpPLD2 cells.

In a further aspect, the phospholipase D (PLD) inhibitor inhibits in vitro PLD1 response. In a still further aspect, the phospholipase D (PLD) inhibitor has a PLD1 $IC_{50}$ of less than about 10 µM, of less than about 1 µM, of less than about 500 nM, of less than about 100 nM, of less than about 60 nM, or of less than about 20 nM. In a yet further aspect, the phospholipase D (PLD) inhibitor exhibits a PLD1:PLD2 inhibition ratio of at least about 2:1, of at least about 3:1, of at least about 5:1, of at least about 10:1, of at least about 20:1, of at least about 50:1, or of at least about 75:1.

In a further aspect, the phospholipase D (PLD) inhibitor inhibits in vitro PLD2 response. In a still further aspect, the phospholipase D (PLD) inhibitor has a PLD2 $IC_{50}$ of less than about 10 µM, of less than about 1 µM, of less than about 500 nM, of less than about 100 nM, of less than about 60 nM, or of less than about 20 nM. In a yet further aspect, the phospholipase D (PLD) inhibitor exhibits a PLD2:PLD1 inhibition ratio of at least about 2:1, of at least about 3:1, of at least about 5:1, of at least about 10:1, of at least about 20:1, of at least about 50:1, or of at least about 75:1.

In a further aspect, the phospholipase D (PLD) inhibitor of the method for inhibiting viral replication within a cell is a compound having a structure represented by a formula:

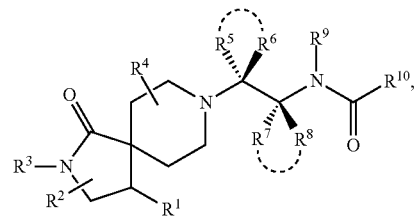

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for inhibiting viral replication within a cell is a compound having a structure represented by a formula:

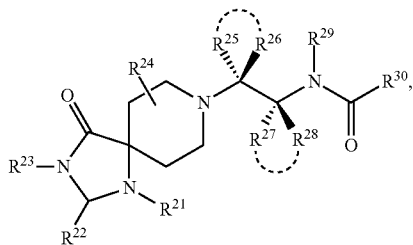

wherein each ---- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for inhibiting viral replication within a cell is a compound having a structure represented by a formula:

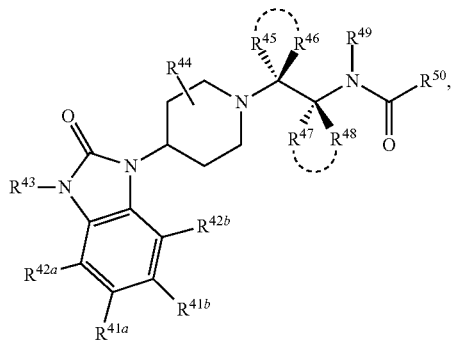

wherein each ---- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D (PLD) inhibitor of the method for inhibiting viral replication within a cell is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the method further comprises administering to the subject a non-PLD anti-viral therapy. In a still further aspect, the method further comprises administering to the subject a non-PLD anti-viral therapy selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In a further aspect, the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

8. Treating a Viral Infection by Administering a Compound that Binds PLD in a Non-Catalytic Domain In one aspect, the invention relates to a method for treating a subject for viral infection, the method comprising the step of administering to the subject an effective amount of a binding agent of phospholipase D (PLD), wherein the binding agent binds to at least one amino acid in a non-catalytic domain of PLD, thereby inhibiting viral entry into the cell.

In a further aspect, the binding to PLD of the method is allosteric binding.

In a further aspect, the non-catalytic domain of the method comprises at least one amino acid residue in amino acids 1-505 of PLD1, or the homologous amino acids of PLD2. In a yet further aspect, the non-catalytic domain comprises at least one amino acid in amino acids 81-425 of PLD1, or the homologous amino acids of PLD2. In a still further aspect, the non-catalytic domain comprises at least one amino acid in amino acids 200-390 of PLD1, or the homologous amino acids of PLD2. In an even further aspect, the non-catalytic domain comprises at least one amino acid in amino acids 310-375, or the homologous amino acids of PLD2. In a still further aspect, the binding agent binds a domain comprising amino acids 310-375.

In a further aspect, the subject of the method has been diagnosed with a need of treatment for viral infection prior to the administering step. In a still further aspect, the method further comprises the step of identifying the subject as having a need of treatment for viral infection.

In a further aspect, the amount administered in the method is a therapeutically effective amount. In a still further aspect, the amount administered in the method is a prophylactically effective amount.

In a further aspect, the method further comprises assessing viral load in the subject following administration.

In a further aspect, the method further comprises administering to the subject a non-PLD anti-viral therapy. In a still further aspect, the non-PLD anti-viral therapy is selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In one aspect, the invention relates to a method for treating a subject for viral infection, the method comprising the step of administering to the subject an effective amount of an allosteric binding agent of phospholipase D (PLD), thereby treating the subject for viral infection.

In a further aspect, the allosteric binding of the method occurs with at least one amino acid residue in amino acids 1-505 of PLD1, or the homologous amino acids of PLD2, thereby inhibiting viral entry into the cell. In a still further aspect, the allosteric binding of the method occurs with at least one amino acid residue in amino acids 81-425 of PLD1, or the homologous amino acids of PLD2. In a yet further aspect, the allosteric binding of the method occurs with at least one amino acid residue in amino acids 200-390, wherein PLD1, or the homologous amino acids of PLD2. In an even further aspect, the allosteric binding of the method occurs with at least one amino acid residue in amino acids 310-375, or the homologous amino acids of PLD2. In a still further aspect, the allosteric binding of the method occurs with a domain comprising amino acids 310-375.

In a further aspect, the subject of the method has been diagnosed with a need of treatment for viral infection prior to the administering step. In a still further aspect, the method further comprises the step of identifying the subject as having a need of treatment for viral infection.

In a further aspect, the amount administered in the method is a therapeutically effective amount. In a still further aspect, the amount administered in the method is a prophylactically effective amount.

In a further aspect, the method further comprises assessing viral load in the subject following administration.

In a further aspect, the method further comprises administering to the subject a non-PLD anti-viral therapy. In a still further aspect, the non-PLD anti-viral therapy is selected from an M2 inhibitor, a neuraminidase inhibitor, and an interferon.

In a further aspect, the administering of the method comprises inhalation or oral administration. In a still further aspect, the administering of the method comprises intravenous or intra-arterial injection.

In one aspect, the invention relates to a method for inhibiting viral entry into a cell, the method comprising the step of contacting the cell an effective amount of a binding agent of phospholipase D (PLD), wherein the binding agent binds to at least one amino acid in a non-catalytic domain of PLD, thereby inhibiting viral entry into the cell.

In a further aspect, the binding to PLD of the method is allosteric binding.

In a further aspect, the non-catalytic domain of the method comprises at least one amino acid residue in amino acids 1-505 of PLD1, or the homologous amino acids of PLD2. In a yet further aspect, the non-catalytic domain comprises at least one amino acid in amino acids 81-425 of PLD1, or the homologous amino acids of PLD2. In a still further aspect, the non-catalytic domain comprises at least one amino acid in amino acids 200-390 of PLD1, or the homologous amino acids of PLD2. In an even further aspect, the non-catalytic domain comprises at least one amino acid in amino acids 310-375, or the homologous amino acids of PLD2. In a still further aspect, the binding agent binds a domain comprising amino acids 310-375.

In one aspect, the invention relates to a method for inhibiting viral entry into a cell, the method comprising the step of contacting the cell with an effective amount of an allosteric binding agent of phospholipase D (PLD), thereby inhibiting viral entry into the cell.

In a further aspect, the allosteric binding of the method occurs with at least one amino acid residue in amino acids 1-505 of PLD1, or the homologous amino acids of PLD2, thereby inhibiting viral entry into the cell. In a still further aspect, the allosteric binding of the method occurs with at least one amino acid residue in amino acids 81-425 of PLD1, or the homologous amino acids of PLD2. In a yet further aspect, the allosteric binding of the method occurs with at least one amino acid residue in amino acids 200-390, wherein PLD1, or the homologous amino acids of PLD2. In an even further aspect, the allosteric binding of the method occurs with at least one amino acid residue in amino acids 310-375, or the homologous amino acids of PLD2. In a still further aspect, the allosteric binding of the method occurs with a domain comprising amino acids 310-375.

In one aspect, the invention relates to a method for inhibiting viral replication within a cell, the method comprising the step of contacting the cell with an effective amount of a binding agent of phospholipase D (PLD), wherein the binding agent binds to at least one amino acid residue in a binding domain comprising amino acids 1-505 of PLD1, or the homologous amino acids of PLD2, thereby inhibiting viral replication within the cell.

In a further aspect, the binding to PLD of the method is allosteric binding.

In a further aspect, the non-catalytic domain of the method comprises at least one amino acid residue in amino acids 1-505 of PLD1, or the homologous amino acids of PLD2. In a yet further aspect, the non-catalytic domain comprises at least one amino acid in amino acids 81-425 of PLD1, or the homologous amino acids of PLD2. In a still further aspect, the non-catalytic domain comprises at least one amino acid in amino acids 200-390 of PLD1, or the homologous amino acids of PLD2. In an even further aspect, the non-catalytic domain comprises at least one amino acid in amino acids 310-375, or the homologous amino acids of PLD2. In a still further aspect, the binding agent binds a domain comprising amino acids 310-375.

In one aspect, the invention relates to a method for inhibiting viral replication within a cell, the method comprising the step of contacting the cell with an effective amount of an allosteric binding agent of phospholipase D (PLD), thereby inhibiting viral replication within the cell.

In a further aspect, the allosteric binding of the method occurs with at least one amino acid residue in amino acids 1-505 of PLD1, or the homologous amino acids of PLD2, thereby inhibiting viral entry into the cell. In a still further aspect, the allosteric binding of the method occurs with at least one amino acid residue in amino acids 81-425 of PLD1, or the homologous amino acids of PLD2. In a yet further aspect, the allosteric binding of the method occurs with at least one amino acid residue in amino acids 200-390, wherein PLD1, or the homologous amino acids of PLD2. In an even further aspect, the allosteric binding of the method occurs with at least one amino acid residue in amino acids 310-375, or the homologous amino acids of PLD2. In a still further aspect, the allosteric binding of the method occurs with a domain comprising amino acids 310-375.

In a further aspect, the binding of the foregoing methods modulates enzymatic activity. In a still further aspect, the binding of the foregoing methods is at a site directly or indirectly involved with protein-protein interaction.

In a further aspect, the cell of the foregoing methods is mammalian. In a still further aspect, the cell of the foregoing methods is human. In a yet further aspect, the cell of the foregoing methods cell has been isolated from a mammal prior to the contacting step. In an even further aspect, the contacting of the cell of the foregoing methods is via administration to a mammal.

In a further aspect, the viral infection of the foregoing methods comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection of the foregoing methods is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection of the foregoing methods comprises influenza virus. In a still further aspect, the viral infection of the foregoing methods comprises an influenza virus subtype selected from H1N1, H2N2, H3N2, H5N1, H7N7, H1N2, H9N2, H7N2, H7N3, and H10N7.

In a further aspect, the agent of the foregoing methods for treating a subject for viral infection is a compound having a structure represented by a formula:

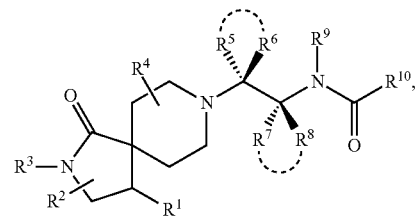

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the agent of the foregoing methods for treating a subject for viral infection is a compound having a structure represented by a formula:

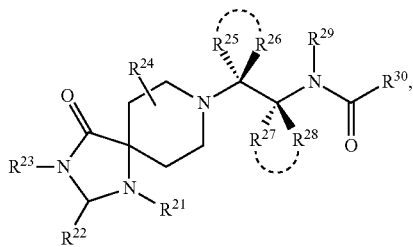

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the agent of the foregoing methods for treating a subject for viral infection is a compound having a structure represented by a formula:

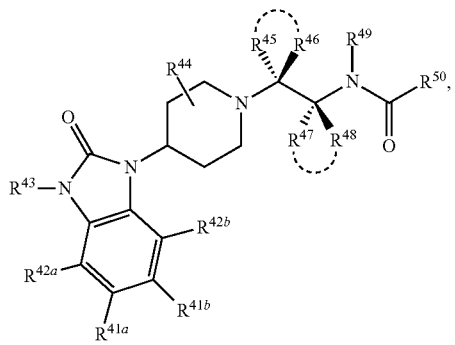

wherein each ----- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkoxy, thiol, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the agent of the foregoing methods for treating a subject for viral infection is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

9. Treating a Viral Infection by Co-Administering Two or More Therapeutic Agents In one aspect, the invention relates to a method for treating a subject comprising the step of co-administering an effective amount of a combination of two or more therapeutic agents to the subject; wherein the subject has been diagnosed with a need for treatment of an influenza infection prior to the administering step; and wherein the combination of two or more therapeutic agents comprises: a) a phospholipase D inhibitor; and b) one or more therapeutic agents selected from: i) a viral protein M2 ion channel inhibitor; ii) a neuraminidase inhibitor, and iii) a nucleoside analog.

In a further aspect, an effective amount is a therapeutically effective amount. In a still further aspect, an effective amount is a prophylactically effective amount.

In a further aspect, the subject is a mammal. In a still further aspect, the mammal is selected from a human, a swine, a horse, a cat, and a dog. In a yet further aspect, the mammal is a human. In an even further aspect, the subject is a bird.

In a further aspect, the influenza infection is caused by a virus selected from a type A influenza virus, type B influenza virus, and type C influenza virus. In a still further aspect, the virus is a type A influenza virus. In a yet further aspect, the type A influenza virus is of subtype H1, H5, H7 or H9. In an even further aspect, the type A influenza virus is of subtype H1N1, H1N2, H2N2, H3N2, H3N8, H5N1, H5N2, H5N3, H5N8, H5N9, H7N1, H7N2, H7N3, H7N4, H7N7, H9N2, or H10N7. In a still further aspect, the type A influenza virus is of subtype H1N1, H1N2, H2N2, H3N2, H5N1, H5N3, H7N2, H7N3, H7N7, H9N2, or H10N7. In a yet further aspect, the type A influenza virus is H5N1. In an even further aspect, the type A influenza virus is H1N1. In a still further aspect, the virus is a type B influenza virus. In a yet further aspect, the virus is a type C influenza virus.

In a further aspect, the virus is treatment resistant. In a still further aspect, the virus is oseltamivir resistant. In a yet further aspect, the virus is not oseltamivir resistant. In an even further aspect, the virus is amantadine resistant. In a still further aspect, the virus is rimantadine resistant. In a yet further aspect, the virus is not amantadine resistant. In an even further aspect, the virus is not rimantadine resistant.

In a further aspect, the co-administration is administration in a substantially simultaneous manner. In a still further aspect, the simultaneous administration comprises a single dose form containing a fixed ratio of the phospholipase D inhibitor and the one or more therapeutic agents. In a yet further aspect, the single dose form containing a fixed ratio of the phospholipase D inhibitor and the one or more therapeutic agents is a capsule or a tablet. In an even further aspect, the single dose form containing a fixed ratio of the phospholipase D inhibitor and the one or more therapeutic agents is an ampule for a single intravenous administration. In a still further aspect, the simultaneous administration comprises a single dose forms for each of the phospholipase D inhibitor and the one or more therapeutic agents. In a yet further aspect, the single dose form for each of the phospholipase D inhibitor and the one or more therapeutic agents is a capsule or a tablet. In an even further aspect, the single dose form for each of the phospholipase D inhibitor and the one or more therapeutic agents an ampule for a single intravenous administration.

In a further aspect, the co-administration is administration in a substantially sequential manner.

In a further aspect, the phospholipase D inhibitor of the method comprising co-administering a combination of two or more therapeutic agents is a disclosed phospholipase D inhibitor. In a still further aspect, the phospholipase D inhibitor inhibits PLD1 and/or PLD2. In a yet further aspect, the phospholipase D inhibitor inhibits PLD1. In an even further aspect, the phospholipase D inhibitor inhibits PLD2.

In a further aspect, the viral protein M2 ion channel inhibitor is selected from amantadine and rimantadine, or a pharmaceutically acceptable prodrug, salt, solvate, or polymorph thereof.

In a further aspect, the neuraminidase inhibitor is selected from oseltamivir, zanamivir, peramivir, laninamivir octanoate, or a pharmaceutically acceptable salt, solvate, or polymorph thereof.

In a further aspect, the nucleoside analog is selected from ribavirin and viramidine.

In a further aspect, the method comprising co-administering a combination of two or more therapeutic agents further comprises a prostaglandin E2 receptor agonist, or a pharmaceutically acceptable prodrug, salt, solvate, or polymorph thereof.

In a further aspect, the method comprising co-administering a combination of two or more therapeutic agents further comprises an interferon, or an isoform, mutein or fused protein thereof.

In a further aspect, the method comprising co-administering a combination of two or more therapeutic agents further comprises an effective amount of an antiviral agent selected from a replication inhibitor, an IMP dehydrogenase inhibitor, an RNA polymerase inhibitor, and an influenza-specific interfering oligonucleotide. In a still further aspect, the IMP dehydrogenase inhibitor is selected from ribavirin, viramidine, mycophenolic acid, and mycophenolate mofetil. In a yet further aspect, the RNA polymerase inhibitor is favipiravir. In an even further aspect, the influenza virus absorption inhibitor is Fludase (DAS181).

In a further aspect, the method comprising co-administering a combination of two or more therapeutic agents further comprises an effective amount of a cysteamine compound.

In a further aspect, the method comprising co-administering a combination of two or more therapeutic agents further comprises a therapeutic agent that is typically considered a standard drug or therapeutic agent during influenza infection.

In a further aspect, the method comprising co-administering a combination of two or more therapeutic agents further comprises an effective amount of an immunomodulator, or a pharmaceutically acceptable prodrug, salt, solvate, or polymorph thereof. In a still further aspect, the immunomodulator is polyoxidonium. In a yet further aspect, the immunomodulator is an anti-inflammatory agent. In an even further aspect, the anti-inflammatory agent is non-steroidal, steroidal, or a combination thereof.

In a further aspect, the phospholipase D inhibitor of the method comprising co-administering a combination of two or more therapeutic agents is a compound having a structure represented by a formula:

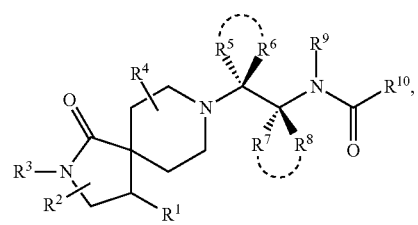

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the method comprising co-administering a combination of two or more therapeutic agents is a compound having a structure represented by a formula:

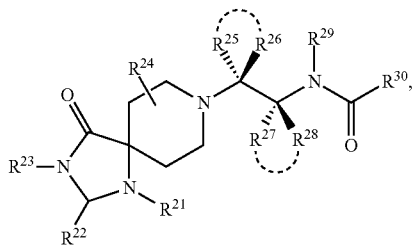

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the method comprising co-administering a combination of two or more therapeutic agents is a compound having a structure represented by a formula:

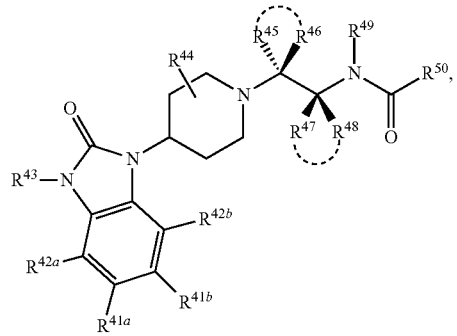

wherein each ----- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the method comprising co-administering a combination of two or more therapeutic agents is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the phospholipase D inhibitor of the method comprising co-administering a combination of two or more therapeutic agents is a compound selected from:

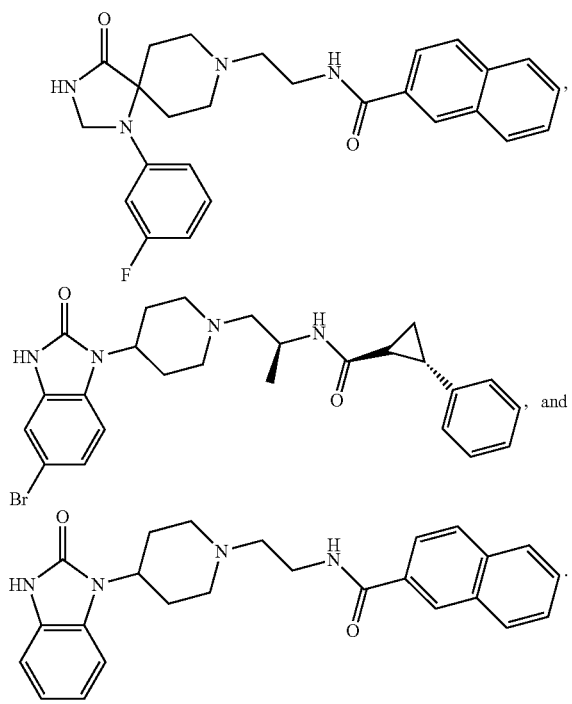

10. Decreasing the Risk to a Subject of Contracting an Influenza Infection

In one aspect, the invention relates to a method for decreasing the risk to a subject of contracting an influenza infection comprising the step of administering a combination of therapeutic agents to the subject; wherein the subject has been determined to be at risk of an influenza infection prior to the administering step; and wherein the combination of therapeutic agents comprises: a) a phospholipase D inhibitor; and b) one or more therapeutic agents selected from: i) a viral protein M2 ion channel inhibitor; ii) a neuraminidase inhibitor; and iii) a nucleotide analog, or prodrug thereof.

In a further aspect, an effective amount is a therapeutically effective amount. In a still further aspect, an effective amount is a prophylactically effective amount.

In a further aspect, the subject is a mammal. In a still further aspect, the mammal is selected from a human, a swine, a horse, a cat, and a dog. In a yet further aspect, the mammal is a human. In an even further aspect, the subject is a bird.

In a further aspect, the influenza infection is caused by a virus selected from a type A influenza virus, type B influenza virus, and type C influenza virus. In a still further aspect, the virus is a type A influenza virus. In a yet further aspect, the type A influenza virus is of subtype H1, H5, H7 or H9. In an even further aspect, the type A influenza virus is of subtype H1N1, H1N2, H2N2, H3N2, H3N8, H5N1, H5N2, H5N3, H5N8, H5N9, H7N1, H7N2, H7N3, H7N4, H7N7, H9N2, or H10N7. In a still further aspect, the type A influenza virus is of subtype H1N1, H1N2, H2N2, H3N2, H5N1, H5N3, H7N2, H7N3, H7N7, H9N2, or H10N7. In a yet further aspect, the type A influenza virus is H5N1. In an even further aspect, the type A influenza virus is H1N1. In a still further aspect, the virus is a type B influenza virus. In a yet further aspect, the virus is a type C influenza virus.

In a further aspect, the virus is treatment resistant. In a still further aspect, the virus is oseltamivir resistant. In a yet further aspect, the virus is not oseltamivir resistant. In an even further aspect, the virus is amantadine resistant. In a still further aspect, the virus is rimantadine resistant. In a yet further aspect, the virus is not amantadine resistant. In an even further aspect, the virus is not rimantadine resistant.

In a further aspect, the co-administration is administration in a substantially simultaneous manner. In a still further aspect, the simultaneous administration comprises a single dose form containing a fixed ratio of the phospholipase D inhibitor and the one or more therapeutic agents. In a yet further aspect, the single dose form containing a fixed ratio of the phospholipase D inhibitor and the one or more therapeutic agents is a capsule or a tablet. In an even further aspect, the single dose form containing a fixed ratio of the phospholipase D inhibitor and the one or more therapeutic agents is an ampule for a single intravenous administration. In a still further aspect, the simultaneous administration comprises a single dose forms for each of the phospholipase D inhibitor and the one or more therapeutic agents. In a yet further aspect, the single dose form for each of the phospholipase D inhibitor and the one or more therapeutic agents is a capsule or a tablet. In an even further aspect, the single dose form for each of the phospholipase D inhibitor and the one or more therapeutic agents an ampule for a single intravenous administration.

In a further aspect, the co-administration is administration in a substantially sequential manner.

In a further aspect, the phospholipase D inhibitor of the a method for decreasing the risk to a subject of contracting an influenza infection is a disclosed phospholipase D inhibitor. In a still further aspect, the phospholipase D inhibitor inhibits PLD1 and/or PLD2. In a yet further aspect, the phospholipase D inhibitor inhibits PLD1. In an even further aspect, the phospholipase D inhibitor inhibits PLD2.

In a further aspect, the viral protein M2 ion channel inhibitor is selected from amantadine and rimantadine, or a pharmaceutically acceptable prodrug, salt, solvate, or polymorph thereof.

In a further aspect, the neuraminidase inhibitor is selected from oseltamivir, zanamivir, peramivir, laninamivir octanoate, or a pharmaceutically acceptable salt, solvate, or polymorph thereof.

In a further aspect, the nucleoside analog is selected from ribavirin and viramidine.

In a further aspect, the a method for decreasing the risk to a subject of contracting an influenza infection further comprises a prostaglandin E2 receptor agonist, or a pharmaceutically acceptable prodrug, salt, solvate, or polymorph thereof.

In a further aspect, the a method for decreasing the risk to a subject of contracting an influenza infection further comprises an interferon, or an isoform, mutein or fused protein thereof.

In a further aspect, the a method for decreasing the risk to a subject of contracting an influenza infection further comprises an effective amount of an antiviral agent selected from a replication inhibitor, an IMP dehydrogenase inhibitor, an RNA polymerase inhibitor, and an influenza-specific interfering oligonucleotide. In a still further aspect, the IMP dehydrogenase inhibitor is selected from ribavirin, viramidine, mycophenolic acid, and mycophenolate mofetil. In a yet further aspect, the RNA polymerase inhibitor is favipiravir. In an even further aspect, the influenza virus absorption inhibitor is Fludase (DAS181).

In a further aspect, the a method for decreasing the risk to a subject of contracting an influenza infection further comprises an effective amount of a cysteamine compound.

In a further aspect, the a method for decreasing the risk to a subject of contracting an influenza infection further comprises an effective amount of an immunomodulator, or a pharmaceutically acceptable prodrug, salt, solvate, or polymorph thereof. In a still further aspect, the immunomodulator is polyoxidonium. In a yet further aspect, the immunomodulator is an anti-inflammatory agent. In an even further aspect, the anti-inflammatory agent is non-steroidal, steroidal, or a combination thereof.

In a further aspect, the phospholipase D inhibitor of the a method for decreasing the risk to a subject of contracting an influenza infection is a compound having a structure represented by a formula:

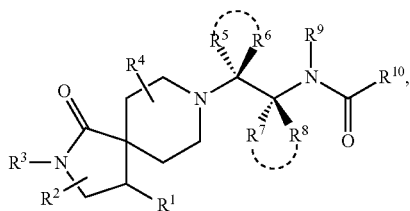

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the a method for decreasing the risk to a subject of contracting an influenza infection is a compound having a structure represented by a formula:

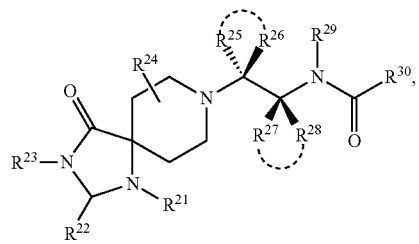

wherein each ----- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the a method for decreasing the risk to a subject of contracting an influenza infection is a compound having a structure represented by a formula:

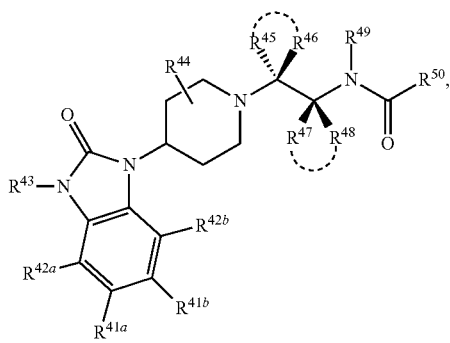

wherein each ---- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the a method for decreasing the risk to a subject of contracting an influenza infection is a compound selected from: trans-diethylstilbestrol, resveratrol, honokiol, SCH420789, presqualene diphosphate, raloxifene, 4-hydroxy tamoxifen, 5-fluoro-2-indoyl des-chlorohalopemide, and halopemide, or a pharmaceutically acceptable salt, hydrate, solvate, or polymorph thereof, thereby treating the subject for viral infection.

In a further aspect, the phospholipase D inhibitor of the a method for decreasing the risk to a subject of contracting an influenza infection is a compound selected from:

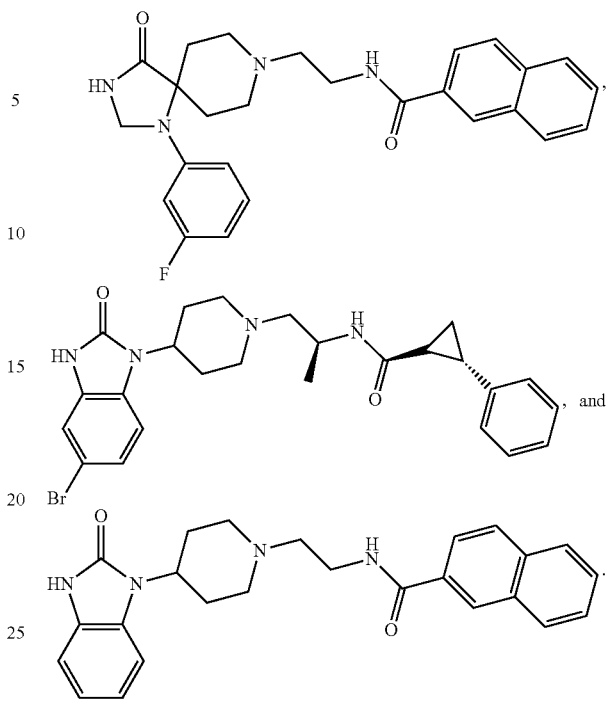

H. Uses

In a further aspect, the invention relates to use of at least one disclosed compound in the manufacture of a medicament for the treatment of a viral infection. In a further aspect, the use is in the manufacture of a medicament for the treatment of a viral infection in a mammal.

In a further aspect, the invention relates to use of at least one disclosed compound in the manufacture of a medicament for the treatment of a viral infection, wherein the viral infection comprises a Paramyxovirus, a Parainfluenza virus, a Morbillivirus, a Respovirus, a Rubalavirus, Varicella-zoster virus, a Variola virus, a Herpesvirus, an Influenza virus, a Pneumovirus, a Metapneumovirus, a Rubivirus, an Astrovirus, a enteric Adenovirus, a Norovirus, a Rotavirus, a Hepatitis virus, an Arbovirus, an Epstein-Barr virus, an Enterovirus, a Coxsackievirus, and an Echovirus. In a still further aspect, the viral infection is associated with a disease comprising chickenpox, herpes, influenza, mumps, measles, viral meningitis, viral pneumonia, rubella, shingles, infectious mononucleosis, smallpox, gastroenteritis and AIDS.

In a further aspect, the viral infection comprises influenza virus. In a still further aspect, the viral infection comprises an influenza virus subtype selected from H1N1, H2N2, H3N2, H5N1, H7N7, H1N2, H9N2, H7N2, H7N3, and H10N7.

In a further aspect, the medicament further comprises a non-PLD anti-viral therapy. In a still further aspect, the non-PLD anti-viral therapy is selected from an M2 inhibitor, a neuraminidase inhibitor, and an interferon.

In a further aspect, the medicament is formulated for inhalation or oral administration. In a still further aspect, the medicament is formulated for intravenous or intra-arterial injection.

It is understood that the disclosed uses can be employed in connection with the disclosed compounds, methods, compositions, and kits.

I. Kits

In a further aspect, the invention relates to a kit comprising a phospholipase D inhibitor, or pharmaceutically acceptable salt, solvate, or polymorph thereof, and one or more of: a) at least one agent known to decrease the severity of symptoms associated with an influenza infection; b) at least one agent known to treat an influenza infection; c) instructions for treating an influenza infection; d) instructions for administering the phospholipase D inhibitor in connection with treating an influenza infection; or e) instructions for administering the phospholipase D inhibitor in connection with reducing the risk of influenza infection.

In a further aspect, the phospholipase D inhibitor and the at least one agent of the kit are co-packaged.

In a further aspect, the phospholipase D inhibitor and the at least one agent of the kit are co-formulated.

In a further aspect, the kit further comprises a plurality of dosage forms, the plurality comprising one or more doses; and each dose comprises an effective amount of each of the phospholipase D inhibitor and the at least one agent. In a still further aspect, the effective amount is a therapeutically effective amount. In a yet further aspect, the effective amount is a prophylactically effective amount.

In a further aspect, each dose of the phospholipase D inhibitor and the at least one agent in the kit are co-formulated.

In a further aspect, each dose of the phospholipase D inhibitor and the at least one agent in the kit are co-packaged.

In a further aspect, the dosage forms in the kit are formulated for oral administration and/or intravenous administration. In a still further aspect, the dosage forms in the kit are formulated for oral administration. In a yet further aspect, the dosage forms in the kit are formulated for intravenous administration. In an even further aspect, the dosage form for the phospholipase D inhibitor in the kit is formulated for oral administration and the dosage for the at least one agent in the kit is formulated for intravenous administration. In a still further aspect, the dosage form for the phospholipase D inhibitor in the kit is formulated for intravenous administration and the dosage for the at least one agent in the kit is formulated for oral administration.

In a further aspect, the phospholipase D inhibitor in the kit is a disclosed phospholipase D inhibitor. In a still further aspect, the phospholipase D inhibitor in the kit inhibits PLD1 and/or PLD2. In a yet further aspect, the phospholipase D inhibitor in the kit inhibits PLD1. In an even further aspect, the phospholipase D inhibitor in the kit inhibits PLD2.

In a further aspect, the at least one agent in the kit is selected from a viral protein M2 ion channel inhibitor, or a pharmaceutically acceptable prodrug, salt, solvate, or polymorph thereof; a neuraminidase inhibitor, or a pharmaceutically acceptable prodrug, salt, solvate, or polymorph thereof; and a nucleoside analog, or a pharmaceutically acceptable prodrug, salt, solvate, or polymorph thereof.

In a further aspect, the viral protein M2 ion channel inhibitor in the kit is selected from amantadine and rimantadine, or a pharmaceutically acceptable prodrug, salt, solvate, or polymorph thereof. In a still further aspect, the neuraminidase inhibitor in the kit is selected from oseltamivir, zanamivir, peramivir, laninamivir octanoate, or a pharmaceutically acceptable salt, solvate, or polymorph thereof. In a yet further aspect, the nucleoside analog in the kit is selected from ribavirin and viramidine.

In a further aspect, the at least one agent in the kit is a viral protein M2 ion channel inhibitor, or a pharmaceutically acceptable prodrug, salt, solvate, or polymorph thereof. In a still further aspect, the viral protein M2 ion channel inhibitor is selected from amantadine and rimantadine, or a pharmaceutically acceptable prodrug, salt, solvate, or polymorph thereof.

In a further aspect, the at least one agent in the kit is a neuraminidase inhibitor, or a pharmaceutically acceptable prodrug, salt, solvate, or polymorph thereof. In a still further aspect, the neuraminidase inhibitor is selected from oseltamivir, zanamivir, peramivir, laninamivir octanoate, or a pharmaceutically acceptable salt, solvate, or polymorph thereof.

The kit of , wherein the at least one agent in the kit is a nucleoside analog, or a pharmaceutically acceptable prodrug, salt, solvate, or polymorph thereof. In a still further aspect, the nucleoside analog is selected from ribavirin and viramidine.

In a further aspect, the phospholipase D inhibitor of the kit is a compound having a structure represented by a formula:

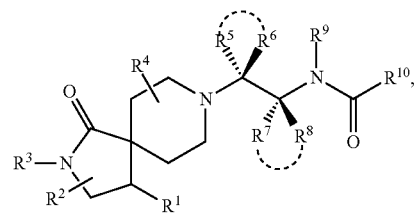

wherein each ----- independently comprises an optional covalent bond; wherein $R^1$ is an optionally substituted C3 to C9 organic residue selected from aryl, heteroaryl, cycloalkyl, heterocycloalkyl, cycloalkenyl, and heterocycloalkenyl; wherein $R^2$ comprises three substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^3$ comprises hydrogen, an optionally substituted C1 to C6 alkyl, an optionally substituted C3 to C6 cycloalkyl, or a hydrolysable residue; wherein $R^4$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^5$ and $R^6$ independently comprises hydrogen, trifluoromethyl, carboxamido, alkylsulfonyl, an optionally substituted C1 to C6 alkyl, or an optionally substituted C3 to C6 cycloalkyl or $R^5$ and $R^6$, together with the intermediate carbon, comprise an optionally substituted C3 to C6 cycloalkyl; wherein each of $R^7$ and $R^8$ independently comprises hydrogen, trifluoromethyl, carboxamido, alkylsulfonyl, an optionally substituted C1 to C6 alkyl, or an optionally substituted C3 to C6 cycloalkyl or $R^7$ and $R^8$, together with the intermediate carbon, comprise an optionally substituted C3 to C6 cycloalkyl; wherein $R^9$ comprises hydrogen, an optionally substituted C1 to C6 alkyl, an optionally substituted C3 to C6 cycloalkyl, or a hydrolysable residue; wherein $R^{10}$ comprises an optionally substituted C1 to C12 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the kit is a compound having a structure represented by a formula:

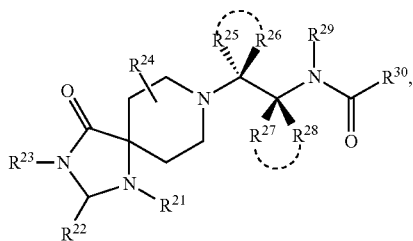

wherein each ---- independently comprises an optional covalent bond; wherein $R^{21}$ is an optionally substituted C3 to C9 organic residue selected from aryl, heteroaryl, cycloalkyl, heterocycloalkyl, cycloalkenyl, and heterocycloalkenyl; wherein $R^{22}$ comprises two substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{23}$ comprises hydrogen, an optionally substituted C1 to C6 alkyl, an optionally substituted C3 to C6 cycloalkyl, or a hydrolysable residue; wherein $R^{24}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{25}$ and $R^{26}$ independently comprises hydrogen, trifluoromethyl, carboxamido, alkylsulfonyl, an optionally substituted C1 to C6 alkyl, or an optionally substituted C3 to C6 cycloalkyl or $R^{25}$ and $R^{26}$, together with the intermediate carbon, comprise an optionally substituted C3 to C6 cycloalkyl; wherein each of $R^{27}$ and $R^{28}$ independently comprises hydrogen, trifluoromethyl, carboxamido, alkylsulfonyl, an optionally substituted C1 to C6 alkyl, or an optionally substituted C3 to C6 cycloalkyl or $R^{27}$ and $R^{28}$, together with the intermediate carbon, comprise an optionally substituted C3 to C6 cycloalkyl; wherein $R^{29}$ comprises hydrogen, an optionally substituted C1 to C6 alkyl, an optionally substituted C3 to C6 cycloalkyl, or a hydrolysable residue; wherein $R^{30}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the kit is a compound having a structure represented by a formula:

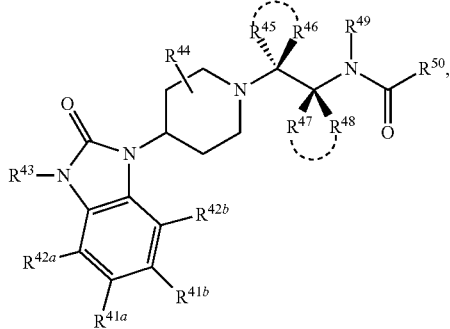

wherein each ---- independently comprises an optional covalent bond; wherein each of $R^{41a}$ and $R^{41b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{42a}$ and $R^{42b}$ is independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein $R^{43}$ comprises hydrogen, an optionally substituted C1 to C6 alkyl, an optionally substituted C3 to C6 cycloalkyl, or a hydrolysable residue; wherein $R^{44}$ comprises eight substituents independently selected from hydrogen, halide, hydroxyl, trifluoromethyl, amino, cyano, nitro, azide, carboxamido, alkoxy, thiol, alkylsulfonyl, and an optionally substituted C1 to C6 organic residue; wherein each of $R^{45}$ and $R^{46}$ independently comprises hydrogen, trifluoromethyl, carboxamido, alkylsulfonyl, an optionally substituted C1 to C6 alkyl, or an optionally substituted C3 to C6 cycloalkyl or $R^{45}$ and $R^{46}$, together with the intermediate carbon, comprise an optionally substituted C3 to C6 cycloalkyl; wherein each of $R^{47}$ and $R^{48}$ independently comprises hydrogen, trifluoromethyl, carboxamido, alkylsulfonyl, an optionally substituted C1 to C6 alkyl, or an optionally substituted C3 to C6 cycloalkyl or $R^{47}$ and $R^{48}$, together with the intermediate carbon, comprise an optionally substituted C3 to C6 cycloalkyl; wherein $R^{49}$ comprises hydrogen, an optionally substituted C1 to C6 alkyl, an optionally substituted C3 to C6 cycloalkyl, or a hydrolysable residue; wherein $R^{50}$ comprises an optionally substituted C1 to C16 organic residue selected from alkyl, aryl, heteroaryl, cycloalkyl, heterocycloalkyl, cycloalkenyl, and heterocycloalkenyl, or a pharmaceutically acceptable salt, hydrate, solvate, or polymorph thereof, thereby treating the subject for viral infection.

In a further aspect, the phospholipase D inhibitor of the kit is a compound selected from: trans-diethylstilbestrol, resveratrol, honokiol, SCH420789, presqualene diphosphate, raloxifene, 4-hydroxy tamoxifen, 5-fluoro-2-indoyl deschlorohalopemide, and halopemide, or a pharmaceutically acceptable salt, hydrate, solvate, or polymorph thereof, thereby treating the subject for viral infection.

In a further aspect, the phospholipase D inhibitor of the kit is a compound selected from:

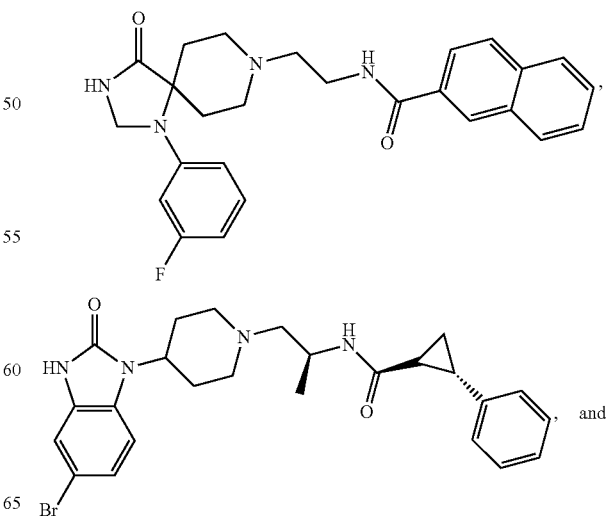

-continued

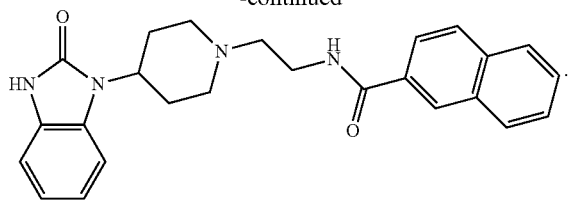

J. Experimental

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. PLD Inhibitor Compounds

The representative PLD inhibitor compounds used in the various studies described herein below are shown below in Table 1, and were synthesized as previously described (Lavieri et al. (2010) J. Med. Chem. 53 6709; and Scott, S. A., et al. (2009) Nat. Chem. Biol. 5:108-117). The inhibitor activity of these representative PLD inhibitors is provided in Table 2.

TABLE 1

| No. | Structure | Reference Codes | Chemical Name |
|---|---|---|---|
| 1 | | JWJ; VU0364739 | N-(2-(1-(3-fluorophenyl)-4-oxo-1,3,8-triazaspiro[4.5]decan-8-yl)ethyl)-2-naphthamide |
| 2 | | EVJ; VU0359595 | (1R,2S)-N-((S)-1-(4-(5-bromo-2-oxo-2,3-dihydro-1H-benzo[d]imidazol-1-yl)piperidin-1-yl)propan-2-yl)-2-phenylcyclopropane carboxamide |
| 3 | | 5WO; VU0155056 | N-(2-(4-(2-oxo-2,3-dihydro-1H-benzo[d]imidazol-1-yl)piperidin-1-yl)ethyl)-2-naphthamide |

TABLE 2

| No. | Reference Codes | PLD1* (IC$_{50}$, nM) | PLD2* (IC$_{50}$, nM) | PLD1** (IC$_{50}$, nM) | PLD2** (IC$_{50}$, nM) |
|---|---|---|---|---|---|
| 1 | JWJ; VU0364739 | 1,500 | 20 | 7,400 | 100 |
| 2 | EVJ; VU0359595 | 3.7 | 6,400 | 15 | 1,100 |
| 3 | 5WO; VU0155056 | 21 | 380 | 80 | 240 |

*Cellular assay
**In vitro enzyme assay

2. In Vitro PLD Activity Assay

In vitro PLD activity is measured with an exogenous substrate assay as previously described (Brown, H. A. et al. (1993) Cell 75:1137-1144). Briefly, PLD activity was measured as the release of [methyl-3H]choline from [choline-methyl-$^3$H]dipalmitoylphosphatidylcholine. PLD enzyme (PLD1=3 nM, or PLD2=15 nM) is reconstituted with phospholipid vesicle substrates. Lipid solutions were dried and resuspended, and small unilamellar vesicles were prepared by bath sonication. All assays were performed at 37° C. with agitation for 30 min. Reactions were stopped by addition of trichloroacetic acid and bovine serum albumin. Free [methyl-$^3$H]choline was separated from precipitated lipids and proteins by centrifugation and analyzed by liquid scintillation counting. Raw data were normalized and are presented as percent total activity. Experiments were performed in triplicate.

3. Cell Culture

Calu-1 cells were purchased from American Type Culture Collection (Manassas, Va.) and are maintained in DMEM supplemented with 10% FBS, 100 μg/mL penicillin-streptomycin and 0.25 μg/mL amphotericin. HEK293 cells stably expressing GFP tagged human PLD2A were generated by the inventors. To sustain selection pressure low passage-number HEK293-gfpPLD2 cells were maintained in DMEM supplemented with 10% FBS, 100 μg/mL penicillin-streptomycin, 2 μg/mL puromycin and 600 μg/mL G418. All HEK293-gfpPLD2 experiments were done on tissue culture plates that had been coated with low levels of poly-lysine. All cells were maintained in a humidified 5% $CO_2$ incubator at 37° C. A549 cells were obtained from American Type Culture Collection (ATCC CCL-185; Manassas, Va.) and were maintained in DMEM media supplemented with 5% FBS, 100 U/mL penicillin, and 100 μg/mL streptomycin.

4. Endogenous PLD Activity Assay

Endogenous PLD activity was determined using a modified in vivo deuterated 1-butanol PLD assay ((Brown, H. A. et al. Methods Enzymol. (2007) 434:49-87). Calu-1 cells are serum-starved 18 h before experiment, whereas aside the stable HEK293-gfpPLD2 cells are not. Cells are pretreated with PLD inhibitor or DMSO for 5 min at room temperature (20° C.). After pretreatment, Calu-1 cells were treated with 1 mM PMA+0.3% (v/v) 1-butanol-d$_{10}$ and either PLD inhibitor or DMSO, or medium alone for 30 min at 37° C. HEK293-gfpPLD2 cells were treated in the presence of 0.3% 1-butanol-d$_{10}$ and PLD inhibitor or vehicle. After treatment, samples are extracted and internal standard is added. The resulting lipids were dried and resuspended in MS solvent. Samples were directly injected into a Finnigan TSQ Quantum triple quadrupole MS, and data are collected in negative ion mode. Data were analyzed as a ratio of major phosphatidylbutanol-d$_9$ lipid products and internal standard. Background signal was subtracted using cells not treated with 1-butanol-d$_{10}$ as a negative control. The data were then expressed as percent of PMA-stimulated PLD activity or as percent of basal PLD activity. Experiments were performed in triplicate.

5. Cell-Based Assay of Influenza Infection

The ability of representative disclosed to block influenza infection was assessed in a cell-based assay using A549 human epithelial cells (ATCC CCL-185). Briefly, a spatial infection model for testing drug efficacy and influenza replication was adapted from Lam et al. (Biotechnol Bioeng. (2005) 90(7):793-804). A549 cells were plated on Lab-Tek™ two well Permanox slides (Nalge Nunc International, Rochester, N.Y.) and allowed to become nearly confluent during an overnight incubation. Culture media used in these experiments was as described above, i.e. in DMEM supplemented with 5% fetal bovine serum, 100 U/ml penicillin, and 100 μg/ml streptomycin. Following overnight incubation, the cells were then washed three times with PBS, and 2 ml of a binary mixture of 2% agar and 2×MEM (with 100 U/ml penicillin, 100 μg/ml streptomycin, 2 mM L-glutamine, and 1×MEM vitamin solution (e.g. Gibco Cat. No. 111120 for 100× solution) was added to the cells. Compounds were added to the overlay at the appropriate concentration, e.g. 10 μM was used in the experiment shown in FIG. 2. Cells were incubated with compound at 37° C. for 1 hour. Then a glass Pasteur pipette was used to create a reservoir in the overlay into which 4 μl of diluted virus was added. The cultures were returned to 37° C. for the duration of the experiment.

After the infection period, the overlay was gently removed, and the cells were fixed with 4% formaldehyde. Then cells were permeabilized with 0.3% Triton X-100 followed by a blocking buffer of 1% bovine serum albumin (BSA) in phosphate-buffered saline (PBS). The presence of influenza virus in cells was detected using a primary antibody that was a monoclonal antibody specific to influenza A nucleoprotein, and an anti-mouse secondary antibody conjugated to an appropriate fluorochrome conjugated. Nuclei were stained with DAPI. Glass coverslips were mounted to the slides using ProLong® Gold (Life Technologies, Inc., Grand Island, N.Y.).

Photomicrograph mosaics of the infection were obtained using Nikon Eclipse Clsi Confocal Microscope (Nikon Instruments, Inc., Melville, N.Y.) and analyzed with the NIS Elements software (Nikon Instruments, Inc., Melville, N.Y.). Infected cells in the cultures were quantified using the Object Count feature of the NIS Elements program. It should be understood that data were acquired in the different experiments using the same software settings. GraphPad Prism was used to process data, and statistical analysis carried out using ANOVA or t-test methods to determine the significance of observations.

Figure 2:
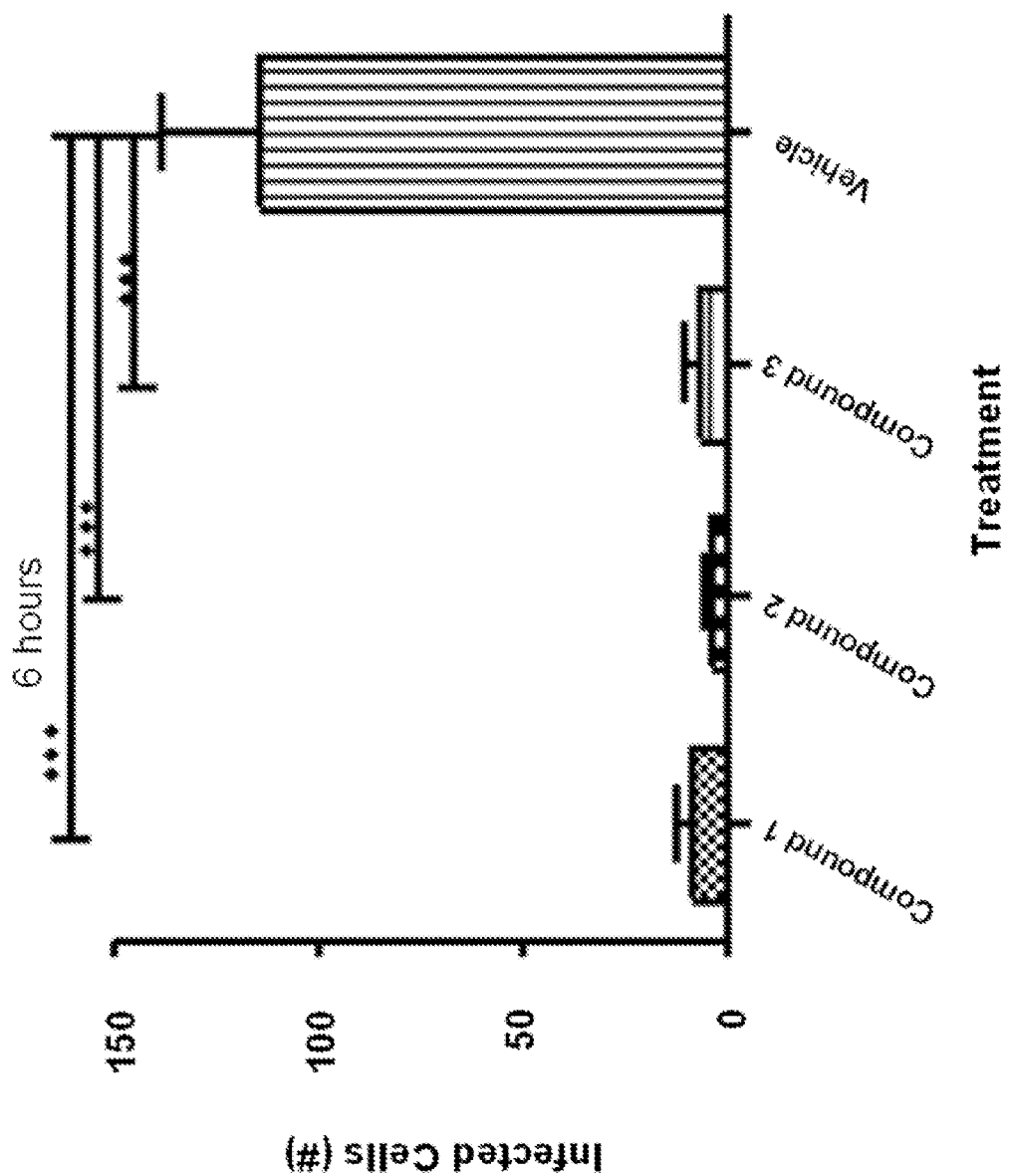
FIG. 2 shows representative data for representative disclosed compounds wherein the compounds inhibit influenza infection in A549 airway cells.

Data in FIG. 2 show that the three compounds tested blocked infection of A549 cells compared to vehicle. The cells were exposed to 10 μM of the specified compound. The three compounds indicated in FIG. 2 are as follows: Compound 1, N-(2-(4-(2-oxo-2,3-dihydro-1H-benzo[d]imidazol-1-yl)piperidin-1-yl)ethyl)-2-naphthamide (5WO); Compound 2: N-(2-(1-(3-fluorophenyl)-4-oxo-1,3,8-triazaspiro[4.5]decan-8-yl)ethyl)-2-naphthamide (JWJ); and Compound 3: (1R,2S)—N—((S)-1-(4-(5-bromo-2-oxo-2,3-dihydro-1H-benzo[d]imidazol-1-yl)piperidin-1-yl)propan-2-yl)-2-phenylcyclopropanecarboxamide (EVJ). In the figure, statistical significance is indicated from paired analysis as follows: *=p<0.05, =p<0.01, and *=p<0.001.

6. In Vivo Model of Influenza Infection

A mouse model of influenza infection was used to test the in vivo efficacy of representative disclosed compounds. Compounds were administered at 30 mg/kg and the mice were infected with PR8 influenza A virus. Briefly, C57BL/6J mice (female 8- to 10-wk-old; purchased from The Jackson Laboratory and held under pathogen-free conditions at St. Jude Children's Research Hospital) were used in these studies. Mice were anesthetized by i.p. injection with Avertin (2,2,2-tribromethanol; prepared in-house) before intranasal (i.n.) infection with 80% infective dose ($EID_{80}$) units of the PR8 influenza A virus in PBS. Mice were administered either the indicated PLD inhibitor (30 mg/kg) or vehicle intraperitoneal starting at 24 hr per exposure. Compounds were administered twice daily for 7 days and subjects were measured for changes in body weight (FIG. 3) or survival (FIG. 4) as a function of PLD inhibitor administration. Mice were sacrificed if moribund.

Figure 3:
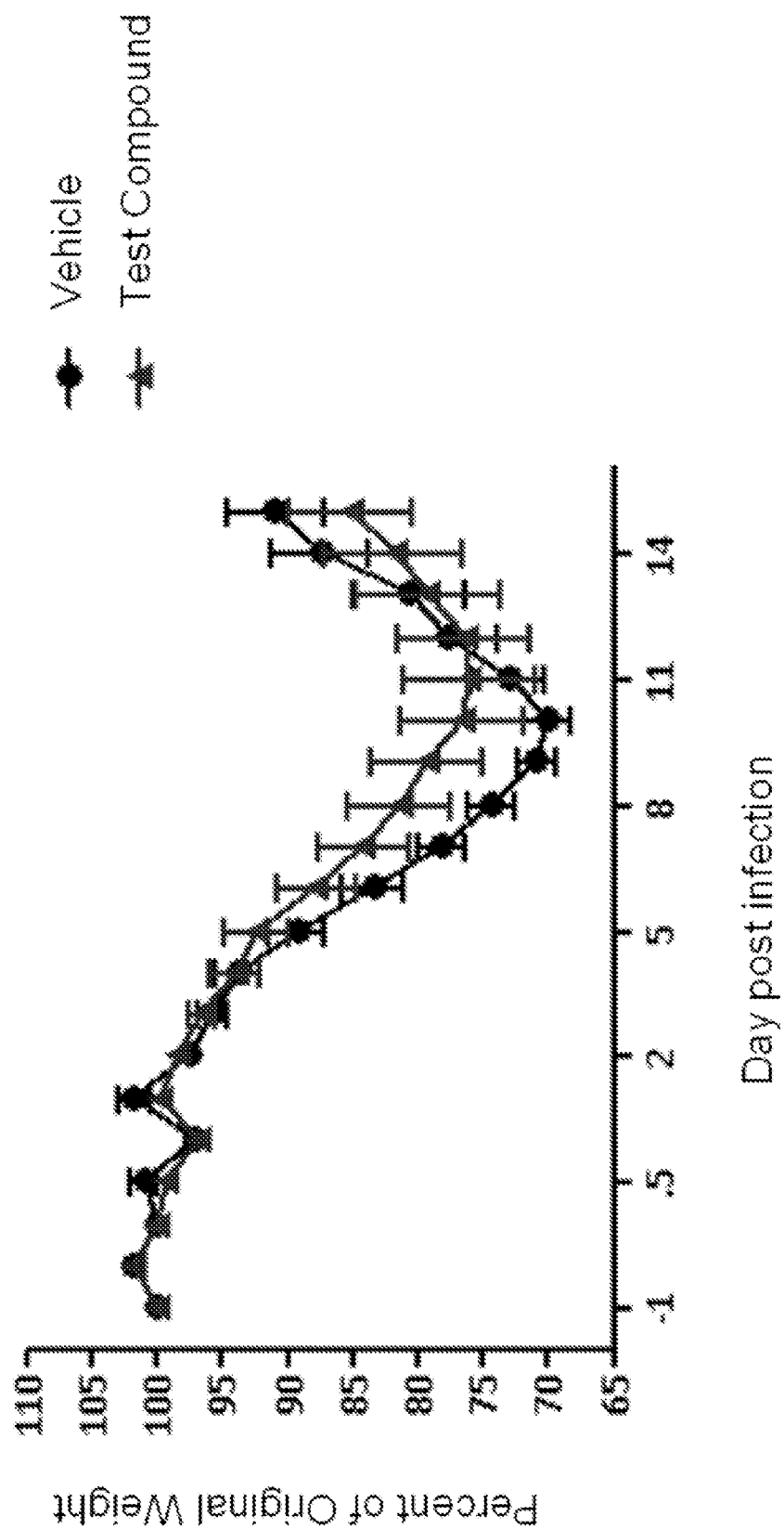
FIG. 3 shows representative data in a mouse model of influenza infection wherein a representative disclosed compound ameliorates weight loss associated with virus infection.
Figure 4:
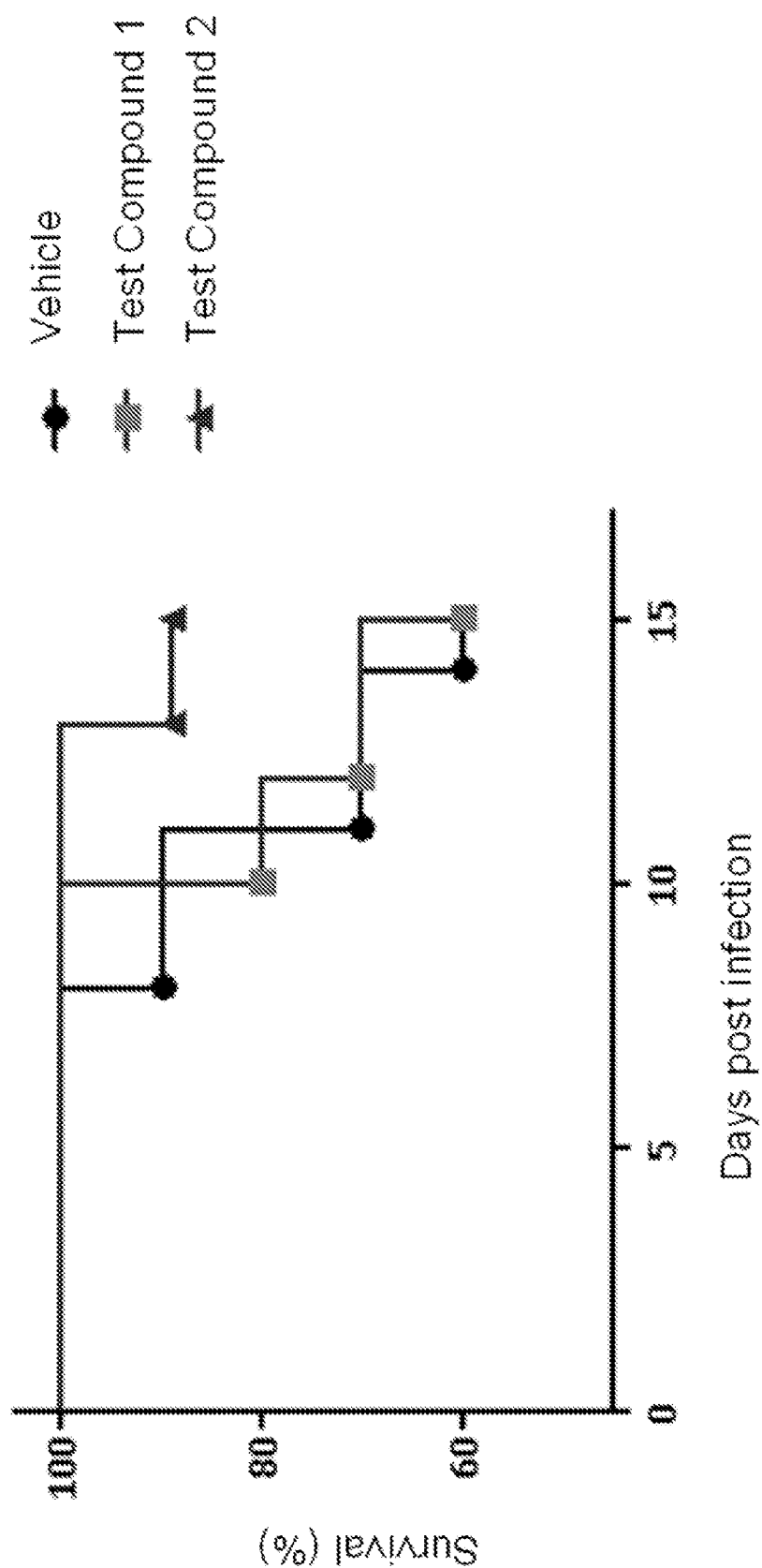
FIG. 4 shows representative data in a mouse model of influenza infection wherein a representative disclosed compounds provide enhanced survival in infected mice.

The data in FIG. 3 shows a trend of the test compound to protect infected mice against weight loss associated with virus infection compared to vehicle (10% Tween 80) through about day 11 post-infection. The test compound used in the study shown in FIG. 3 was (1R,2S)-N-((S)-1-(4-(5-bromo-2-oxo-2,3-dihydro-1H-benzo[d]imidazol-1-yl)piperidin-1-yl)propan-2-yl)-2-phenylcyclopropanecarboxamide. The ability of representative compounds to increase the survival rate of infected is shown in FIG. 4. The test compounds were as follows: Test Compound 1 was N-(2-(1-(3-fluorophenyl)-4-oxo-1,3,8-triazaspiro[4.5]decan-8-yl)ethyl)-2-naphthamide; and Test Compound 2 was (1R,2S)-N-((S)-1-(4-(5-bromo-2-oxo-2,3-dihydro-1H-benzo[d]imidazol-1-yl)piperidin-1-yl)propan-2-yl)-2-phenylcyclopropanecarboxamide. The data in FIG. 4 show that when mice were dosed with 30 mg/kg of the indicated compound that survival improved. The ability of Test Compound 2 to enhance survival was particularly profound at the dose tested.

7. Effect of N-Butanol on Influenza Virus Infection of A549 Cells

The A549 cell-line was used as a model of influenza virus infection as described above. In the representative experiment shown in FIG. 5, the effect of n-butanol on the ability the indicated influenza virus strains to infect A549 cells was determined. Briefly, cells were cultured and infected as described above. The cells were treated with either tert-butanol or n-butanol (0.6% v/v for either alcohol) for one hour prior to infection with the indicated virus. Virus was infected at an MOI of 1. Twenty-four hours after infection, cells were fixed and processed for immunofluorescence to determine the number of infected cells. Differences determined after an unpaired, two-tailed t-test (* $p<0.05$;  $p<0.01$; * $p<0.001$). Data are from three independent experiments, each conducted in quadruplicate.

It should be understood, as described above, that PLD catalyzes a transphosphatidylation reaction wherein a primary alcohol is a substrate in this reaction. Exposure of cells to a primary alcohol, e.g. n-butanol, would bias the enzymatic activity of PLD to the transphosphatidylation reaction and significantly decrease the ability of the PLD to catalyze the normal cellular reaction, i.e. hydrolysis of phosphatidylcholine to yield phosphatidic acid and choline.

Figure 5:
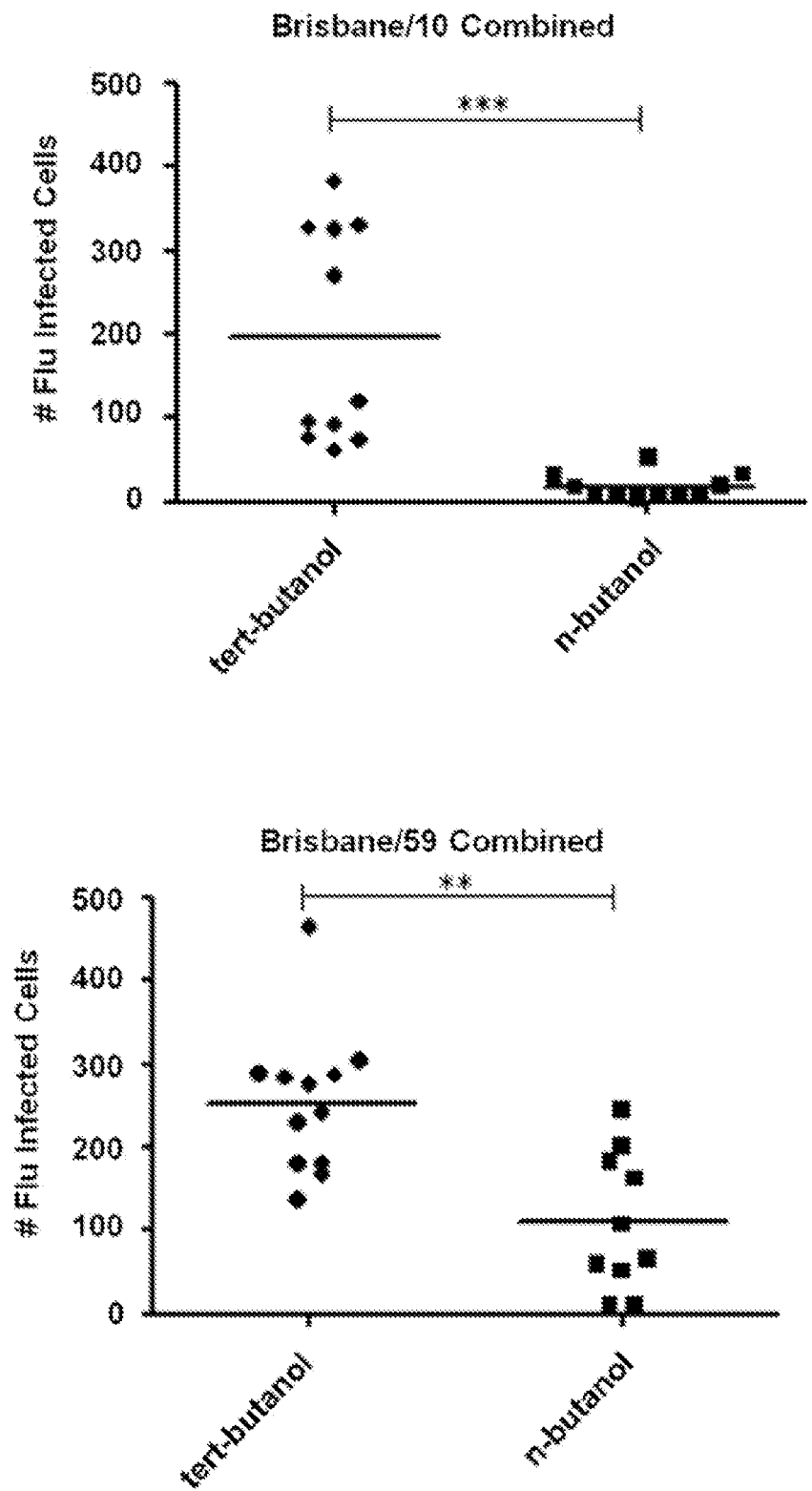
FIG. 5 shows representative data for the effect on n-butanol on infection of A549 cells by different influenza virus strains.
Figure 5:
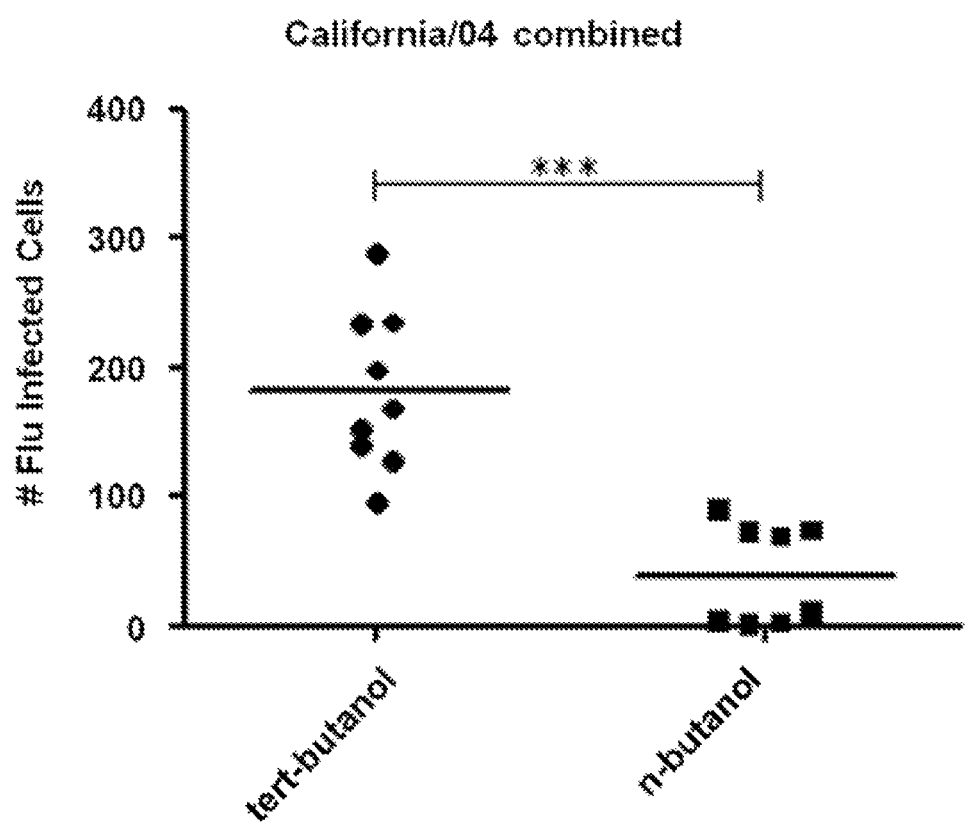

The data in FIG. 5 show that tert-butanol (which is not a substrate in the transphosphatidylation reaction catalyzed by PLD) does not have any effect on virus infection of A549 cells, whereas n-butanol (which is a substrate in transphosphatidylation reaction) has a significant effect on virus infection of A549 cells. Without wishing to be bound by a particular theory, these data suggest that formation of phosphatidic acid via PLD is a key event in the infection process. These data suggest that PLD can be a key target in blocking influenza infection.

8. Mass Spectrometry-Based Lipid Analysis

A549 cells infected with California/04/2009 virus at 1 multiplicity of infection (MOI) were monitored for changes in glycerophospholipids and phosphatidylbutanol in a time course (0, 1, 2, 4, and 6 h post infection) following treatment with 10 μM of PLD inhibitors VU0359595 (EVJ) and VU0364739 (JWJ).

For analysis of cellular lipids, A549 cells were serum starved for 1 hour, infected at 1 MOI with A/California/04/2009, and then maintained in 6-well plates for the desired treatment times. Mock-infected and California/04/2009-infected cells were harvested at various times after infection and treatment with PLD inhibitors. To extract phospholipids, ~1×106 cells were washed with ice-cold PBS, scraped into 1 ml of ice-cold PBS and aliquots were taken for protein analysis. After centrifugation and PBS aspiration, the pellet was extracted with 800 µl ice-cold 0.1 N HCl:MeOH (1:1) and 400 µl of ice-cold CHCl3 (modified Bligh-Dyer extraction). Following vortexing for 1 min at 4° C. phases were separated by centrifugation in a microfuge (18,000×g for 5 min, 4° C.). The lower organic layer was isolated, synthetic odd-carbon phospholipids (four per each phospholipid class) were added as internal standards, and solvent was evaporated. The resulting lipid film was dissolved in 100 µl of isopropanol (IPA): hexane:100 mM $NH_4COOH$ (aq) 58:40:2 (mobile phase A) (2). Samples containing n-butanol were extracted similarly and 5 µl of 10 µg/ml 32:0 phosphatidylmethanol (PtdMeOH) was added as an internal standard before analysis.

Mass spectrometric analysis and quantitation were performed essentially as described (Ivanova, P. T., et al. Methods Enzymol. 432, 21-57 (2007); Myers, D. S., Ivanova, P. T., Milne, S. B., and Brown, H. A. Biochim. Biophys. Acta 1811, 748-757 (2011)). MDS SCIEX 4000QTRAP hybrid triple quadrupole/linear ion trap mass spectrometer (Applied Biosystems, Foster City, Calif.) was used for the analyses. Coupled to it was a Shimadzu HPLC system (Shimadzu Scientific Instruments, Inc., Columbia, Md.) consisting of a SCL 10 APV controller, two LC 10 ADVP pumps and a CTC HTC PAL autosampler (Leap Technologies, Carrboro, N.C.). Phospholipids were separated on a Phenomenex Luna Silica column (Phenomenex, Torrance, Calif.) (2×250 mm, 5 µm particle size) using a 20 µL sample injection. A binary gradient consisting of IPA:Hexane: 100 mM $NH_4COOH$ (aq) 58:40:2 (mobile phase A) and IPA:Hexane: 100 mM $NH_4COOH$ (aq) 50:40:10 (mobile phase B) was used for the separation. Instrumentation parameters and solvent gradient were as described in (Ivanova et al., ibid).

Time courses were performed in two independent experiments each in triplicate. Statistical analysis was by two-way ANOVA with Bonferroni's post test.

9. Spatial Infection Model

A spatial infection model for testing drug efficacy and influenza replication was adapted from Lam, V., Duca, K. A., and Yin, J. (2005) 90(7):793-804. Briefly, A549 cells in DMEM supplemented with 5% FBS and 100 U/ml penicillin/streptomycin were placed on Lab-Tek two well Permanox slides and allowed to become nearly confluent during an overnight incubation. The cells were then washed three times with PBS, and 2 ml of a binary mixture of 2% agar and 2×MEM (MEM with 0.2% BSA, sodium bicarbonate, 2× vitamins, 2× l-glutamine, and 2× penicillin/streptomycin) was added to the cells. Compounds being tested were added to the overlay at the appropriate concentration. Cells were allowed to rest at 37° C. for 1 hour. Then a glass Pasteur pipette was used to create a reservoir in the overlay into which 4 µl of diluted virus was added. The cultures were returned to 37° C. for the duration of the infection.

After the infection, the overlay was gently removed, and the cells were fixed with 4% formaldehyde. Then cells were permeabilized with 0.3% Triton X-100 followed by a blocking buffer of 1% BSA in PBS. Cultures were probed with a monoclonal antibody specific to Influenza A nucleoprotein, and appropriate fluorophore conjugated secondary antibodies were used to identify the infected cells. To stain nuclei, DAPI was used. Glass coverslips were mounted to the slides using ProLong Gold.

Photomicrograph mosaics of the infection were created with a Nikon C1Si and analyzed with the NIS Elements software. Infected cells in the cultures were quantified using the Object Count feature of the NIS Elements program, and data was always acquired using the same settings. GraphPad Prism was used to process data, and ANOVA with Dunnett's post test was used when testing PLD inhibitors. When comparing alcohol treatments, t-tests were used to determine the significance of observations. Data is represented as mean±SEM and *=$p<0.05$, =$p<0.01$, and *=$p<0.001$, ****=$p<0.0001$.

10. Diffuse Infection Model

A549 cells were seeded onto chamber slides and allowed to adhere overnight. The cells were washed with PBS, and serum-free medium containing treatment was added to the cells. After one hour of treatment, the medium was removed and replaced with serum-free medium containing treatment and 0.05 MOI influenza virus. The infected cultures were kept at 4° C. for 15 minutes before being incubated at 37° C. At appropriate times, cultures were removed and fixed with 0.4% formaldehyde and processed for microscopy as above. Z stacks were acquired using a Zeiss LSM 510 microscope, and images were analyzed with ImageJ (Java-based software available from NIH). Data was processed as above.

11. Phospholipase D (PLD) Knockdown in Cultured Cells

A549 cells were transfected with siRNA (Life Technologies, Inc.) specific to PLD isoforms using NeoFX (Life Technologies, Inc.) and were infected with 1 MOI A/Brisbane/59/2007 for 24 hours. Knockdown was confirmed with gene specific Taqman® assays and the $2^{\Delta\Delta Ct}$ method using GAPDH to normalize.

12. Toxicity Assessment in Cells

Annexin V and propidium iodide staining was conducted on cells that had been treated with 10 µM of drugs or DMSO control for 24 hours. Data was collected using a FACScalibur. Annexin V staining was carried as previously described by Keating, R., et al., J. Immunol. (2007) 178(5):1737-1745.

13. Immunofluorescence Methods

Samples were fixed in 4% formaldehyde, permeabilized with 0.3% Triton X-100, and then exposed to antisera targeting proteins of interest and corresponding fluorescent secondary antibodies alongside DAPI to visualize nuclei. Focal infections were imaged and processed using a Nikon C1Si and NIS Elements software. Confocal images were captured with a Zeiss LSM 510 NLO Meta and analyzed with Zeiss Zen 2011 software and ImageJ.

14. $TCID_{50}$ Determination

Cultures of A549 cells were infected with 1 MOI A/California/04/2009 for 8 hours. Monolayers of MDCK cells were prepared in 96 well plates. A549 supernatant was diluted into the MDCK supernatant (Infection medium with 1 mg/ml TPCK trypsin). After 3 days at 37° C., the MDCK were stained and $TCID_{50}$ was calculated using the Reed-Meunch method. The A549 cells were fixed and processed for immunofluoresence. Briefly, 36 fields of each sample were collected and the number of nucleoprotein (NP) positive cells was divided by the number of nuclei in the images to generate a ratio of infected cells in the cultures.

15. Animal Studies

Female C57Bl/6 8-10 weeks old were anesthetized and infected with 4000 $EID_{50}$ A/Puerto Rico/8/1934. Mice were weighed and monitored daily; tissues were collected at the specified times and kept at −80° C. for analysis. For drug treatment, mice were given 13 mg/kg JWJ or Vehicle (10% DMSO, 90% PEG) every 8 hours from day −1 to day 3 after infection. The drugs were then given twice a day until day 10 after infection.

Mice were anesthetized with 2,2,2-tribromoethanol (Avertin) prior to intranasal (i.n.) infection with 8000 $EID_{50}$ PR8. Illness was monitored by daily weighing after virus challenge. Mice were sacrificed if moribund. Data collected were weight change as percent of original weight and survival. GraphPad Prism was used to analyze data. Changes in weight were compared using a two-way ANOVA with repeating measures and Bonferroni's post test; data is expressed as mean±SEM. Survival differences were examined with both Log-Rank test and Gehan-Breslow-Wilcoxon Test. *=p<0.05, =p<0.01, and *=p<0.001, ****=p<0.0001 for all statistical results.

Infected animal lungs were titered using a plaque assay. Supernatant from infected cultures were titered using $TCID_{50}$, and immunofluoresence was used to enumerate the number of infected cells in a sample.

RNA was isolated from lungs and used in a reverse transcriptase PCR. The cDNA was then used in Gene specific Taqman assays to determine host gene expression, and the differences in expression were quantified using the $2^{\Delta\Delta Ct}$ method. The same amount of RNA was used in each reaction and samples were run in triplicate.

16. Plaque Assay

The right lung from infected mice was washed with Hank's Balanced Salt Solution and flash frozen after excision. Monolayers of Madin-Darby Canine Kidney (MDCK) cells were grown on 6 well plates. The infected lungs were homogenized in infection medium (MEM containing 0.1% BSA, sodium bicarbonate, vitamins, 1-glutamine, and penicillin/streptomycin). 10 fold dilutions of the homogenized lungs were inoculated on the MDCK cells, allowed to adhere at 4° C. for 15 minutes, and then incubated at 37° C. for 1 hour. The homogenate was removed and overlain with the same agar based medium used in the spatial infection model, except containing 1 mg/ml TPCK treated trypsin. After 72 hours at 37° C., the overlay was removed, and the monolayer was stained with a 10% formaldehyde and 1 g/L crystal violet solution to allow counting of plaques in the monolayer.

17. PCR Analysis of Host Response

The left lungs of the mice used for plaque assay (as described) were collected in RNAlater® (QIAgen, Inc., Valencia, Calif.). The lung was homogenized and RNA was extracted using the RNeasy® kit (QIAgen, Inc.). Briefly, 250 ng of RNA was used in an iScript® (Bio-Rad Laboratories, Inc., Hercules, Calif.) Reverse Transcription reaction to prepare cDNA, and 2 μl of the cDNA thus generated was used in gene specific Taqman® assays (Life Technologies, Inc.). Each reaction was done in triplicate. The $2^{\Delta\Delta Ct}$ method was used to calculate the relative quantification of mRNA levels, and samples were compared to an uninfected mouse.

18. Lipid Analysis of Airway Epithelial Cells

Figure 6:
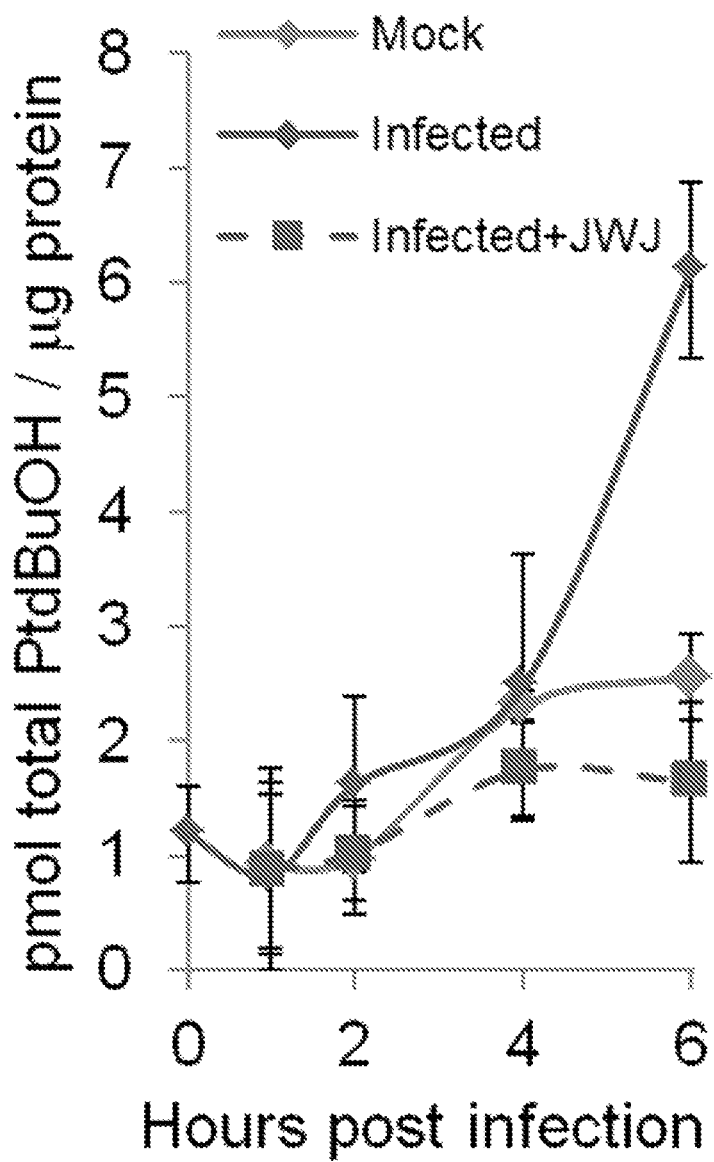
FIG. 6 shows representative data for phosphatidylbutanol (PtdBuOH) in A549 cells mock-infected or infected with influenza virus and then left untreated or treated with a representative PLD inhibitor.

Lipidomic analysis of A549 airway epithelial cells infected with strains of influenza showed systematic increases in phosphatidylbutanol (PtdBuOH), a lipid product of the transphosphatidylation reaction of the PLD enzymes (FIG. 6). Other lipid species (see FIGS. 10 and 11) failed to show significant changes as a function of infection alone when grouped together by class. Without wishing to be bound by a particular theory, PLD activity may be an important lipid signaling event. Moreover, without wishing to be bound by a particular theory, the time dependent increase in PtdBuOH accumulation is consistent with a potential role for host cell PLD in viral entry and infectivity.

Infection with California/04/2009 leads to elevated formation of PtdBuOH by 6 hours post-infection, which is inhibited by phospholipase D (PLD) inhibitor VU0364739 (FIG. 6). Addition of primary alcohol (n-butanol) leads to formation of PtdBuOH by transphosphatidylation instead of phosphatidic acid in the reaction of PLD with phospholipids.

The data shown in FIG. 6 are the mean±SEM of two experiments each in triplicate. The various treatments are as indicated in the figure (mock infection; and cells infected with California/04/2009 that were either untreated or treated with 10 μM PLD2-selective inhibitor compound VU0364739 at t=−1 (dashed line). A two-way ANOVA with Bonferroni's post test was used to compare differences in the time courses and yielded p<0.0001 across treatments. Post-test results (* p<0.05 and *** p<0.001) indicate differences between infected and infected+VU0364739.

Figure 10:
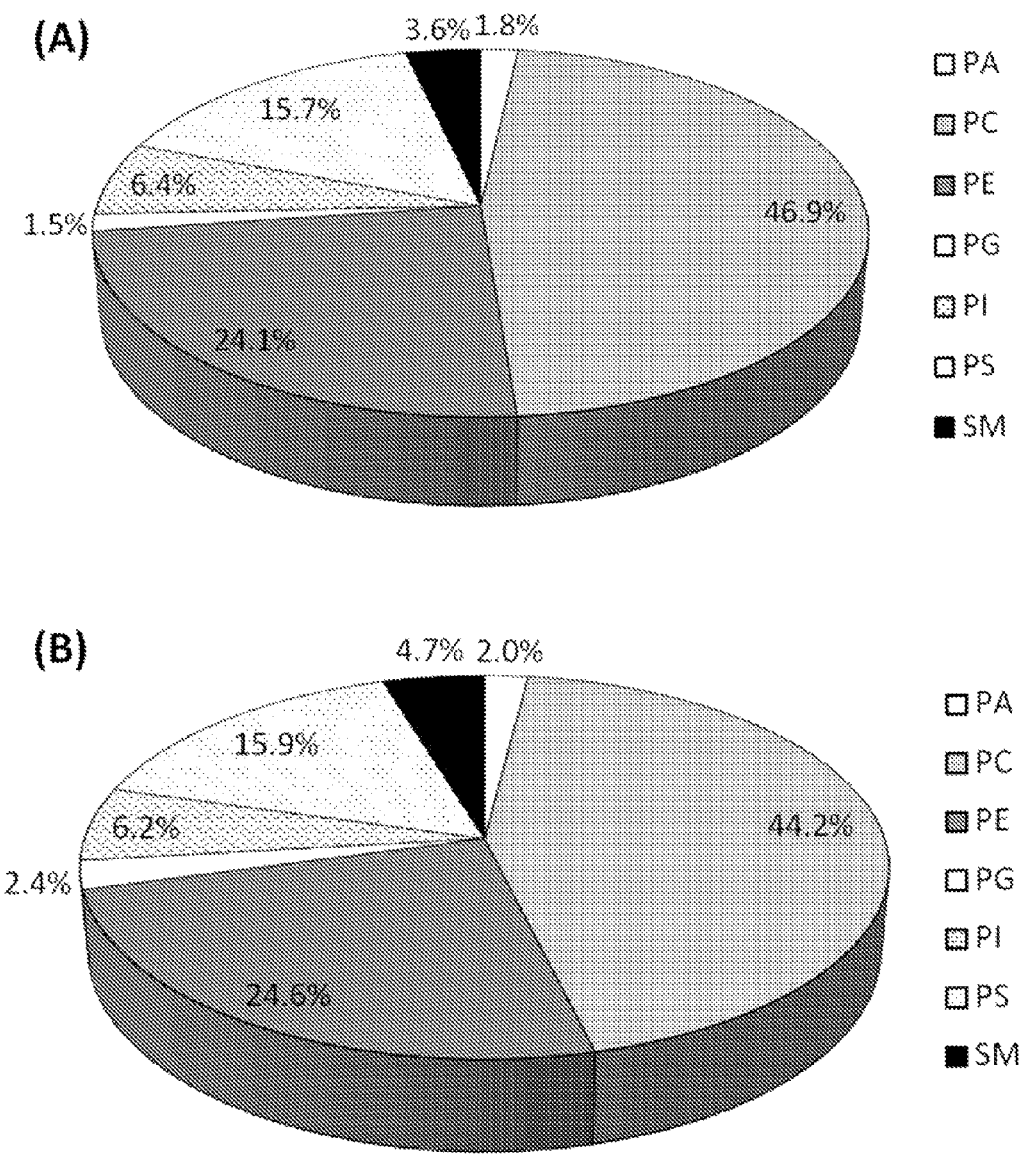
FIG. 10 shows representative data on the distribution of phospholipid classes by headgroup in A549 cells following infection with influenza virus.
Figure 10:
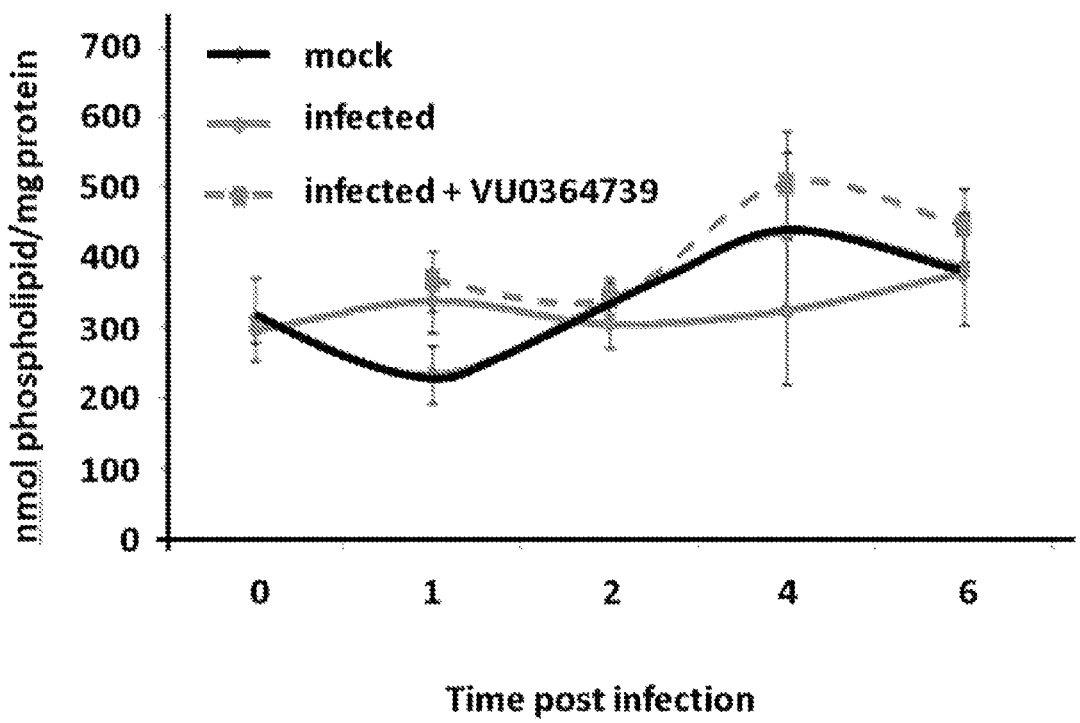

The distribution among glycerophospholipid (GPL) classes is relatively unchanged during infection by California/04/2009 (FIG. 10). The ratio between the largest classes represented (PC, PE) also remains stable over time. There is a roughly two-fold increase in the amount of GPL per unit protein in each class by 6 h and this can be compared to the larger fold increase in phosphatidylbutanol at that time (FIG. 6). For GPL classes and individual species (FIGS. 11 and 16), there is little difference between mock, infected, and infected+PLD inhibitors at most time points. This is true for phosphatidic acid (PA) species as well. Some important exceptions include phosphatidylglycerol (PG) and certain major species of short chain lysophosphatidylinositol and lysophosphatidylcholine, which show increases with the PLD2 selective inhibitor at the later time points (4 h and 6 h) and smaller increases at 6 h with the PLD1 selective inhibitor compared to infected cells without inhibitor treatment (see FIG. 12 for 18:0 species of these classes and Table 2 for others). By contrast, species of lysophosphatidylethanolamine, another major lysolipid class, did not show this behavior.

FIG. 10: Shows the distribution of phospholipid classes by headgroup during infection of A549 cells with California/04/2009 for (a) 0 h and (b) 6 h post-infection. The time course of total phospholipid per unit protein (means±SEM) is shown in (c) for mock-infection and California/04/2009-infected cells either untreated or treated with PLD2-selective inhibitor VU0364739 (10 μM).

Figure 11:
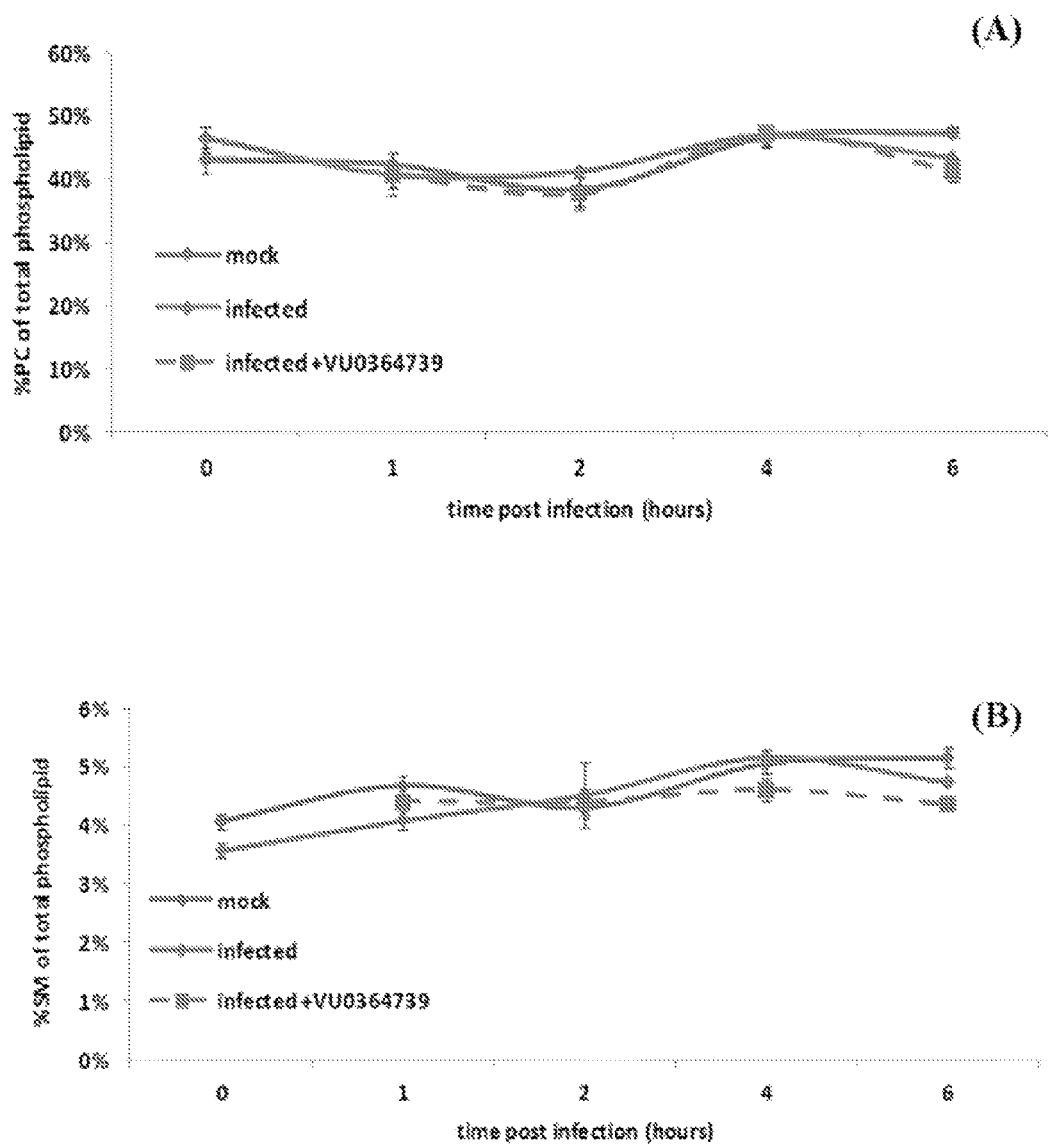
FIG. 11 shows representative data on the time course of each phospholipid class in A549 cells following infection with influenza virus.
Figure 11:
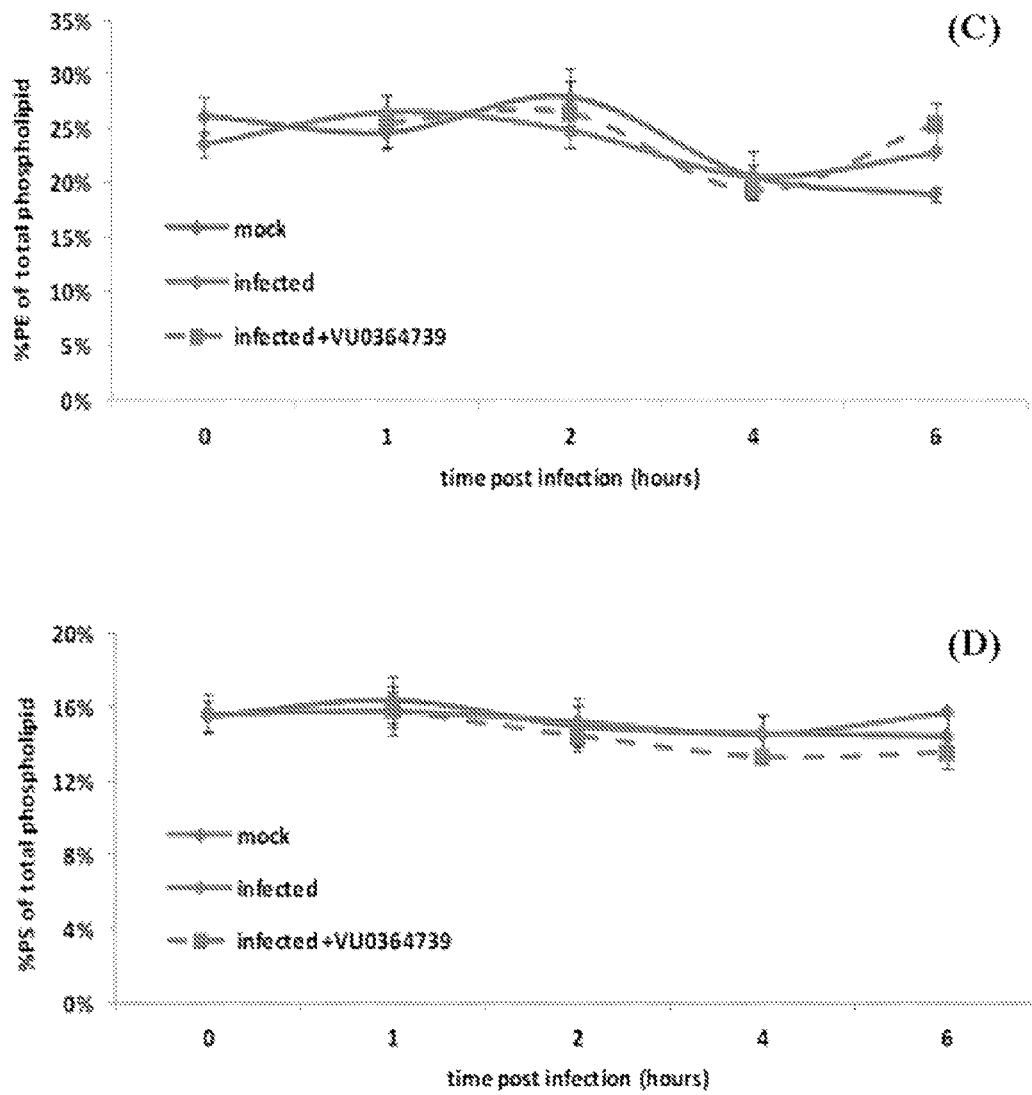
Figure 11:
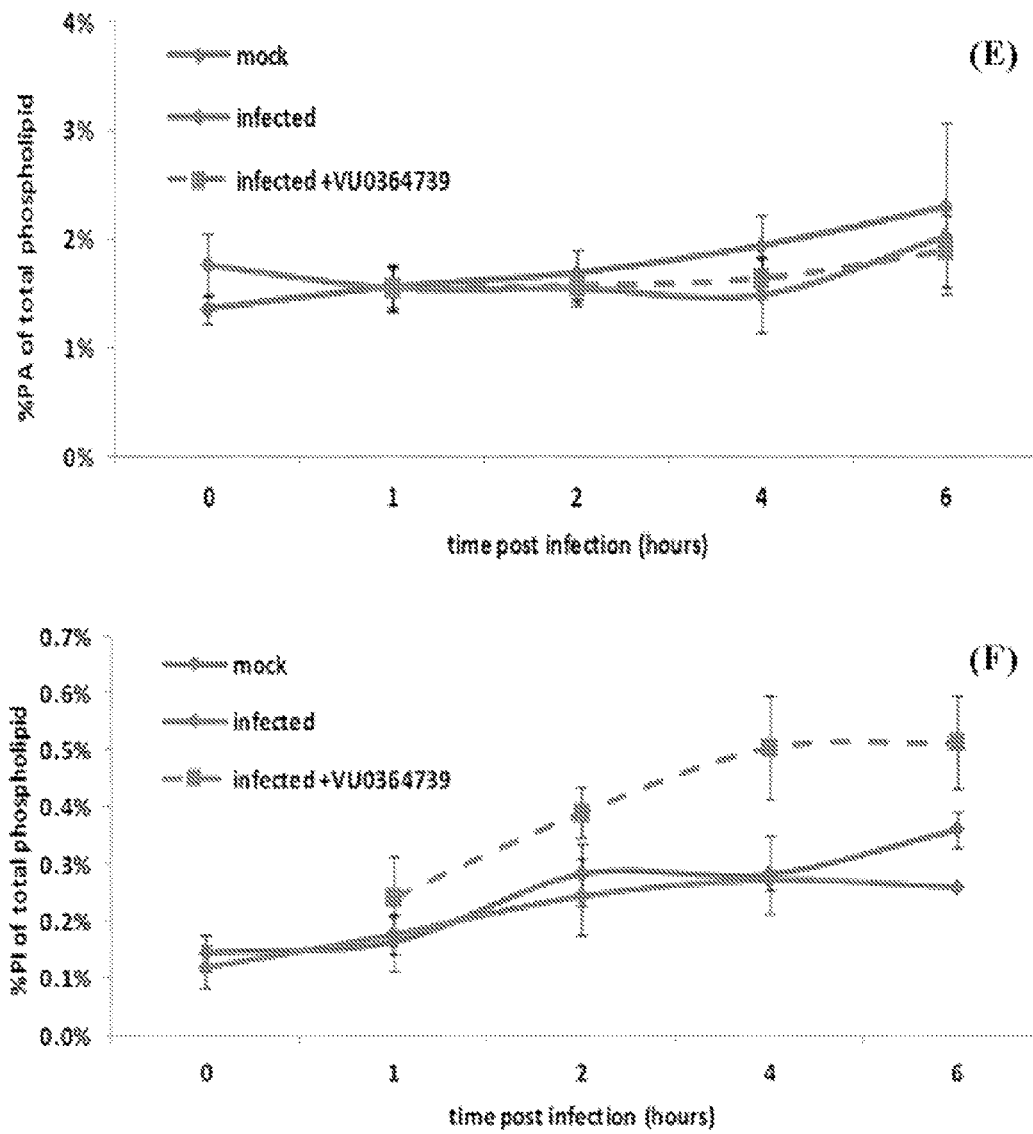
Figure 11:
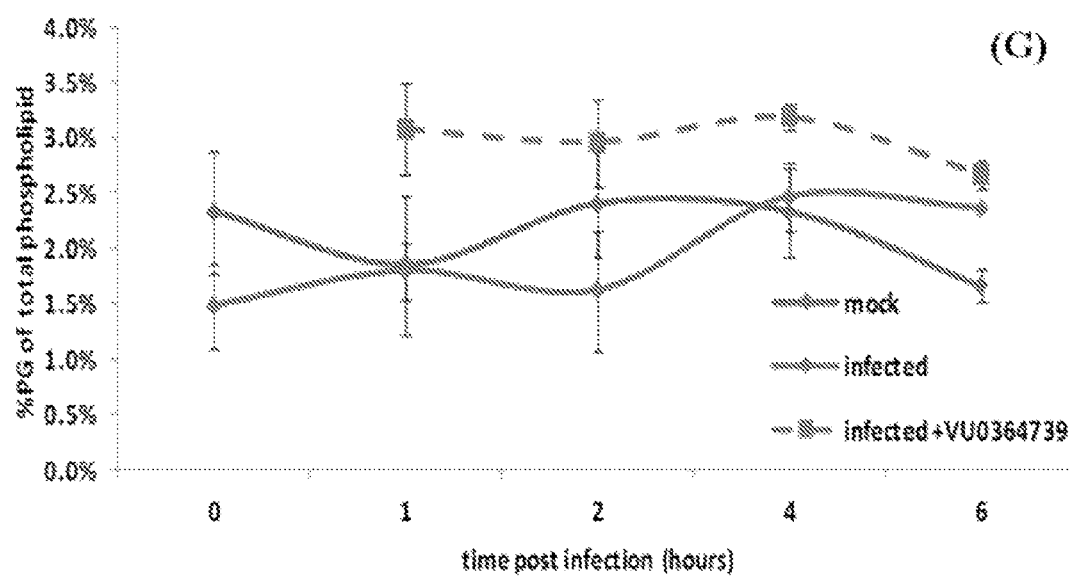

FIG. 11: Shows the time course for each phospholipid class measured in A549 cells, expressed as percentage of total phospholipid for mock-infection and cells infected with California/04/2009 that were either untreated or treated with VU0364739 (10 μM). Means and standard errors shown for (a) PC—phosphatidylcholine, (b) SM—sphingomyelin, (c) PE—phosphatidylethanolamine, (d) PS—phosphatidylserine, (e) PA—phosphatidic acid, (f) PS—phosphatidylinositol, and (g) PG—phosphatidylglycerol.

Figure 12:
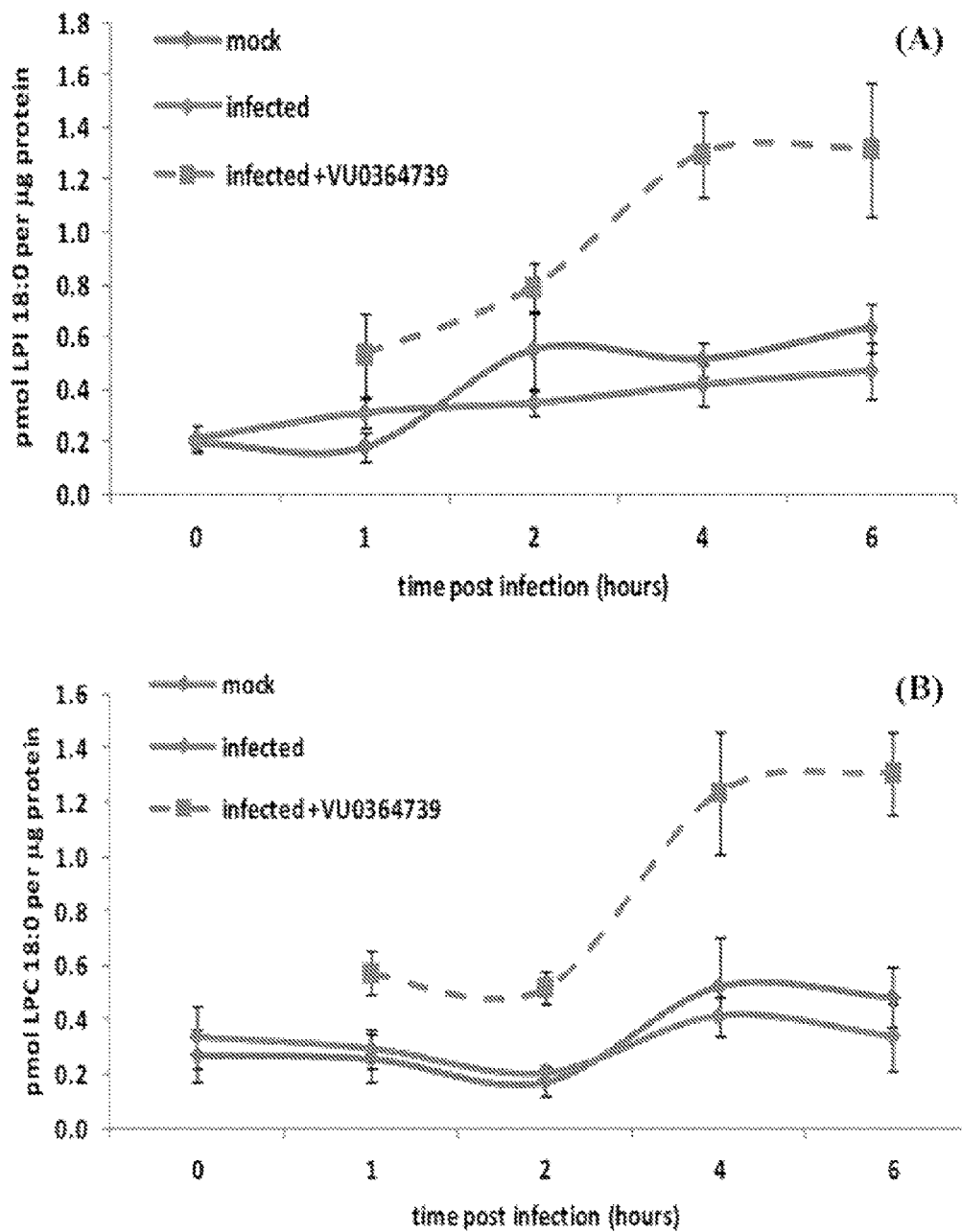
FIG. 12 shows representative data on the time course LPI 18:0 and LPC 18:0 in A549 cells following infection with influenza virus.

FIG. 12: Shows the time course for (a) LPI 18:0 and (b) LPC 18:0 measured in A549 cells that were mock-infected or infected with California/04/2009 that were untreated or treated with VU0364739 (10 μM). Means and standard errors shown.

FIG. 16: Means and standard errors for phospholipid species in A549 cells during infection with California/04/2009 (0, 1, 2, 4, 6 h) and for mock-infected cells. Infected cells were treated either with vehicle or PLD2-preferring inhibitor VU0364739 (10 μM).

19. Protection of A549 Cells from Productive Influenza Infection by PLD Inhibition A focal infection model wherein influenza virus was used to create a lesion in cultured A549 cells, and the infection was allowed to propagate through the culture (FIG. 7a). In order to assess whether a loss of PLD activity can affect influenza infection, A549 cells were treated with PLD isoform specific siRNA and infected with 1 MOI A/Brisbane/59/2007 for 24 hours. Following an approximately 70% reduction in PLD expression, cells treated with PLD2 siRNA and a combination of PLD1 and PLD2 siRNAs were significantly ($p<0.01$) protected from infection (FIG. 7b).

Figure 13:
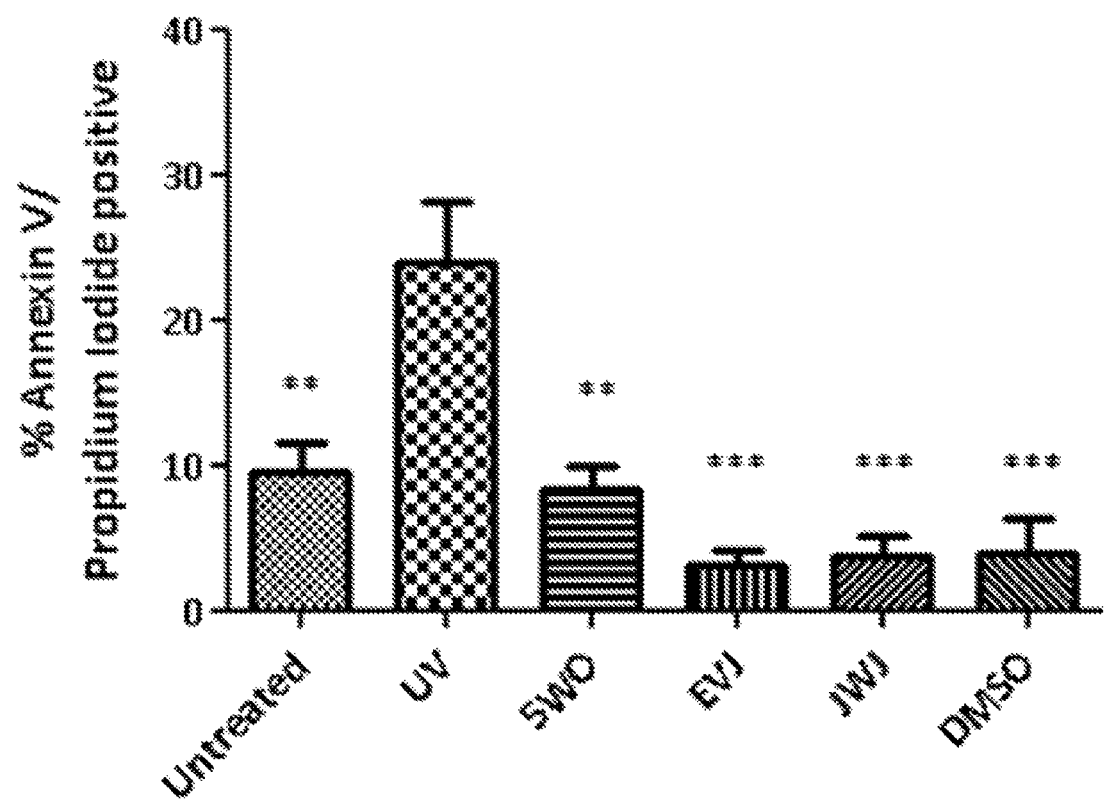
FIG. 13 shows representative data on the lack of toxicity to A549 cells following treatment with PLD inhibitors.

Addition of PLD inhibitors (10 μM) of the present invention to the semisolid overlay resulted in a marked protection from infection of two different clinically relevant influenza viruses, A/Brisbane/59/2007 and A/California/04/2009 (both H1N1) when compared to the DMSO treated cells (FIG. 7c-d). At six hours after infection, cultures that had been treated with PLD inhibitors (5WO, EVJ, and JWJ, see Table 1; 10 μM) and infected with MOI 1 A/Brisbane/59/2007 contained significantly fewer ($p<0.001$) infected cells than cultures treated with the DMSO vehicle (FIG. 7b). At the same time, PLD inhibitors 5WO and JWJ conferred a significant protection ($p<0.001$ for both) from a MOI 1 A/California/04/2009 infection when compared to the vehicle control (FIG. 7c). Using the same experimental model, the data show that at 24 hours post-infection, cells that had been treated with 5WO, EVJ, and JWJ were still significantly protected from A/Brisbane/59/2007 infection ($p<0.001$) (FIG. 7d), but only cultures treated with JWJ were protected ($p<0.05$) from A/California/04/2009 (FIG. 7d). Importantly, no toxicity was observed when using the PLD inhibitors (FIG. 13).

The protective effects of PLD inhibition during an influenza infection were confirmed with more traditional assays as well Inhibition of PLD with 10 μM EVJ or JWJ in MDCK cells lead to less plaque formation in a traditional plaque assay compared to a DMSO treated control (FIG. 14a). Additionally, the protective effects of the drugs were observed in TCID50 and immunofluoresence assays (FIG. 14c-d).

The protective effect of PLD inhibition during an influenza infection was further demonstrated in analysis of cells treated with a primary alcohol. Primary alcohol treatment is the canonical method of abrogating the function of PLD in order to study the effects of the loss of phosphatidic acid. Phospholipase D normally converts phosphatidylcholine to phosphatidic acid (PA) by hydrolysis. However, in the presence of a primary alcohol, PLD preferentially uses the primary alcohol as a substrate in a transphosphatidylation reaction to convert phosphatidylcholine to a phosphatidyl alcohol, a biologically inert product. Using the focal infection model, 0.6% of n-butanol or tert-butanol was added to the semisolid overlay to interfere with PA production by PLD. Consistent with the PLD inhibitor results described herein above, cultures that had been treated with n-butanol were significantly protected from a productive infection after a 24 hour, MOI 1 infection of A/Brisbane/59/2007 ($p<0.01$) and A/California/04/2009 ($p<0.001$) when compared to cells treated with tert-butanol (FIG. 7e). Similar protective results were seen using traditional assays such as plaque assay, $TCID_{50}$, and immunofluorescence (see FIGS. 14b, e, and f).

Figure 7:
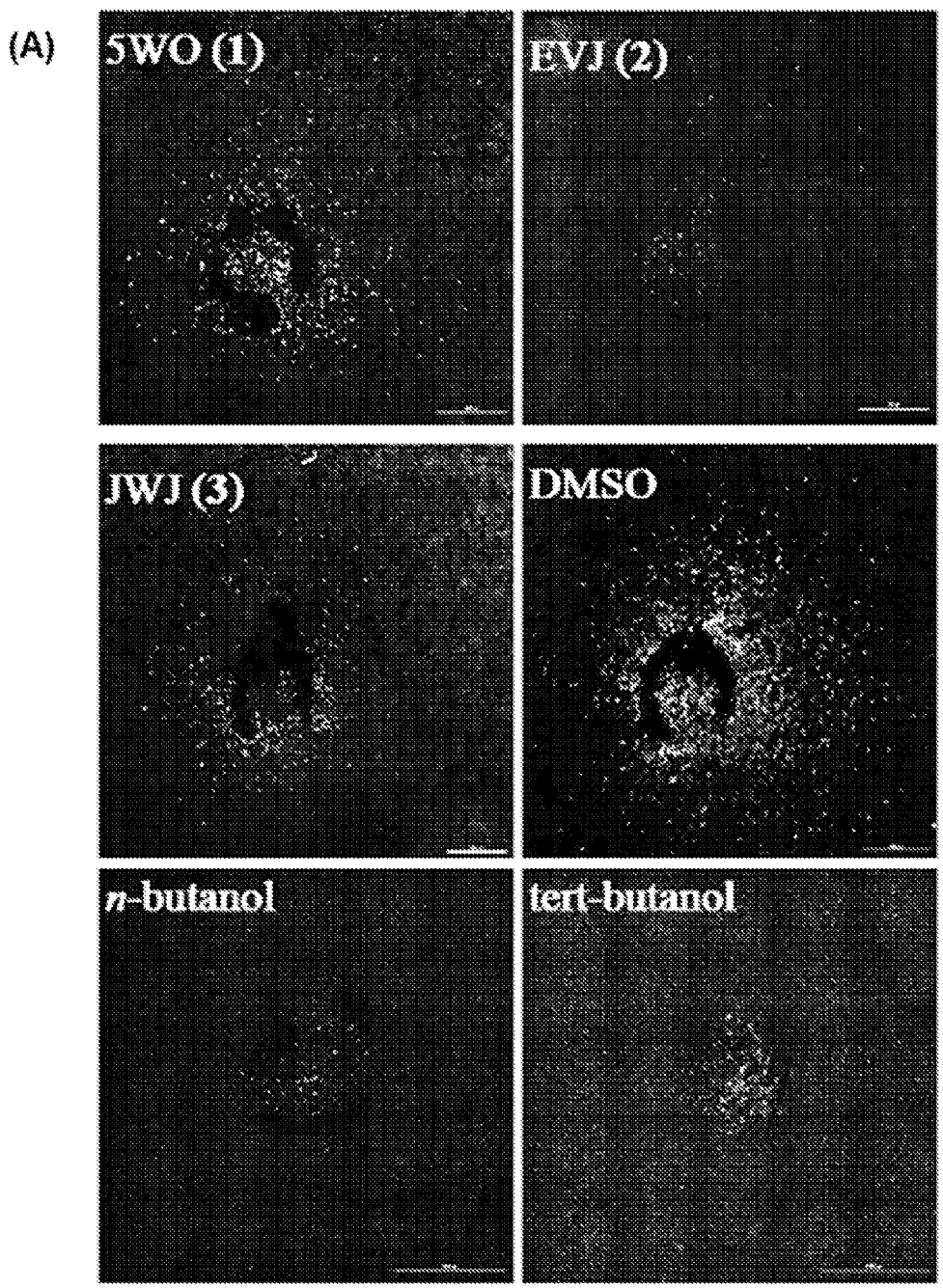
FIG. 7 shows representative data for protection of A549 cells from influenza virus when exposed to PLD inhibitors.
Figure 7:
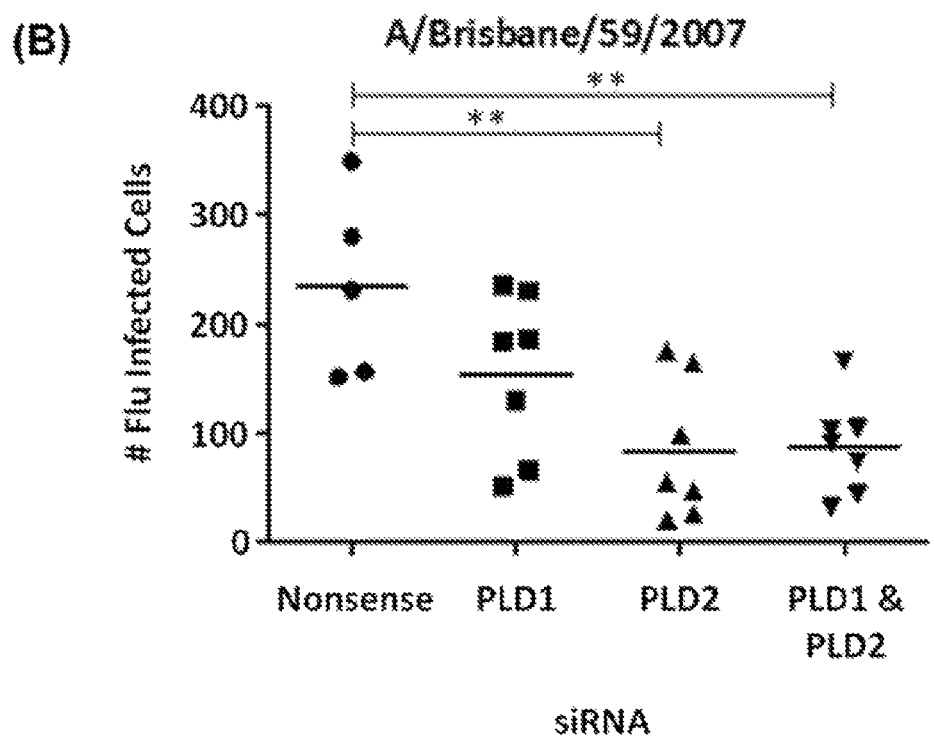
Figure 7:
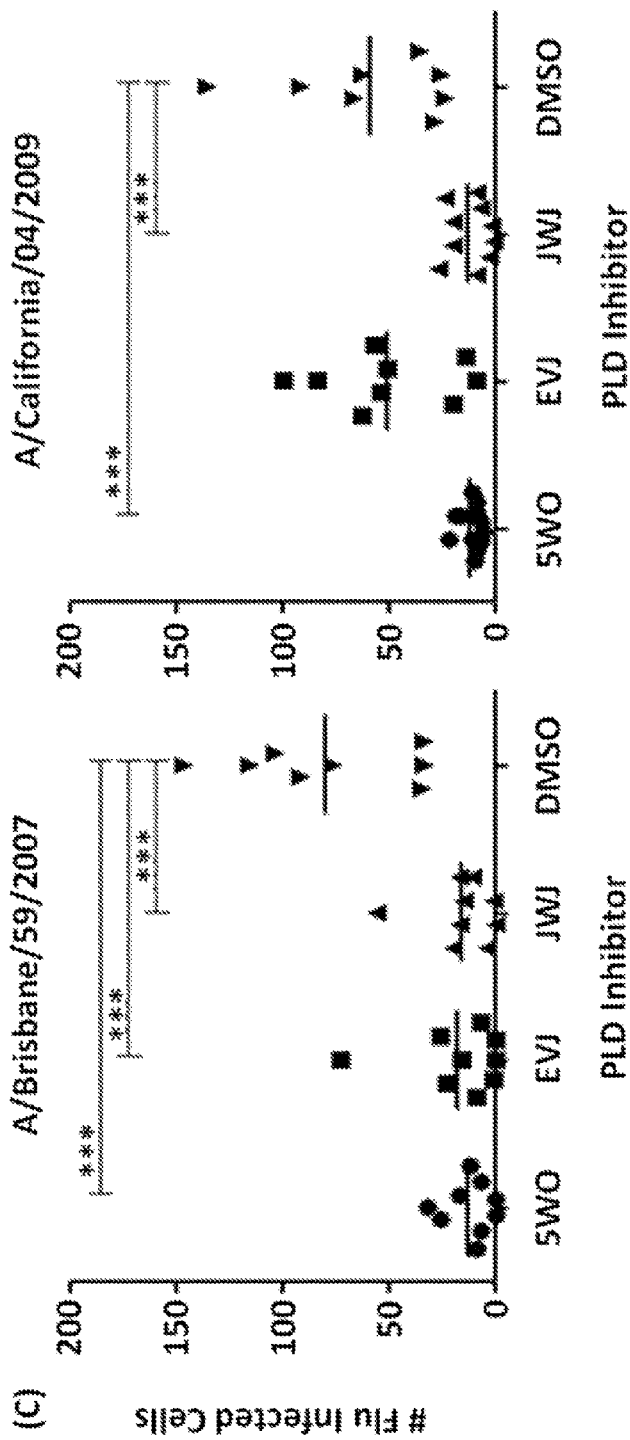
Figure 7:
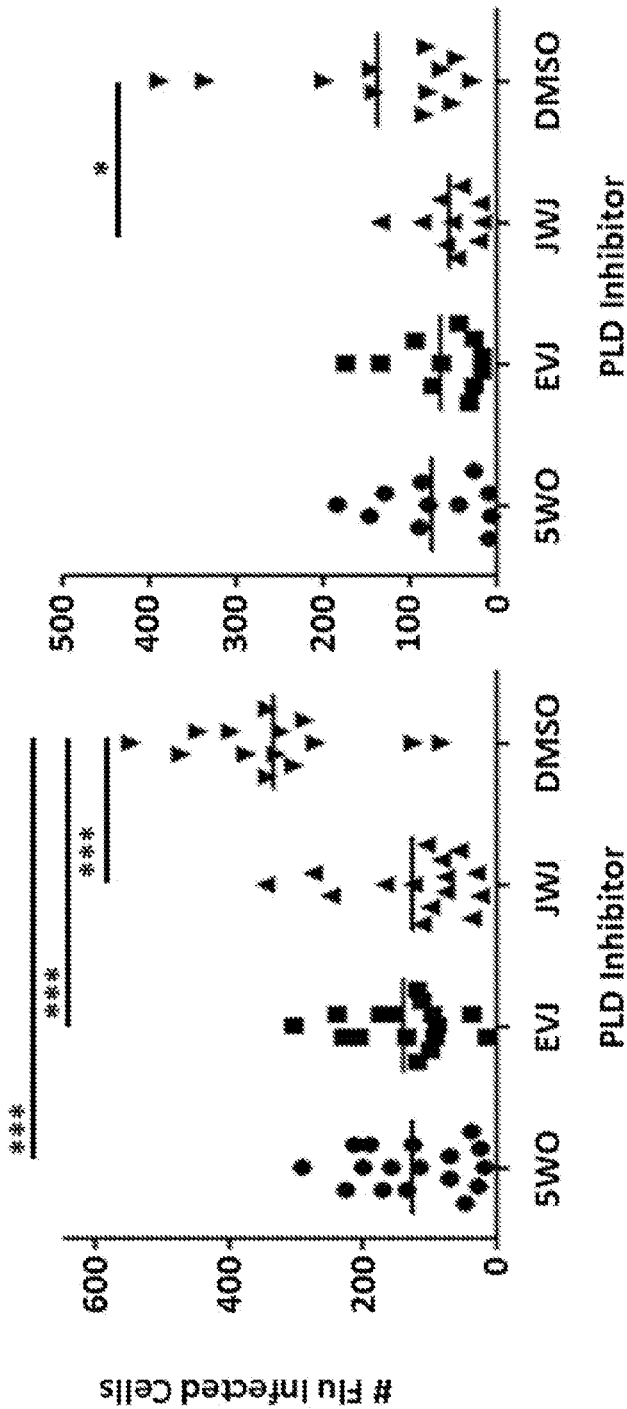
Figure 7:
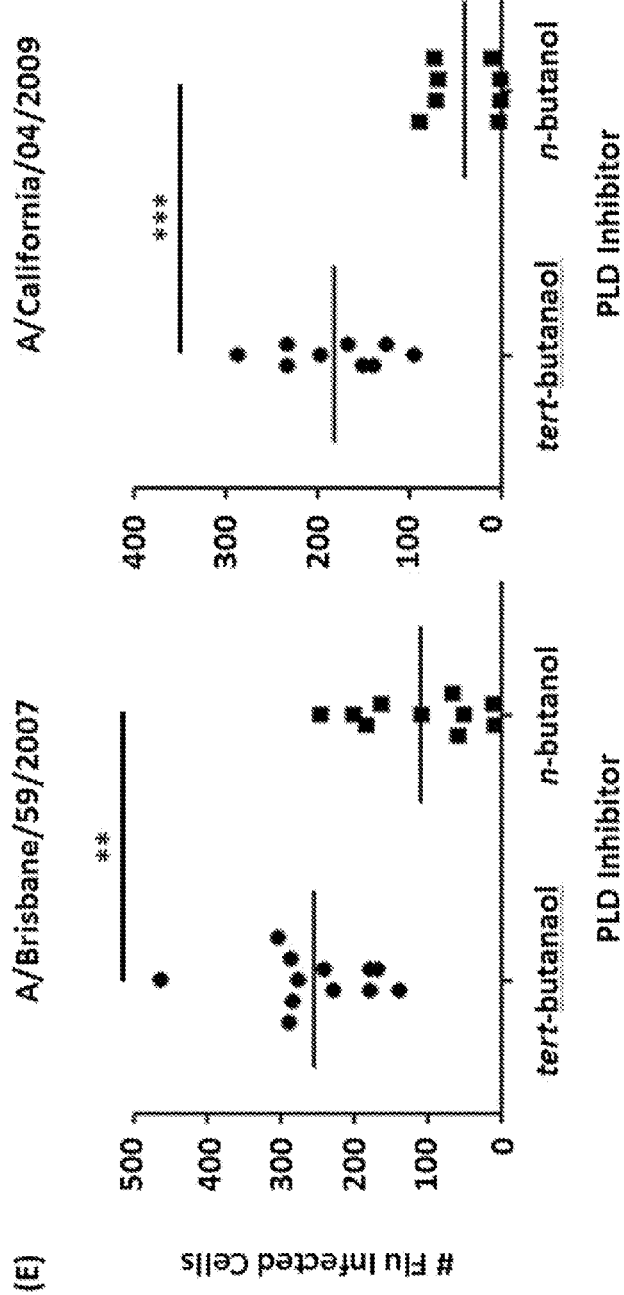

FIG. 7: (a) Fluorescent micrograph mosaics of A549 cells following a 24 hour influenza infection using the focal infection technique. Photos of culture treated with 10 μM PLD inhibitors (as labeled), DMSO vehicle control, or 0.6% primary or tertiary alcohols; in a color image, the green signal is influenza NP, and blue signal is DAPI; the figure as shown has been converted to grayscale; bar=1 mm; (a) A549 cells infected with 1 MOI A/Brisbane/59/2007 for 24 hours after a 70% siRNA mediated knockdown of PLD isoforms. (c & d) Cells treated with 10 μM PLD inhibitor or DMSO and focally infected with 1 MOI A/Brisbane/59/2007 or A/California/04/2009 for 6 hours (c) or 24 hours (d); (e) 24 hour focal infection of A549 cells with 1 MOI A/Brisbane/59/2007 or A/California/04/2009 treated with 0.6% tert-butanol or n-butanol. Data in each panel are from at least three independent experiments. One-way ANOVA and Dunnett's post-test was used to evaluate differences in (a), (b), and (c). Unpaired t-test was used for (e), * $p<0.05$,  $p<0.01$, *, $p<0.001$. The bar in (a), (b), (c), (d), and (e) is the mean of the data set.

FIG. 13: A549 cells were exposed to 10 μM PLD inhibitors or DMSO control and assayed for apoptosis 24 hours after treatment using an Annexin V/propidium iodide staining kit. Cells UV irradiated served as a positive control. A one-way ANOVA and Dunnett's post test was used to compare differences. For ANOVA based statistical analyses, * $p<0.05$,  $p<0.01$, *, $p<0.001$, **** $p<0.0001$.

Figure 14:
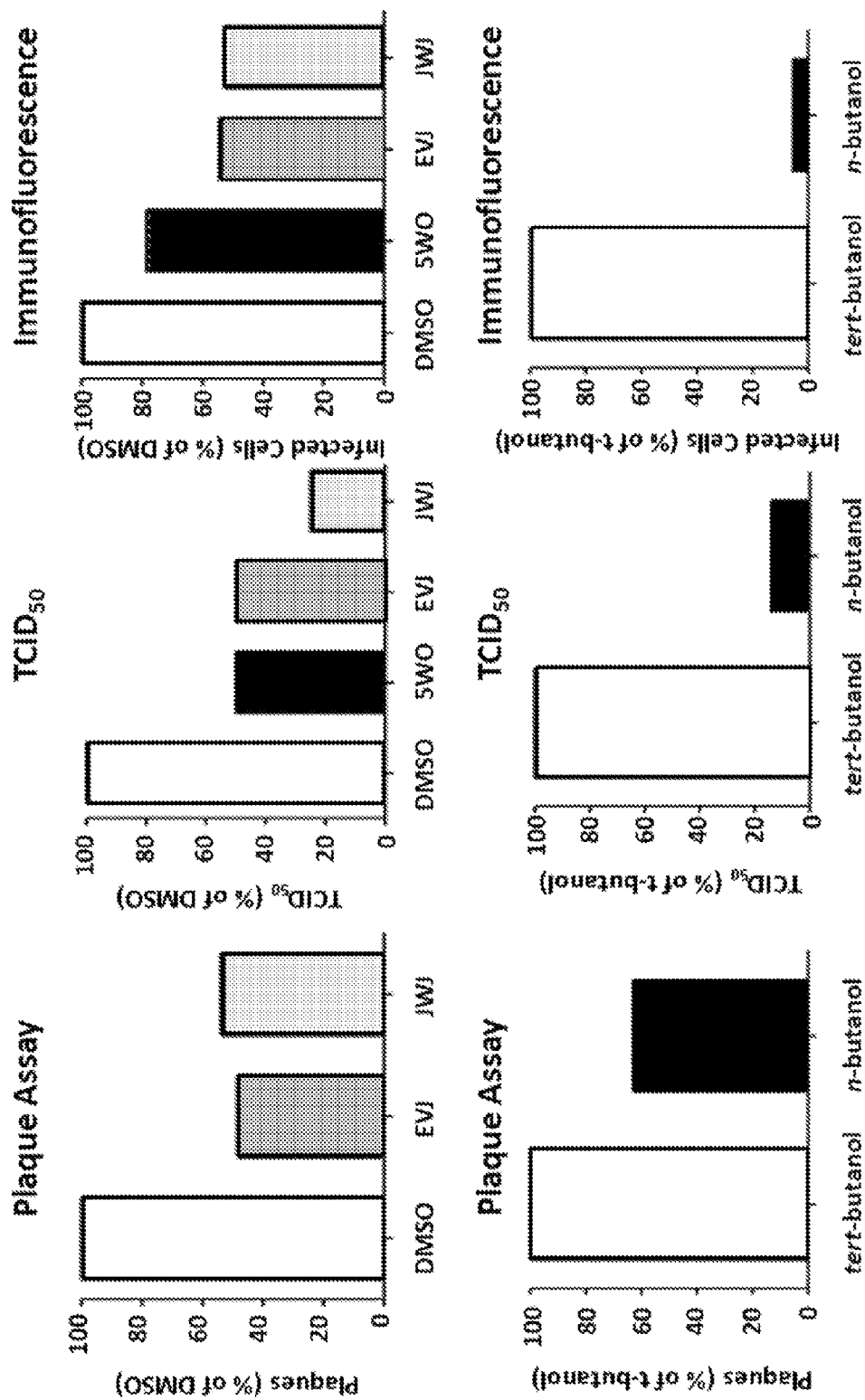
FIG. 14 shows representative data on the protection of cultured cells from influenza infection.

FIG. 14: (a & b) MDCK cells were treated with 10 μM of drug or DMSO, or 0.6% alcohol for 1 hour before infection. The treatment was removed and 10 fold dilutions of A/Puerto Rico/8/1934 were used to perform a traditional plaque assay. The plaques in the 100 pfu/ml well were counted and compared between treatments. (c-f) A549 were treated with 10 μM drugs or vehicle or 0.6% alcohol for 1 hour before an 8 hour 1 MOI infection of A/California/04/2009. (c & e) Supernatant was collected and titered using the $TCID_{50}$ method. (d & f) The same samples were fixed and processed for immunofluoresence; 36 fields were collected for each sample and NP positive cells were divided by the number of nuclei in the 36 fields to give a percentage of infected cells.

20. PLD Inhibition Alters the Dynamics of Influenza Entry into Cells

It is known that a successful influenza infection requires an intact and efficient endocytosis pathway (e.g. see review by Lakadamyali M, Rust M J, and Zhuang X. Microbes Infect. (2004) 6(10):929-936). Briefly, the virus must enter the cell, and then is trafficked to the late endosome where low pH causes the viral hemagglutinin to undergo a conformational change to fuse the viral and endosomal membranes, releasing the viral genome into the cytoplasm. In order to ascertain whether PLD inhibition affected endocytosis, a cell-based model of diffuse infection was used to study trafficking in the presence and absence of PLD inhibition. Briefly, A549 cells were infected with MOI 0.05 influenza virus and at selected time points, cells were fixed and processed for confocal microscopy. Cells treated with PLD inhibitors or n-butanol accumulated less clathrin after 0.05 MOI A/Brisbane/59/07 infection (FIG. 8a). At 50 minutes post-infection, cells that were treated with 5WO, EVJ, and JWJ had accumulated less clathrin than cells treated with vehicle control (DMSO; see FIG. 8b) and the observed effect persisted at least until 80 minutes in cells that were treated with EVJ and JWJ. Likewise, when cells were treated with n-butanol, significantly less clathrin had accumulated compared to cells treated with tert-butanol at 80 minutes after infection (FIG. 8b).

As endosomes mature, they recruit waves of early (RAB5) and late (CD63) proteins that orchestrate trafficking. After treatment with PLD inhibitors (1 h; 10 μM), treated cells accumulated significantly less RAB5 compared to the vehicle treated cells (DMSO; FIGS. 8c-d). Primary alcohol treatment had a similar effect (FIG. 8d). The level of CD63 recruited was also measured. In the presence of PLD inhibitors 5WO, EVJ, and JWJ, as well as in the presence of n-butanol, there was significantly less CD63 to accumulated compared to the respective control treatment (FIG. 8e-f). The data show that PLD inhibition, either by specific inhibitor or primary alcohol treatment, delayed the temporal dynamics of clathrin, RAB5, and CD63 recruitment after influenza infection.

Late in the infection cycle, viral proteins and RNA are trafficked to the budding virion. Viral nucleoprotein (NP) trafficking was disrupted when PLD was inhibited by exposure of the cells to EVJ or JWJ (each at 5 µM) during infection with A/Puerto Rico/8/1934 (16 hr infection; MOI=5). The discreet NP positive Rab11 positive puncta seen in DMSO treated samples were not seen when cells had been treated with PLD inhibitors (FIG. 8g). Instead, more diffuse and less intense staining of NP is seen when cells had been exposed to one of the PLD inhibitors. Without wishing to be bound by a particular theory, PLD inhibition affects the transport of newly made NP to the cell surface.

Concomitant with the shift in trafficking of the virus, the accumulation of innate immune effector protein Mx1 (Myxovirus resistance 1) increased relative to controls during the infection when cells were exposed to PLD inhibitors (FIGS. 8h and 8i). The accumulation of Mx1 was cytoplasmic and co-localized with influenza NP. Mx1 accumulation was higher cells exposed to PLD inhibitors at all time points measured through the first two hours of infection (data not shown).

Figure 8:
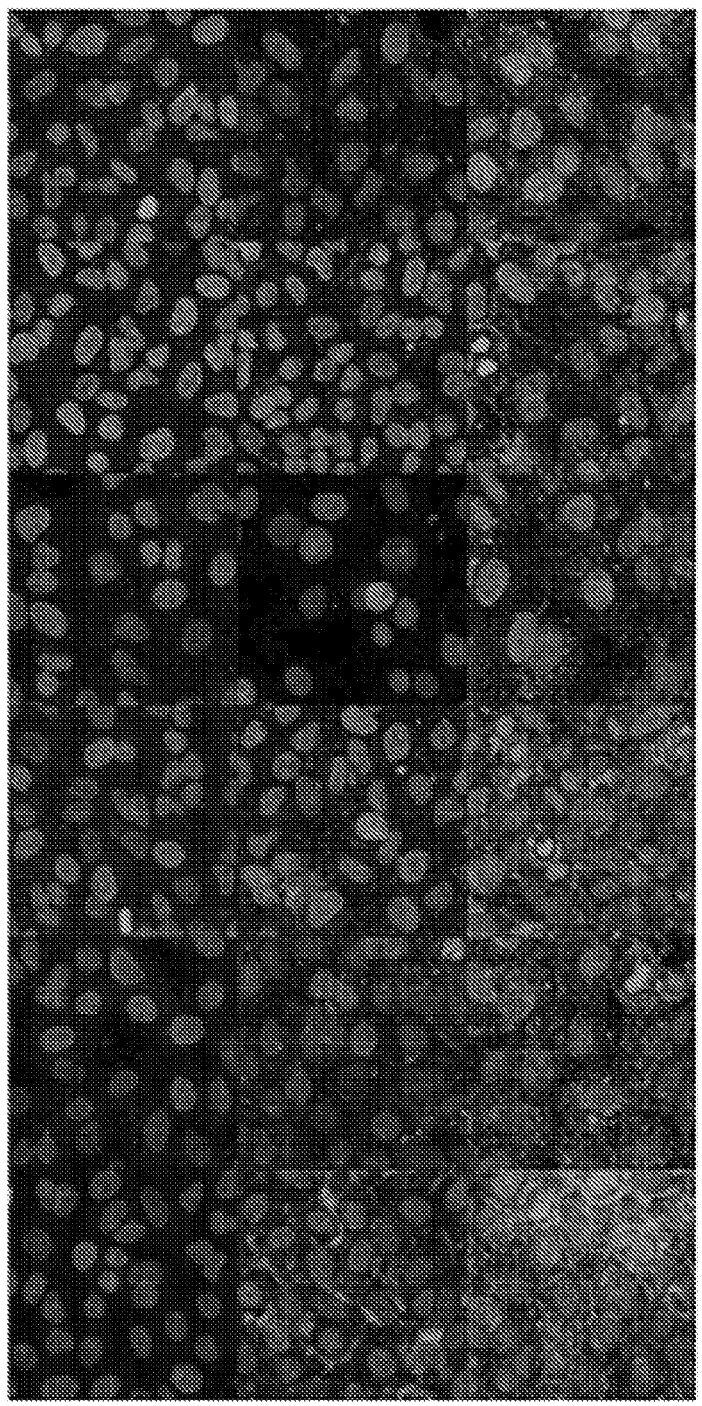
FIG. 8 shows representative data on the effect of PLD inhibition on influenza trafficking kinetics and innate immune effector activation.
Figure 8:
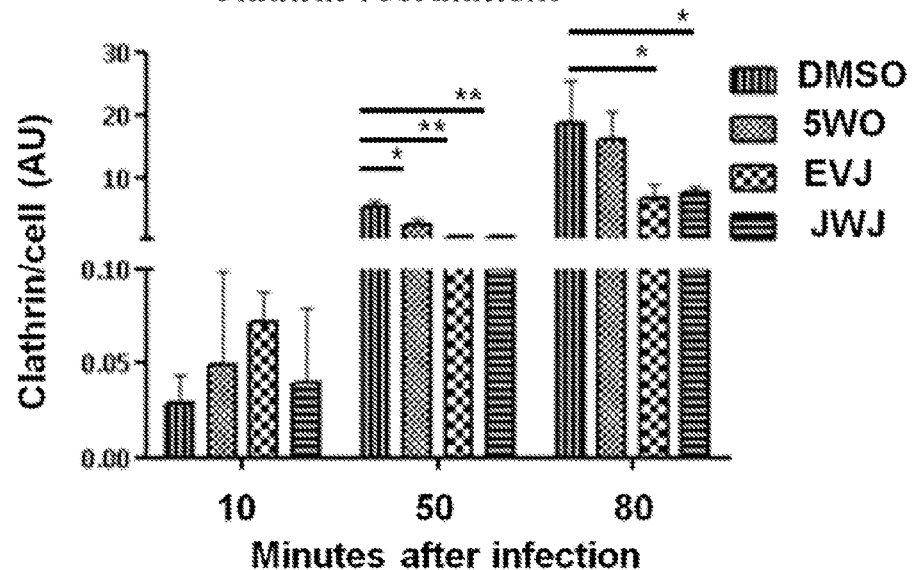
Figure 8:
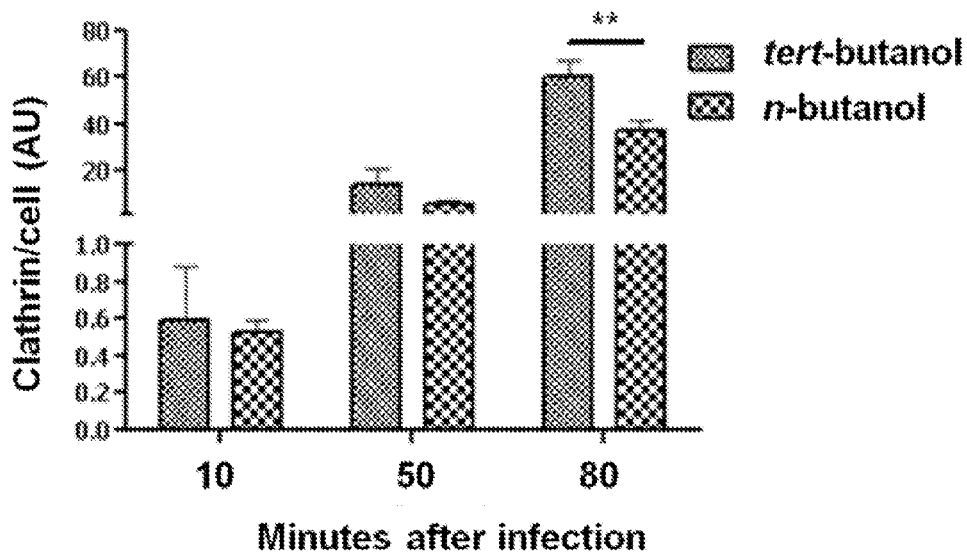
Figure 8:
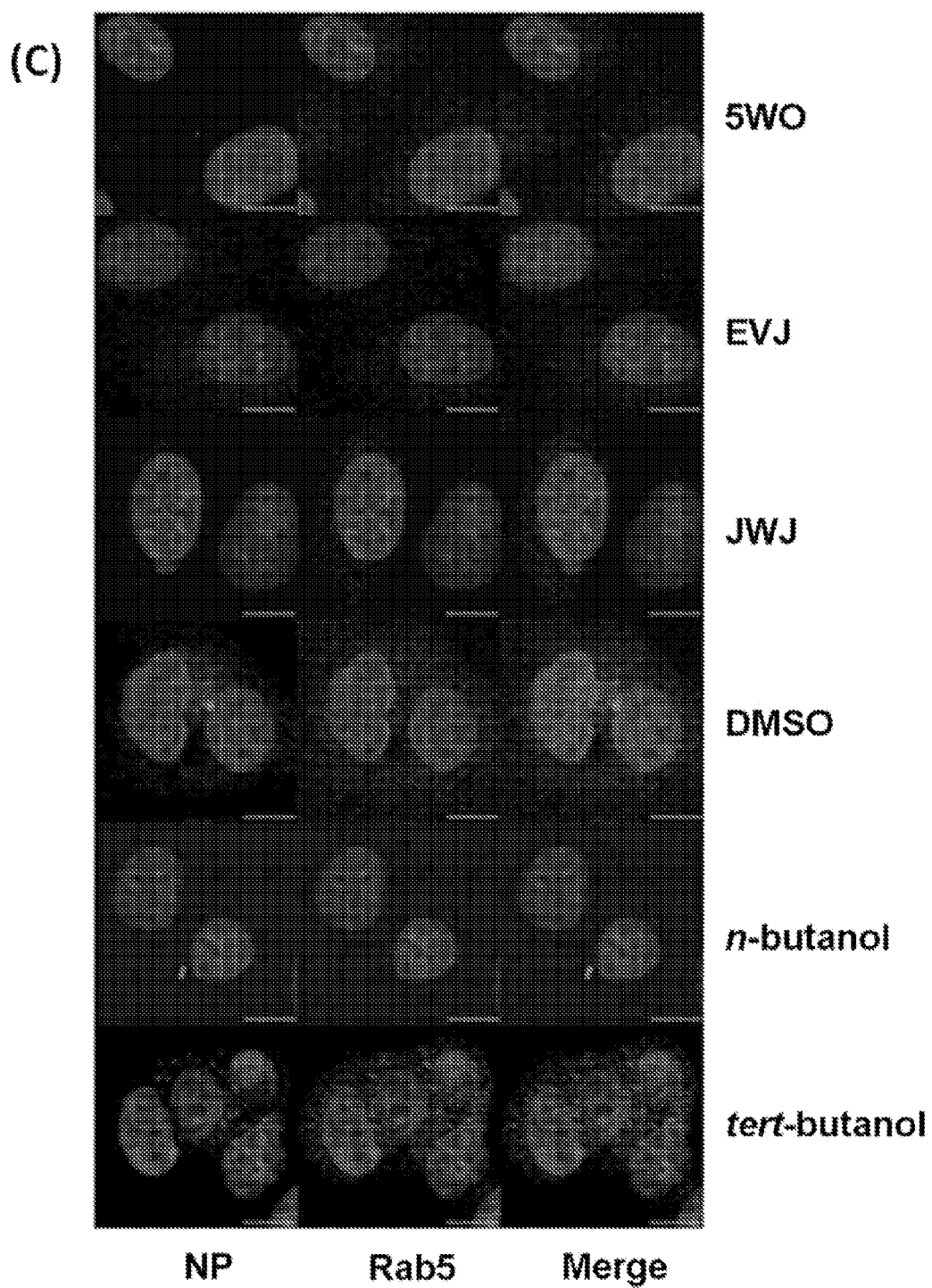
Figure 8:
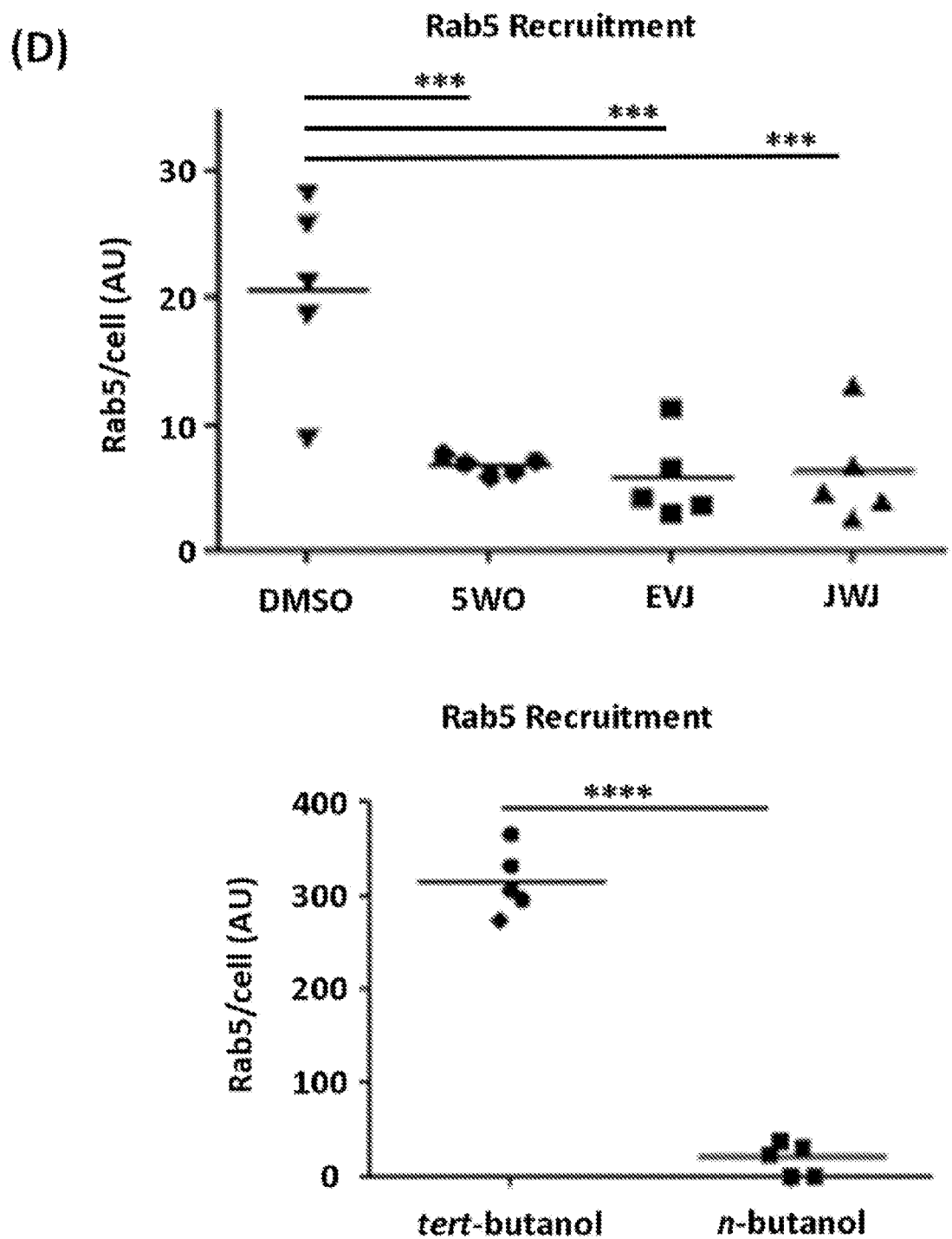
Figure 8:
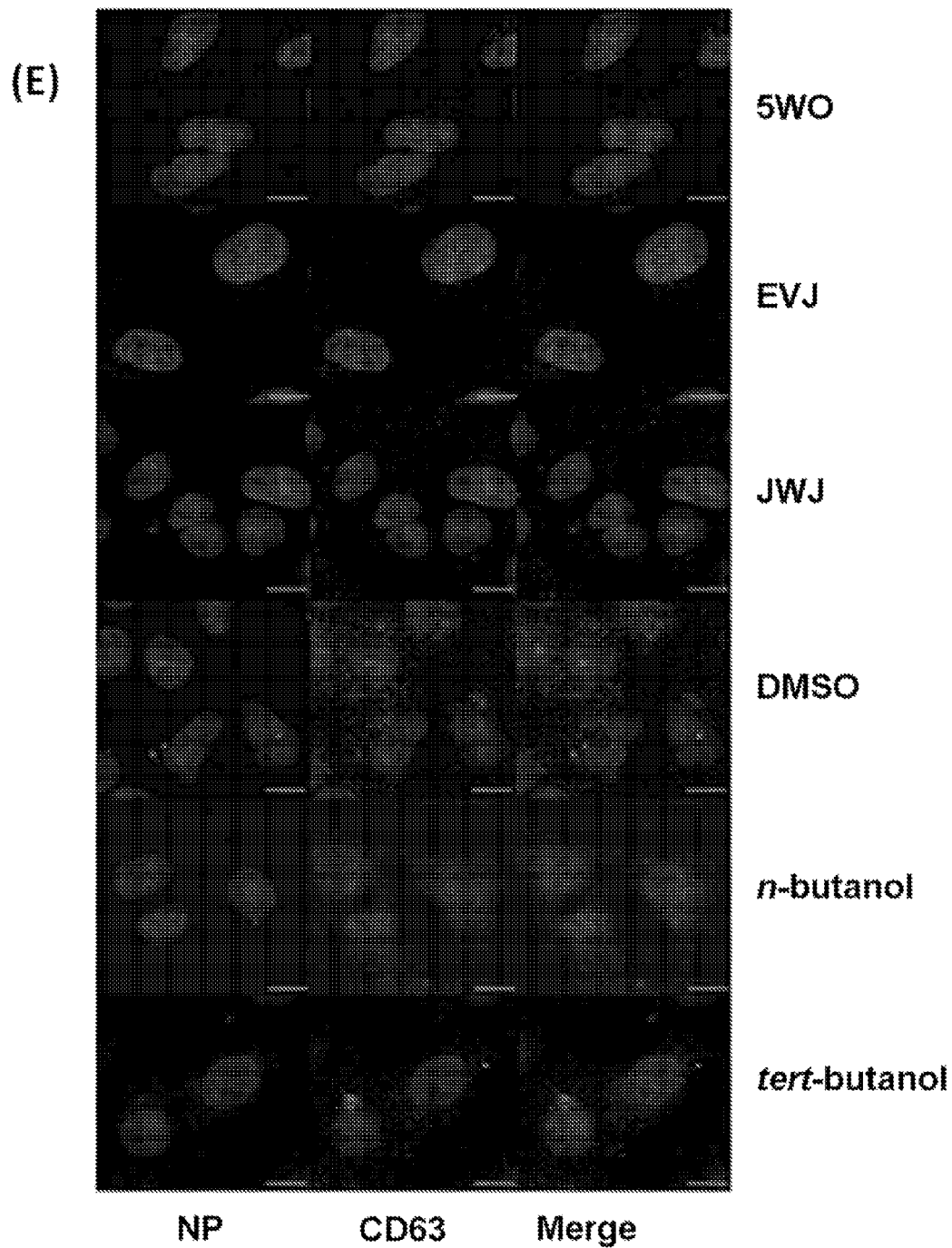
Figure 8:
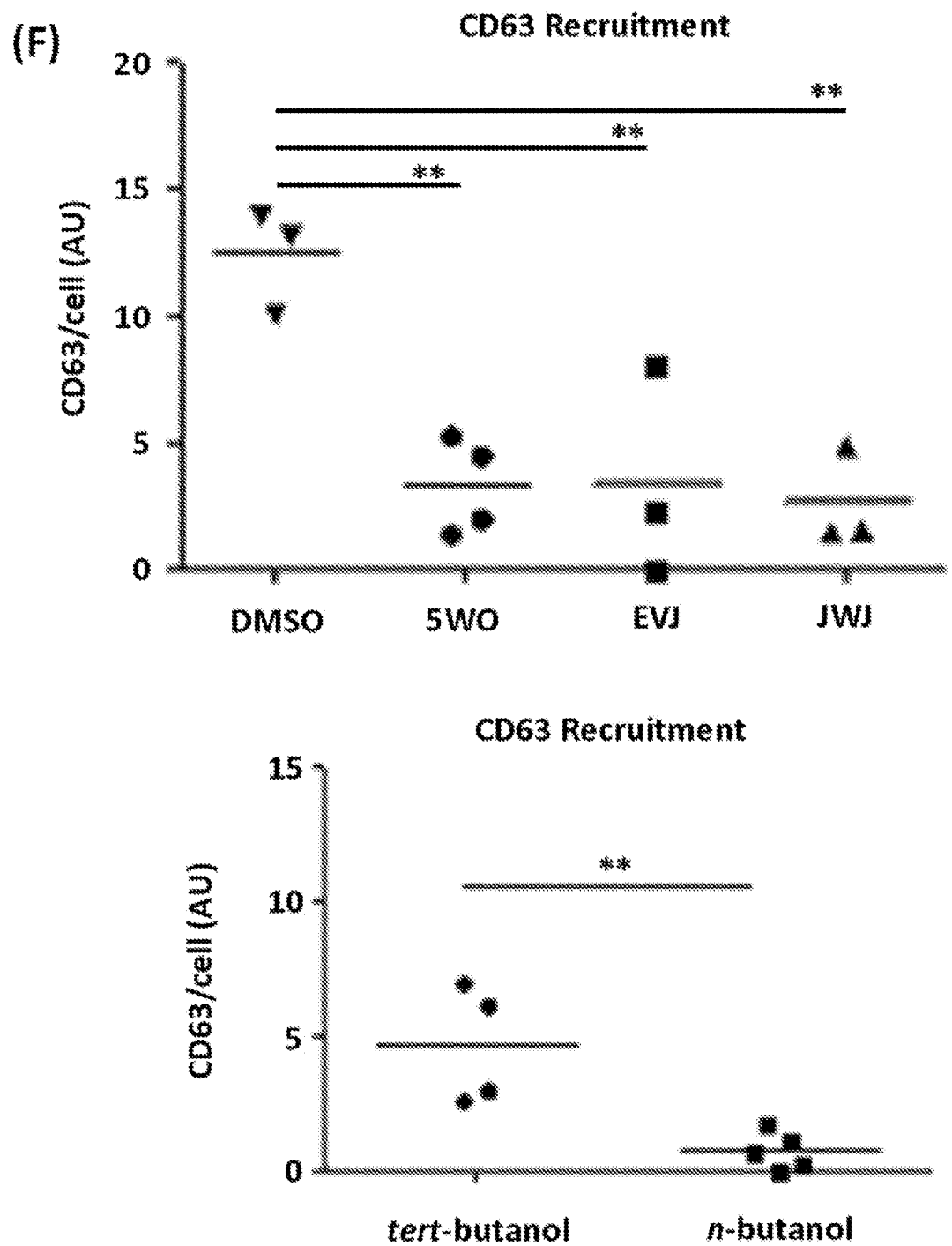
Figure 8:
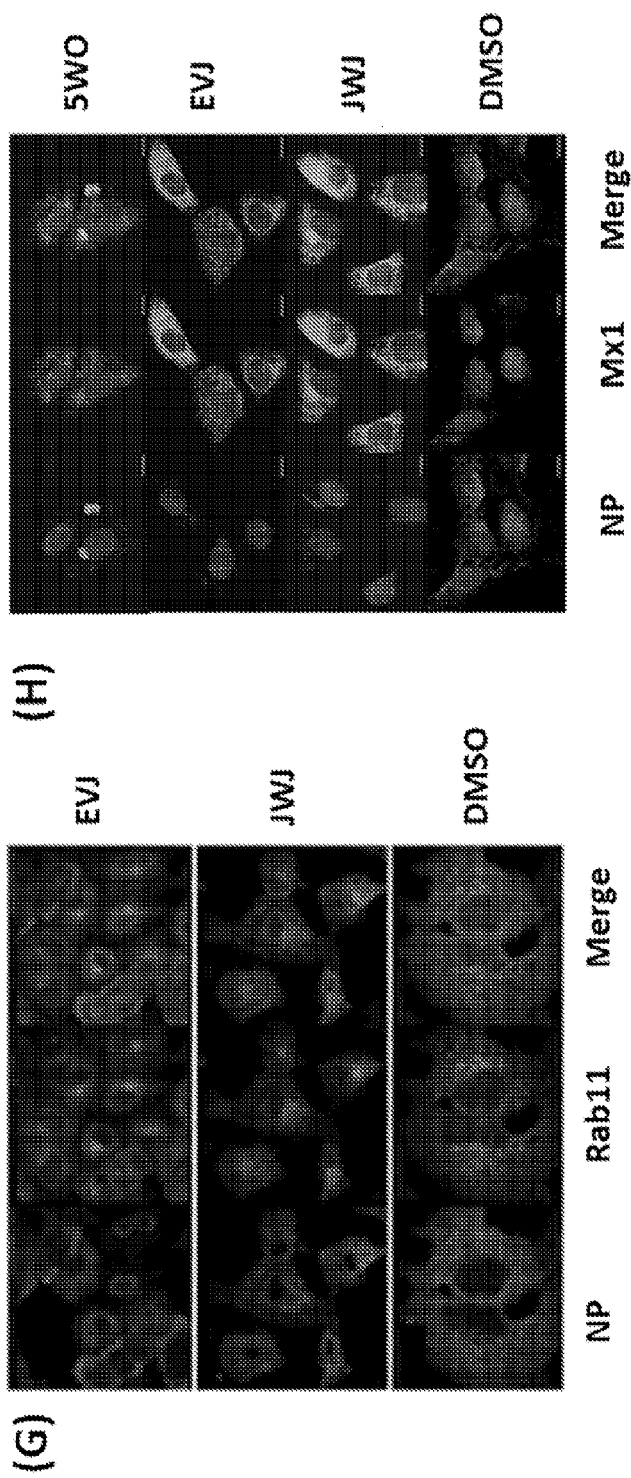
Figure 8:
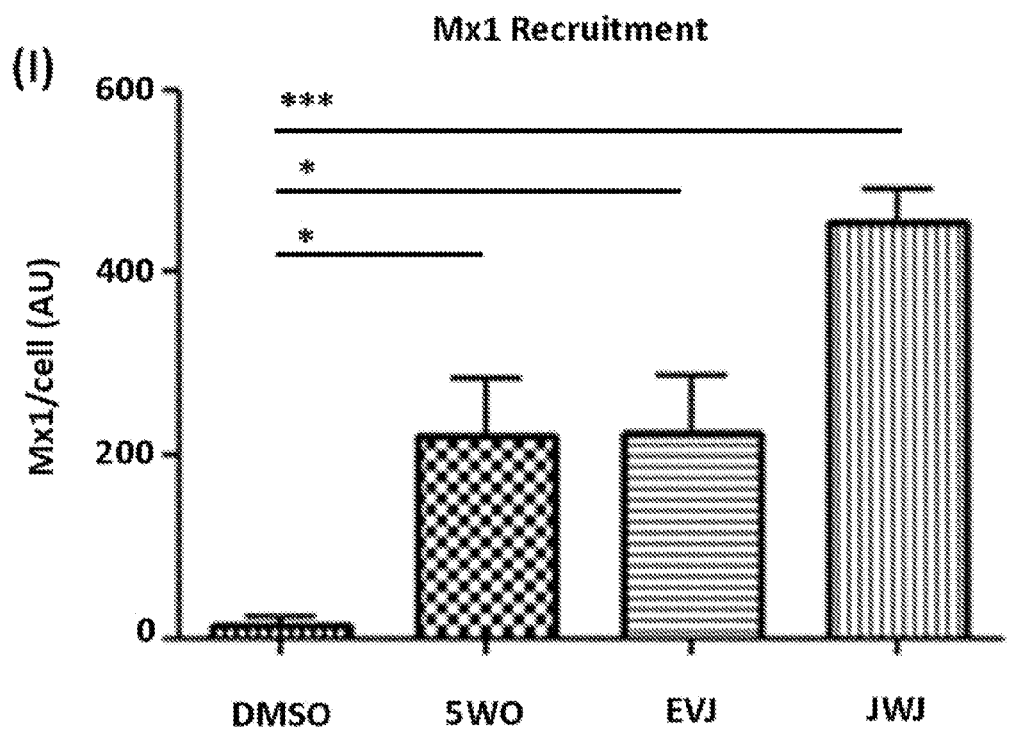

FIG. 8: (a) Confocal micrographs of cells treated with PLD inhibitors or 0.6% alcohol and infected with 0.05 MOI A/Brisbane/5/2007 for 10 minutes; clathrin is stained red and nuclei are stained blue with DAPI, however, the figure as shown is converted to grayscale; (b) quantitation of clathrin staining in treated cells after infection; (c) confocal micrographs of cells treated with 10 µM PLD inhibitor as indicated, DMSO, or 0.6% (v/v) of the indicated alcohol and infected with 0.05 MOI A/California/04/2009 for 10 minutes; Rab5 is stained red, influenza NP is stained green, and nuclei are stained blue with DAPI, however, the figure as shown is converted to grayscale; bar=10 µm; (d) quantitation (area) of Rab5 staining in treated cells after infection; (e) the data show that recruitment of the late endosomal marker CD63 is delayed when PLD is inhibited by either specific inhibitors as indicated or primary alcohol after 10 minutes of infection with 0.05 MOI of A/California/04/2009; (f) quantitation of CD63 staining; (g) the data show that Rab11 trafficking of NP is altered after PLD inhibitor treatment; for data shown in (g), A549 cells were treated with 5 µM DMSO or drug for 30 minutes before a 5 MOI infection of A/Puerto Rico/8/1934; cells were fixed and processed for immunofluoresence 10 hours after infection; (h) representative confocal images of Mx1 accumulation in cells treated for 1 hour with 10 µM PLD inhibitors or DMSO control 30 minutes after a 0.05 MOI infection of A/California/04/2009. (i) Quantitation of the area of positive Mx1 staining, n=4 for DMSO and n=5 for drug treatments. ANOVA and Dunnett's post test were used to determine significance of changes when PLD inhibitors were used, and a t-test was used when cells were treated with alcohol, * $p<0.05$,  $p<0.01$, *, $p<0.001$, **** $p<0.0001$. Data in (b, d, f, i) is mean±SEM, n=3 fields of at least 15 cells.

21. In Vivo PLD Inhibition Confers Survival Benefits

Having demonstrated that PLD inhibition affords protection from influenza infection in vitro, we next tested the effects of PLD inhibition during a lethal influenza infection in a mouse model. Mice were given an intraperitoneal injection of the JWJ compound (13 mg/kg) every eight hours from day −1 to day 3 after infection, and from day 4 to day 10 after infection, the injections were every twelve hours. On day 0, mice were intranasally infected with 4000 $EID_{50}$ PR8, approximately 2 $MLD_{50}$, and weight loss and survival were monitored every day. Mice that received injections of JWJ lost significantly less weight than mice receiving vehicle alone (FIG. 9a), and they also recovered the weight lost more quickly. Additionally, mice that received JWJ treatment were about 27% less likely to die, a significant difference (p=0.0061) using the Log-Rank test (FIG. 9b). Only one mouse out of 42 in the vehicle group survived and recovered from the infection whereas 12/38 in the JWJ cohort survived.

To investigate the mechanism of protection from a lethal influenza infection, viral titers were measured in the lungs of infected mice by plaque assay. Infected mice treated with JWJ (n=7) had significantly less virus (p=0.0017) in their lungs at 8 hours after infection when compared to mice who did not receive JWJ treatments (n=8) (FIG. 9c). Mice treated with PLD inhibitors had lower viral titers, experienced less severe disease, and were less likely to die during a lethal influenza infection. Additionally, mice treated with JWJ (n=9) displayed a more activated innate immune response than mice treated with vehicle (n=10) 8 hours after infection. Significant differences were noted in the expression levels of the antiviral effector molecules (FIG. 9d) Mx1 (p=0.0023), OASL (p=0.0146), and IFITM3 (p=0.0162).

Figure 9:
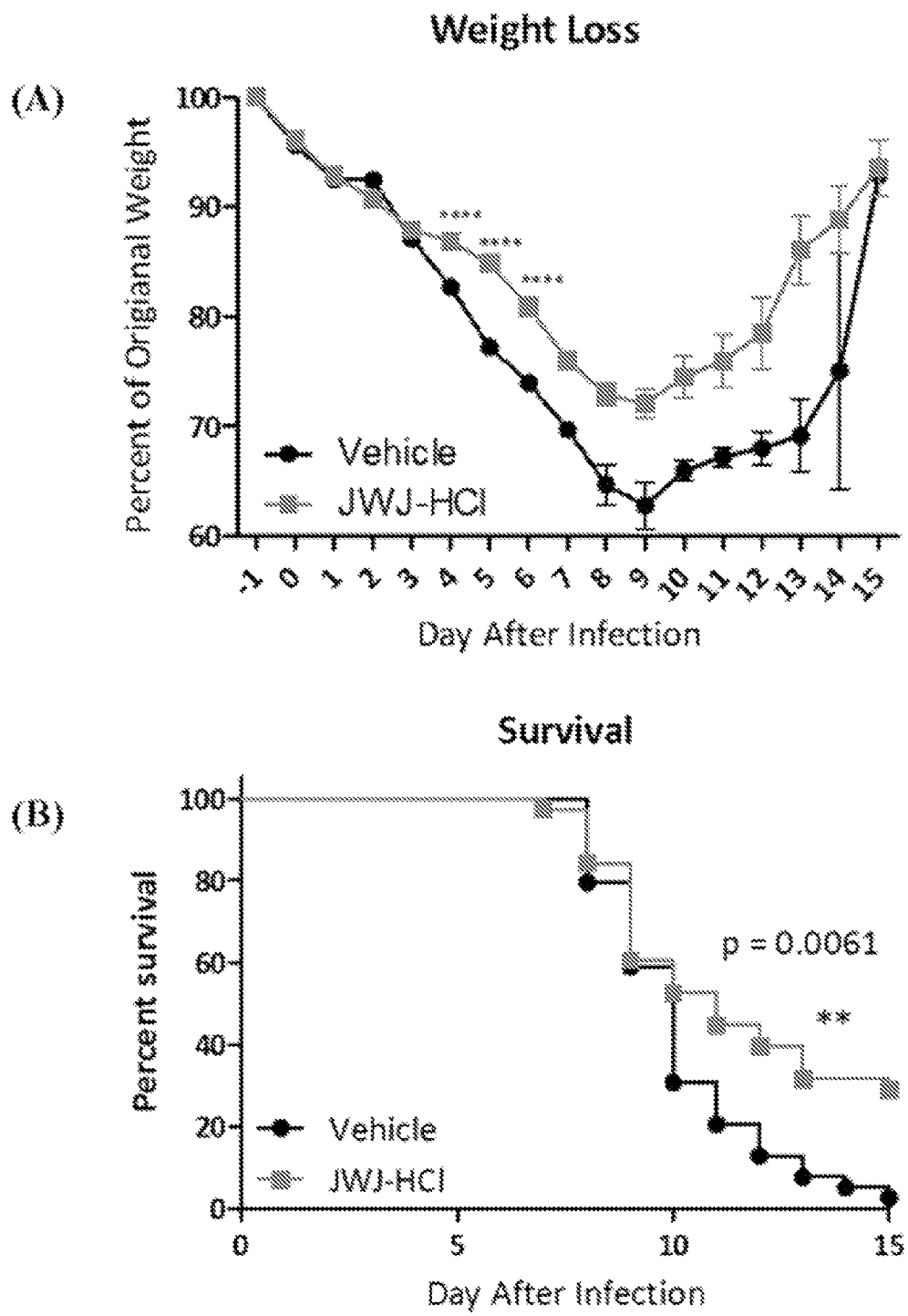
FIG. 9 shows representative data on increased survival and decreased viral titers in influenza infected mice that had been treated with a PLD inhibitor.
Figure 9:
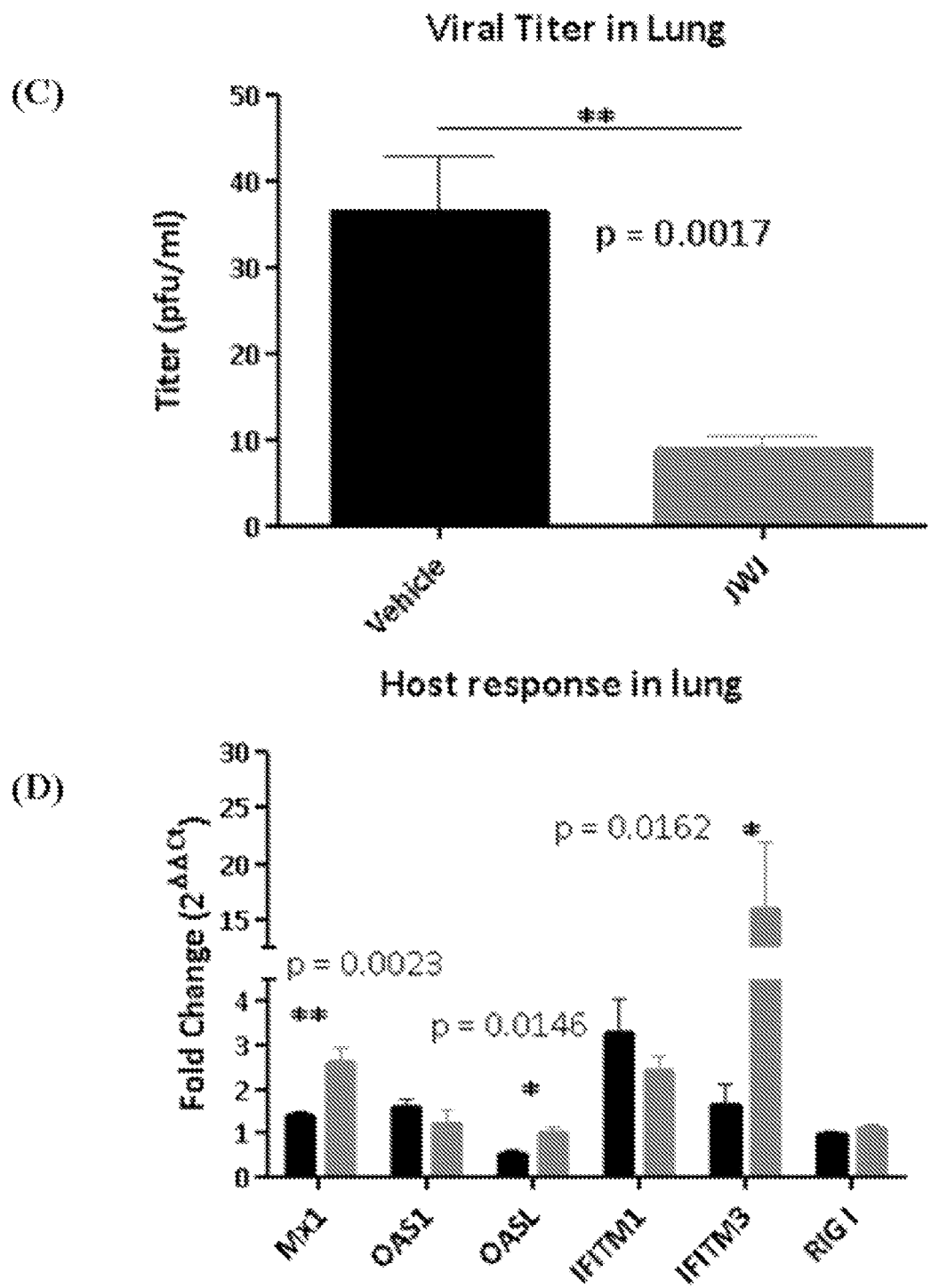

FIG. 9: Mice were treated with vehicle (Black) or JWJ (Blue) every 8 hours from day −1 to day 3 after infection and every 12 hours from day 4 to day 10 after infection. The animals were infected intranasally with 4000 EID50 PR8 on day 0 and weighed everyday. Weight loss (a), survival (b) and viral titer (c) in JWJ (blue) or vehicle treated animals (black). Lung viral titers were determined 8 hours after infection in lung homogenates by plaque assay. (d) Expression of the indicated antiviral effectors measured by qPCR from lung homogenates 8 hours after infection in JWJ-(blue) and vehicle-treated (black) animals. For panels (a) and (b), n=42 in the vehicle group, and n=38 in the JWJ group. For panel (c) n=8 for Vehicle group and, n=7 for JWJ group, and data is representative of two independent experiments; in (d) n=10 in the vehicle group, and n=9 for the JWJ group, and data is representative of two independent experiments. A two-way ANOVA with repeated measures and Bonferroni's post test was used to compare differences in (a), and differences were compared from day −1 to day 7 post infection, the day of the first death. The log-rank test was used to determine the significance of the survival phenotype in panel (b). In panel (c), a t-test was used to compare differences at each time point. A two-way ANOVA and Bonferroni's post test was used to compare gene expression in (d). For ANOVA based statistical analyses, * $p<0.05$,  $p<0.01$, *, $p<0.001$, **** $p<0.0001$.

22. Pharmacokinetics of PLD Inhibitor Administered in a Mouse Model

Figure 15:
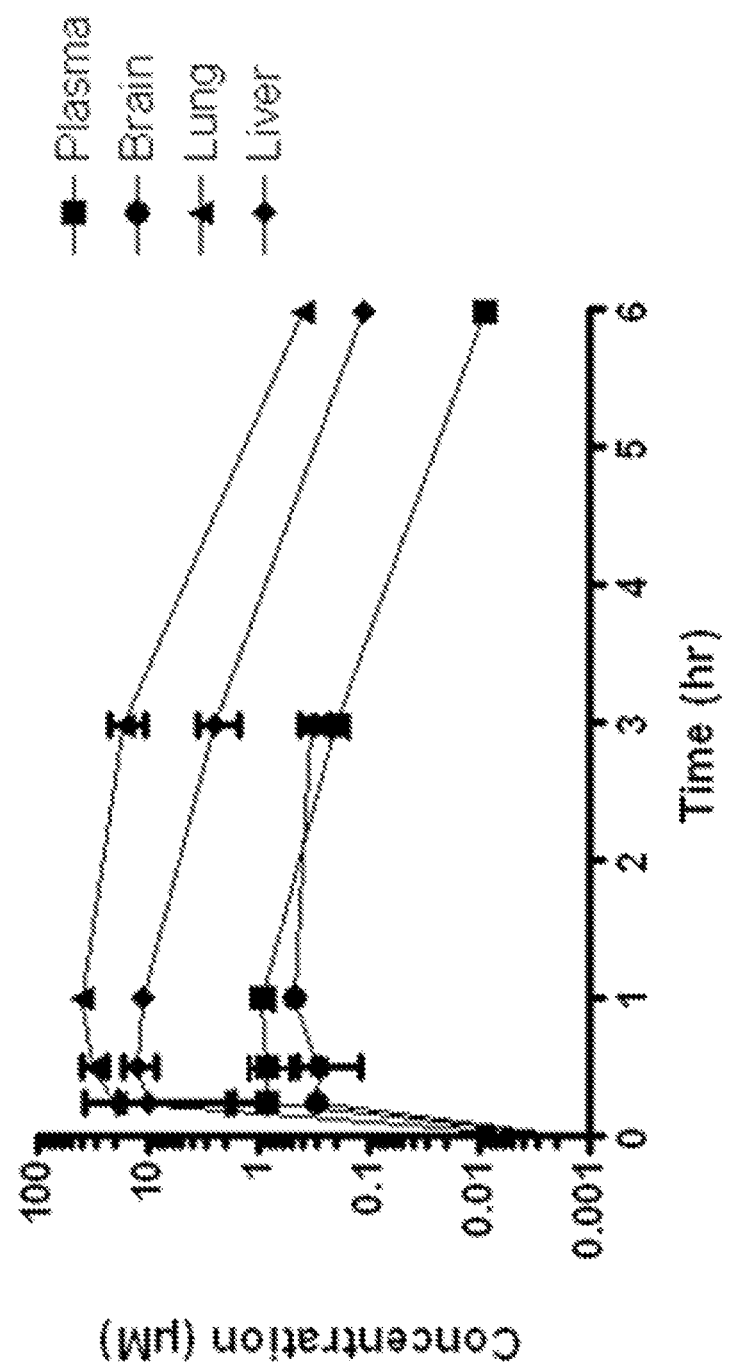
FIG. 15 shows representative data on the pharmacokinetics of a PLD inhibitor following intraperitoneal injection.

The pharmacokinetic behavior of a representative disclosed PLD inhibitor of the present invention was assessed following intraperitoneal administration in a mouse model. Briefly, mice were administered a single dose of the PLD inhibitor VU0364739 (10 mg/kg) by intraperitoneal injection. Tissue (brain, lung, and liver) and plasma samples were isolated following euthanizing animals (N=2 for each time point) at the indicated time points (see FIG. 15). The samples were flash frozen and stored at −80° C. Analysis was carried out by LC-MS/MS following extraction. The data in FIG. 15 show sustained exposure in the tissues examined and in plasma over a period of at least three hours. The representative PLD inhibitor had elevated accumulation in liver and lung compared to plasma. The accumulation in brain appeared to be constant in the window of 15 min to 3 hr post-administration.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a subject comprising the step of co-administering an effective amount of a combination of two or more therapeutic agents to the subject;
    wherein the subject has been diagnosed with a need for treatment of an influenza infection prior to the administering step; and
    wherein the combination of two or more therapeutic agents comprises:
    (a) an phospholipase D inhibitor; and
    (b) one or more therapeutic agents selected from:
        (i) a viral protein M2 ion channel inhibitor,
        (ii) a neuraminidase inhibitor, and
        (iii) a nucleoside analog selected from ribavirin, viramidine, 6-fluoro-3-hydroxy-2-pyrazinecarboxamide, 2'-deoxy-2'-fluoroguanosine, pyrazofurin, carbodine, and cyclopenenyl cytosine;
    wherein the phospholipase D inhibitor is a compound having a structure represented by a formula:

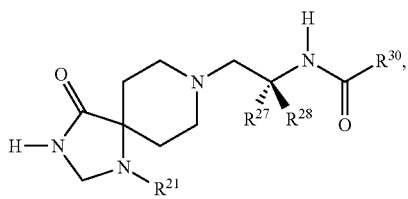

Wherein $R^{21}$ is a phenyl or halophenyl; each of $R^{27}$ and $R^{28}$ is, independently, a hydrogen or a C1 to C6 alkyl; $R^{30}$ is an optionally substituted organic residue selected from aryl and heteroaryl, wherein the organic residue is up to C16,
or a pharmaceutically acceptable salt thereof.

2. The method of claim 1, wherein the influenza infection is caused by a type A influenza virus.

3. The method of claim 2, wherein the type A influenza virus is of subtype H1, H5, H7 or H9.

4. The method of claim 2, wherein the type A influenza virus is of subtype H1N1, H1N2, H2N2, H3N2, H3N8, H5N1, H5N2, H5N3, H5N8, H5N9, H7N1, H7N2, H7N3, H7N4, H7N7, H9N2, or H10N7.

5. The method of claim 4, wherein the type A influenza virus is of subtype H1N1, H1N2, H2N2, H3N2, H5N1, H5N3, H7N2, H7N3, H7N7, H9N2, or H10N7.

6. The method of claim 4, wherein type A influenza virus is H1N1.

7. The method of claim 1, wherein co-administration is administration in a substantially simultaneous manner.

8. The method of claim 1, wherein co-administration is administration in a substantially sequential manner.

9. The method of claim 1, wherein the phospholipase D inhibitor is a phospholipase D2-selective inhibitor.

10. The method of claim 1, wherein one of $R^{27}$ and $R^{28}$ is hydrogen and the other is methyl.

11. The method of claim 10, the compound has the structure represented by a formula:

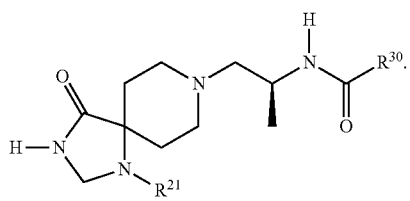

12. The method of claim 1, the compound has the structure represented by a formula:

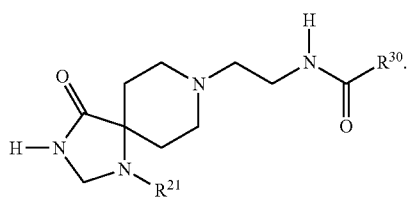

13. The method of claim 1, wherein $R^{21}$ is selected from:

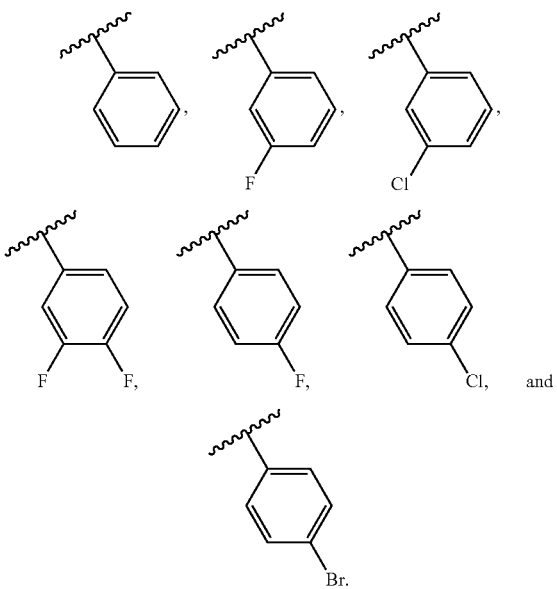

14. The method of claim 1, wherein $R^{30}$ is selected from:

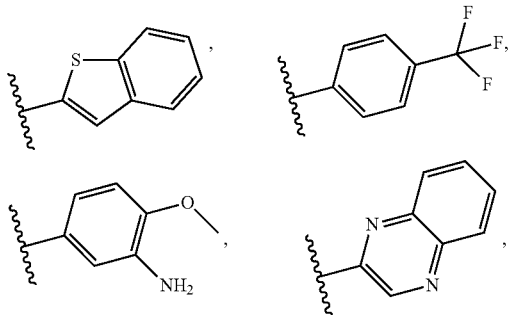

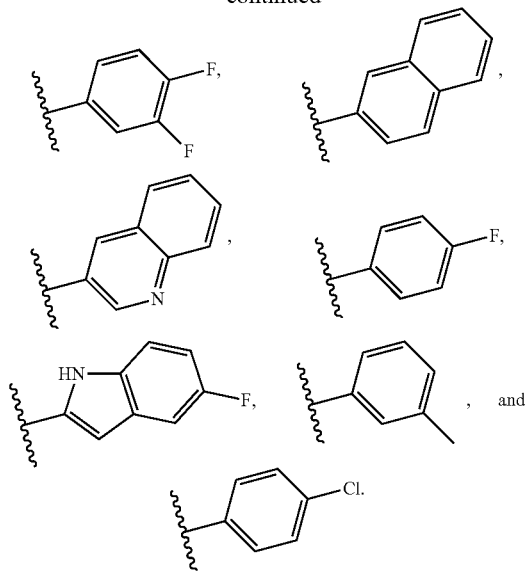
15. The method of claim 1, wherein the phospholipase D inhibitor is selected from:
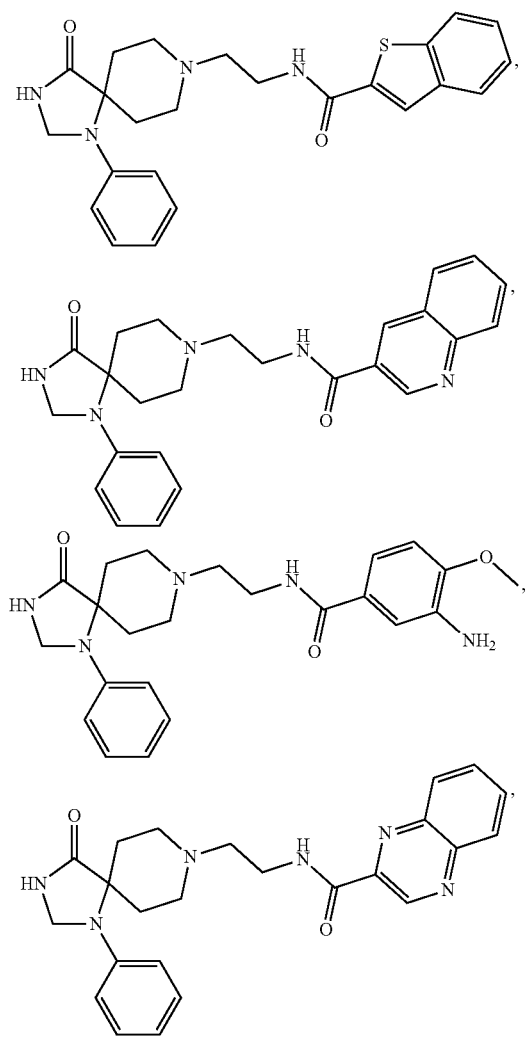
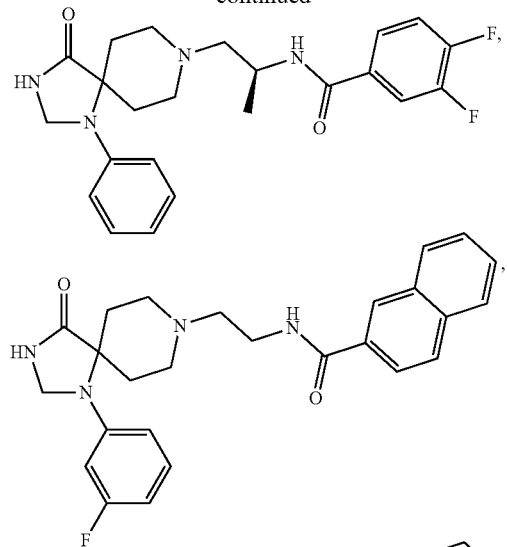

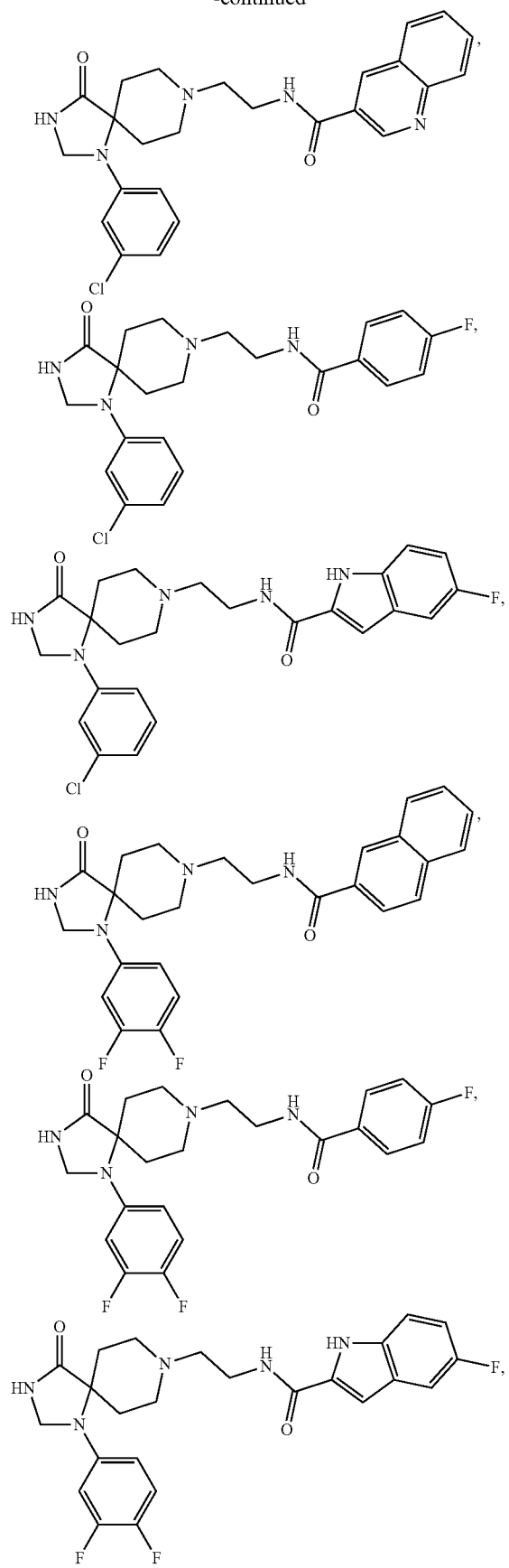
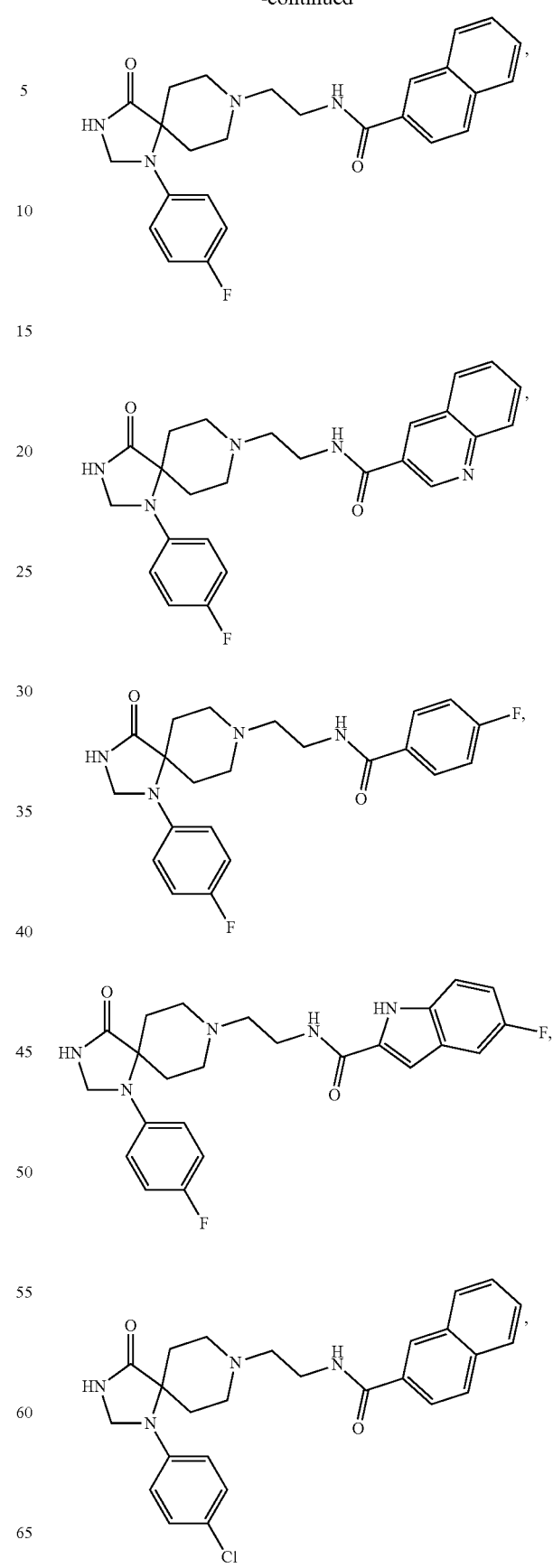

-continued
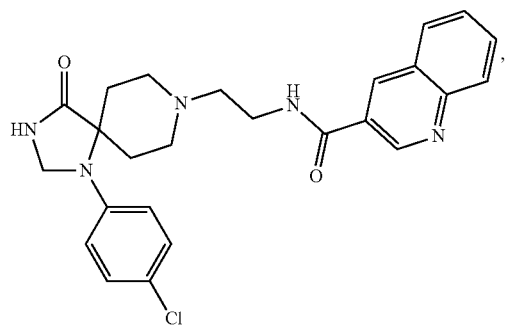
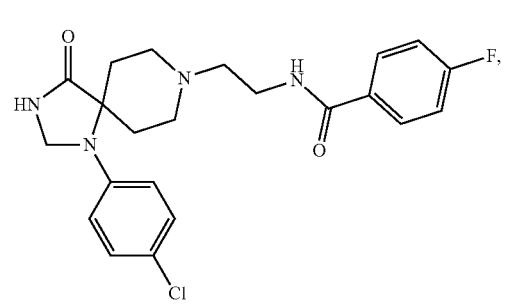
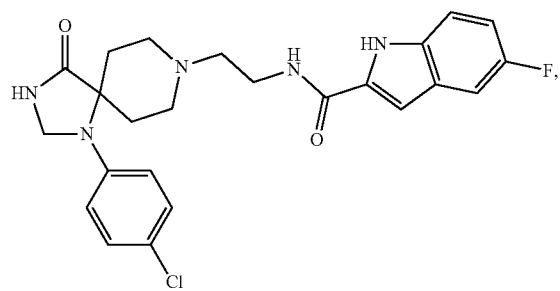
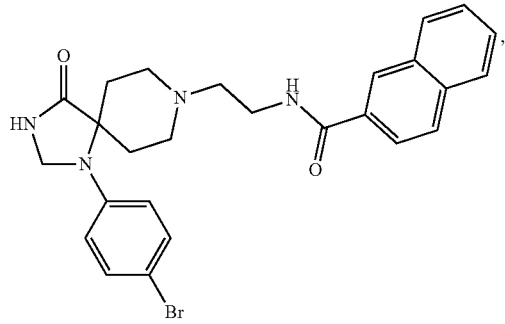
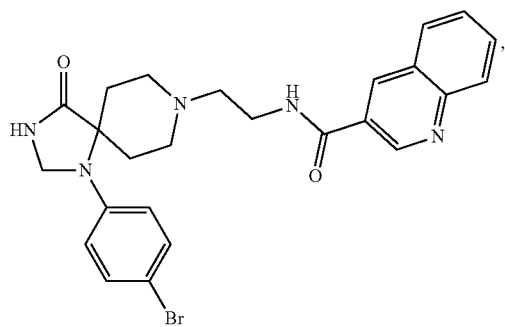
-continued
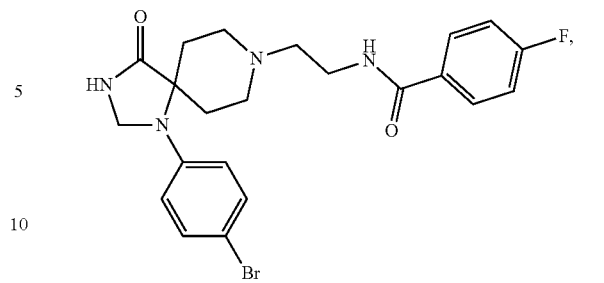
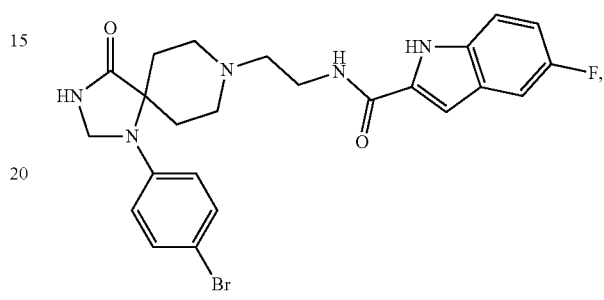
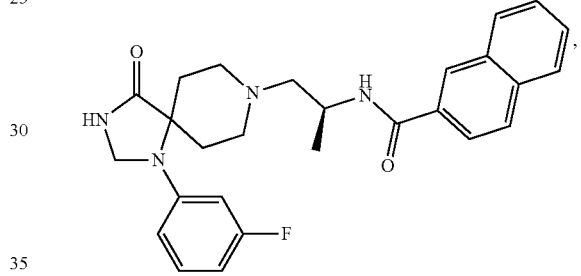
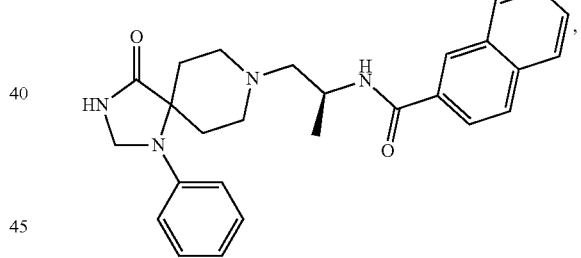
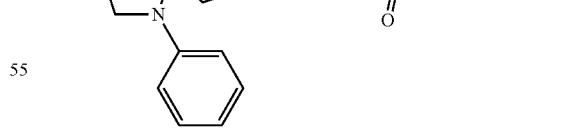
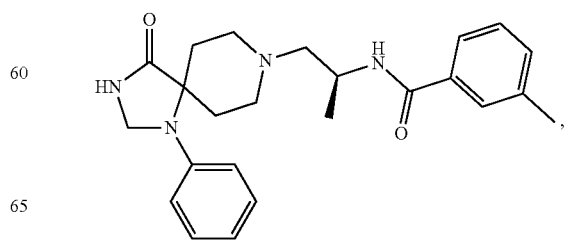

-continued

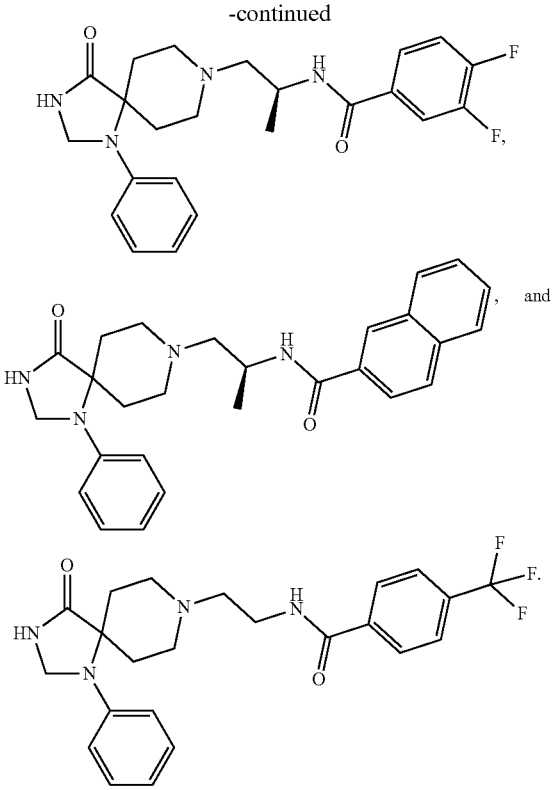

16. The method of claim 1, wherein the phospholipase D inhibitor is a PLD1-selective inhibitor.

17. The method of claim 1, wherein the phospholipase D inhibitor is

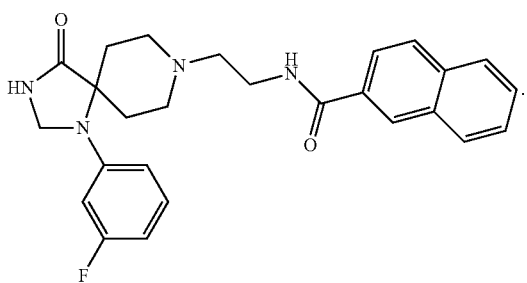 [SMILES: O=C(NCCN1CCC2(CC1)C(=O)NCN2c1cccc(F)c1)c1ccc2ccccc2c1]

18. The method of claim 1, wherein the viral protein M2 ion channel inhibitor is present and selected from the group consisting of amantadine, rimantadine, 1-amino-1,3,5-trimethylcyclohexane, 1-amino-1(trans),3(trans),5-trimethylcyclohexane, 1-amino-1 (cis),3(cis),5-trimethylcyclohexane, 1-amino-1,3,3,5-tetramethylcyclohexane, 1-amino-1,3,3,5,5-pentamethylcyclohexane(neramexane), 1-amino-1,3,5,5-tetramethyl-3-ethylcyclohexane, 1-amino-1,5,5-trimethyl-3,3-diethylcyclohexane, 1-amino-1,5,5-trimethyl-cis-3-ethylcyclohexane, 1-amino-(1S,5S)cis-3-ethyl-1,5,5-trimethylcyclohexane, 1-amino-1,5,5-trimethyl-trans-3-ethylcyclohexane, 1-amino-(1R,5S)trans-3-ethyl-1,5,5-trimethylcyclohexane, 1-amino-1-ethyl-3,3,5,5-tetramethylcyclohexane, 1-amino-1-propyl-3,3,5,5-tetramethylcyclohexane, N-methyl-1-amino-1,3,3,5,5-pentamethylcyclohexane, N-ethyl-1-amino-1,3,3,5,5-pentamethyl-cyclohexane, N-(1,3,3,5,5-pentamethylcyclohexyl)pyrrolidine, 3,3,5,5-tetramethylcyclohexylmethylamine, 1-amino-1-propyl-3,3,5,5-tetramethylcyclohexane, 1 amino-1,3,3,5(trans)-tetramethylcyclohexane(axial amino group), 3-propyl-1,3,5,5-tetramethylcyclohexylamine semihydrate, 1-amino-1,3,5,5-tetramethyl-3-ethylcyclohexane, 1-amino-1,3,5-trimethylcyclohexane, 1-amino-1,3-dimethyl-3-propylcyclohexane, 1-amino-1,3(trans),5(trans)-trimethyl-3(cis)-propylcyclohexane, 1-amino-1,3-dimethyl-3-ethylcyclohexane, 1-amino-1,3,3-trimethylcyclohexane, cis-3-ethyl-1(trans)-3(trans)-5-trimethylcyclohexamine, 1-amino-1,3(trans)-dimethylcyclohexane, 1,3,3-trimethyl-5,5-dipropylcyclohexylamine, 1-amino-1-methyl-3(trans)-propylcyclohexane, 1-methyl-3 (cis)-propylcyclohexylamine, 1-amino-1-methyl-3 (trans)-ethylcyclohexane, 1-amino-1,3,3-trimethyl-5(cis)-ethylcyclohexane, 1-amino-1,3,3-trimethyl-5 (trans)-ethylcyclohexane, cis-3-propyl-1,5,5-trimethylcyclohexylamine, trans-3-propyl-1,5,5-trimethylcyclohexylamine, N-ethyl-1,3,3,5,5-pentamethylcyclohexylamine, N-methyl-1-amino-1,3,3,5,5-pentamethylcyclohexane, 1-amino-1-methylcyclohexane, N,N-dimethyl-1-amino-1,3,3,5,5-pentamethylcyclohexane, 2-(3,3,5,5-tetramethylcyclohexyl)ethylamine, 2-methyl-1-(3,3,5,5-tetramethylcyclohexyl)propyl-2-amine, 2-(1,3,3,5,5-pentamethylcyclohexyl-1)-ethylamine semihydrate, N-(1,3,3,5,5-pentamethylcyclohexyl)-pyrrolidine, 1-amino-1,3 (trans),5(trans)-trimethylcyclohexane, 1-amino-1,3(cis),5(cis)-trimethylcyclohexane, 1-amino-(1R,5S)trans-5-ethyl-1,3,3-trimethylcyclohexane, 1-amino-(1S,5S)cis-5-ethyl-1,3,3-trimethylcyclohexane, 1-amino-1,5,5-trimethyl-3(cis)-isopropyl-cyclohexane, 1-amino-1,5,5-trimethyl-3(trans)-isopropyl-cyclohexane, 1-amino-1-methyl-3 (cis)-ethyl-cyclohexane, 1-amino-1-methyl-3(cis)-methyl-cyclohexane, 1-amino-5,5-diethyl-1,3,3-trimethyl-cyclohexane, 1-amino-1,3,3,5,5-pentamethylcyclohexane, 1-amino-1,5,5-trimethyl-3,3-diethylcyclohexane, 1-amino-1-ethyl-3,3,5,5-tetramethylcyclohexane, N-ethyl-1-amino-1,3,3,5,5-pentamethylcyclohexane, N-(1,3,5-trimethylcyclohexyl)pyrrolidine, N-(1,3,5-trimethylcyclohexyl) piperidine, N-[1,3(trans),5(trans)-trimethylcyclohexyl]pyrrolidine, N-[1,3(trans),5(trans)-trimethylcyclohexyl]piperidine, N-[1,3(cis),5(cis)-trimethylcyclohexyl]pyrrolidine, N-[1,3(cis),5(cis)-trimethylcyclohexyl]piperidine, N-(1,3,3,5-tetramethylcyclohexyl)pyrrolidine, N-(1,3,3,5-tetramethylcyclohexyl)piperidine, N-(1,3,3,5,5-pentamethylcyclohexyl)pyrrolidine, N-(1,3,3,5,5-pentamethylcyclohexyl)piperidine, N-(1,3,5,5-tetramethyl-3-ethylcyclohexyl)pyrrolidine, N-(1,3,5,5-tetramethyl-3-ethylcyclohexyl)piperidine, N-(1,5,5-trimethyl-3,3-diethylcyclohexyl)pyrrolidine, N-(1,5,5-trimethyl-3,3-diethylcyclohexyl)piperidine, N-(1,3,3-trimethyl-cis-5-ethylcyclohexyl)pyrrolidine, N-(1,3,3-trimethyl-cis-5-ethylcyclohexyl)piperidine, N-[(1S,5S)cis-5-ethyl-1,3,3-trimethylcyclohexyl]pyrrolidine, N-[(1S,5S)cis-5-ethyl-1,3,3-trimethylcyclohexyl]piperidine, N-(1,3,3-trimethyl-trans-5-ethylcyclohexyl)pyrrolidine, N-(1,3,3-trimethyl-trans-5-ethylcyclohexyl)piperidine, N-[(1R,5S)trans-5-ethyl, 3,3-trimethylcyclohexyl]pyrrolidine, N-[(1R,5S)trans-5-ethyl, 3,3-trimethylcyclohexyl]piperidine, N-(1-ethyl-3,3,5,5-tetramethylcyclohexyl)pyrrolidine, N-(1-ethyl-3,3,5,5-tetramethylcyclohexyl)piperidine, N-(1-propyl-3,3,5,5-tetramethylcyclohexyl)pyrrolidine, N-(1-propyl-3,3,5,5-tetramethylcyclohexyl)piperidine, N-(1,3,3,5,5-pentamethylcyclohexyl)pyrrolidine, spiro[cyclopropane-1,2-adamantan]-2-amine, spiro[pyrrolidine-2,2'-adamantane], spiro[piperidine-2,2-adamantane], 2-(2-adamantyl)piperidine, 3-(2-adamantyl)pyrrolidine, 2-(1-adamantyl)piperidine, 2-(1-adamantyl)pyrrolidine, 2-(1-adamantyl)-2-methyl-pyrrolidine, 1-amino-3-phenyl adamantane, 1-amino-methyl adamantane, 1-amino-3-ethyl adamantane, 1-amino-3-isopropyl adamantane, 1-amino-3-n-butyl adamantane, 1-amino-3,5-diethyl adamantane, 1-amino-3,5-diisopropyl adamantane, 1-amino-3,5-di-n-butyl adamantane, 1-amino-3-methyl-5-ethyl adamantane, 1-N-methylamino-3,5-dimethyl adamantane, 1-N-ethylamino-3,5-dimethyl adamantane, 1-N-isopropyl-amino-3,5-dimethyl adamantane, 1-N,N-dimethyl-amino-3,5-dimethyl adamantane, 1-N-methyl-N-isopropyl-amino-3-methyl-5-ethyl adamantane, 1-amino-3-butyl-5-phenyl adamantane, 1-amino-3-pentyl adamantane, 1-amino-3,5-dipentyl adamantane, 1-amino-3-pentyl-5-hexyl adamantane, 1-amino-3-pentyl-5-cyclohexyl adamantane, 1-amino-3-pentyl-5-phenyl adamantane, 1-amino-3-hexyl adamantane, 1-amino-3,5-dihexyl adamantane, 1-amino-3-hexyl-5-cyclohexyl adamantane, 1-amino-3-hexyl-5-phenyl adamantane, 1-amino-3-cyclohexyl adamantane, 1-amino-3,5-dicyclohexyl adamantane, 1-amino-3-cyclohexyl-5-phenyl adamantane, 1-amino-3,5-diphenyl adamantane, 1-amino-3,5,7-trimethyl adamantane, 1-amino-3,5-dimethyl-7-ethyl adamantane, 1-amino-3,5-diethyl-7-methyl adamantane, 1-N-pyrrolidino and 1-N-piperidine derivatives, 1-amino-3-methyl-5-propyl adamantane, 1-amino-3-methyl-5-butyl adamantane, 1-amino-3-methyl-5-pentyl adamantane, 1-amino-3-methyl-5-hexyl adamantane, 1-amino-3-methyl-5-cyclohexyl adamantane, 1-amino-3-methyl-5-phenyl adamantane, 1-amino-3-ethyl-5-propyl adamantane, 1-amino-3-ethyl-5-butyl adamantane, 1-amino-3-ethyl-5-pentyl adamantane, 1-amino-3-ethyl-5-hexyl adamantane, 1-amino-3-ethyl-5-cyclohexyl adamantane, 1-amino-3-ethyl-5-phenyl adamantane, 1-amino-3-propyl-5-butyl adamantane, 1-amino-3-propyl-5-pentyl adamantane, 1-amino-3-propyl-5-hexyl adamantane, 1-amino-3-propyl-5-cyclohexyl adamantane, 1-amino-3-propyl-5-phenyl adamantane, 1-amino-3-butyl-5-pentyl adamantane, 1-amino-3-butyl-5-hexyl adamantane, and 1-amino-3-butyl-5-cyclohexyl adamantine.

19. The method of claim 1, wherein the neuraminidase inhibitor is present and selected from the group consisting of oseltamivir, oseltamivir phosphate, oseltamivir carboxylate zanamivir, peramivir, laninamivir octanoate, 2,3-didehydro-2-deoxy-N-acetylneuraminic acid (DANA), 2-deoxy-2,3-dehydro-N-trifluoroacetylneuraminic acid (FANA), N-[(1R,2S)-2-methoxy-2-methyl-1-[(2R,3S,5R)-5-(2-methylpropanoyl)-3-[(Z)-prop-1-enyl]pyrrolidin-2-yl]pentyl]acetamide (A-322278), and (2R,4S,5R)-5-[(1R,2S)-1-acetamido-2-methoxy-2-methylpentyl]-4-[(Z)-prop-1-enyl]pyrrolidine-2-carboxylic acid (A-315675).

20. The method of claim 1, wherein the phospholipase D inhibitor is

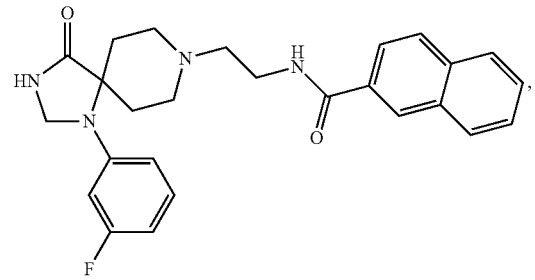 [SMILES: O=C(NCCN1CCC2(CC1)C(=O)NCN2c1cccc(F)c1)c1ccc2ccccc2c1]

and wherein the one or more therapeutic agents comprises ribavirin and/or oseltamivir.

21. A method for treating a subject comprising the step of co-administering an effective amount of a combination of two or more therapeutic agents to the subject;
   wherein the subject has been diagnosed with a need for treatment of an influenza infection prior to the administering step; and
   wherein the combination of two or more therapeutic agents comprises:
      (a) an phospholipase D inhibitor; and
      (b) one or more therapeutic agents selected from:
         (i) a viral protein M2 ion channel inhibitor,
         (ii) a neuraminidase inhibitor, and
         (iii) a nucleoside analog selected from ribavirin, viramidine, 6-fluoro-3-hydroxy-2-pyrazinecarboxamide, 2'-deoxy-2'-fluoroguanosine, pyrazofurin, carbodine, and cyclopenenyl cytosine;
   wherein the phospholipase D inhibitor is a compound having a structure represented by a formula:

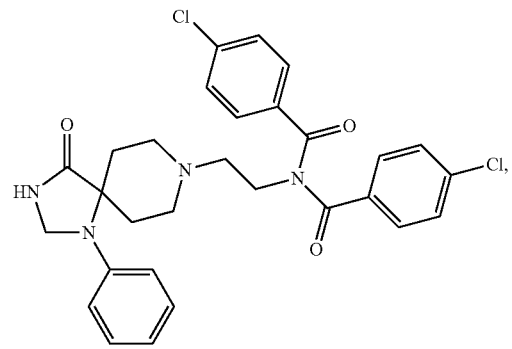 [SMILES: O=C(c1ccc(Cl)cc1)N(CCN1CCC2(CC1)C(=O)NCN2c1ccccc1)C(=O)c1ccc(Cl)cc1]

or a pharmaceutic acceptable salt thereof.

* * * * *

UNITED STATES PATENT AND TRADEMARK OFFICE
CERTIFICATE OF CORRECTION

PATENT NO. : 9,453,017 B2  
APPLICATION NO. : 14/348036  
DATED : September 27, 2016  
INVENTOR(S) : Craig W. Lindsley et al.

Page 1 of 1

It is certified that error appears in the above-identified patent and that said Letters Patent is hereby corrected as shown below:

In the Claims

In Column 157, insert the following at Line 45

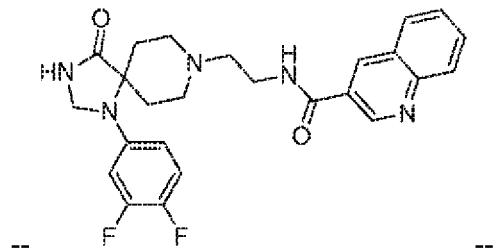

-- --

Signed and Sealed this  
Third Day of January, 2017

Michelle K. Lee  
*Director of the United States Patent and Trademark Office*